US012559533B2

(12) United States Patent
Bosch Tubert et al.

(10) Patent No.: US 12,559,533 B2
(45) Date of Patent: Feb. 24, 2026

(54) VIRAL EXPRESSION CONSTRUCT COMPRISING A FIBROBLAST GROWTH FACTOR 21 (FGF21) CODING SEQUENCE

(71) Applicant: Universitat Autònoma de Barcelona, Cerdanyola del Valles (ES)

(72) Inventors: Fàtima Bosch Tubert, Cerdanyola del Valles (ES); Verónica Jiménez Cenzano, Cerdanyola del Valles (ES); Claudia Jambrina Pallares, Cerdanyola del Valles (ES)

(73) Assignee: UNIVERSITAT AUTÒNOMA DE BARCELONA, Cerdanyola del Valles (ES)

( * ) Notice: Subject to any disclaimer, the term of this patent is extended or adjusted under 35 U.S.C. 154(b) by 0 days.

(21) Appl. No.: 18/484,279

(22) Filed: Oct. 10, 2023

(65) Prior Publication Data

US 2024/0182534 A1 Jun. 6, 2024

Related U.S. Application Data

(63) Continuation of application No. 16/615,854, filed as application No. PCT/EP2018/063707 on May 24, 2018, now abandoned.

(30) Foreign Application Priority Data

May 24, 2017 (EP) ...................................... 17172818

(51) Int. Cl.

| | |
|---|---|
| *C07K 14/50* | (2006.01) |
| *A01K 67/0275* | (2024.01) |
| *A61K 35/761* | (2015.01) |
| *A61K 38/00* | (2006.01) |
| *A61K 48/00* | (2006.01) |
| *C12N 15/113* | (2010.01) |
| *C12N 15/86* | (2006.01) |
| *C12N 15/85* | (2006.01) |

(52) U.S. Cl.
CPC .......... *C07K 14/50* (2013.01); *A01K 67/0275* (2013.01); *A61K 35/761* (2013.01); *C12N 15/113* (2013.01); *C12N 15/86* (2013.01); *A01K 2207/25* (2013.01); *A01K 2227/105* (2013.01); *A01K 2267/0362* (2013.01); *C12N 2015/8518* (2013.01); *C12N 2310/141* (2013.01); *C12N 2750/14143* (2013.01); *C12N 2799/02* (2013.01)

(58) Field of Classification Search
CPC ....... C07K 14/50; C12N 15/86; A61K 48/005
See application file for complete search history.

(56) References Cited

U.S. PATENT DOCUMENTS

| | | | |
|---|---|---|---|
| 5,139,941 A | 8/1992 | Muzyczka et al. |
| 5,436,146 A | 7/1995 | Shenk et al. |
| 5,464,758 A | 11/1995 | Gossen et al. |
| 5,478,745 A | 12/1995 | Samulski et al. |
| 5,741,683 A | 4/1998 | Zhou et al. |
| 6,001,650 A | 12/1999 | Colosi et al. |
| 6,057,152 A | 5/2000 | Samulski et al. |
| 6,136,597 A | 10/2000 | Hope et al. |
| 6,156,303 A | 12/2000 | Russell et al. |
| 6,165,782 A | 12/2000 | Naldini et al. |
| 6,204,059 B1 | 3/2001 | Samulski et al. |
| 6,207,455 B1 | 3/2001 | Chang |
| 6,218,181 B1 | 4/2001 | Verma et al. |
| 6,268,213 B1 | 7/2001 | Samulski et al. |
| 6,277,633 B1 | 8/2001 | Olsen et al. |
| 6,323,031 B1 | 11/2001 | Cichutek |
| 6,432,705 B1 | 8/2002 | Yee et al. |
| 6,531,456 B1 | 3/2003 | Kurtzman et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,056,502 B2 | 6/2006 | Hildinger et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,198,951 B2 | 4/2007 | Gao et al. |
| 7,201,898 B2 | 4/2007 | Monahan et al. |
| 7,220,577 B2 | 5/2007 | Zolotukhin |
| 7,229,823 B2 | 6/2007 | Samulski et al. |
| 7,282,199 B2 | 10/2007 | Gao et al. |
| 7,319,002 B2 | 1/2008 | Wilson et al. |
| 7,439,065 B2 | 10/2008 | Ferrari et al. |

(Continued)

FOREIGN PATENT DOCUMENTS

| | | |
|---|---|---|
| CN | 105916990 A | 8/2016 |
| EP | 2394667 A1 | 12/2011 |

(Continued)

OTHER PUBLICATIONS

NCBI in Genes and Diseases (Year: 1998).*
Kharitonenkov et al (The Metabolic State of Diabetic Monkeys Is Regulated by Fibroblast Growth Factor-21. Endocrinology 148(2): 774-781) (Year: 2006).*
Mingozzi et al (Therapeutic in vivo gene transfer for genetic disease using AAV: progress and challenges. Nature Reviews Genetics, vol. 12, May 2011) (Year: 2011).*

(Continued)

*Primary Examiner* — Emily A Cordas
*Assistant Examiner* — Matasha Dhar
(74) *Attorney, Agent, or Firm* — Sterne, Kessler, Goldstein & Fox P.L.L.C.

(57) ABSTRACT

The invention relates to a viral expression construct and related viral vector and nucleic acid molecule and composition and to their use wherein said construct and vector are suitable for expression in a mammal and comprise a nucleotide sequence encoding a Fibroblast growth factor 21 (FGF21) to be expressed in liver, adipose tissue and/or skeletal muscle.

16 Claims, 52 Drawing Sheets

Figure 1D:
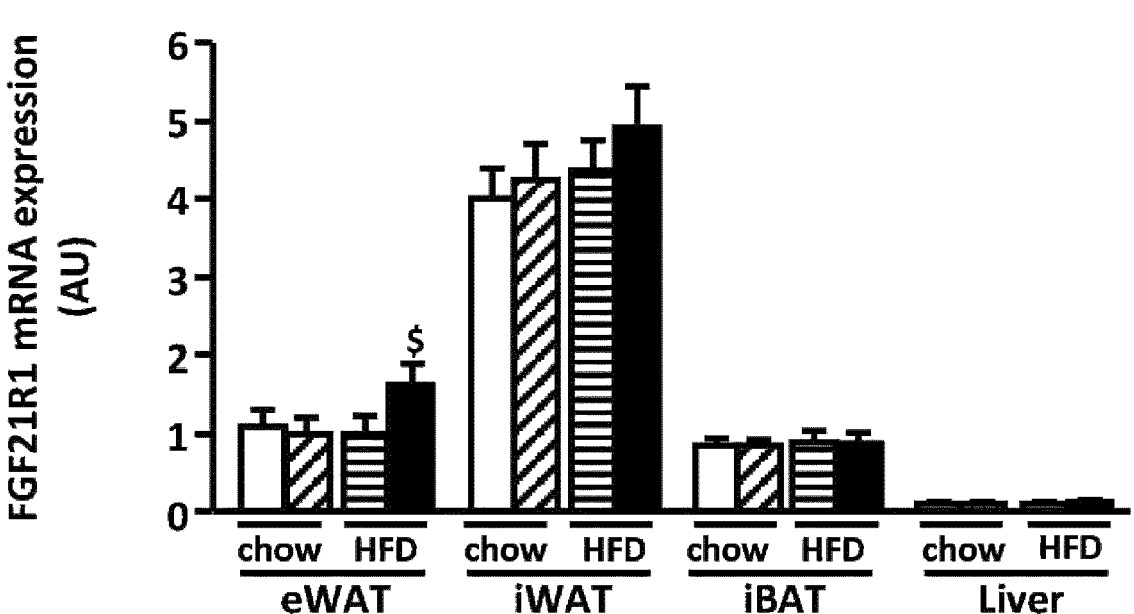
Figure 1E:
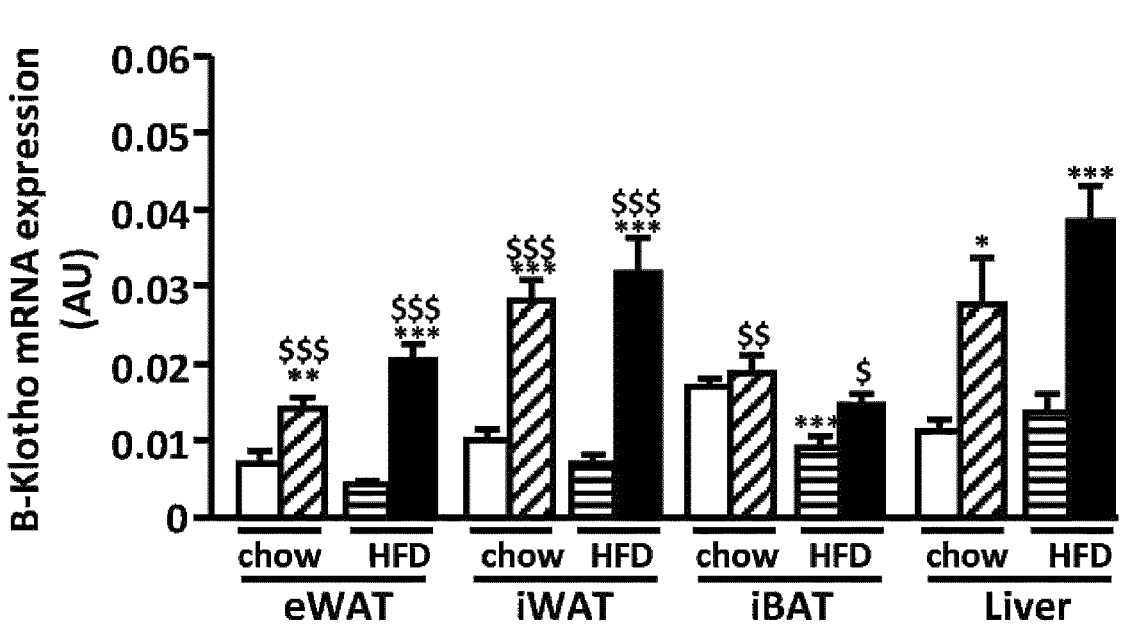

Specification includes a Sequence Listing.

(56) References Cited

U.S. PATENT DOCUMENTS

| | | | |
|---|---|---|---|
| 7,790,449 | B2 | 9/2010 | Gao et al. |
| 9,023,791 | B2 | 5/2015 | Boettcher et al. |
| 9,079,971 | B2 | 7/2015 | Cujec et al. |
| 9,309,534 | B2 | 4/2016 | Bosch et al. |
| 9,464,126 | B2 | 10/2016 | Mohammadi et al. |
| 2002/0065239 | A1 | 5/2002 | Caplan et al. |
| 2003/0219409 | A1 | 11/2003 | Coffin et al. |
| 2004/0055023 | A1 | 3/2004 | Bosch et al. |
| 2005/0187154 | A1 | 8/2005 | Kahn et al. |
| 2008/0075740 | A1 | 3/2008 | Gao et al. |
| 2010/0216709 | A1 | 8/2010 | Scheule et al. |
| 2010/0240029 | A1 | 9/2010 | Guarente et al. |
| 2011/0166210 | A1 | 7/2011 | Felber et al. |
| 2012/0040401 | A1 | 2/2012 | Ellis et al. |
| 2014/0194352 | A1 | 7/2014 | Ling et al. |
| 2018/0186849 | A1 | 7/2018 | Mohammadi et al. |
| 2020/0102361 | A1 | 4/2020 | Bosch Tubert et al. |
| 2021/0386870 | A1 | 12/2021 | Bosch Tubert et al. |

FOREIGN PATENT DOCUMENTS

| | | | |
|---|---|---|---|
| EP | 2453019 A1 | 5/2012 | |
| EP | 2492347 A1 | 8/2012 | |
| EP | 2634253 A1 | 9/2013 | |
| EP | 2692868 A1 | 2/2014 | |
| EP | 3101125 A1 | 12/2016 | |
| EP | 3269823 A2 | 1/2018 | |
| JP | 2014506787 A | 3/2014 | |
| JP | 2016530360 A | 9/2016 | |
| WO | WO-1996040954 A1 | 12/1996 | |
| WO | WO-199749827 A2 | 12/1997 | |
| WO | WO-199809524 A1 | 3/1998 | |
| WO | WO-199811244 A2 | 3/1998 | |
| WO | WO-1998032869 A1 | 7/1998 | |
| WO | WO-199961601 A2 | 12/1999 | |
| WO | WO-200028004 A1 | 5/2000 | |
| WO | WO-200028061 A2 | 5/2000 | |
| WO | WO-2001083692 A2 | 11/2001 | |
| WO | WO-2001091803 A2 | 12/2001 | |
| WO | WO-2001094605 A2 | 12/2001 | |
| WO | WO-0224234 A2 | 3/2002 | |
| WO | WO-2002049423 A1 | 6/2002 | |
| WO | WO-2003014367 A1 | 2/2003 | |
| WO | WO-2003042397 A2 | 5/2003 | |
| WO | WO-2003052051 A2 | 6/2003 | |
| WO | WO-2003052052 A2 | 6/2003 | |
| WO | WO-2005033321 A2 | 4/2005 | |
| WO | WO-2006001982 A2 | 1/2006 | |
| WO | WO-2006110689 A2 | 10/2006 | |
| WO | WO-2007000668 A2 | 1/2007 | |
| WO | WO-2007058902 A1 | 5/2007 | |
| WO | WO-200170276 A2 | 9/2007 | |
| WO | WO-2007127264 A2 | 11/2007 | |
| WO | WO-2008027084 A2 | 3/2008 | |
| WO | WO-2008061011 A2 | 5/2008 | |
| WO | WO-2008071959 A1 | 6/2008 | |
| WO | WO-2008103755 A1 | 8/2008 | |
| WO | WO-2009120978 A2 | 10/2009 | |
| WO | WO-2009149171 A2 | 12/2009 | |
| WO | WO-2009151172 A1 | 12/2009 | |
| WO | WO-2010010887 A1 | 1/2010 | |
| WO | WO-2010139741 A1 | 12/2010 | |
| WO | WO-2011004051 A1 | 1/2011 | |
| WO | WO-2011127337 A2 | 10/2011 | |
| WO | WO-2011154520 A1 | 12/2011 | |
| WO | WO-2012007458 A1 | 1/2012 | |
| WO | WO-2012106465 A2 | 8/2012 | |
| WO | WO 2013/006486 A2 * | 1/2013 | |
| WO | WO-2013033452 A2 | 3/2013 | |
| WO | WO-2013063379 A1 | 5/2013 | |
| WO | WO-2014020149 A1 | 2/2014 | |
| WO | WO-2014085365 A2 | 6/2014 | |
| WO | WO-2014130659 A1 | 8/2014 | |
| WO | WO-2015009480 A1 | 1/2015 | |
| WO | WO-2015044292 A1 | 4/2015 | |
| WO | WO-2015060722 A1 | 4/2015 | |
| WO | WO-2015173308 A1 | 11/2015 | |
| WO | WO-2016041588 A1 | 3/2016 | |
| WO | WO-2016087678 A1 | 6/2016 | |
| WO | WO-2016110518 A1 | 7/2016 | |
| WO | WO-2016193431 A1 | 12/2016 | |
| WO | WO-2017021893 A1 | 2/2017 | |
| WO | WO-2017201527 A2 | 11/2017 | |
| WO | WO-2018060097 A1 | 4/2018 | |

OTHER PUBLICATIONS

Issa et al (Various AAV Serotypes and Their Applications in Gene Therapy: An Overview. Cells 2023, 12, 785) (Year: 2023).*

Gao et al (Clades of Adeno-Associated Viruses Are Widely Disseminated in Human Tissues. Journal of Virology, Jun. 2004, p. 6381-6388) (Year: 2004).*

Yan et al (The Roles and Pharmacological Effects of FGF21 in Preventing Aging-Associated Metabolic Diseases. Frontiers in Cardiovascular Medicine, vol. 8, Mar. 30, 2021). (Year: 2021).*

Mingozzi et al (Immune responses to AAV vectors: overcoming barriers to successful gene therapy. Blood First Edition paper, Apr. 17, 2013) (Year: 2013).*

NM_019113.4 (mRNA and CDS sequence of human FGF21 gene, available at least since Mar. 2016). (Year: 2016).*

NP_061986.1 (protein sequence of human FGF21 gene, available at least since Mar. 2016 (Year: 2016).*

Sequence alignment NP_061986.1with SEQ 1 (Year: 2025).*

Huang, X., et al., "Forced expression of hepatocyte-specific fibroblast growth factor 21 delays initiation of chemically induced hepatocarcinogenesis," Mol Carcinog 45(12):934-942, Wiley, United States (Aug. 2006).

UniProtKB/Swiss-Prot, "FGF21_MOUSE," Acession No. Q9JJN, accessed at https://www.uniprot.org/uniprot/Q9JJN1.txt?version=119, accessed on May 10, 2017, 3 pages.

UniProtKB/TrEMBL, "E2RRP8_CANLF," Acession No. E2RRP, accessed at https://www.uniprot.org/uniprot/E2RRP8.txt?version=47, accessed on May 10, 2017, 3 pages.

Kuznik, B.I., et al. "Growth Factors of Fibroblasts FGF19, FGF21, FGF23 as Endocrine regulators of Physiological Functions and Geroprotectors. Epigenetic Regulatory Mechanisms," Uspehi Sovremennoj Biologii (Advances In Modern Biology) 137(1):84-99, Russian Academy of Sciences, Russia (2017).

Sequence alignment between Mus musculus FGF21 and Seq ID No. 4 from U.S. Appl. No. 16/615,854, cited as "SEQUENCE_ALIGNMENT_US-16-615-854-4.align.pdf Year: 2022)" in U.S. Appl. No. 16/615,854 in an Office Action mailed Apr. 12, 2023.

Ayuso, E., and Bosch, F., "Highlights on AAV Mediated Gene Transfer: Introduction," in The Clinibook: Clinical Gene Transfer State of the Art, Cohen-Haguenauer, O., ed., pp. 31-34, Editions EDK, Paris, France (2012).

Ayuso, E., et al., "AAV Gene Therapy for Diabetes Mellitus," in The Clinibook: Clinical Gene Transfer State of the Art, Cohen-Haguenauer, O., ed., pp. 62-70, Editions EDK, Paris, France (2012).

Ayuso, E., et al., "High AAV vector purity results in serotype- and tissue-independent enhancement of transduction efficiency," Gene Ther 17(4):503-510, Nature Publishing Group, United Kingdom (Apr. 2010).

Ayuso, E., et al., "Reference Materials for the Characterization of Adeno-Associated Viral Vectos," in The Clinibook: Clinical Gene Transfer State of the Art, Cohen-Haguenauer, O., ed., pp. 83-90, Editions EDK, Paris, France (2012).

Casana, E., et al., "AAV-mediated BMP7 gene therapy counteracts insulin resistance and obesity," Mol Ther Methods Clin Dev 25:190-204, Cell Press, United States (Mar. 2022).

Casana, E., et al., "BMP7 overexpression in adipose tissue induces white adipogenesis and improves insulin sensitivity in ob/ob mice," Int J Obes (Lond) 45(2):449-460, Nature Publishing Group, United Kingdom (Feb. 2021).

Garcia, M., et al., "Phosphofructo-1-kinase deficiency leads to a severe cardiac and hematological disorder in addition to skeletal muscle glycogenosis," PLoS Genet 5(8):e1000615, Public Library of Science, United States (Aug. 2009), 12 pages.

(56) References Cited

OTHER PUBLICATIONS

Gros, L., et al., "Insulin production by engineered muscle cells," Hum Gene Ther 10(7):1207-1217, Mary Ann Liebert Inc., United States (May 1999).

Haurigot, V., et al., "Future Directions: Gene Therapy for Diabetes," in Textbook of Diabetes, Holt, R., ed., pp. 1029-1037, Wiley-Blackwell, United States (2017).

Haurigot, V., et al., "Increased intraocular insulin-like growth factor-I triggers blood-retinal barrier breakdown," J Biol Chem 284(34):22961-22969, American Society for Biochemistry and Molecular Biology Inc., United States (Aug. 2009).

Haurigot, V., et al., "Long-term retinal PEDF overexpression prevents neovascularization in a murine adult model of retinopathy," PLoS One 7(7):e41511, Public Library of Science, United States (2012), 12 pages.

Jimenez, V., et al., "In vivo adeno-associated viral vector-mediated genetic engineering of white and brown adipose tissue in adult mice," Diabetes 62(12):4012-4022, American Diabetes Association Inc., United States (Dec. 2013).

Mann, C.J., et al., "Molecular signature of the immune and tissue response to non-coding plasmid DNA in skeletal muscle after electrotransfer," Gene Ther 19(12):1177-1186, Nature Publishing Group, United Kingdom (Dec. 2012).

Mann, C.J., et al., "Skeletal muscle metabolism in the pathology and treatment of type 1 diabetes," Curr Pharm Des 16(8):1002-1020, Bentham Science Publishers B.V., United Arab Emirates (2010).

Marco, S., et al., "In Vivo Gene Therapy for Mucopolysaccharidosis Type III (Sanfilippo Syndrome): A New Treatment Horizon," Hum Gene Ther 30(10):1211-1221, Mary Ann Liebert Inc., United States (Oct. 2019).

Munoz, S., et al., "Treatment of infantile-onset Pompe disease in a rat model with muscle-directed AAV gene therapy," Mol Metab 81:101899, Elsevier GmbH, Germany (Mar. 2024), 17 pages.

Otaegui, P.J., et al., "Expression of glucokinase in skeletal muscle: a new approach to counteract diabetic hyperglycemia," Hum Gene Ther 11(11):1543-1552, Mary Ann Liebert Inc., United States (Jul. 2000).

Otaegui, P.J., et al., "Glucose-regulated glucose uptake by transplanted muscle cells expressing glucokinase counteracts diabetic hyperglycemia," Hum Gene Ther 13(18):2125-2133, Mary Ann Liebert Inc., United States (Dec. 2002).

Riu, E., et al., "Counteraction of type 1 diabetic alterations by engineering skeletal muscle to produce insulin: insights from transgenic mice," Diabetes 51(3):704-711, American Diabetes Association Inc., United States (Mar. 2002).

Roca, C., et al., "Disease correction by AAV-mediated gene therapy in a new mouse model of mucopolysaccharidosis type IIID," Hum Mol Genet 26(8):1535-1551, Oxford University Press, United Kingdom (Apr. 2017).

Ruberte, J., et al., "Increased ocular levels of IGF-1 in transgenic mice lead to diabetes-like eye disease," J Clin Invest 113(8):1149-1157, The American Society for Clinical Investigation, United States (Apr. 2004).

Vila, L., et al., "AAV8-mediated Sirt1 gene transfer to the liver prevents high carbohydrate diet-induced nonalcoholic fatty liver disease," Mol Ther Methods Clin Dev 1:14039, Cell Press, United States (Oct. 2014), 10 pages.

Villacampa, P., et al., "Insulin-like growth factor I (IGF-I)-induced chronic gliosis and retinal stress lead to neurodegeneration in a mouse model of retinopathy," J Biol Chem 288(24):17631-17642, American Society for Biochemistry and Molecular Biology Inc., United States (Jun. 2013).

Villacampa, P., et al., "Proliferative retinopathies: animal models and therapeutic opportunities," Curr Neurovasc Res 12(2):189-198, Bentham Science Publishers B.V., United Arab Emirates (2015).

Jimenez, V., et al., "FGF21 Gene Therapy as Treatment for Obesity and Insulin Resistance," EMBO Mol Med 10(8):e8791, Wiley-Blackwell, United Kingdom (Aug. 2018).

Konishi, M., et al., "Secreted Factor, FG21, Regulates Diverse Biological Processes," Journal of Japanese Biochemical Society 88(1): 86-93, The Japanese Biochemical Society, Japan (Feb. 2016).

Inagaki, T., et al., "Endocrine Regulation of the Fasting Response by PPAR-alpha—Mediated Induction of Fibroblast Growth Factor 21," Cell Metab. 5(6):415-25, Cell Press, United States (2007).

Yang, H., et al., "Recombinant AAV-DJ Vector-Mediated FGF-21/FGF-21-GLP-1 Long-Term Expression in db/db Mice With Type 2 Diabetes Mellitus," Abstracts of the ASGCT 17th Annual Meeting, May 21-24, 2014, Washington, DC, Mol Ther. (22):S367 (Jun. 2014), 1 page.

Gao, M., et al., "Hydrodynamics-Based FGF21 Gene Transfer for Treatment and Prevention of High Fat Diet Induced Obesity and Insulin Resistance," Abstracts of the ASGCT 17th Annual Meeting, May 21-24, 2014, Washington, DC, Mol Ther. (22):S588 (Jun. 2014), 1 page.

Ahi, Y., et al., "Adenoviral vector immunity: its implications and circumvention strategies," Curr Gene Ther 11(4):307-320, NIH, United States (Aug. 2011).

Al-Dosari, M., et al., "Evaluation of viral and mammalian promoters for driving transgene expression in mouse liver," Biochem Biophyc Res Commun 339(2):673-678, Elsevier, Netherlands (Jan. 2006).

Allera-Moreau, C., et al., "Long term expression of bicistronic vector driven by the FGF-1 IRES in mouse muscle," BMC Biotechnol 7:74, BioMed Cental Ltd., United Kingdom (Oct. 2007).

Ayuso, C., et al., "Production, purification and characterization of adeno-associated vectors," Curr Gene Ther 10(6):423-436, Bentham Science Publishers Ltd., United Arab Emirates (Dec. 2010).

Berglund E., et al., "Fibroblast growth factor 21 controls glycemia via regulation of hepatic glucose flux and insulin sensitivity," Endocrinology 150(9):4084-4093, The Endocrine Society, United States (Sep. 2009).

Borel, F., et al., "Recombinant AAV as a platform for translating the therapeutic potential of RNA interference," Molecular Therapy 22(4):692-701, The American Society of Gene & Cell Therapy, United States (Apr. 2014).

Boulos, S., et al., "Assessment of CMV, RSV and SYN1 promoters and the woodchuck post-transcriptional regulatory element in adenovirus vectors for transgene expression in cortical neuronal cultures," Brain Res 1102(1):27-38, Elsevier, Netherlands (Aug. 2006).

Brown, B., and Naldini, L., "Exploiting and antagonizing microRNA regulation for therapeutic and experimental applications," Nat Rev Genet 10(8):578-585, Nature Publishing Group, United Kingdom (Aug. 2009).

Callejas, D., et al., "Gene Therapy for Type I Diabetes by Engineering Skeletal Muscle to Express Insulin and Glucokinase (GK): Pre-clinical studies in Diabetic Dogs" Poster presentation, 2008.

Callejas, D., et al., "Treatment of diabetes and long-term survival after insulin and glucokinase gene therapy," Diabetes 62(5):1718-1729, American Diabetes Association, United States (May 2013).

Camacho, R., et al., "Pegylated Fgf21 rapidly normalizes insulin-stimulated glucose utilization in diet-induced insulin resistant mice," Eur J Pharmacol 715(1-3):41-45, Elsevier, Netherlands (Sep. 2013).

Card, P., et al., "MicroRNA silencing improves the tumor specificity of adenoviral transgene expression," Cancer Gene Therapy 19(7):451-459, Nature Publishing Group, United Kingdom (May 2012).

Casteilla, L., et al., "Virus-based gene transfer approaches and adipose tissue biology," Curr Gene Ther 8(2):79-87, Bentham Science Publishers Ltds., United Arab Emirates (Apr. 2008).

Chao, H., et al., "Several log increase in therapeutic transgene delivery by distinct adeno-associated viral serotype vectors," Mol Ther 2(6):619-623, The American Society of Gene Therapy, United States (Dec. 2000).

Charoenphandhu, N., et al., "Fibroblast growth factor-21 restores insulin sensitivity but induces aberrant bone microstructure in obese insulin-resistant rats," J Bone Miner Metab 35(2):142-149, The Japanese Society for Bone and Mineral Research and Springer Japan, Japan (Mar. 2017).

Chen, J., et al., "The role of microRNA-1 and microRNA-133 in skeletal muscle proliferation and differentiation," Nat Genet 38(2):228-233, Nature Publishing Group, United Kingdom (Feb. 2006).

(56)　　　　References Cited

OTHER PUBLICATIONS

Chiorini, J., et al., "Cloning of adeno-associated virus type 4 (AAV4) and generation of recombinant AAV4 particles," Journal of Virology 71(9):6823-6833, American Society for Microbiology, United States (Sep. 1997).

Collaco, A., and Geusz, M., "Monitoring immediate-early gene expression through firefly luciferase imaging of HRS/J hairless mice," BMC Physiology 3:8, BioMed Central Ltd., United Kingdom (Aug. 2003).

Connelly, S., and Mech, C., "Delivery of adenoviral DNA to mouse liver," in Gene Delivery to Mammalian Cells vol. 2: Viral Gene Transfer Techniques, Methods Mol Biol 246:37-52, Humana Press Inc., United States (2004).

Croyle, M., "Development of novel formulations that enhance adenoviral-mediated gene expression in the lung in vitro and in vivo," Mol Ther 4(1):22-28, The American Society of Gene Therapy, United States (Jul. 2001).

Douris, N., et al., "Central Fibroblast Growth Factor 21 Browns White Fat via Sympathetic Action in Male Mice," Endocrinology 156(7):2470-2481, The Endocrine Society, United States (Apr. 2015).

Duarte, N., et al., "How Inflammation Impinges on NAFLD: A Role for Kupffer Cells," Biomed Res Int 2015:984578, Hindawi Publishing Corporation, United States (Mar. 2015).

Emanuelli, B., et al., "Interplay between FGF21 and insulin action in the liver regulates metabolism," J Clin Invest 124(2):515-527, The Journal of Clinical Investigation, United States (Feb. 2014).

Erion, D., et al., SirT1 knockdown in liver decreases basal hepatic glucose production and increases hepatic insulin responsiveness in diabetic rats, Proc Natl Acad Sci USA 106(27):11288-11293, PNAS, United States Jul. (Jul. 2009).

Esau, C., et al., "miR-122 regulation of lipid metabolism revealed by in vivo antisense targeting," Cell Metab 3(2):87-98, Cell Press, United States (Feb. 2006).

Fagoe, N., et al., "A compact dual promoter adeno-associated viral vector for efficient delivery of two genes to dorsal root ganglion neurons," Gene Therapy 21(3):242-252, Nature Publishing Group, United Kingdom (Nov. 2023).

Gaich, G., et al., "The effects of LY2405319, an FGF21 analog, in obese human subjects with type 2 diabetes," Cell Metabolism 18(3):333-340, Elsevier, Netherlands (Sep. 2013).

Gao, G., et al., "Novel adeno-associated viruses from rhesus monkeys as vectors for human gene therapy," Proc Natl Acad Sci USA 99(18):11854-11859, PNAS, United States (Sep. 2002).

Geisler, A., et al., "microRNA122-regulated transgene expression increases specificity of cardiac gene transfer upon intravenous delivery of AAV9 vectors," Gene Therapy 18(2):199-209, Nature Publishing Group, United Kindgom (Feb. 2011).

GenBank, "insulin-like growth factor I isoform 5 precursor [Mus musculus]," Accession No. NP 001104746.1, accessed at https://www.ncbi.nlm.nih.gov/protein/NP_001104746.1, access on Oct. 4, 2023, 3 pages.

Gray, J., and Zolotukhin, S., "Design and construction of functional AAV vectors," in Adeno-Associated Virus Methods and Protocols, Methods Molecular Biology 807:25-46, Springer Humana Press, United States (2011).

Grundy, S., et al., "Definition of metabolic syndrome: Report of the National Heart, Lung, and Blood Institute/American Heart Association conference on scientific issues related to definition," Circulation 109(3):433-438, Lippincott Williams & Wilkins, United States (Jan. 2004).

Grundy, S., "Obesity, metabolic syndrome, and coronary atherosclerosis," Circulation 105(23):2696-2698, Lippincott Williams & Wilkins, United States (Jun. 2002).

Hafenrichter, D., et al., "Quantitative evaluation of liver-specific promoters from retroviral vectors after in vivo transduction of hepatocytes," Blood 84(10):3394-3404, The American Society of Hematology, United States (1994).

Hagopian, K., et al., "Influence of age and caloric restriction on liver glycolytic enzyme activities and metabolite concentrations in mice," Exp Gerontol 38(3):253-266, Elsevier, Netherlands (Mar. 2003).

Hoffman, J., et al., "BMP4 gene therapy enhances insulin sensitivity but not adipose tissue browning in obese mice," Molecular Metabolism 32:15-26, Elsevier GmbH, Germany (Dec. 2019).

Huang, J., et al., "Development of a novel long-acting antidiabetic FGF21 mimetic by targeted conjugation to a scaffold antibody," J Pharmacol Exp Ther 346(2):270-280, The American Society for Pharmacology and Experimental Therapeutics, United States (Aug. 2013).

Jaen, M., et al., "Long-Term Efficacy and Safety of Insulin and Glucokinase Gene Therapy for Diabetes: 8-Year Follow-Up in Dogs," Mol Ther Methods Clin Dev 6:1-7, Cell Press, United States (Sep. 2017).

Jaffe, H., et al., "Adenovirus-mediated in vivo gene transfer and expression in normal rat liver," Nat Genet 1(5):372-378, Nature Publishing Group, United Kingdom (Aug. 1992).

Jimenez, V., "In vivo genetic engineering of murine pancreatic beta cells mediated by single-stranded adeno-associated viral vectors of serotypes 6, 8 and 9," Diabetologia 54(5):1075-1086, Springer Verlag, Germany (May 2011).

Kamata, K., et al., "Structural basis for allosteric regulation of the monomeric allosteric enzyme human glucokinase," Structure 12(3):429-438, Cell Press, United States (Mar. 2004).

Kaneko, J., "Carbohydrate Metabolism and Its Diseases," in *Clinical biochemistry of domestic animals 6th edition*, pp. 45-80, Academic Press, United States (2008).

Kapturczak, M., et al., "Transduction of human and mouse pancreatic islet cells using a bicistronic recombinant adeno-associated viral vector," Molecular Therapy 5(2):154-160, Cell Press, United States (Feb. 2002).

Kelly, E., and Russell, S., "MicroRNAs and the regulation of vector tropism," Molecular Therapy 17(3):406-416, Cell Press, United States (Mar. 2009).

Kelly, E., et al., "Attenuation of vesicular stomatitis virus encephalitis through microRNA targeting," J Virol 83(4):1550-1562, American Society for Microbiology, United States (Feb. 2010).

Kim, A., et al., "Once-weekly administration of a long-acting fibroblast growth factor 21 analogue modulates lipids, bone turnover markers, blood pressure and body weight differently in obese people with hypertriglyceridaemia and in non-human primates," Diabetes Obes Metab 19(12):1762-1772, Wiley-Blackwell Publishing Ltd., United Kingdom (Jul. 2017).

Kim, J., et al., "Combined expression of miR-122a, miR-1, and miR-200b can differentiate degraded RNA samples from liver, pancreas, and stomach," Pathol Int 61(2):67-72, Wiley-Blackwell Publishing Ltd., United Kingdom (Feb. 2011).

Kim, Y., et al., "Codon-optimized human sodium iodide symporter (opt-hNIS) as a sensitive reporter and efficient therapeutic gene," Theranostics 5(1):86-96, IvySpring International Publisher, Australia (Jan. 2015).

Koichi Miyake et al., (Journal of The Medical Association of Nippon Medical School), 2012, vol. 8, pp. 216-221; Translation of abstract included.

Kotronen, A., and Yki-Jarvinen, H., "Fatty liver: a novel component of the metabolic syndrome," Arerioscler Thromb Vasc Biol 28(1):27-38, Lippincott Williams & Wilkins, United States (Jan. 2008).

Lagos-Quintana, M., et al., "Identification of tissue-specific microRNAs from mouse," Current Biology 12(9):735-739, Cell Press, United States (Apr. 2002).

Lee, Y., et al., "Optimizing regulatable gene expression using adenoviral vectors," Exp Physiol 90(1):33-37, Wiley-Blackwell Publishing Ltd., United Kindom (Dec. 2004).

Li, C., et al., "A small regulatory element from chromosome 19 enhances liver-specific gene expression," Gene Therapy 16(1):43-51, Nature Publishing Group, United Kingdom (Jan. 2009).

Liu, Y., et al., "Promoter effects of adeno-associated viral vector for transgene expression in the cochlea in vivo," Exp Mol Med 39(2):170-175, Nature Publishing Group, United Kingdom (Apr. 2007).

(56) References Cited

OTHER PUBLICATIONS

Mingozzi, F., et al., "Induction of immune tolerance to coagulation factor IX antigen by in vivo hepatic gene transfer," J Clin Invest 111(9):1347-1356, The American Society for Clinical Investigation, United States (May 2003).

Mizukami, H., et al., "Adipose tissue as a novel target for in vivo gene transfer by adeno-associated viral vectors," Hum Gene Ther 17(9):921-928, Mary Ann Liebert Inc., United States (Jan. 2006).

Muise, E., et al., "Adipose fibroblast growth factor 21 is up-regulated by peroxisome proliferator-activated receptor gamma and altered metabolic states," Mol Pharmacol 74(2):403-412, The American Society for Pharmacology and Experimental Therapeutics, United States (May 2008).

Nathwani, A., et al., "Safe and efficient transduction of the liver after peripheral vein infusion of self-complementary AAV vector results in stable therapeutic expression of human FIX in nonhuman primates," Blood 109(4):1414-1421, The American Society of Hematology, United States (Feb. 2007).

Niemeyer, G., et al., "Long-term correction of inhibitor-prone hemophilia B dogs treated with liver-directed AAV2-mediated factor IX gene therapy," Blood 113(4):797-806, The American Society of Hematology, United States (Jan. 2009).

O'Brien, T., "Gene therapy for type 1 diabetes moves a step closer to reality," Diabetes 62(5):1396-1397, American Diabetes Assoication Inc., United States (May 2013).

Pfluger, P., et al., "Sirt1 protects against high-fat diet-induced metabolic damage," Proc Natl Acad Sci USA 105(28):9793-9798, PNAS, United States (Jul. 2008).

Pinkert, C., et al., "An albumin enhancer located 10 kb upstream functions along with its promoter to direct efficient, liver-specific expression in transgenic mice," Genes Dev 1(3):268-276, Cold Spring Harbor Laboratory Press, United States (May 1987).

Purushotham, A., et al., "Hepatocyte-specific deletion of SIRT1 alters fatty acid metabolism and results in hepatic steatosis and inflammation," Cell Metabolism 9(4):327-338, Cell Press, United States (Apr. 2009).

Qiao, C., et al., "Liver-specific microRNA-122 target sequences incorporated in AAV vectors efficiently inhibits transgene expression in the liver," Gene Therapy 18(4);403-410, Nature Publishing Group, United Kingdom (Apr. 2011).

Rabinowitz, J., et al., "Cross-packaging of a single adeno-associated virus (AAV) type 2 vector genome into multiple AAV serotypes enables transduction with broad specificity," Journal of Virology 76(2):791-801, American Society for Microbiology, United States (Jan. 2002).

Samms, R., et al., "Discrete Aspects of FGF21 In Vivo Pharmacology Do Not Require UCP1," Cell Rep 11(7):991-999, Cell Press, United States (May 2015).

Smith, G., et al., "The structure of T6 human insulin at 1.0 A resolution," Acta Custallogr D Biol Crystallogr 59(Pt 3):474-482, International Union of Crystallography, United Kingdom (Mar. 2003).

Talukdar, S., et al., "A Long-Acting FGF21 Molecule, PF-05231023, Decreases Body Weight and Improves Lipid Profile in Non-human Primates and Type 2 Diabetic Subjects," Cell Metabolism 23(3):427-440, Cell Press, United States (Mar. 2016).

Tian, J., and Andreadis, S., "Independent and high-level dual-gene expression in adult stem-progenitor cells from a single lentiviral vector," Gene Therapy 16(7):874-884, Nature Publishing Group, United Kingdom (Jul. 2009).

Tomlinson, E., et al., "Transgenic mice expressing human fibroblast growth factor-19 display increased metabolic rate and decreased adiposity," Endocrinology 143(5):1741-1771, Endocrine Society, United States (May 2002).

Translation of Office Action issued by JPO on Mar. 22, 2022 wherein Koichi Miyake et al was cited.

Tsai, W., et al., "MicroRNA-122 plays a critical role in liver homeostasis and hepatocarcinogenesis," Journal of Clinical Investigation 122(8):2884-2897, The American Society for Clinical Investigation, United States (Aug. 2012).

Van Linthout, S., et al., "Persistent hepatic expression of human apo A-I after transfer with a helper-virus independent adenoviral vector," Gene Therapy 9(22):1520-1528, Nature Publishing Group, United Kingdom (Nov. 2002).

Vila, L., et al., "AAV-mediated Sirt1 overexpression in skeletal muscle activates oxidative capacity but does not prevent insulin resistance," Mol Ther Methods Clin Dev 5:16072, The American Society of Gene & Cell Therapy, United States (Nov. 2016).

Wang, R., et al., "Liver steatosis and increased ChREBP expression in mice carrying a liver specific SIRT1 null mutation under a normal feeding condition," Int J Biol Sci 6(7):682-690, Ivyspring International Publisher, United States (Nov. 2010).

Wang, Z., et al., "Widespread and stable pancreatic gene transfer by adeno-associated virus vectors via different routes," Diabetes 55(4):875-884, American Diabetes Association, United States (Apr. 2006).

Wang, R., et al., "Bone Morphogenetic Protein (BMP) signaling in development and human diseases," Genes Dis 1(1):87-105, Elsevier, Netherlands (Sep. 2014).

Wang, X., et al., "A Liver-Bone Endocrine Relay by IGFBP1 Promotes Osteoclastogenesis and Mediates FGF21-Induced Bone Resorption," Cell Metabolism 22(5):811-824, Cell Press, United States (Nov. 2015).

Wei, W., et al., "Fibroblast growth factor 21 promotes bone loss by potentiating the effects of peroxisome proliferator-activated receptor $\gamma$," Proc Natl Acad Sci USA 109(8):3143-3148, PNAS, United States (Feb. 2012).

Xie, J., et al., "MicroRNA-regulated, systemically delivered rAAV9: a step closer to CNS-restricted transgene expression," Molecular Therapy 19(3):526-535, Cell Press, United States (Mar. 2011).

Xu, J., et al., "Acute glucose-lowering and insulin-sensitizing action of FGF21 in insulin-resistant mouse models—association with liver and adipose tissue effects," Am J Physiol Endocrinol Metab 297(5):E1105-E1114, The American Physiological Society, United States (Aug. 2009).

Xu, J., et al., "Fibroblast growth factor 21 reverses hepatic steatosis, increases energy expenditure, and improves insulin sensitivity in diet-induced obese mice," Diabetes 58(1):250-259, American Diabetes Association, United States (Jan. 2009).

Yan, Z., et al., "Inverted terminal repeat sequences are important for intermolecular recombination and circularization of adeno-associated virus genomes," Journal of Virology 79(1):364-379, American Society for Microbiology, United States (Jan. 2005).

Zarrin, A., et al., "Comparison of CMV, RSV, SV40 viral and Vlambda1 cellular promoters in B and T lymphoid and non-lymphoid cell lines," Biochim Biophys Acta 1446(1-2):135-139, Elsevier, Netherlands (Jul. 1999).

Zhang, J., and Yang, L., "Fibroblast Growth Factor 21 Analogs for Treating Metabolic Disorders," Front Endocrinol (Lausanne) 6:168, Frontiers Media S.A., Switzerland (Nov. 2015).

Zhang, Y., et al., "862. Adipose Tissue Transduction Using AAV8-Based Vectors: Inadvertent Gene Transfer into Liver," Molecular Therapy 11(1):S335, Elsevier, Netherlands (May 2005).

Zhang, H., et al., "Adenovirus-adeno-associated virus hybrid for large-scale recombinant adeno-associated virus production," Hum Gene Ther 20(9):922-929, Mary Ann Liebert, Inc., United States (Aug. 2009).

Zincarelli, C., et al., "Analysis of AAV serotypes 1-9 mediated gene expression and tropism in mice after systemic injection," Molecular Therapy 16(6):1073-1080, Cell Press, United States (Jun. 2008).

Mas, A., et al., "Reversal of Type 1 Diabetes by Engineering a Glucose Sensor in Skeletal Muscle," Diabetes 55(6):1546-1553, The American Diabetes Association, United States (Jun. 2006).

Zhang, J., et al. "Chronic Over-expression of Fibroblast Growth Factor 21 Increases Bile Acid Biosynthesis by Opposing FGF15/19 Action." eBioMedicine 15: 173-183, Elsevier, Netherlands (Feb. 2017).

Bordone, L., et al., "Sirt1 regulates insulin secretion by repressing UCP2 in pancreatic beta cells," PLoS Biol 4(2):e31, Public Library of Science, United States (Dec. 2005).

Dressman, D., "AAV-Mediated Gene Transfer to Models of Muscular Dystrophy: Insights into Assembly of Multi-22 Subunit Membrane Proteins," University of Pittsburgh, Graduate Facility of the School of Medicine, Dept. of Biochemistry and Molecular Genetics

(56) References Cited

OTHER PUBLICATIONS in partial fulfillment of the requirements for the degree of Doctor of Philosophy, 183 pp., United States (2001).

GenBank, "Mus musculus BAC clone RP24-92J3 from 10, complete sequence," Accession No. AC139754, accessed at https://www.ncbi.nlm.nih.gov/nucleotide/AC139754.4, accessed on Mar. 2005, pages.

Anguela, X., et al., "Nonviral-mediated hepatic expression of IGF-I increases Treg levels and suppresses autoimmune diabetes in mice," Diabetes 62(2):551-560, The American Diabetes Association, United States (Feb. 2013).

Ng, R., et al., "miRNA-32 Drives Brown Fat Thermogenesis and Trans-activates Subcutaneous White Fat Browning in Mice," Cell Reports, 19(6):1229-1246, Cell Press, United States (May 2017).

Fisher, F., et al., "FGF21 regulates PGC-1α and browning of white adipose tissues in adaptive thermogenesis," Genes Dev 26(3):271-281, Cold Spring Harbor Laboratory Press, United States (Feb. 2021).

Kharitonenkov, A., et al., "FGF-21 as a novel metabolic regulator", J Clin Invest 115(6):1627-1635, The American Society for Clinical Investigation, United States (Jun. 2005).

Coskun, T., et al., "Fibroblast Growth Factor 21 Corrects Obesity in Mice," Endocrinology 149(12):6018-6027, Endocrine Society, United States (Dec. 2008).

Sarruf, D., et al., "Fibroblast Growth Factor 21 Action in the Brain Increases Energy Expenditure and Insulin Sensitivity in Obese Rats," Diabetes 2010; 59:1817-1824, The American Diabetes Association, United States (Jul. 2010).

Office Action mailed Dec. 7, 2022, in U.S. Appl. No. 16/615,854, Tubert, F., filed Nov. 22, 2019, 11 pages.

Office Action mailed Apr. 12, 2023, in U.S. Appl. No. 16/615,854, Tubert, F., filed Nov. 22, 2019, 10 pages.

Advisory Action mailed Jul. 25, 2023, in U.S. Appl. No. 16/615,854, Tubert, F., filed Nov. 22, 2019, 3 pages.

Beqvez FDA Package Insert, Retrieved from the internet: https://www.fda.gov/media/178140/download, (2024), 20 pages.

Boisgerault, F., and Mingozzi, F., "The Skeletal Muscle Environment and Its Role in Immunity and Tolerance to AAV Vector-Mediated Gene Transfer," Current Gene Therapy 15(4):381-394, Bentham Science Publishers, United Arab Emirates (2015).

George, L.A., et al., "Hemophilia B Gene Therapy with a High-Specific-Activity Factor IX Variant," The New England Journal of Medicine 377(23):2215-2227, Massachusetts Medical Society, United States (Dec. 2017).

Harding, T.C., et al., "Intravenous Administration of an AAV-2 Vector for the Expression of Factor IX in Mice and a Dog Model of Hemophilia B," Gene Therapy 11(2):204-213, Nature Publishing Group, United Kingdom (Jan. 2004).

High, K.A., and Anguela, X.M., "Adeno-associated Viral Vectors for the Treatment of Hemophilia," Human Molecular Genetics 25(R1):R36-R41, IRL Press at Oxford University Press, United Kingdom (Apr. 2016).

Kurosu, H., et al., "Tissue-specific Expression of Betaklotho and Fibroblast Growth Factor (FGF) Receptor Isoforms Determines Metabolic Activity of FGF19 and FGF21," The Journal of Biological Chemistry 282(37):26687-26695, Elsevier Inc, United States (Sep. 2007).

Robinson, S.D., and Safavi-Hemami, H., "Insulin as a Weapon," Toxicon 123:56-61, Pergamon Press, United Kingdom (Dec. 2016).

Nathwani, A.C., et al., "Long-term safety and efficacy following systemic administration of a self-complementary AAV vector encoding human FIX pseudotyped with serotype 5 and 8 capsid proteins," Molecular Therapy 19(5):876-885, Academic Press, United States (May 2011).

Flotte, T.R., et al., "Phase 2 clinical trial of a recombinant adeno-associated viral vector expressing α1-antitrypsin: interim results," Human Gene Therapy 22(10):1239-1247, Mary Ann Liebert, Inc., United States (Oct. 2011).

National Center for Biotechnology Information, "PubChem Compound Summary for Insulin," PubChem CID 70678557, accessed at https://pubchem.ncbi.nlm.nih.gov/compound/Insulin, accessed on Jul. 3, 2025, 44 pages.

Yang, C., et al., "Control of lipid metabolism by adipocyte FGFR1-mediated adipohepatic communication during hepatic stress," Nutrition & Metabolism 9:94, pp. 1-12, BioMed Central, United Kingdom (Oct. 2012).

Hale, C., et al., "Lack of Overt FGF21 Resistance in Two Mouse Models of Obesity and Insulin Resistance," Endocrinology 153(1):69-80, The Endocrine Society, United States (Jan. 2012).

Priddy, F., et al., "Adeno-associated virus vectored immunoprophylaxis to prevent HIV in healthy adults: a phase 1 randomised controlled trial," Lancet HIV 6:e230-239 (Mar. 2019).

Ding, X., et al., "ßKlotho is required for fibroblast growth factor 21 effects on growth and metabolism," Cell Metabolism 16(3):387-393, Cell Press, United States (Sep. 2012).

Urabe, M., et al., "A novel dicistronic AAV vector using a short IRES segment derived from hepatitis C virus genome," Gene 200(1-2):157-162, Elsevier Netherlands (Oct. 1997).

Vinod, M., et al., "MiR-206 is expressed in pancreatic islets and regulates glucokinase activity," American Journal of Physiology, Endocrinology, and Metabolism 311(1):E175-E185, American Physiological Society, Untied States (Jul. 2016).

Adams, A.C., et al., "Fundamentals of FGF19 & FGF21 action in vitro and in vivo," PLoS One 7(5):e38438, 11 pages, Public Library of Science, United States (May 2012).

Chao, L., et al., "Adipose tissue is required for the antidiabetic, but not for the hypolipidemic, effect of thiazolodinediones," The Journal of Clinical Investigation 106(10):1221-1228, American Society for Clinical Investigation, United States (Nov. 2000).

Hajer, G.R., et al., "Adipose tissue dysfunction in obesity, diabetes, and vascular diseases," European Heart Journal 29(24):2959-2971, Oxford University Press, United Kingdom (Dec. 2008).

Hondares, E., et al., "Hepatic FGF21 expression is induced at birth via PPARα in response to milk intake and contributes to thermogenic activation of neonatal brown fat," Cell Metabolism 11(3):206-212, Cell Press, United States (Mar. 2010).

Lisowski, L., et al., "Adeno-associated virus serotypes for gene therapeutics," Current Opinion in Pharmacology 24:59-67, Elsevier, United Kingdom (Oct. 2015).

Moller, D.E., and Flier, J.S., "Insulin resistance—mechanisms, syndrones, and implications," New England Journal of Medicine 325(13):938-948, Massachusetts Medical Society, United States (Sep. 1991).

Nakagawa, H., "Recent advances in mouse models of obesity- and nonalcoholic steatohepatitus-associated hepatocarcinogenesis," World Journal of Hepatology 7(17):2110-2118, Baishideng Publishing Group, China (Aug. 2015).

Peeters, A., et al., "Obesity in adulthood and its consequences for life expectancy: a life-table analysis," Annuals of Internal Medicine 138(1):24-32, American College of Physicians, United States (Jan. 2003).

So, W.Y., and Leung, P.S., "Fibroblast Growth Factor 21 As an Emerging Therapeutic Target for Type 2 Diabetes Mellitus," Medicinal Research Reviews 36(4):672-704, Wiley, United States (Jul. 2016).

Spiegelman, B.M., et al., "Regulation of adipocyte gene expression in differentiation and syndromes of obesity/diabetes," Journal of Biological Chemistry 268(10):6823-6826, American Society for Biochemistry and Molecular Biology, united States (Apr. 1993).

Wu, Z., et al., "α2,3 and α2,6 N-Linked Sialic Acids Facilitate Efficient Binding and Transduction by Adeno-Associated Virus Types 1 and 6," Journal of Virology 80(18):9093-9103, American Society for Microbiology, United States (Sep. 2006).

* cited by examiner

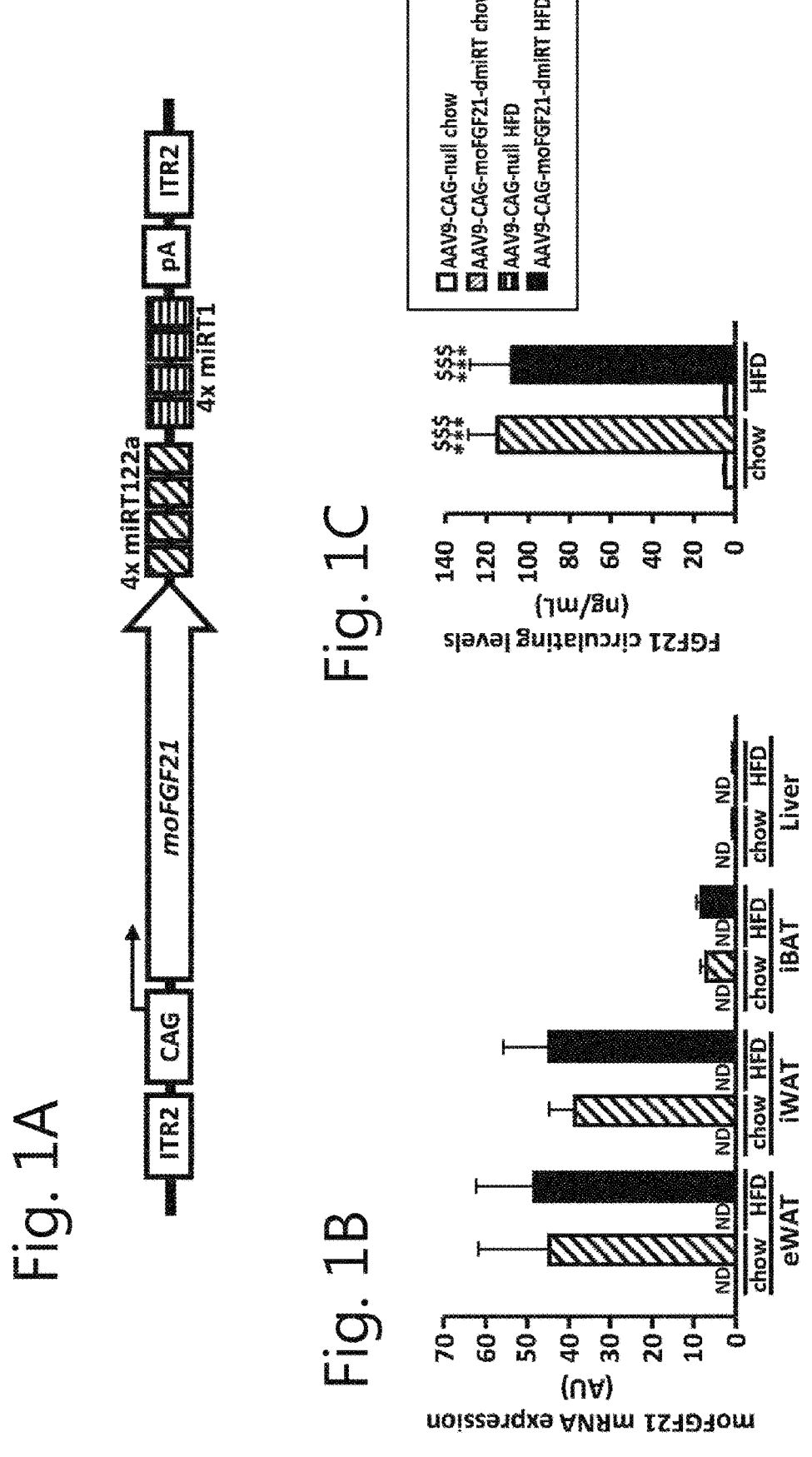

Chow AAV8-hAAT-null 5x10$^{10}$vg
HFD AAV8-hAAT-null 5x10$^{10}$vg
HFD AAV8-hAAT-moFGF21 10$^{10}$vg
HFD AAV8-hAAT-moFGF21 2x10$^{10}$vg
HFD AAV8-hAAT-moFGF21 5x10$^{10}$vg chow AAV8-hAAT-null 5x10$^{10}$vg
HFD AAV8-hAAT-null 5x10$^{10}$vg
HFD AAV8-hAAT-moFGF21 10$^{10}$vg
HFD AAV8-hAAT-moFGF21 2x10$^{10}$vg
HFD AAV8-hAAT-moFGF21 5x10$^{10}$vg

Fig. 14A
Fig. 14B
AAV8-CAG-null ☐ 1x10¹³vg
AAV8-CAG-FGF21-dmiRT
☐ 1x10¹⁰vg
▦ 5x10¹⁰vg
▨ 2x10¹¹vg
■ 1x10¹²vg
Fig. 14C
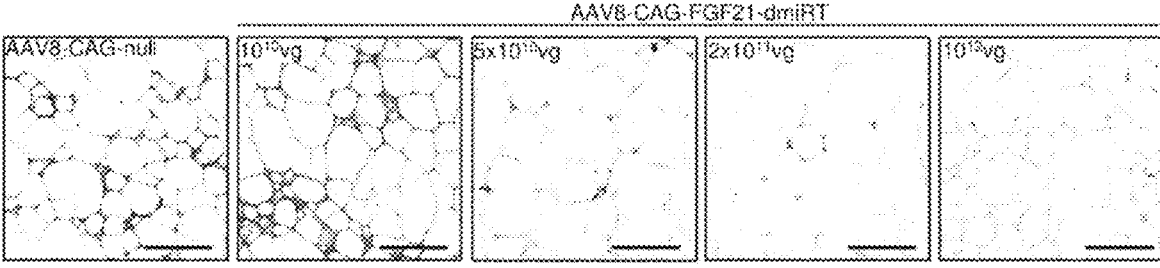
Fig. 14D
Fig. 14E
Fig. 14F
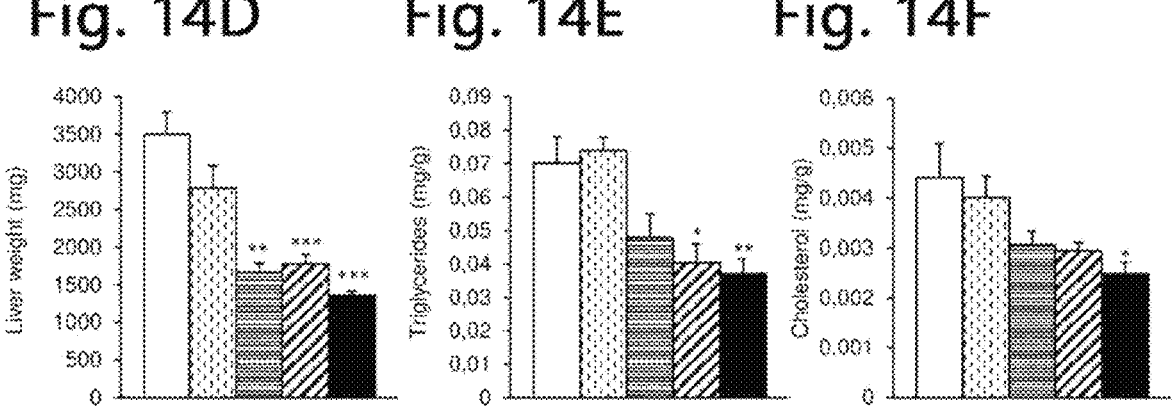

Fig. 15A
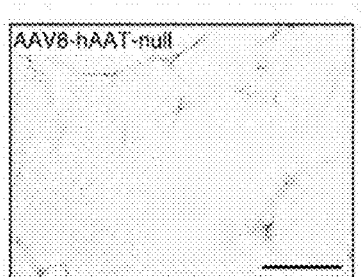
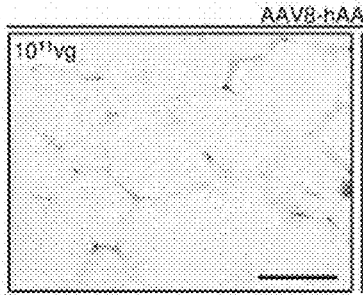
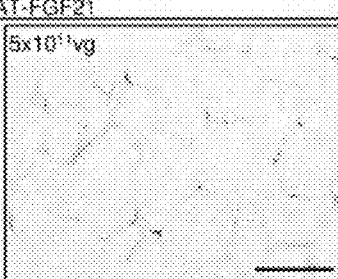
Fig. 15B
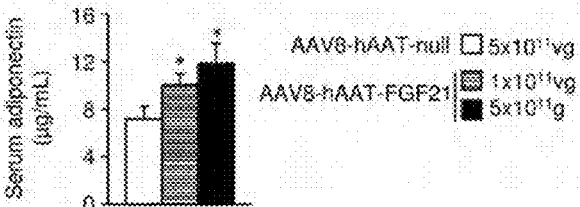
Fig. 15C
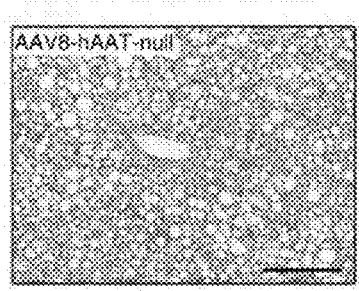
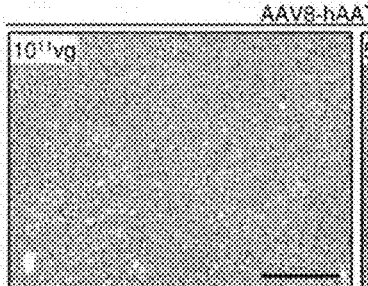
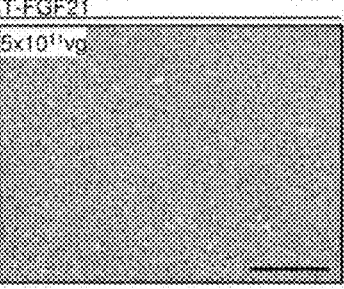
Fig. 15D
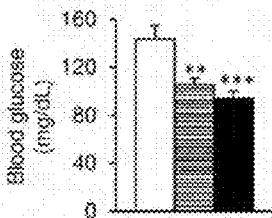
Fig. 15E
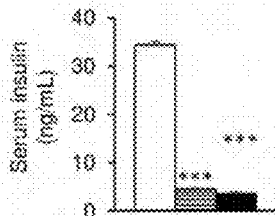

Fig. 16A
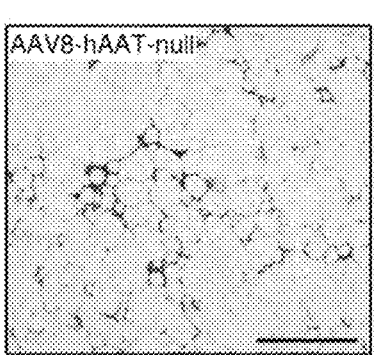
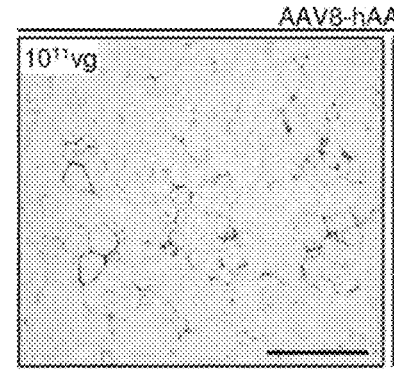
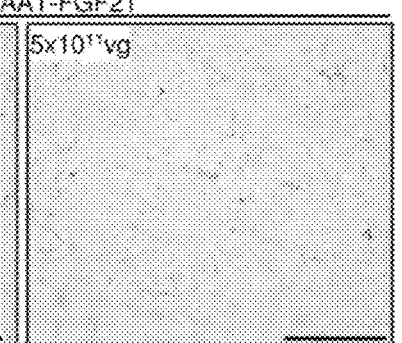
AAV8-hAAT-FGF21
AAV8-hAAT-null    10¹¹vg    5x10¹¹vg
Fig. 16B
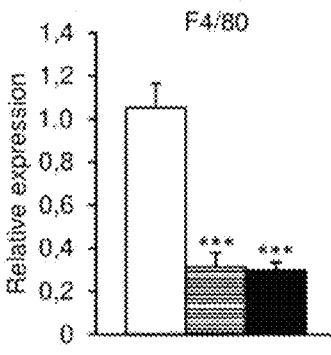
F4/80
Fig. 16C
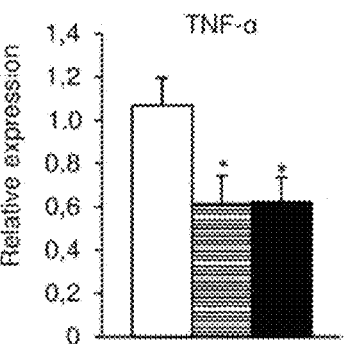
TNF-α
Fig. 16D
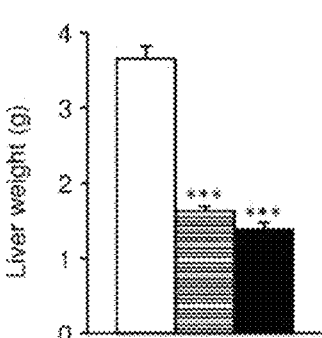
Fig. 16E
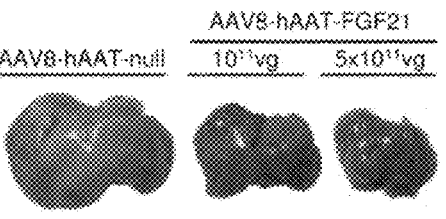
AAV8-hAAT-null
AAV8-hAAT-FGF21
10¹¹vg    5x10¹¹vg
Fig. 16F
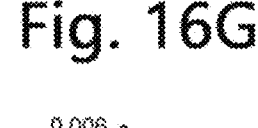
Fig. 16G
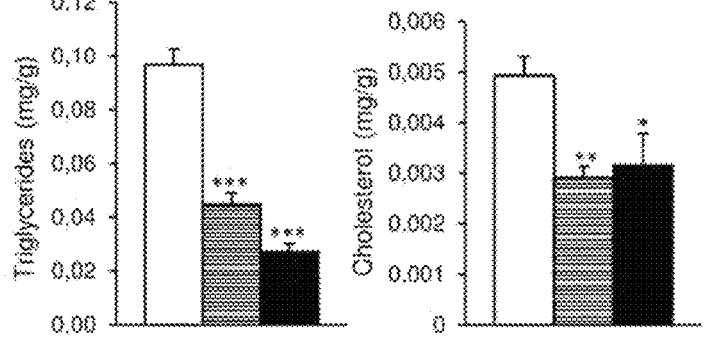

Fig. 19A
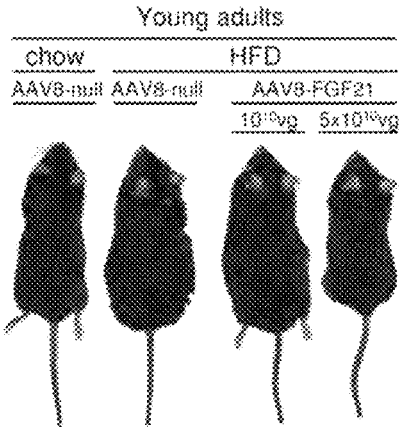
Fig. 19B
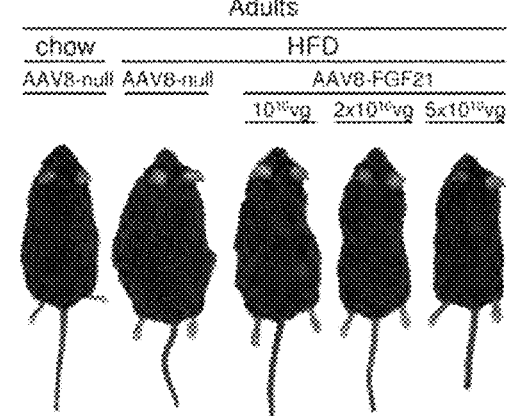
Fig. 19C
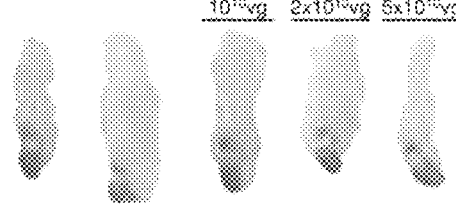
Fig. 19D
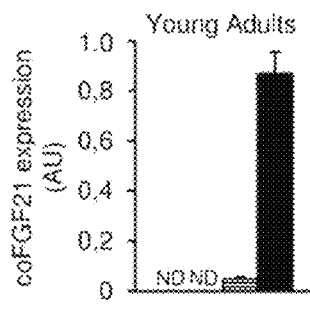
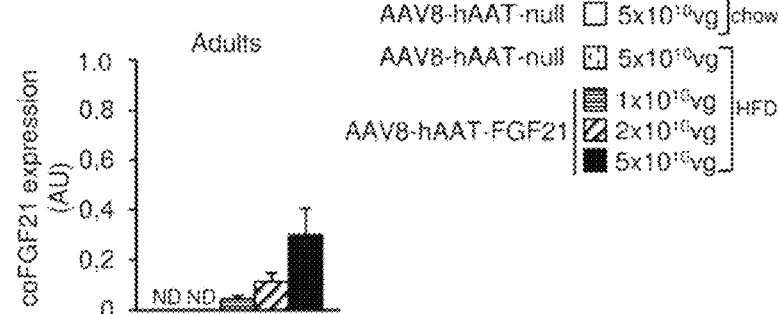
Fig. 19E

Fig. 21A
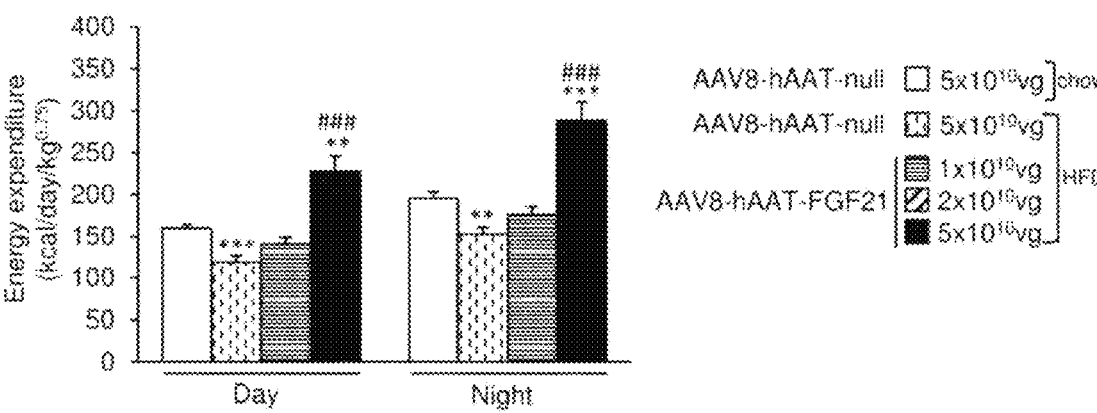
Fig. 21B
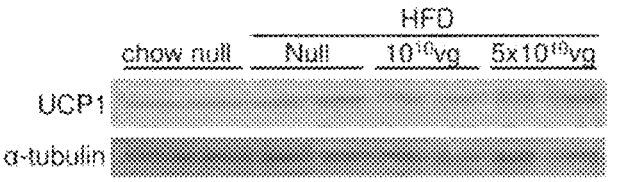
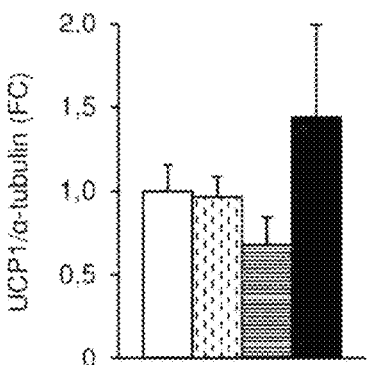
Fig. 21C
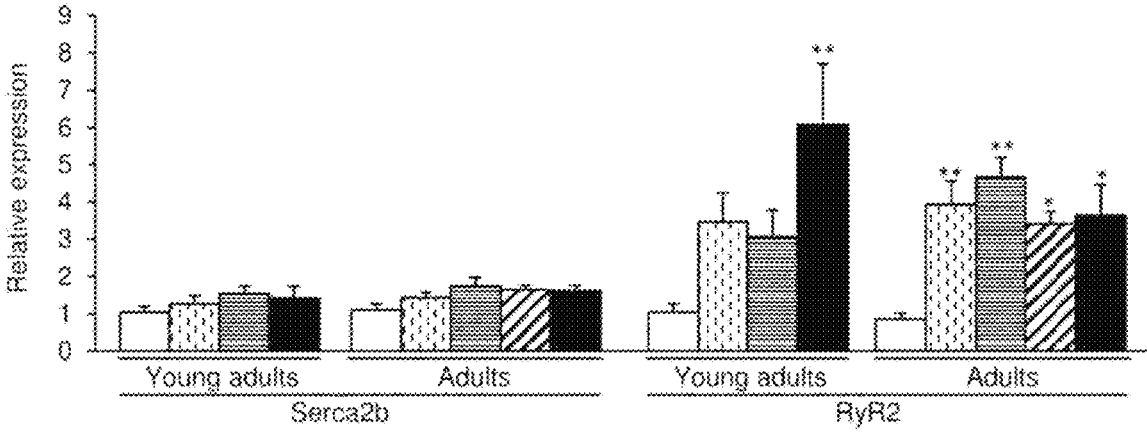

Fig. 22A    Fig. 22B
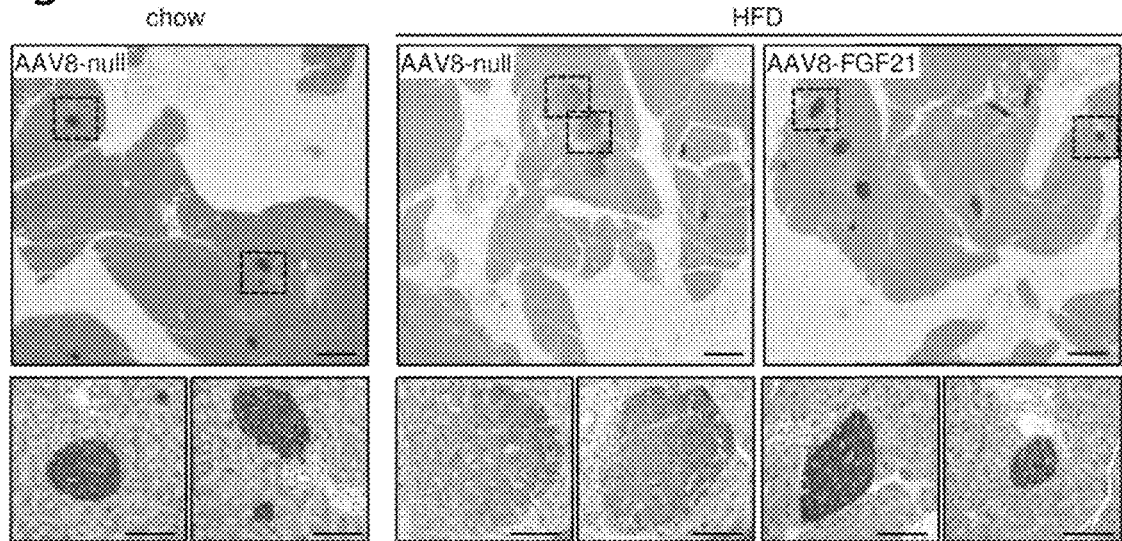
Fig. 22C
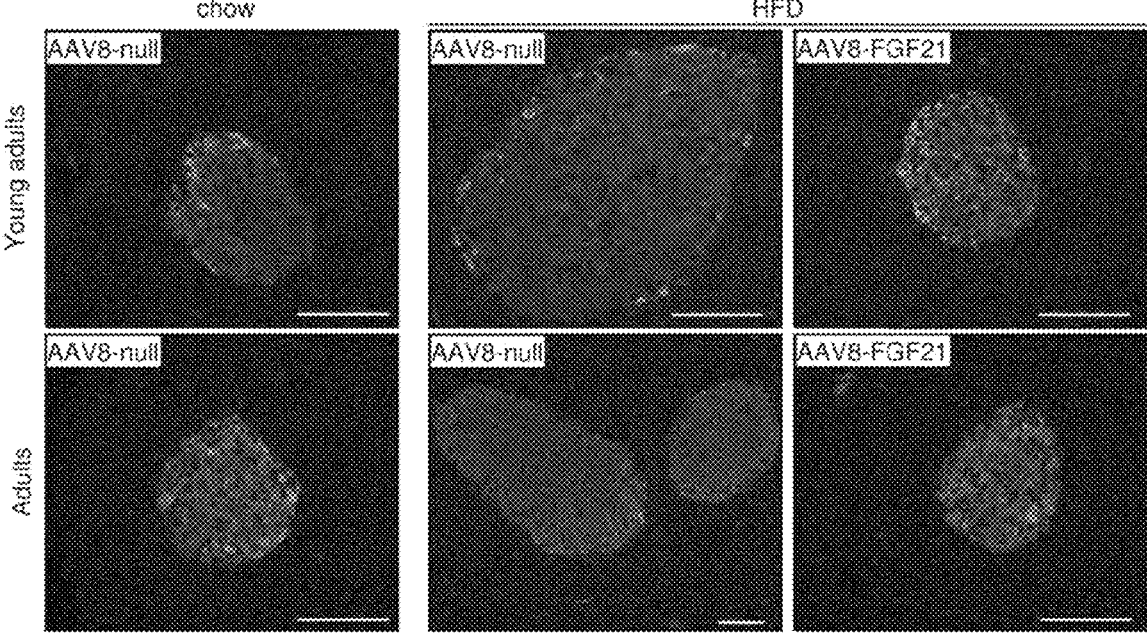
Fig. 22D

Fig. 24A
Fig. 24E
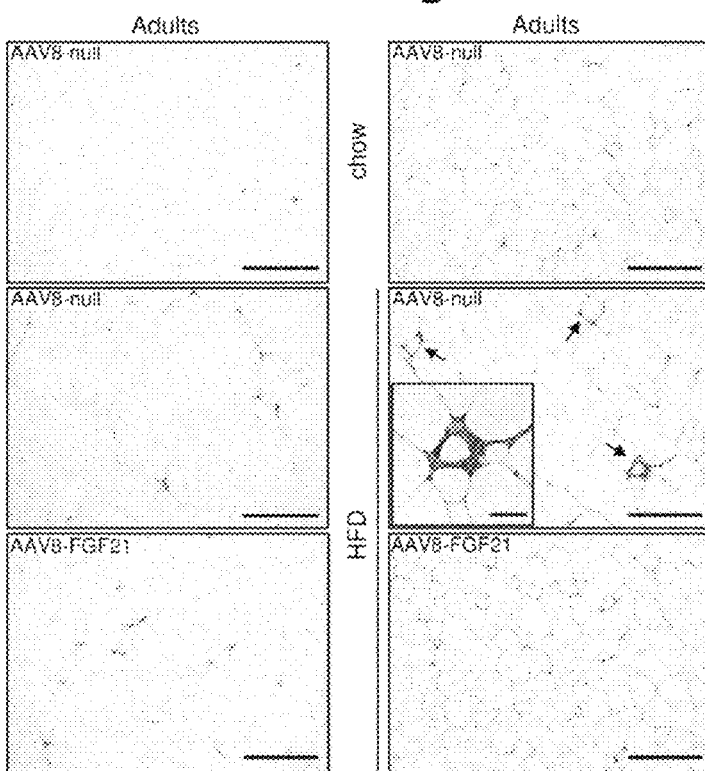
Fig. 24B
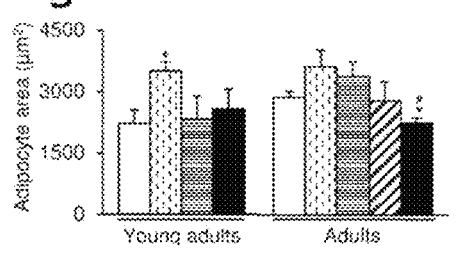
AAV8-hAAT-null ☐ 5x10¹⁰vg ] chow
AAV8-hAAT-null ☐ 5x10¹⁰vg
☐ 1x10¹⁰vg
AAV8-hAAT-FGF21 ☐ 2x10¹⁰vg HFD
■ 5x10¹⁰vg
Fig. 24C
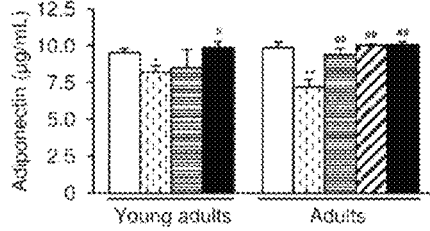
Fig. 24F
F4/80
Fig. 24G
IL-1β
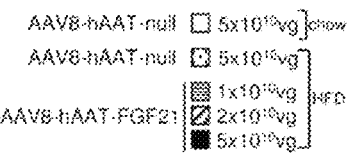
Fig. 24D
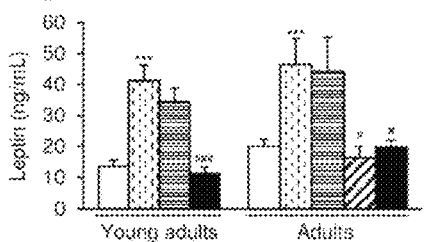
Fig. 24H
TNF-α
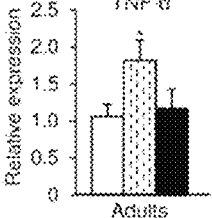

Fig. 25A
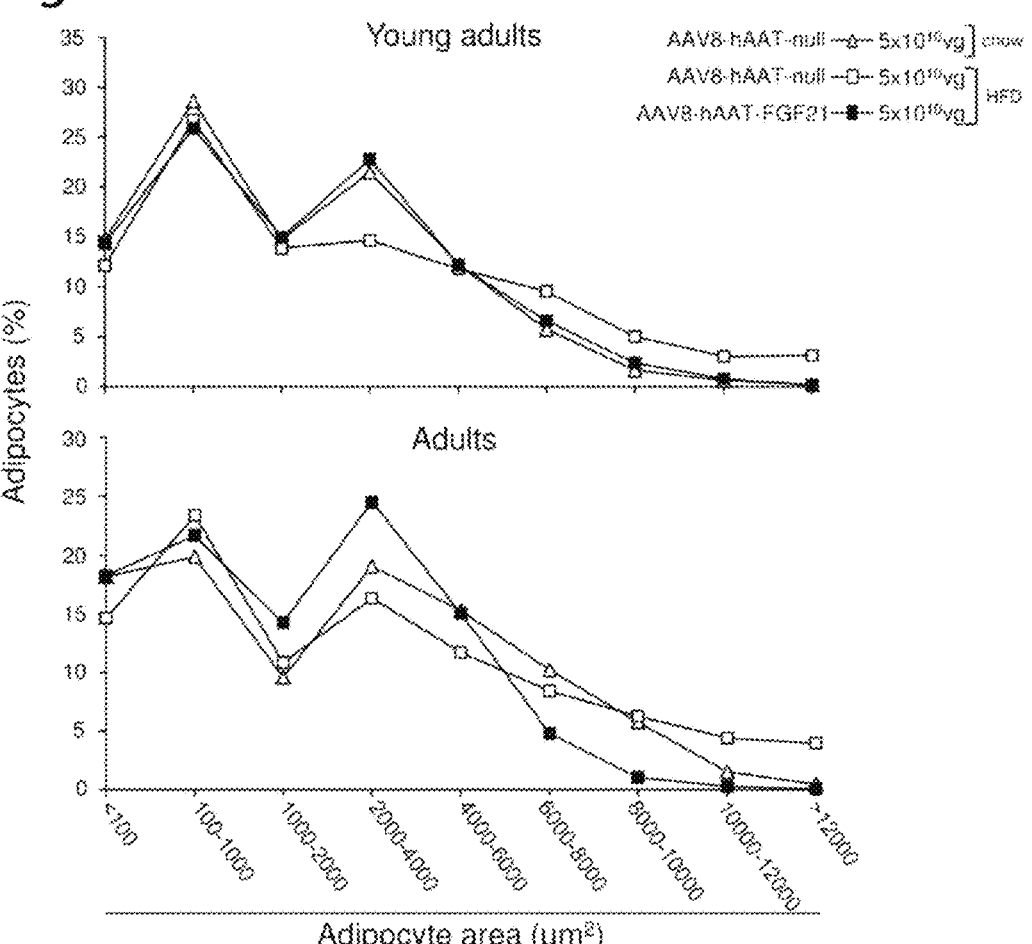
Fig. 25B
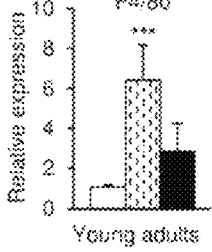
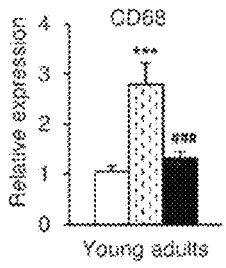
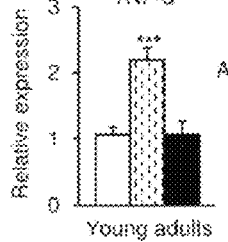
Fig. 25C    Fig. 25D    Fig. 25E
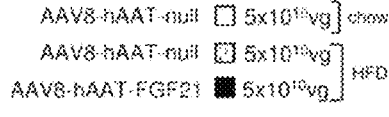

Fig. 28B        # Fig. 28C

Collagen I        Collagen I        AAV8-hAAT-null  ☐ 5x10¹⁰vg ⌉chow

AAV8-hAAT-null  ▦ 5x10¹⁰vg ⌉

AAV8-hAAT-FGF21  ■ 5x10¹⁰vg ⌋ HFD

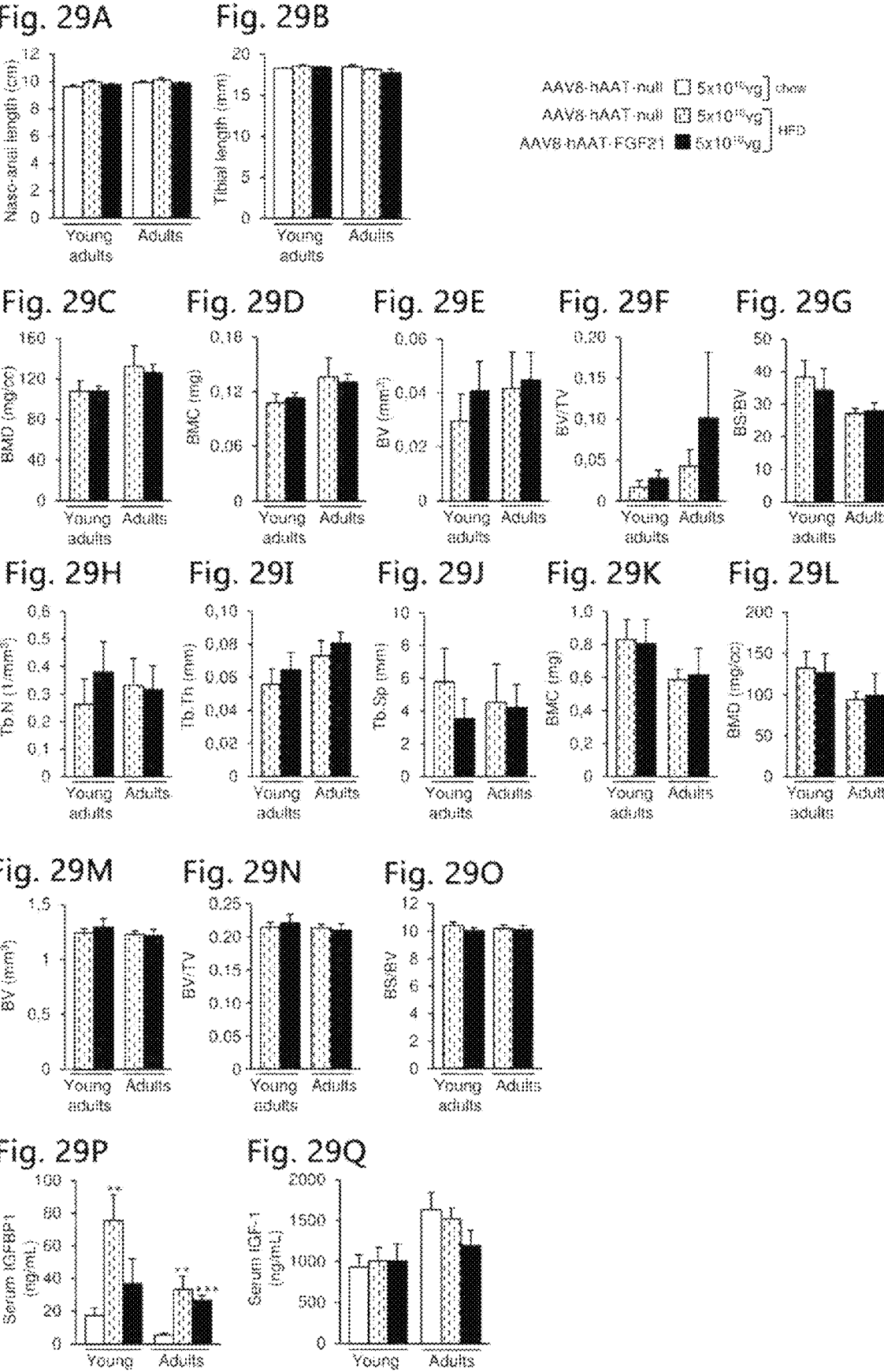

Fig. 31A
Fig. 31B
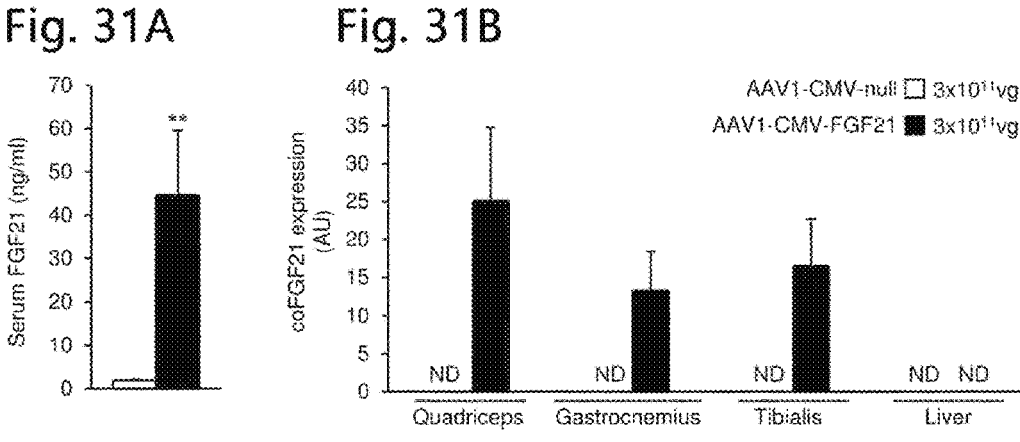
Fig. 31C
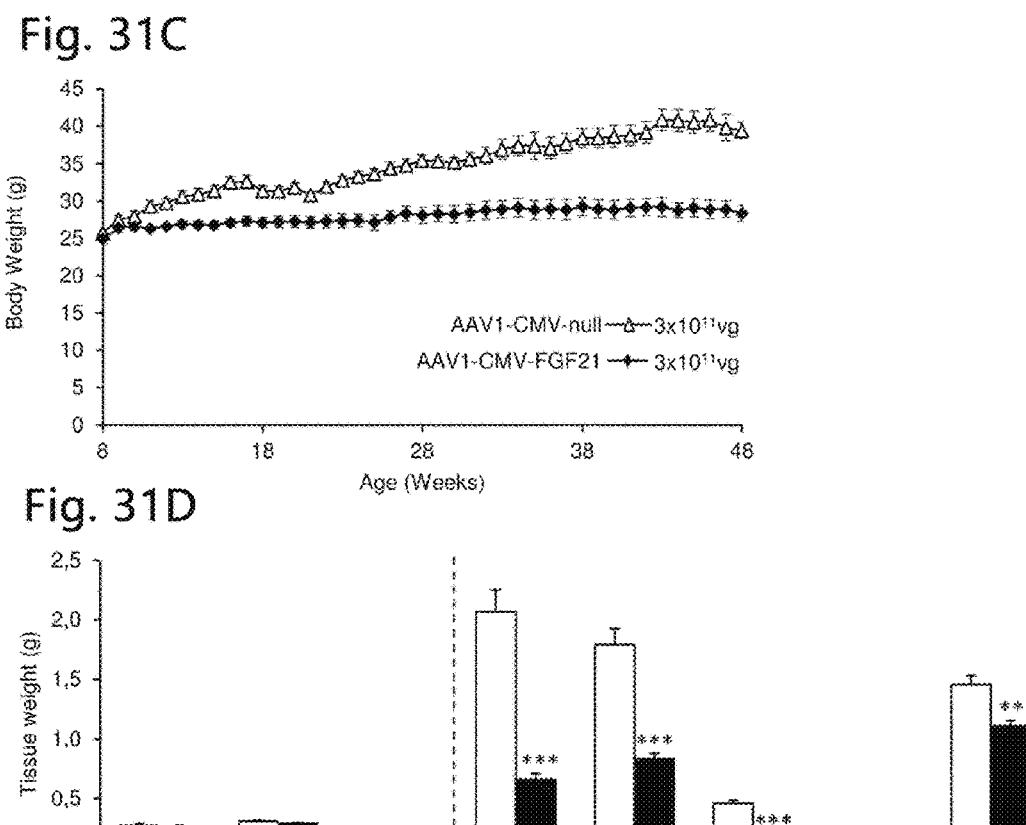
Fig. 31D
Fig. 31E    Fig. 31F    Fig. 31G    Fig. 31H
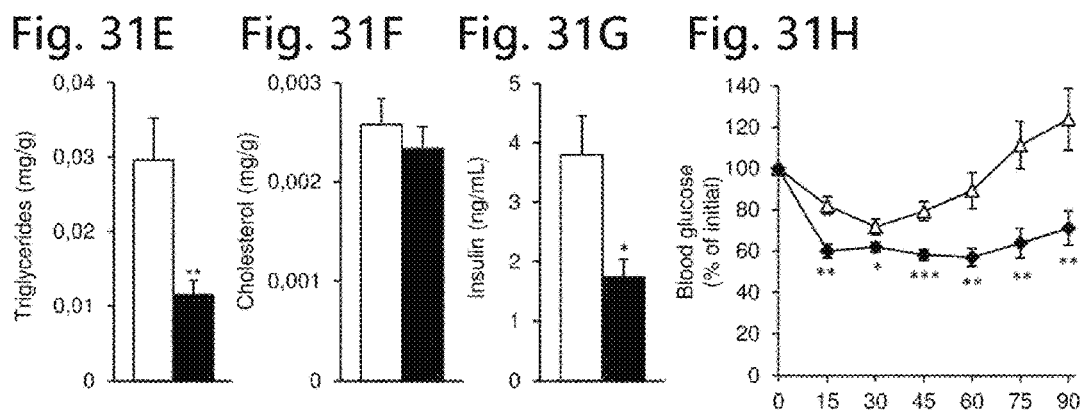

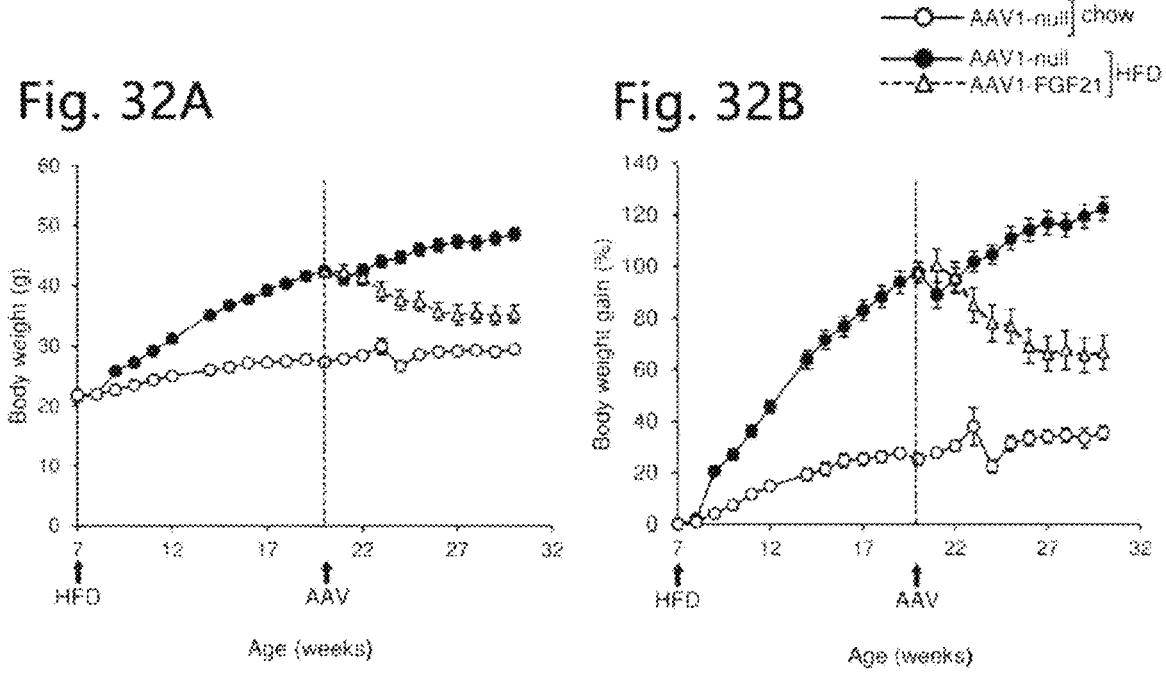
Fig. 32A
Fig. 32B
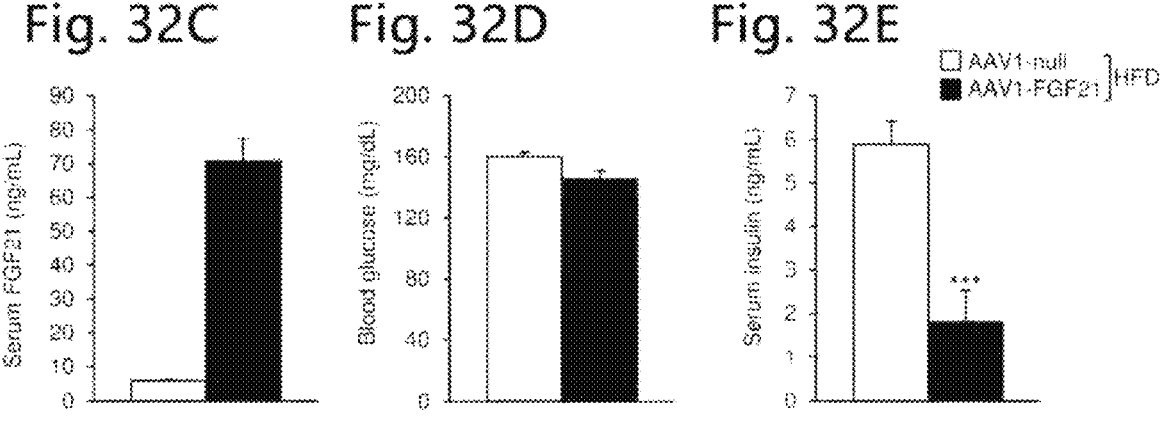
Fig. 32C
Fig. 32D
Fig. 32E
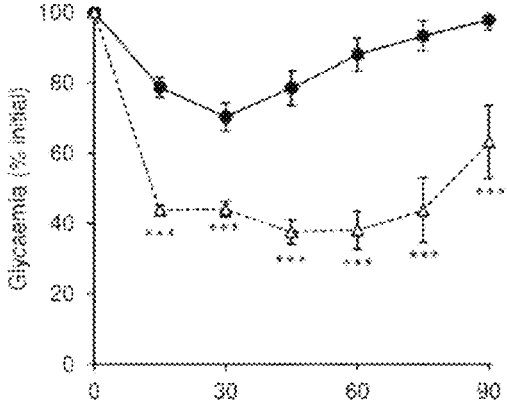
Fig. 32F

VIRAL EXPRESSION CONSTRUCT COMPRISING A FIBROBLAST GROWTH FACTOR 21 (FGF21) CODING SEQUENCE

REFERENCE TO SEQUENCE LISTING SUBMITTED ELECTRONICALLY

The content of the electronically submitted sequence listing (Name: 5344_0040003_Seqlisting_ST26.xml; Size: 161,336 bytes; Date of Creation: Oct. 3, 2023) filed with the application is incorporated herein by reference in its entirety.

FIELD OF THE INVENTION

The invention pertains to the medical field, comprising gene therapy compositions for use in the treatment of a metabolic disorder, use in the treatment of liver inflammation and/or fibrosis, use in the treatment of cancer and/or use in extending healthy lifespan in mammals, particularly in human beings.

BACKGROUND OF THE INVENTION

The prevalence of diabetes is growing at an alarming rate and is a major health problem worldwide. Obesity is strongly associated with insulin resistance and type 2 diabetes (T2D) (Moller, D. E., and Flier, J. S., 1991. *N. Engl. J. Med.* 325:938-948). Moreover, obesity increases the risk of mortality (Peeters, A. et al., 2003. *Ann. Intern. Med.* 138:24-32) and is also a significant risk factor for heart disease, immune dysfunction, hypertension, arthritis, neurodegenerative diseases, and certain types of cancer (Roberst, D. L. et al., 2010. *Annu. Rev. Med.* 61:301-316: Spiegelman. B. M. et al., 1993. *J. Biol. Chem.* 268:6823-6826: Whitmer, R. A., 2007. *Curr. Alzheimer Res.* 4:117-122). Despite the clinical significance of T2D and obesity, no effective treatments are available. Hence, there is an urgent need for novel and safe approaches to prevent and combat the current T2D-obesity epidemic. Recently, it has become widely accepted that obesity is an important risk factor for cancer (Roberst, D. L. et al., 2010. *Annu. Rev. Med.* 61:301-316). Given the current obesity epidemic, obesity-related cancer risks are a clinically important concern for which novel and safe approaches are urgently needed. An increase in weight and insulin resistance is also associated with aging. Hence, novel and safe approaches to prevent and reverse obesity and diabetes are needed to extend healthy lifespan. Liver fibrosis is an excessive accumulation of extracellular matrix proteins, e.g. collagen, resulting predominantly from chronic liver inflammation. Advanced liver fibrosis will lead to liver cirrhosis, portal hypertension and liver failure. Thus, novel and safe antifibrotic therapeutics are required.

Fibroblast growth factor 21 (FGF21), a growth factor predominantly secreted by the liver, but also by adipose tissue and pancreas (Muise, E. S. et al., 2008. *Mol. Pharmacol.* 74:403-412), has been shown to increase brown adipose tissue (BAT) growth and expression of thermogenic genes in BAT and white adipose tissue (WAT), stimulating energy expenditure (Coskun, T. et al., 2008. *Endocrinology* 149:6018-6027; Fisher, F. M. et al., 2012. *Genes Dev.* 26:271-281; Kharitonenkov, A. et al., 2005. *J. Clin. Invest* 115:1627-1635; Konishi, M. et al., 2000. *J. Biol. Chem.* 275:12119-12122; Tomlinson, E. et al., 2002. *Endocrinology* 143:1741-1747; Xu, J. et al., 2009. *Diabetes* 58:250-259). Overexpression of FGF21 in transgenic mice protected them from diet-induced obesity (Kharitonenkov, A. et al., 2005. *J. Clin. Invest* 115:1627-1635) and the administration of FGF21 to ob/ob, db/db or high fat diet (HFD)-fed mice or to obese ZDF rats promoted a robust reduction in adiposity, significantly lowered blood glucose and triglycerides, decreased fasting insulting levels and improved insulin sensitivity (Coskun, T. et al., 2008. *Endocrinology* 149:6018-6027; Kharitonenkov, A. et al., 2005. *J. Clin. Invest* 115:1627-1635; Xu, J. et al., 2009. *Diabetes* 58:250-259; Adams, A. C. et al., 2012. *PLoS. One.* 7:e38438.; Berglund, E. D. et al., 2009. *Endocrinology* 150:4084-4093). Moreover, the administration of FGF21 to obese diabetic rhesus monkeys dramatically reduced fasting plasma glucose, fructosamine, triglyceride, insulin and glucagon levels and induced a small but significant weight loss (Kharitonenkov, A. et al., 2007. *Endocrinology* 148:774-781).

Native FGF21 protein exhibits poor pharmacokinetic characteristics. It has a short half-life, and it is susceptible to in vivo proteolytic degradation and in vitro aggregation (Huang, J. et al., 2013. *J Pharmacol Exp Ther.* 346(2):270-80; So, W. Y. and Leung, P. S. 2016. *Med Res Rev.* 36(4): 672-704; Zhang, J. and Li, Y. 2015. Front Endocrinol (Lausanne). 6:168). Various engineering approaches have been developed to extend the half-life and to improve the stability and solubility of FGF21. Currently, two engineered FGF21 mimetics (LY2405319 and PF-05231023) are being tested in humans. Nevertheless, those FGF21 mimetics require multiple administrations, which poses a significant burden to the patients. Moreover, engineered FGF21 mimetics/analogs may exhibit a higher risk of immunogenicity than native FGF21, e.g. patients treated with LY2405319 developed injection site reactions, anti-drug antibodies and a serious hypersensitivity reaction (Gaich, G. et al., 2013. *Cell Metab.* 18(3):333-40).

Therefore there is still a need for new treatments for diabetes and/or obesity and/or liver inflammation and/or fibrosis and/or cancer and/or extending healthy lifespan which do not have all the drawbacks of existing treatments.

DESCRIPTION OF THE INVENTION

The inventors designed improved gene therapy strategies based on adeno-associated viral (AAV) vector-mediated FGF21 gene transfer to liver, adipose tissue and/or skeletal muscle to counteract metabolic disorders, preferably diabetes and/or obesity. The gene therapy of the invention may also be used to counteract liver inflammation and/or fibrosis. Additionally, the gene therapy of the invention may also be used for the extension of healthy lifespan by counteracting metabolic disorders associated with aging, preferably diabetes and/or obesity. Additionally, the gene therapy of the invention may also be used to counteract cancer, preferably liver cancer.

Generation of single-vector gene constructs allows the in vivo production of native FGF21, which should result in reduced risk of immunogenicity or other toxicities. However, the skilled person knows that native FGF21 may be susceptible to in vivo proteolytic degradation and/or have a fast in vivo clearance rate. All vectors tested in the experimental part were found to be able to enable long-lasting secretion of stable native FGF21 into the bloodstream. Efficacy is maintained even with a single administration of gene transfer vectors.

Therefore the generation of such AAV vectors for in vivo production of native FGF21 is not routine for a person skilled in the art, as demonstrated in the experimental part.

Viral Expression Construct

In a first aspect there is provided a viral expression construct suitable for expression in a mammal and comprising a nucleotide sequence encoding a Fibroblast growth factor 21 (FGF21) to be expressed in liver, adipose tissue and/or skeletal muscle.

The definition of "viral expression construct", "suitable for expression in a mammal" "liver", "adipose tissue" and "skeletal muscle" has been provided in the part of the description entitled "general definitions".

A preferred nucleotide sequence encoding a FGF21 present in the viral expression construct of the invention has at least 60%, 65%, 70%, 75%, 80%, 85%, 90%, 95%, 97%, 98%, 99%, 100% identity with SEQ ID NO: 4, 5, 6, 7, 8, 9, 10 or 11. Identity may be assessed over the whole SEQ ID NO or over part thereof as explained in the part of the description entitled "general definitions".

A more preferred nucleotide sequence encoding a human FGF21 present in the viral expression construct of the invention has at least 60%, 65%, 70%, 75%, 80%, 85%, 90%, 95%, 97%, 98%, 99%, 100% identity with SEQ ID NO: 4, 5, 6 or 7. Identity may be assessed over the whole SEQ ID NO or over part thereof as explained in the part of the description entitled "general definitions". SEQ ID NO: 4 is a nucleotide sequence encoding human FGF21. SEQ ID NO: 5 is a codon optimized nucleotide sequence encoding human FGF21, variant 1. SEQ ID NO: 6 is a codon optimized nucleotide sequence encoding human FGF21, variant 2. SEQ ID NO: 7 is a codon optimized nucleotide sequence encoding human FGF21, variant 3. Variant 1, variant 2 and variant 3 encode for the same human FGF21 protein and were obtained by different algorithms of codon optimization. Another preferred nucleotide sequence encoding mouse FGF21 present in the viral expression construct of the invention has at least 60%, 65%, 70%, 75%, 80%, 85%, 90%, 95%, 97%, 98%, 99%, 100% identity with SEQ ID NO: 8 or 9. Identity may be assessed over the whole SEQ ID NO or over part thereof as explained in the part of the description entitled "general definitions". SEQ ID NO: 8 is a nucleotide sequence encoding mouse FGF21. SEQ ID NO: 9 is a codon optimized nucleotide sequence encoding mouse FGF21. Another preferred nucleotide sequence encoding canine FGF21 present in the viral expression construct of the invention has at least 60%, 65%, 70%, 75%, 80%, 85%, 90%, 95%, 97%, 98%, 99%, 100% identity with SEQ ID NO: 10 or 11. Identity may be assessed over the whole SEQ ID NO or over part thereof as explained in the part of the description entitled "general definitions". SEQ ID NO: 10 is a nucleotide sequence encoding canine FGF21. SEQ ID NO: 11 is a codon optimized nucleotide sequence encoding canine FGF21. The nucleotide sequence encoding a FGF21 may be derived from any FGF21 gene or FGF21 coding sequence, preferably from human, mouse or dog; or a mutated FGF21 gene or FGF21 coding sequence, or a codon optimized FGF21 gene or FGF21 coding sequence, preferably from human, mouse or dog.

A FGF21 as used herein exerts at least a detectable level of an activity of a FGF21 as known to the skilled person. An activity of a FGF21 is to increase insulin sensitivity. This activity could be assessed using the insulin tolerance test, as described in the experimental part, preferably as in example 8 or 9.

In an embodiment there is provided a viral expression construct as described above, wherein the nucleotide sequence encoding a FGF21 suitable for expression in a mammal is selected from the group consisting of:

(a) a nucleotide sequence encoding a polypeptide comprising an amino acid sequence that has at least 60% sequence identity with the amino acid sequence of SEQ ID NO: 1, 2 or 3.

(b) a nucleotide sequence that has at least 60% sequence identity with the nucleotide sequence of SEQ ID NO: 4, 5, 6, 7, 8, 9, 10 or 11.

(c) a nucleotide sequence the sequence of which differs from the sequence of a nucleotide sequence of (b) due to the degeneracy of the genetic code.

A preferred nucleotide sequence encoding a FGF21 suitable for expression in a mammal encodes a polypeptide comprising an amino acid sequence that has at least 60%, 65%, 70%, 75%, 80%, 85%, 90%, 95%, 97%, 98%, 99%, 100% identity with SEQ ID NO: 1, 2 or 3. Identity may be assessed over the whole SEQ ID NO or over part thereof as explained in the part of the description entitled "general definitions". SEQ ID NO: 1 is an amino acid sequence of human FGF21. SEQ ID NO: 2 is an amino acid sequence of murine FGF21. SEQ ID NO: 3 is an amino acid sequence of canine FGF21.

In an embodiment there is provided a viral expression construct as described above comprising a nucleotide sequence encoding a FGF21 suitable for expression in a mammal and at least one of elements a), b), c), d) and e):

(a) a liver-specific promoter (b) an adipose tissue-specific promoter (c) a combination of an ubiquitous promoter and at least one nucleotide sequence encoding a target sequence of a microRNA expressed in the liver and at least one nucleotide sequence encoding a target sequence of a microRNA expressed in the heart, wherein said combination enables specific expression in adipose tissue (d) a skeletal muscle promoter and (e) a combination of an ubiquitous promoter and an adeno-associated virus (AAV) vector sequence, wherein said combination enables specific expression in skeletal muscle.

A "target sequence of a microRNA expressed in the liver" or "target sequence of a miRNA expressed in the liver" or "binding site of a microRNA expressed in the liver" refers to a nucleotide sequence which is complementary or partially complementary to at least a portion of a microRNA expressed in the liver. Similarly, a "target sequence of a microRNA expressed in the heart" or "target sequence of a miRNA expressed in the heart" or "binding site of a microRNA expressed in the heart" refers to a nucleotide sequence which is complementary or partially complementary to at least a portion of a microRNA expressed in the heart. A portion of a microRNA expressed in the liver or a portion of a microRNA expressed in the heart, as defined herein, means a nucleotide sequence of at least five or at least six consecutive nucleotides of said microRNA. The binding site sequence can have perfect complementarity to at least a portion of an expressed microRNA, meaning that the sequences can be a perfect match, no mismatch may occur. Alternatively, the binding site sequence can be partially complementary to at least a portion of an expressed microRNA, meaning that one mismatch/five, six consecutive nucleotides may occur. Partially complementary binding sites preferably contain perfect or near perfect complementarity to the seed region of the microRNA, meaning that no mismatch (perfect complementarity) or one mismatch/five, six consecutive nucleotides (near perfect complementarity) may occur between the seed region of the microRNA and its binding site. The seed region of the microRNA consists of the 5' region of the microRNA from about nucleotide 2 to about nucleotide 8 of the microRNA (i.e. 6 nucleotides). The portion as defined herein is preferably the seed region of said microRNA. Degradation of the messenger RNA (mRNA) containing the target sequence for a microRNA expressed in the liver or a microRNA expressed in the heart may be through the RNA interference pathway or via direct translational control (inhibition) of the mRNA. The invention is not limited by the pathway ultimately utilized by the miRNA in inhibiting expression of the transgene or encoded protein.

In the context of the invention, a nucleotide sequence encoding a target sequence of a microRNA expressed in the liver may be replaced by a nucleotide sequence comprising a nucleotide sequence that has at least 60% sequence identity or similarity with SEQ ID NO: 12 or 14-23. A more preferred nucleotide sequence has at least 60%, 65%, 70%, 75%, 80%, 85%, 90%, 95%, 97%, 98%, 99%, 100% identity with SEQ ID NO: 12 or 14-23. Identity may be assessed over the whole SEQ ID NO or over part thereof as explained in the part of the description entitled "general definitions". In one embodiment, the nucleotide sequence encoding a target sequence of a microRNA expressed in the liver may be replaced by a nucleotide sequence comprising a nucleotide sequence that has at least 60% sequence identity or similarity with SEQ ID NO: 12. A more preferred nucleotide sequence has at least 60%, 65%, 70%, 75%, 80%, 85%, 90%, 95%, 97%, 98%, 99%, 100% identity with SEQ ID NO: 12. In a further embodiment, at least one copy of a nucleotide sequence encoding a target sequence of a microRNA expressed in the liver, as defined in SEQ ID NO: 12 or 14-23, is present in the viral expression construct of the invention. In a further embodiment, two, three, four, five, six, seven or eight copies of a nucleotide sequence encoding a target sequence of a liver-specific microRNA, as defined in SEQ ID NO: 12 or 14-23, are present in the viral expression construct of the invention. In a preferred embodiment one, two, three, four, five, six, seven or eight copies of a nucleotide sequence encoding miRT122a (SEQ ID NO: 12) are present in the viral expression construct of the invention.

A target sequence of a microRNA expressed in the liver as used herein exerts at least a detectable level of activity of a target sequence of a microRNA expressed in the liver as known to the skilled person. An activity of a target sequence of a microRNA expressed in the liver is to bind to its cognate, microRNA expressed in the liver and, when operatively linked to a transgene, to mediate detargeting of transgene expression in the liver. This activity may be assessed by measuring the levels of transgene expression in the liver by qPCR, as described in the experimental part.

In the context of the invention, a nucleotide sequence encoding a target sequence of a microRNA expressed in the heart may be replaced by a nucleotide sequence comprising a nucleotide sequence that has a least 60% sequence identity or similarity with SEQ ID NO: 13 or 23-30. A preferred nucleotide sequence has at least 60%, 65%, 70%, 75%, 80%, 85%, 90%, 95%, 97%, 98%, 99%, 100% identity with SEQ ID NO: 13 or 23-30. Identity may be assessed over the whole SEQ ID NO or over part thereof as explained in the part of the description entitled "general definitions". In one embodiment, the nucleotide sequence encoding a target sequence of a microRNA expressed in the heart may be replaced by a nucleotide sequence comprising a nucleotide sequence that has at least 60% sequence identity or similarity with SEQ ID NO: 13. A preferred nucleotide sequence has at least 60%, 65%, 70%, 75%, 80%, 85%, 90%, 95%, 97%, 98%, 99%, 100% identity with SEQ ID NO: 13. In a further embodiment, at least one copy of a nucleotide sequence encoding a target sequence of a microRNA expressed in the heart, as defined in SEQ ID NO: 13 or 23-30, is present in the viral expression construct of the invention. In a further embodiment, two, three, four, five, six, seven or eight copies of a nucleotide sequence encoding a target sequence of a heart-specific microRNA, as defined in SEQ ID NO: 13 or 23-30, are present in the viral expression construct of the invention. In a preferred embodiment one, two, three, four, five, six, seven or eight copies of a nucleotide sequence encoding miRT1 (SEQ ID NO: 13), are present in the viral expression construct of the invention.

An activity of a target sequence of a microRNA expressed in the heart is to bind to its cognate, microRNA expressed in the heart and, when operatively linked to a transgene, to mediate detargeting of transgene expression in the heart. This activity may be assessed by measuring the levels of transgene expression in the heart by qPCR, as described in the experimental part.

In an embodiment there is provided a viral expression construct as described above, wherein the nucleotide sequence encoding a target sequence of a microRNA expressed in the liver and the nucleotide sequence encoding a target sequence of a microRNA expressed in the heart is selected from a group consisting of sequences SEQ ID NO: 12 to 30 and/or combinations thereof.

In one embodiment, at least one copy of a nucleotide sequence encoding a target sequence of a microRNA expressed in the liver, as defined in SEQ ID NO: 12 or 14-23, and at least one copy of a nucleotide sequence encoding a target sequence of a microRNA expressed in the heart, as defined in SEQ ID NO: 13 or 23-30, are present in the viral expression construct of the invention. In a further embodiment, two, three, four, five, six, seven or eight copies of a nucleotide sequence encoding a target sequence of a microRNA expressed in the liver, as defined in SEQ ID NO: 12 or 14-23, and two, three, four, five, six, seven or eight copies of a nucleotide sequence encoding a target sequence of a microRNA expressed in the heart, as defined in SEQ ID NO: 13 or 23-30, are present in the viral expression construct of the invention. In a further embodiment one, two, three, four, five, six, seven or eight copies of a nucleotide sequence encoding miRT122a (SEQ ID NO: 12) and one, two, three, four, five, six, seven or eight copies nucleotide sequence encoding miRT1 (SEQ ID NO: 13) are combined in the viral expression construct of the invention. In a further embodiment, four copies of a nucleotide sequence encoding miRT122a (SEQ ID NO: 12) and four copies of nucleotide sequence encoding miRT1 (SEQ ID NO: 13) are combined in the viral expression construct of the invention.

The definition "promoter", "liver-specific promoter", "adipose tissue-specific promoter", "ubiquitous promoter", "skeletal muscle promoter" has been provided in the part of the description entitled "general definitions".

A preferred ubiquitous promoter is a CAG promoter.

In the context of the invention, a nucleotide sequence of a CAG promoter may be replaced by a nucleotide sequence comprising a nucleotide sequence that has at least 60% sequence identity or similarity with SEQ ID NO: 44. A preferred nucleotide sequence has at least 60%, 65%, 70%, 75%, 80%, 85%, 90%, 95%, 97%, 98%, 99%, 100% identity with SEQ ID NO: 44. Identity may be assessed over the whole SEQ ID NO or over part thereof as explained in the part of the description entitled "general definitions".

Another preferred ubiquitous promoter is a cytomegalovirus (CMV) promoter.

In the context of the invention, a nucleotide sequence of a CMV promoter may be replaced by a nucleotide sequence comprising a nucleotide sequence that has at least 60% sequence identity or similarity with SEQ ID NO: 45. A preferred nucleotide sequence has at least 60%, 65%, 70%, 75%, 80%, 85%, 90%, 95%, 97%, 98%, 99%, 100% identity with SEQ ID NO: 45. Identity may be assessed over the whole SEQ ID NO or over part thereof as explained in the part of the description entitled "general definitions".

Preferably said CMV promoter is used together with an intronic sequence. In this context an intronic sequence may be replaced by a nucleotide sequence comprising a nucleotide sequence that has at least 60% sequence identity or similarity with SEQ ID NO: 43. A preferred nucleotide sequence has at least 60%, 65%, 70%, 75%, 80%, 85%, 90%, 95%, 97%, 98%, 99%, 100% identity with SEQ ID NO: 43. Identity may be assessed over the whole SEQ ID NO or over part thereof as explained in the part of the description entitled "general definitions".

A preferred liver-specific promoter is a human al-antitrypsin (hAAT) promoter.

In the context of the invention, a nucleotide sequence of a hAAT promoter may be replaced by a nucleotide sequence comprising a nucleotide sequence that has at least 60% sequence identity or similarity with SEQ ID NO: 47. A preferred nucleotide sequence has at least 60%, 65%, 70%, 75%, 80%, 85%, 90%, 95%, 97%, 98%, 99%, 100% identity with SEQ ID NO: 47. Identity may be assessed over the whole SEQ ID NO or over part thereof as explained in the part of the description entitled "general definitions".

Preferably said hAAT promoter is used together with an intronic sequence. A preferred intronic sequence is a hepatocyte control region (HCR) enhancer from apolipoprotein E. A most preferred intronic sequence is the HCR enhancer from apolipoprotein E as defined in SEQ ID NO: 53. In this context an intronic sequence may be replaced by a nucleotide sequence comprising a nucleotide sequence that has at least 60% sequence identity or similarity with SEQ ID NO: 53. A preferred nucleotide sequence has at least 60%, 65%, 70%, 75%, 80%, 85%, 90%, 95%, 97%, 98%, 99%, 100% identity with SEQ ID NO: 53. Identity may be assessed over the whole SEQ ID NO or over part thereof as explained in the part of the description entitled "general definitions". In an embodiment, said hAAT promoter is used together with one, two, three, four or five copies of an intronic sequence. In a preferred embodiment, said hAAT promoter is used together with one, two, three, four or five copies of the HCR enhancer from apolipoprotein E as defined in SEQ ID NO: 53.

Other liver-specific promoters are the albumin promoter, the major urinary protein promoter, the phosphoenolpyruvate carboxykinase (PEPCK) promoter, the liver-enriched protein activator promoter, the transthyretin promoter, the thyroxine binding globulin promoter, the apolipoprotein A1 promoter, the liver fatty acid binding protein promoter and the phenylalanine hydroxylase promoter.

Adipose tissue-specific promoters are the adipocyte protein 2 (aP2, also known as fatty acid binding protein 4 (FABP4)) promoter, the PPARy promoter, the adiponectin promoter, the phosphoenolpyruvate carboxykinase (PEPCK) promoter, the promoter derived from human aromatase cytochrome p450 (p450arom) the mini/aP2 promoter (composed of the adipose-specific aP2 enhancer and the basal aP2 promoter), the uncoupling protein 1 (UCP1) promoter, the mini/UCP1 promoter (composed of the adipose-specific UCP1 enhancer and the basal UCP1 promoter), the adipsin promoter, the leptin promoter, or the Foxa-2 promoter. Preferred adipose tissue-specific promoters are the mini/aP2 promoter (SEQ ID NO: 54) and the mini/UCP1 promoter (SEQ ID NO 55). In this context an adipose tissue-specific promoter sequence may be replaced by a nucleotide sequence comprising a nucleotide sequence that has at least 60% sequence identity or similarity with SEQ ID NO: 53 or SEQ ID NO: 54. A preferred nucleotide sequence has at least 60%, 65%, 70%, 75%, 80%, 85%, 90%, 95%, 97%, 98%, 99%, 100% identity with SEQ ID NO: 53 or SEQ ID NO: 54. Identity may be assessed over the whole SEQ ID NO or over part thereof as explained in the part of the description entitled "general definitions".

Preferred skeletal muscle promoters are the myosin light-chain promoter, the myosin heavy-chain promoter, the desmin promoter, the muscle creatine kinase (MCK) promoter, the smooth muscle alpha-actin promoter, the CK6 promoter, the Unc-45 Myosin Chaperone B promoter, the basal MCK promoter in combination with copies of the MCK enhancer, the Enh358MCK promoter (combination of the MCK enhancer with the 358 bp proximal promoter of the MCK gene). A most preferred skeletal muscle promoter is the C5-12 promoter as defined in SEQ ID NO: 56. In this context a skeletal muscle promoter sequence may be replaced by a nucleotide sequence comprising a nucleotide sequence that has at least 60% sequence identity or similarity with SEQ ID NO: 56. A preferred nucleotide sequence has at least 60%, 65%, 70%, 75%, 80%, 85%, 90%, 95%, 97%, 98%, 99%, 100% identity with SEQ ID NO: 56. Identity may be assessed over the whole SEQ ID NO or over part thereof as explained in the part of the description entitled "general definitions".

A promoter as used herein (especially when the promoter sequence is defined as having a minimal identity percentage with a given SEQ ID NO) should exert at least an activity of a promoter as known to the skilled person. Please be referred to the part of the description entitled "general definitions" for a definition of such activity. Preferably a promoter defined as having a minimal identity percentage with a given SEQ ID NO should control transcription of the nucleotide sequence it is operably linked thereto (i.e. a nucleotide sequence encoding a FGF21) as assessed in an assay known to the skilled person. In the context of the invention, said promoter is operatively linked to the FGF21 nucleotide sequence defined above. In one embodiment, the promoter is cell-specific and/or tissue-specific, preferably specific for liver, adipose tissue and/or skeletal muscle.

Several viral expression constructs are therefore encompassed by the present invention:

A viral expression construct comprising a nucleotide sequence encoding a FGF21 suitable for expression in a mammal and comprising element a), A viral expression construct comprising a nucleotide sequence encoding a FGF21 suitable for expression in a mammal and comprising element b), A viral expression construct comprising a nucleotide sequence encoding a FGF21 suitable for expression in a mammal and comprising element c), A viral expression construct comprising a nucleotide sequence encoding a FGF21 suitable for expression in a mammal and comprising element d), A viral expression construct comprising a nucleotide sequence encoding a FGF21 suitable for expression in a mammal and comprising element e), A viral expression construct comprising a nucleotide sequence encoding a FGF21 suitable for expression in a mammal and comprising element b) and a nucleotide sequence of element c), A viral expression construct comprising a nucleotide sequence encoding a FGF21 suitable for expression in a mammal and comprising element e) and a nucleotide sequence of element c).

In an embodiment there is provided a viral expression construct as described herein, wherein the liver-specific promoter is the human α1-antitrypsin (hAAT) promoter and/or the adipose tissue-specific promoter is the mini/ap2 promoter and/or the mini/UCP1 promoter and/or the skeletal muscle promoter is the C5-12 promoter and/or the ubiquitous promoter is the cytomegalovirus (CMV) promoter and/or the CAG promoter.

In an embodiment, a viral expression construct is encompassed comprising a nucleotide sequence encoding FGF21 suitable for expression in a mammal and element a), wherein the liver-specific promoter is a hAAT promoter (SEQ ID NO: 47).

Figures 6A, 6B, 6C:
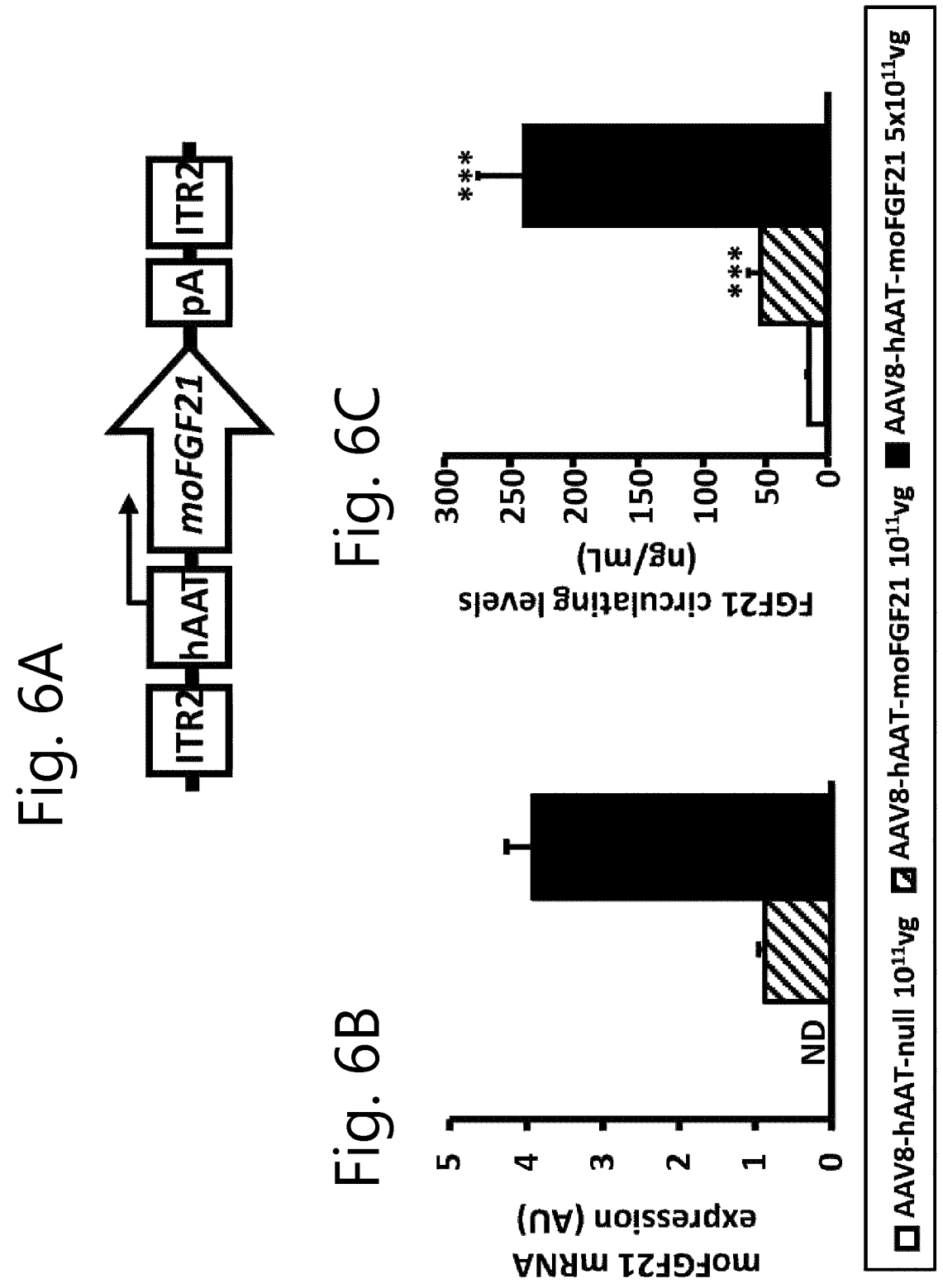

In a preferred embodiment, a viral expression construct is encompassed comprising a nucleotide sequence encoding FGF21 suitable for expression in a mammal and element a) wherein said construct is AAV8-hAAT-moFGF21. This construct for example contains a viral expression construct as depicted in FIG. 6A: ITR2-hAAT-moFGF21-polyA-ITR2; the sequence of this expression construct is comprised in SEQ ID NO:34. For this construct, Example 3 surprisingly reveals high and stable liver-specific expression after intravenous administration. Expression was shown to be stable for up to 1 year (Example 12). Extensive beneficial therapeutic effects for the reversion and treatment of obesity and diabetes are shown in ob/ob mice (Examples 3 and 11), high fat diet (HFD)-fed mice (Examples 4, 12-14) and old HFD-fed mice (Examples 5, 12-14). Examples 11 and 16 also reveal marked improvement of hepatic steatosis, hepatic inflammation and hepatic fibrosis. Example 15 shows improvement of the inflammation of WAT associated to obesity. Example 17 indicates the long-term safety of the therapy. Example 18 reveals a beneficial effect in preventing liver tumors. Example 19 shows therapeutic potential in a model for type I diabetes.

In an embodiment, a viral expression construct is encompassed comprising a nucleotide sequence encoding FGF21 suitable for expression in a mammal and element b), wherein the adipose tissue-specific promoter is a mini/aP2 promoter (SEQ ID NO: 54) and/or a mini/UCP1 promoter (SEQ ID NO 55).

In an embodiment, a viral expression construct is encompassed comprising a nucleotide sequence encoding FGF21 suitable for expression in a mammal and element c), wherein the ubiquitous promoter is a CAG Promoter (SEQ ID NO: 44) and wherein the at least one nucleotide sequence encoding a target sequence of a microRNA expressed in the liver is selected from the group consisting of SEQ ID NO: 12 or 14-23 and the at least one nucleotide sequence encoding a target sequence of a microRNA expressed in the heart is selected from the group consisting of SEQ ID NO: 13 or 23-30.

In a preferred embodiment, a viral expression construct is encompassed comprising a nucleotide sequence encoding FGF21 suitable for expression in a mammal and element c) wherein said construct is AAV9-CAG-moFGF21-dmiRT or AAV8-CAG-moFGF21-dmiRT. The notations dmiRT and doublemiRT are equivalent. These constructs for example contain a viral expression construct as depicted in FIG. 1A: ITR2-CAG-moFGF21-4×miRT122a-4×miRT1-polyA-ITR2; the sequence of this expression construct is comprised in SEQ ID NO:32.

For these constructs, Examples 1-2 surprisingly reveal high and stable adipose-specific expression after intra-eWAT administration. Extensive beneficial therapeutic effects for the prevention, reversion and treatment of obesity and diabetes are shown in normal mice (Example 1) and ob/ob mice (Examples 2 and 10). Example 10 also reveals improvement of hepatic steatosis.

In an embodiment, a viral expression construct is encompassed comprising a nucleotide sequence encoding FGF21 suitable for expression in a mammal and element d), wherein the skeletal muscle promoter is a C5-12 promoter (SEQ ID NO: 56).

In an embodiment, a viral expression construct is encompassed comprising a nucleotide sequence encoding FGF21 suitable for expression in a mammal and element e), wherein the ubiquitous promoter is a CMV promoter (SEQ ID NO: 45) and the AAV serotype is AAV1.

Figures 11A, 11B, 11C, 11D:
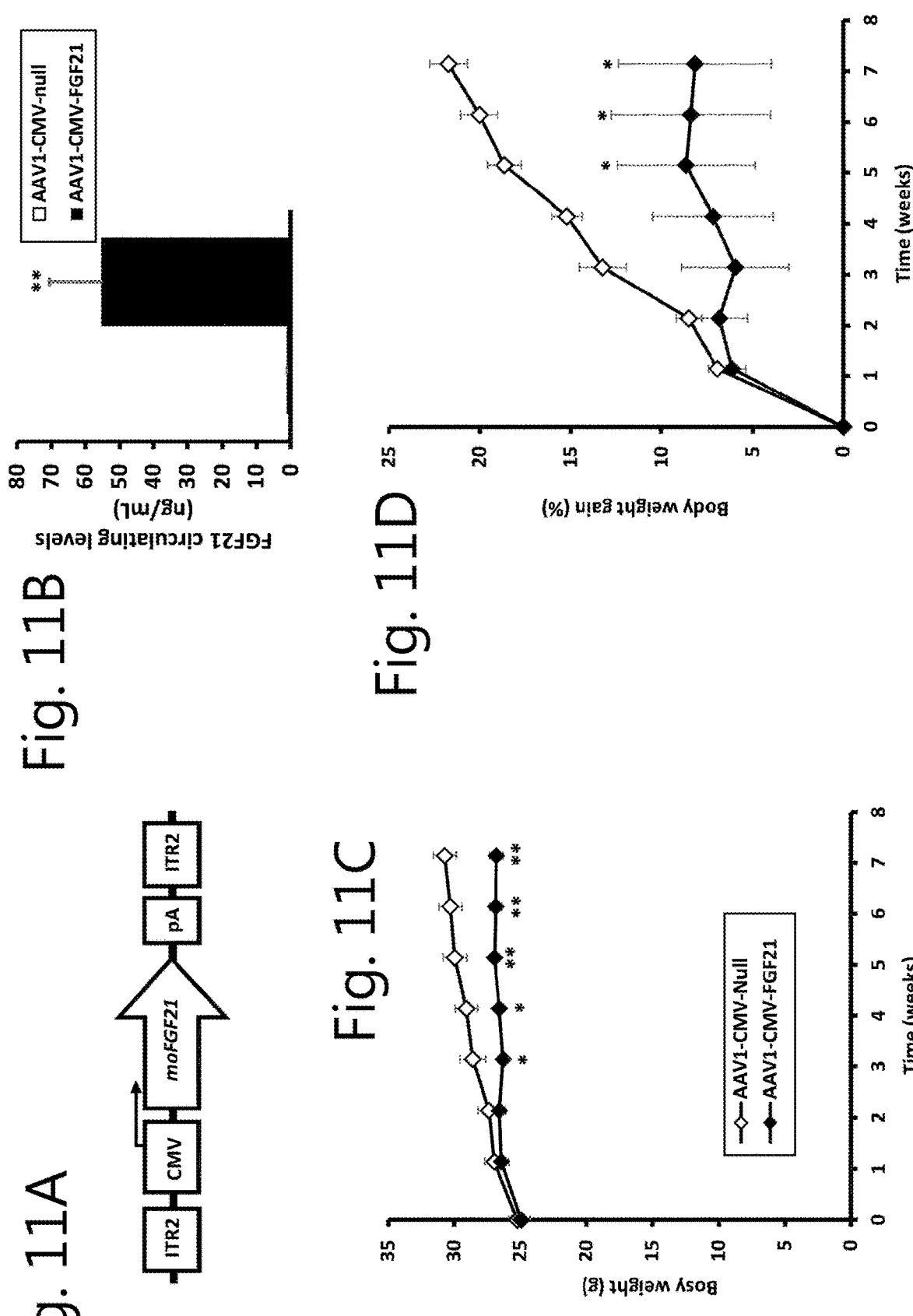

In a preferred embodiment, a viral expression construct is encompassed comprising a nucleotide sequence encoding FGF21 suitable for expression in a mammal and element e) wherein said construct is AAV1-CMV-moFGF21. This construct for example contains a viral expression construct as depicted in FIG. 11A: ITR2-CMV-moFGF21-polyA-ITR2; the sequence of this expression construct is comprised in SEQ ID NO:36.

For this construct, Example 20 reveals high and stable skeletal muscle-specific expression after intramuscular administration. Extensive beneficial therapeutic effects for the prevention, reversion and treatment of obesity and diabetes are shown in HFD-fed mice (Examples 6 and 21). Example 20 reveals a beneficial effect in extending healthy lifespan by preventing obesity and diabetes.

In an embodiment, a viral expression construct is encompassed comprising a nucleotide sequence encoding FGF21 suitable for expression in a mammal and element b) and a nucleotide sequence of element c), wherein the adipose tissue-specific promoter is a mini/aP2 promoter (SEQ ID NO: 54) and/or the mini/UCP1 promoter (SEQ ID NO 55).

In an embodiment, a viral expression construct is encompassed comprising a nucleotide sequence encoding FGF21 suitable for expression in a mammal and element e) and a nucleotide sequence of element c), wherein the ubiquitous promoter is a CMV promoter (SEQ ID NO: 45) and the AAV serotype is AAV1.

All constructs of the invention are more attractive than the ones of the prior art, such as the one disclosed in Zhang et al., EBioMedicine 15 (2017) 173-183, especially the ones comprising element a) which is a liver-specific promoter, preferably hAAT, and/or element c) which is a combination of an ubiquitous promoter and at least one nucleotide sequence encoding a target sequence of a microRNA expressed in the liver, preferably miRT122a, and at least one nucleotide sequence encoding a target sequence of a microRNA expressed in the heart, preferably miRT1, wherein said combination enables specific expression in adipose tissue, and/or element e) which is a combination of an ubiquitous promoter, preferably CMV, and an adeno-associated virus (AAV) vector sequence, preferably AAV1, wherein said combination enables specific expression in skeletal muscle. Zhang et al. discloses wild type murine FGF21 coding sequence under the control of the elongation factor 1a (EF1a) promoter (EF1a-mFGF21) (Zhang et al., EBioMedicine 15 (2017) 173-183). This construct was compared with constructs of the invention in Examples 23 and 24. In all the in vitro and in vivo experiments, all expression cassettes and AAV vectors of the invention mediated higher expression of FGF21 in the target tissue or cell type and lower expression of FGF21 in off-target tissues, demonstrating higher efficiency of the expression cassettes and AAV vectors of the invention as well as higher tissue-specificity. In addition, constructs CMV-moFGF21 and CAG-moFGF21-double miRT also mediated higher protein production and secretion to the culture media in HEK293 cells in comparison to EF1a-mFGF21. Moreover, hAAT-moFGF21 and AAV8-hAAT-moFGF21 also mediated higher secretion of FGF21 to the bloodstream than EF1a-mFGF21 and AAV8-EF1a-mFGF21.

Additional sequences may be present in the viral expression construct of the invention as explained in detail in the part of the description entitled "general definitions". Preferred additional sequences include inverted terminal repeats (ITRs), a SV40 polyadenylation signal (SEQ ID NO: 50), a rabbit β-globin polyadenylation signal (SEQ ID NO: 51), a CMV enhancer sequence (SEQ ID NO: 46) and a HCR enhancer from apolipoprotein E (SEQ ID NO: 53). Within the context of the invention, "ITRs" is intended to encompass one 5'ITR and one 3'ITR, each being derived from the genome of an AAV. Preferred ITRs are from AAV2 and are represented by SEQ ID NO: 48 (5' ITR) and SEQ ID NO: 49 (3' ITR). Within the context of the invention, it is encompassed to use the CMV enhancer sequence (SEQ ID NO: 46) and the CMV promoter sequence (SEQ ID NO: 45) as two separate sequences or as a single sequence (SEQ ID NO: 52).

Each of these additional sequences may be present in the viral expression construct of the invention (see for example as depicted in FIGS. 1, 2, 3, 4, 5, 6, 7, 8 and 9 and also as depicted in FIGS. 11, 31 and 32).

In an embodiment, the viral expression construct comprising a nucleotide sequence encoding FGF21 suitable for expression in a mammal and at least one of elements a) and/or b) and/or c) and/or d) and/or e) as earlier defined further comprises:

ITRs that flank the expression cassette of said construct,

SV40 or rabbit β-globin polyadenylation signals that are located at the 3' of the nucleotide sequence encoding the FGF21 and/or a CMV enhancer sequence or a HCR enhancer sequence that is located at the 5' of the nucleotide sequence encoding the FGF21.

In a preferred embodiment, the viral expression construct comprising a nucleotide sequence encoding FGF21 suitable for expression in a mammal and at least one of elements a) and/or b) and/or c) and/or d) and/or e) as earlier defined further comprises ITRs that flank the expression cassette of said construct and optionally SV40 or rabbit β-globin polyadenylation signals that are located at the 3' of the nucleotide sequence encoding the FGF21 and/or a CMV enhancer sequence or a HCR enhancer sequence that is located at the 5' of the nucleotide sequence encoding the FGF21.

These sequences were used in the experimental part in some of the constructs identified herein.

Therefore, in one embodiment, for each of these preferred viral expression constructs defined above an additional sequence may be present selected from the group consisting of: ITRs, SV40 polyadenylation signal, rabbit β-globin polyadenylation signal, CMV enhancer sequence, HCR enhancer sequence from apolipoprotein E.

In a preferred embodiment, the viral expression construct comprises a nucleotide sequence encoding FGF21 suitable for expression in a mammal and at least one of elements a) and/or b) and/or c) and/or d) and/or e), wherein an additional sequence is present which is selected from the group consisting of: ITRs, SV40 polyadenylation signal, rabbit β-globin polyadenylation signal, CMV enhancer sequence, HCR enhancer sequence. Preferred ITRs are those of AAV2 which are represented by SEQ ID NO: 48 (5' ITR) and SEQ ID NO: 49 (3' ITR).

Preferred viral expression constructs comprise elements a) and/or b) and/or c) and/or d) and/or e) and are such that the expression cassette is flanked by a 5'ITR and a 3'ITR.

Other preferred viral expression constructs comprise elements a) and/or b) and/or c) and/or d) and/or e) and are such that the expression cassette is flanked by a 5'ITR and a 3'ITR. In addition, SV40 polyadenylation signals are present.

Other preferred viral expression constructs comprise elements a) and/or b) and/or c) and/or d) and/or e) and are such that the expression cassette is flanked by a 5'ITR and a 3'ITR. In addition, rabbit β-globin polyadenylation signals are present.

Other preferred viral expression constructs comprise elements a) and/or b) and/or c) and/or d) and/or e) and are such that the expression cassette is flanked by a 5'ITR and a 3'ITR. In addition, CMV enhancer sequence is present.

Other preferred viral expression constructs comprise elements a) and/or b) and/or c) and/or d) and/or e) and are such that the expression cassette is flanked by a 5'ITR and a 3'ITR. In addition, HCR enhancer sequence from apolipoprotein E is present.

Most preferred designed viral expression constructs include:

Construct B (represented by a nucleotide sequence comprising SEQ ID NO: 32),

Construct D (represented by a nucleotide sequence comprising SEQ ID NO: 34),

Construct F (represented by a nucleotide sequence comprising SEQ ID NO: 36),

Construct G (represented by a nucleotide sequence comprising SEQ ID NO: 37),

Construct H (represented by a nucleotide sequence comprising SEQ ID NO: 38),

Construct I (represented by a nucleotide sequence comprising SEQ ID NO: 39),

Construct J (represented by a nucleotide sequence comprising SEQ ID NO: 40),

Construct K (represented by a nucleotide sequence comprising SEQ ID NO: 41).

Construct L (represented by a nucleotide sequence comprising SEQ ID NO: 42).

As the skilled person will understand, each of these viral expression constructs already comprise two ITRs from AAV2 (i.e. SEQ ID NO: 48 (5' ITR) and SEQ ID NO: 49 (3' ITR)).

Constructs B and G comprise a rabbit β-globin polyadenylation signal. Construct F comprises a SV40 polyadenylation signal, a CMV enhancer sequence and a nucleotide sequence of a chimeric intron (composed of introns from human β-globin and immunoglobulin heavy chain genes). Constructs D, H-L comprise a SV40 polyadenylation signal, a HCR enhancer sequence and a nucleotide sequence of chimeric intron (composed of introns from human β-globin and immunoglobulin heavy chain genes).

As explained in the general part entitled "general definitions", throughout this application, each time one refers to a specific nucleotide sequence SEQ ID NO (take SEQ ID NO: A, B or C) representing the preferred constructs designed herein, one may replace it by:

i. a nucleotide sequence comprising a nucleotide sequence that has at least 60% sequence identity or similarity with SEQ ID NO: A, B or C;

ii. a nucleotide sequence the sequence of which differs from the sequence of a nucleic acid molecule of (i) due to the degeneracy of the genetic code.

Each nucleotide sequence described herein by virtue of its identity percentage (at least 60%) with a given nucleotide sequence respectively has in a further preferred embodiment an identity of at least 65%, 70%, 75%, 80%, 85%, 90%, 95%, 97%, 98%, 99% or more identity with the given nucleotide respectively. In a preferred embodiment, sequence identity is determined by comparing the whole length of the sequences as identified herein. Unless otherwise indicated herein, identity with a given SEQ ID NO means identity or similarity based on the full length of said sequence (i.e. over its whole length or as a whole).

A construct defined by its minimum identity (i.e. at least 60%) to a given SEQ ID NO as identified above is encompassed within the scope of the invention when this construct or a viral expression construct or a viral vector comprising this construct or a composition comprising this construct or vector is able to induce the expression of FGF21 in a cell, preferably in a liver cell, cell of adipose tissue or in a cell of skeletal muscle. The expression of FGF21 could be assessed using techniques known to the skilled person. In a preferred embodiment, said expression is assessed as carried out in the experimental part.

In a preferred embodiment, a viral expression construct is such that the construct is represented by a nucleotide sequence comprising SEQ ID NO: 4, 5, 6, 7, 8, 9, 10 or 11 or a sequence having at least 60% identity with SEQ ID NO: 4, 5, 6, 7, 8, 9, 10 or 11 or a sequence having at least 60%, 65%, 70%, 75%, 80%, 85%, 90%, 95%, 97%, 98%, 99%, 100% identity with SEQ ID NO: 4, 5, 6, 7, 8, 9, 10 or 11.

Viral Vector

In a further aspect, there is provided a viral vector comprising a viral expression construct as defined above, wherein said viral vector is an adenovirus vector, an adeno-associated virus vector, a retrovirus vector or a lentivirus vector, preferably an adeno-associated virus vector selected from the group consisting of an adeno-associated virus 1 (AAV1) vector, an adeno-associated virus 8 (AAV8) vector, and an adeno-associated virus 9 (AAV9) vector.

A "viral vector" and an "adeno-associated virus vector (AAV vector)" are further defined in the part of the description entitled "general definitions".

In an embodiment, an AAV vector is used comprising each of the elements defined earlier herein and a recombinant AAV (rAAV) based genome comprising a ITR or a part thereof. Preferred ITRs are those of AAV2 which are represented by SEQ ID NO: 48 (5' ITR) and SEQ ID NO: 49 (3' ITR).

Preferably, said AAV vector is an AAV1 vector, an AAV8 vector or an AAV9 vector.

A viral expression construct and a viral vector of the invention are preferably for use as a medicament. The medicament is preferably for preventing, delaying, curing, reverting and/or treating a metabolic disorder, preferably a diabetes and/or obesity. Diabetes may be Type 1 Diabetes, Type 2 Diabetes or Monogenic Diabetes. In another preferred embodiment, the medicament is for preventing, delaying, curing, reverting and/or treating liver inflammation and/or fibrosis. In yet another preferred embodiment, the medicament is for extending healthy lifespan, preferably by preventing, delaying, curing, reverting and/or treating a metabolic disorder associated with aging, preferably a diabetes and/or obesity. In yet another preferred embodiment, the medicament is for preventing, delaying, curing, reverting and/or treating cancer, preferably liver cancer.

The subject treated may be a higher mammal, e.g. cats, rodents, (preferably mice, rats, gerbils and guinea pigs, and more preferably mice and rats), or dogs, or human beings.

Nucleic Acid Molecule

In a further aspect, there is provided a nucleic acid molecule suitable for expression in a mammal and represented by a mammalian codon optimized nucleotide sequence encoding a FGF21 to be expressed in liver, adipose tissue and/or skeletal muscle.

The definition of "codon optimization" has been provided in the part of the description entitled "general definitions".

In an embodiment, a nucleic acid molecule is encompassed as described above, wherein the nucleotide sequence has at least 60% sequence identity with the nucleotide sequence of SEQ ID NO: 4, 5, 6, 7, 8, 9, 10 or 11. A preferred nucleotide sequence has at least 65%, 70%, 75%, 80%, 85%, 90%, 95%, 97%, 98%, 99%, 100% identity with SEQ ID NO: 4, 5, 6, 7, 8, 9, 10 or 11.

Composition

In a further aspect there is provided a composition comprising a viral expression construct as defined above and/or a viral vector as defined above and/or a nucleic acid molecule as defined above, together with one or more pharmaceutically acceptable excipients or vehicles.

This composition is preferably called a gene therapy composition. Preferably, the composition is a pharmaceutical composition said pharmaceutical composition comprising a pharmaceutically acceptable carrier, adjuvant, diluents, solubilizer, filler, preservative and/or excipient.

Such pharmaceutically acceptable carrier, filler, preservative, solubilizer, diluent and/or excipient may for instance be found in Remington: The Science and Practice of Pharmacy, 20th Edition. Baltimore, MD: Lippincott Williams & Wilkins, 2000.

In a preferred embodiment, said composition is for use as a medicament, preferably for preventing, delaying, curing, reverting and/or treating a metabolic disorder, preferably a diabetes and/or obesity. Diabetes may be Type 1 Diabetes, Type 2 Diabetes or Monogenic Diabetes. In another preferred embodiment, the medicament is for preventing, delaying, curing, reverting and/or treating liver inflammation and/or fibrosis. In yet another preferred embodiment, the medicament is for extending healthy lifespan, preferably by preventing, delaying, curing, reverting and/or treating a metabolic disorder associated with aging, preferably a diabetes and/or obesity. In yet another preferred embodiment, the medicament is for preventing, delaying, curing, reverting and/or treating cancer, preferably liver cancer. The subject treated may be a higher mammal, e.g. cats, rodent, (preferably mice, rats, gerbils and guinea pigs, and more preferably mice and rats), or dogs, or a human being.

Said viral expression construct, viral vector and/or nucleic acid molecule and/or composition are preferably said to be able to be used for preventing, delaying, reverting, curing and/or treating a metabolic disorder, preferably a diabetes and/or obesity, when said viral expression construct, viral vector and/or nucleic acid molecule and/or composition are able to exhibit an anti-diabetes effect and/or an anti-obesity effect.

Said viral expression construct, viral vector and/or nucleic acid molecule and/or composition are preferably said to be able to be used for preventing, delaying, curing, reverting and/or treating liver inflammation and/or fibrosis, when said viral expression construct, viral vector and/or nucleic acid molecule and/or composition are able to exhibit an anti-fibrotic effect.

Said viral expression construct, viral vector and/or nucleic acid molecule and/or composition are preferably said to be able to be used for extending healthy lifespan, preferably by preventing, delaying, curing, reverting and/or treating a metabolic disorder associated with aging, preferably a diabetes and/or obesity, when said viral expression construct, viral vector and/or nucleic acid molecule and/or composition are able to exhibit an anti-diabetes effect and/or an anti-obesity effect during aging.

Said viral expression construct, viral vector and/or nucleic acid molecule and/or composition are preferably said to be able to be used for preventing, delaying, curing, reverting and/or treating cancer, preferably liver cancer, when said viral expression construct, viral vector and/or nucleic acid molecule and/or composition are able to exhibit an anti-cancer effect.

An anti-diabetes effect may be reached when glucose disposal in blood is increased and/or when glucose tolerance is improved and/or when insulin sensitivity is increased. This could be assessed using techniques known to the skilled person or as done in the experimental part, preferably as assessed in example 8 or 9. In this context, "increase" (respectively "improvement") means at least a detectable increase (respectively a detectable improvement) using an assay known to the skilled person or using assays as carried out in the experimental part, such as measurement of glycaemia, insulinemia and/or performance of an insulin tolerance test and/or of a glucose tolerance test. The increase may be an increase of at least 5%, at least 10%, at least 20%, at least 30%, at least 40%, at least 50%, at least 60%, at least 70%, at least 80%, at least 90% or at least 100% using assays such as the measurement of glycaemia, insulinemia and/or performance of an insulin tolerance test and/or of a glucose tolerance test.

An anti-obesity effect may be reached when body weight, body weight gain and/or body fat percentage is decreased. An anti-obesity effect may also be reached when body mass index (BMI), waist circumference, waist-to-hip ratio (WHR) and/or waist-to-height ratio (WHtR) is decreased. This could be assessed using techniques known to the skilled person or as done in the experimental part. In this context, "decrease" (respectively "improvement") means at least a detectable decrease (respectively a detectable improvement) using an assay known to the skilled person or using assays as carried out in the experimental part. Anti-obesity effects include both prevention of obesity and reversion of obesity, as evaluated by measurement of body weight of the individual, the BMI and/or weight of the tissues.

An anti-inflammatory effect in the liver may be reached by a decrease in macrophage infiltration, decreased pro-inflammatory cytokines. This could be assessed using techniques known to the skilled person or as done in the experimental part. In this context, "decrease" (respectively "improvement") means at least a detectable decrease (respectively a detectable improvement) using an assay known to the skilled person or using assays as carried out in the experimental part.

An anti-fibrotic effect in the liver may be reached by a decrease in deposited extracellular matrix proteins, blood markers (e.g. including N-terminal propeptide of type III collagen, hyaluronic acid, tissue inhibitor of metalloproteinase type 1 (TIMP-1), YKL-40, serum glutamate oxaloacetate transaminase (SGOT), serum glutamate pyruvic transaminase (SGPT) levels in the plasma). An anti-fibrotic effect may also be reached by an improvement in a fibrosis scoring system such as Metavir or Ishak. This could be assessed using techniques known to the skilled person or as done in the experimental part. In this context, "decrease" (respectively "improvement") means at least a detectable decrease (respectively a detectable improvement) using an assay known to the skilled person or using assays as carried out in the experimental part.

A healthy lifespan-extending effect may be reached when an anti-diabetes and/or anti-obesity effect as defined earlier herein is used to prevent, delay, cure, reverse or treat the onset or progression of a metabolic disorder associated with aging, preferably of a diabetes and/or obesity. A healthy lifespan-extending effect may also be reached by an increase in the healthy lifespan, wherein symptoms associated with metabolic disorders, preferably of a diabetes and/or obesity, are absent or reduced. A healthy-lifespan extending effect may also be reached by improved coordination and balance (assessed by Rota-Rod test), memory (assessed by Object Recognition Test), and/or neuromuscular coordination (assessed by Tightrope Test), decreased mitochondrial and metabolic deterioration (assessed by measurement of expression levels of genes involved in metabolism and mitochondrial function such as PGC-1alpha, ATP synthase and ERRalpha). This could be assessed using techniques known to the skilled person or as done in the experimental part. In this context, "increase" (respectively "improvement") means at least a detectable increase (respectively a detectable improvement) using an assay known to the skilled person or using assays as carried out in the experimental part. An anti-cancer effect may be reached by a decrease in the cumulative incidence of cancer over the lifetime. This could be assessed using techniques known to the skilled person or as done in the experimental part. In this context, "decrease" (respectively "improvement") means at least a detectable decrease (respectively a detectable improvement) using an assay known to the skilled person or using assays as carried out in the experimental part.

An anti-diabetes effect and/or anti-obesity effect may also be observed when the progression of a typical symptom (e.g. insulitis, beta cell loss, increase of body weight) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of diabetes and/or obesity, including clinical examination and routine laboratory tests. Such methods include both macroscopic and microscopic methods, as well as molecular methods, X-rays, biochemical, immunohistochemical and others.

An anti-inflammatory effect in the liver may also be observed when the progression of a typical symptom (e.g. fatigue, flu-like symptoms, dark urine, pale stool, abdominal pain, loss of appetite, unexplained weight loss, jaundice) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of liver fibrosis, including clinical examination and routine laboratory tests. Such methods include both macroscopic and microscopic methods, as well as molecular methods, imaging methods (elastography, X-rays, MRI, CT, ultrasonography, angiography), biochemical, immunohistochemical and others.

An anti-fibrotic effect in the liver may also be observed when the progression of a typical symptom (e.g. liver stiffness, jaundice, appetite loss, difficulty thinking clearly, fluid buildup in the legs or stomach, nausea, unexplained weight loss, weakness) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of liver fibrosis, including clinical examination and routine laboratory tests. Such methods include both macroscopic and microscopic methods, as well as molecular methods, imaging methods (elastography, X-rays, MRI, CT, ultrasonography, angiography), biochemical, immunohisto-chemical and others.

An healthy lifespan-extending effect may also be observed when the progression of a typical symptom of metabolic disorders associated with aging (e.g. insulin resistance, glucose intolerance, increase of body weight) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of diabetes and/or obesity, including clinical examination and routine laboratory tests. Such methods include both macroscopic and microscopic methods, as well as molecular methods, X-rays, biochemical, immunohistochemical and others.

An anti-cancer effect may also be observed when the progression of a typical symptom (e.g. tumor size, unexplained weight loss, loss of appetite, feeling very full after a small meal, nausea or vomiting, enlarged liver, enlarged spleen, pain in the abdomen or near the right shoulder blade, swelling or fluid build-up in the abdomen, itching, jaundice) has been slowed down as assessed by a physician. A decrease of a typical symptom may mean a slow down in progression of symptom development or a complete disappearance of symptoms. Symptoms, and thus also a decrease in symptoms, can be assessed using a variety of methods, to a large extent the same methods as used in diagnosis of cancer, including clinical examination and routine laboratory tests. Such methods include both macroscopic and microscopic methods, as well as molecular methods, imaging methods (X-rays, MRI, CT, ultrasonography, angiography), biochemical, immunohistochemical and others.

A medicament as defined herein (viral expression construct, viral vector, nucleic acid molecule, composition) is preferably able to alleviate one symptom or one characteristic of a patient or of a cell, tissue or organ of said patient if after at least one week, one month, six months, one year or more of treatment using a viral expression construct and/or a viral vector and/or a nucleic acid molecule and/or a composition of the invention, said symptom or characteristic has decreased (e.g. is no longer detectable or has slowed down), as defined above.

A viral expression construct and/or a viral vector and/or a nucleic acid molecule and/or a composition as defined herein for use according to the invention may be suitable for administration to a cell, tissue and/or an organ in vivo of individuals affected by or at risk of developing a metabolic disorder, such as a diabetes and/or obesity, liver inflammation and/or fibrosis, a metabolic disorder associated with aging, and/or cancer, and may be administered in vivo, ex vivo or in vitro. Said viral expression construct and/or a viral vector and/or a nucleic acid molecule and/or composition may be directly or indirectly administrated to a cell, tissue and/or an organ in vivo of an individual affected by or at risk of developing a metabolic disorder, such as a diabetes and/or obesity, liver inflammation and/or fibrosis, a metabolic disorder associated with aging, and/or cancer, and may be administered directly or indirectly in vivo, ex vivo or in vitro. An administration mode may be intravenous, subcutaneous, intramuscular, intrathecal, intraarticular, intraventricular, intraperitoneal, intra-adipose tissue, via inhalation, oral, intranasal, intrahepatic, intrasplanchnic, intra-ocular, intra-ear, topic administration and/or via retrograde intraductal pancreatic administration. A preferred administration mode is intramuscular, intravenous or intra-adipose tissue, as described in the "General procedures to the Examples" as part of this application.

A viral expression construct and/or a viral vector and/or a nucleic acid molecule and/or a composition of the invention may be directly or indirectly administered using suitable means known in the art. Improvements in means for providing an individual or a cell, tissue, organ of said individual with a viral expression construct and/or a viral vector and/or a nucleic acid molecule and/or a composition of the invention are anticipated, considering the progress that has already been achieved. Such future improvements may of course be incorporated to achieve the mentioned effect of the invention. A viral expression construct and/or a viral vector and/or a nucleic acid molecule and/or a composition can be delivered as is to an individual, a cell, tissue or organ of said individual. Depending on the disease or condition, a cell, tissue or organ of said individual may be as earlier defined herein. When administering a viral expression construct and/or a viral vector and/or a nucleic acid molecule and/or a composition of the invention, it is preferred that such viral expression construct and/or vector and/or nucleic acid and/or composition is dissolved in a solution that is compatible with the delivery method.

As encompassed herein, a therapeutically effective dose of a viral expression construct, vector, nucleic acid molecule and/or composition as mentioned above is preferably administered in a single and unique dose hence avoiding repeated periodical administration. More preferably, the single dose is administered to skeletal muscle, to adipose tissue or intravenously.

A further compound may be present in a composition of the invention. Said compound may help in delivery of the composition. Below is provided a list of suitable compounds: compounds capable of forming complexes, nanoparticles, micelles and/or liposomes that deliver each constituent as defined herein, complexed or trapped in a vesicle or liposome through a cell membrane. Many of these compounds are known in the art. Suitable compounds comprise polyethylenimine (PEI), or similar cationic polymers, including polypropyleneimine or polyethylenimine copolymers (PECs) and derivatives, synthetic amphiphiles (SAINT-18), Lipofectin™, DOTAP.

Depending on their identity, the skilled person will know which type of formulation is the most appropriate for the composition as defined herein.

Method/Use

In a further aspect there is provided a viral expression construct as defined above and/or a viral vector as defined above and/or a nucleic acid molecule as defined above and/or a composition as defined above, for use as a medicament.

In an embodiment, said viral expression construct and/or viral vector and/or nucleic acid molecule and/or composition is provided for use in the treatment and/or prevention of a metabolic disorder, preferably a diabetes and/or obesity. Complications of a metabolic disorder may also be encompassed.

In another embodiment, said viral expression construct and/or viral vector and/or nucleic acid molecule and/or composition is provided for use in the treatment and/or prevention of liver inflammation and/or fibrosis. Complications of liver inflammation and/or fibrosis may also be encompassed.

In yet another embodiment, said viral expression construct and/or viral vector and/or nucleic acid molecule and/or composition is provided for use in extending healthy lifespan, preferably by preventing, delaying, curing, reverting and/or treating a metabolic disorder associated with aging, preferably a diabetes and/or obesity.

In yet another embodiment, said viral expression construct and/or viral vector and/or nucleic acid molecule and/or composition is provided for use in the treatment and/or prevention of cancer, preferably liver cancer. Complications of a cancer may also be encompassed.

In a further aspect there is provided a method for preventing, delaying, reverting, curing and/or treating a metabolic disorder, preferably a diabetes and/or obesity and their complications, comprising the use of a viral expression construct as defined above and/or a viral vector as defined above and/or a nucleic acid molecule as defined above and/or a composition as defined above.

Such a method is preferably for alleviating one or more symptom(s) of a metabolic disorder, such as a diabetes and/or obesity, in an individual, in a cell, tissue or organ of said individual or alleviate one or more characteristic(s) or symptom(s) of a cell, tissue or organ of said individual, the method comprising administering to said individual a viral expression construct and/or a viral vector and/or a nucleic acid molecule and/or a composition as defined herein.

In a further aspect there is provided a method for preventing, delaying, reverting, curing and/or treating liver inflammation and/or fibrosis and its complications, comprising the use of a viral expression construct as defined above and/or a viral vector as defined above and/or a nucleic acid molecule as defined above and/or a composition as defined above. Such a method is preferably for alleviating one or more symptom(s) of liver inflammation and/or fibrosis, in an individual, in a cell, tissue or organ of said individual or alleviate one or more characteristic(s) or symptom(s) of a cell, tissue or organ of said individual, the method comprising administering to said individual a viral expression construct and/or a viral vector and/or a nucleic acid molecule and/or a composition as defined herein.

In a further aspect there is provided a method for extending healthy lifespan, preferably by preventing, delaying, curing, reverting and/or treating a metabolic disorder associated with aging, preferably a diabetes and/or obesity, comprising the use of a viral expression construct as defined above and/or a viral vector as defined above and/or a nucleic acid molecule as defined above and/or a composition as defined above.

Such a method is preferably for alleviating one or more symptom(s) of a metabolic disorder associated with aging, such as a diabetes and/or obesity, in an individual, in a cell, tissue or organ of said individual or alleviate one or more characteristic(s) or symptom(s) of a cell, tissue or organ of said individual, the method comprising administering to said individual a viral expression construct and/or a viral vector and/or a nucleic acid molecule and/or a composition as defined herein.

In a further aspect there is provided a method for preventing, delaying, reverting, curing and/or treating cancer, preferably liver cancer and its complications, comprising the use of a viral expression construct as defined above and/or a viral vector as defined above and/or a nucleic acid molecule as defined above and/or a composition as defined above. Such a method is preferably for alleviating one or more symptom(s) of cancer, such as liver cancer, in an individual, in a cell, tissue or organ of said individual or alleviate one or more characteristic(s) or symptom(s) of a cell, tissue or organ of said individual, the method comprising administering to said individual a viral expression construct and/or a viral vector and/or a nucleic acid molecule and/or a composition as defined herein.

In the context of the invention there is provided a use of a viral expression construct and/or a viral vector and/or a nucleic acid molecule and/or a composition as defined herein for the manufacture of a medicament for preventing, delaying, reverting, curing and/or treating a metabolic disorder, preferably a diabetes and/or obesity.

In the context of the invention there is provided a use of a viral expression construct and/or a viral vector and/or a nucleic acid molecule and/or a composition as defined herein for the manufacture of a medicament for preventing, delaying, curing, reverting and/or treating liver inflammation and/or fibrosis.

In the context of the invention there is provided a use of a viral expression construct and/or a viral vector and/or a nucleic acid molecule and/or a composition as defined herein for the manufacture of a medicament for extending healthy lifespan, preferably by preventing, delaying, curing, reverting and/or treating a metabolic disorder associated with aging, preferably a diabetes and/or obesity.

In the context of the invention there is provided a use of a viral expression construct and/or a viral vector and/or a nucleic acid molecule and/or a composition as defined herein for the manufacture of a medicament for preventing, delaying, reverting, curing and/or treating cancer, preferably liver cancer.

Metabolic disorders include metabolic syndrome, diabetes, obesity, obesity-related comorbidities, diabetes-related comorbidities, hyperglycaemia, insulin resistance, glucose intolerance, hepatic steatosis, alcoholic liver diseases (ALD), non-alcoholic fatty liver disease (NAFLD), non-alcoholic steatohepatitis (NASH), coronary heart disease (CHD), hyperlipidemia, atherosclerosis, endocrinophaties, osteosarcopenic obesity syndrome (OSO), diabetic nephropaty, chronic kidney disease (CKD), cardiac hypertrophy, diabetic retinopathy, diabetic nephropathy, diabetic neuropathy, arthritis, sepsis, ocular neovascularization, neurodegeneration, dementia, and may also include depression, adenoma, carcinoma.

Diabetes includes prediabetes, hyperglycaemia, Type 1 diabetes, Type 2 diabetes, maturity-onset diabetes of the young (MODY), monogenic diabetes, neonatal diabetes, gestational diabetes, brittle diabetes, idiopathic diabetes, drug- or chemical-induced diabetes, Stiff-man syndrome, lipoatrophic diabetes, latent autoimmune diabetes in adults (LADA).

Obesity includes overweight, central/upper body obesity, peripheral/lower body obesity, morbid obesity, osteosarcopenic obesity syndrome (OSO), pediatric obesity, Mendelian (monogenic) syndromic obesity, Mendelian non-syndromic obesity, polygenic obesity. Metabolic disorders, diabetes, obesity and the type of subject treated have been earlier defined herein.

Liver inflammation and/or fibrosis includes autoimmune hepatitis, viral hepatitis including hepatitis A, B, C, D and E, alcoholic hepatitis, non-alcoholic steatohepatitis (NASH) and liver cirrhosis.

Cancer includes astrocytoma, glioma, leukemia, lymphoma, melanoma, myeloma, neuroblastoma, sarcoma (including chondrosarcoma, fibrosarcoma, rhabdomyosarcoma, and osteosarcoma), schwannoma, seminoma, and carcinomas of the bladder, breast, cervix, colon, endometrium, esophagus, gallbladder, kidney, liver, lung, ovary, prostate, pancreas, rectum, skin, stomach and thyroid. A preferred cancer is liver cancer, preferably hepatocellular carcinoma. In one embodiment said method or use is performed in vitro, for instance using a cell culture. Preferably, said method or use is in vivo. Each feature of these methods/uses has already been defined herein.

In a method of the invention, a viral expression construct and/or a vector and/or a nucleic acid molecule and/or a composition may be combined with an additional compound known to be used for treating metabolic disorders, preferably diabetes and/or obesity in an individual.

In another method of the invention, a viral expression construct and/or a vector and/or a nucleic acid molecule and/or a composition may be combined with an additional compound known to be used for treating liver inflammation and/or fibrosis.

In yet another method of the invention, a viral expression construct and/or a vector and/or a nucleic acid molecule and/or a composition may be combined with an additional compound known to be used for extending healthy lifespan.

In yet another method of the invention, a viral expression construct and/or a vector and/or a nucleic acid molecule and/or a composition may be combined with an additional compound known to be used for treating cancer, preferably liver cancer.

In a preferred embodiment, a treatment in a use or in a method according to the invention does not have to be repeated. Alternatively in a use or a method according to the invention said administration of the viral expression construct or of said composition may be repeated each year or each 2, 3, 4, 5, 6 years.

General Definitions

Identity/Similarity

In the context of the invention, a protein fragment or a polypeptide or a peptide or a derived peptide as Fibroblast growth factor 21 (FGF21) is represented by an amino acid sequence.

In the context of the invention, a nucleic acid molecule as a nucleic acid molecule encoding a FGF21 is represented by a nucleic acid or nucleotide sequence which encodes a protein fragment or a polypeptide or a peptide or a derived peptide. A nucleic acid molecule may comprise a regulatory region.

It is to be understood that each nucleic acid molecule or protein fragment or polypeptide or peptide or derived peptide or construct as identified herein by a given Sequence Identity Number (SEQ ID NO) is not limited to this specific sequence as disclosed. Each coding sequence as identified herein encodes a given protein fragment or polypeptide or peptide or derived peptide or construct or is itself a protein fragment or polypeptide or construct or peptide or derived peptide. Throughout this application, each time one refers to a specific nucleotide sequence SEQ ID NO (take SEQ ID NO: X as example) encoding a given protein fragment or polypeptide or peptide or derived peptide, one may replace it by:

i. a nucleotide sequence comprising a nucleotide sequence that has at least 60% sequence identity or similarity with SEQ ID NO: X;

ii. a nucleotide sequence the sequence of which differs from the sequence of a nucleic acid molecule of (i) due to the degeneracy of the genetic code; or, iii. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

Each non-coding nucleotide sequence (i.e. of a promoter or of another regulatory region) could be replaced by a nucleotide sequence comprising a nucleotide sequence that has at least 60% sequence identity or similarity with a specific nucleotide sequence SEQ ID NO (take SEQ ID NO: A as example). A preferred nucleotide sequence has at least 60%, 65%, 70%, 75%, 80%, 85%, 90%, 95%, 97%, 98%, 99%, 100% identity with SEQ ID NO: A. Identity may be assessed over the whole SEQ ID NO or over part thereof as explained herein. In a preferred embodiment, such non-coding nucleotide sequence such as a promoter exhibits or exerts at least an activity of such a non-coding nucleotide sequence such as an activity of a promoter as known to the skilled person.

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10%, 20%, 30%, 40%, 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994;

Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, WI. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Gene or Coding Sequence

"Gene" or "coding sequence" or "nucleic acid" or "nucleotide sequence" or "nucleic" refers to a DNA or RNA region (the transcribed region) which "encodes" a particular protein such as a FGF21. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3' nontranslated sequence or 3' untranslated region (3' UTR), comprising a polyadenylation site or a signal sequence. A chimeric or recombinant gene (such as a FGF21 gene) is a gene not normally found in nature, such as a gene in which for example the promoter is not associated in nature with part or all of the transcribed DNA region. "Expression of a gene" refers to the process wherein a gene is transcribed into an RNA and/or translated into an active protein.

Promoter

As used herein, the term "promoter" refers to a nucleic acid fragment that functions to control the transcription of one or more genes (or coding sequence), located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "organ-specific" or "tissue-specific" promoter is a promoter that is active in a specific type of organ or tissue, respectively. Organ-specific and tissue-specific promoters regulate expression of one or more genes (or coding sequence) primarily in one organ or tissue, but can allow detectable level ("leaky") expression in other organs or tissues as well. Leaky expression in other organs or tissues means at least one-fold, at least two-fold, at least three-fold, at least four-fold or at least five-fold lower, but still detectable expression as compared to the organ-specific or tissue-specific expression, as evaluated by standard assays known to the skilled person (e.g. PCR, Western blot analysis, ELISA). The maximum number of organs or tissues where leaky expression may be detected is five, six, seven or eight. An "adipose tissue-specific promoter" is a promoter that is capable of initiating transcription in the adipose tissue, whilst still allowing for any leaky expression in other (maximum five, six, seven or eight) organs and parts of the body. Transcription in the adipose tissue can be detected in adipose tissue and adipose cells, such as white adipocytes, brown adipocytes, beige adipocytes, preadipocytes, stromal vascular cells. A "liver-specific promoter" is a promoter that is capable of initiating transcription in the liver, whilst still allowing for any leaky expression in other (maximum five, six, seven or eight) organs and parts of the body. Transcription in the liver can be detected in liver tissue and liver cells, such as hepatocytes, Kupffer cells and/or oval cells. Similarly, a "skeletal muscle promoter" is a promoter that is capable of initiating transcription in skeletal muscle, whilst still allowing for any leaky expression in other (maximum five, six, seven or eight) organs and parts of the body. Transcription in the skeletal muscle can be detected in skeletal muscle cells, such as myocytes, myoblasts, satellite cells.

A "ubiquitous promoter" is active in substantially all tissues, organs and cells of an organism.

Suitable promoters for organ-specific and/or tissue-specific expression of a nucleotide sequence encoding a FGF21 include the human al-antitrypsin promoter, the al-antitrypsin promoter in combination with the hepatocyte control region (HCR) enhancer from the apolipoprotein E, the albumin promoter, the major urinary protein promoter, the phosphoenolpyruvate carboxykinase (PEPCK) promoter, the liver-enriched protein activator promoter, the transthyretin promoter, the thyroxine binding globulin promoter, the apolipoprotein A1 promoter, the liver fatty acid binding protein promoter, the phenylalanine hydroxylase promoter, the adipocyte protein 2 (aP2, also known as fatty acid binding protein 4 (FABP4)) promoter, the PPARγ promoter, the adiponectin promoter, the phosphoenolpyruvate carboxykinase (PEPCK) promoter, the promoter derived from human aromatase cytochrome p450 (p450arom) the mini/aP2 promoter (composed of the adipose-specific aP2 enhancer and the basal aP2 promoter), the uncoupling protein 1 (UCP1) promoter, the mini/UCP1 promoter (composed of the adipose-specific UCP1 enhancer and the basal UCP1 promoter), the adipsin promoter, the leptin promoter, the Foxa-2 promoter, the myosin light-chain promoter, the myosin heavy-chain promoter, the desmin promoter, the C5-12 promoter, the muscle creatine kinase (MCK) promoter, the smooth muscle alpha-actin promoter, the CK6 promoter, the Unc-45 Myosin Chaperone B promoter, the basal MCK promoter in combination with copies of the MCK enhancer, the Enh358MCK promoter (combination of the MCK enhancer with the 358 bp proximal promoter of the MCK gene).

Operably Linked

"Operably linked" is defined herein as a configuration in which a control sequence such as a promoter sequence or regulating sequence is appropriately placed at a position relative to the nucleotide sequence of interest, preferably coding for a FGF21 such that the promoter or control or regulating sequence directs or affects the transcription and/or production or expression of the nucleotide sequence of interest, preferably encoding a FGF21 in a cell and/or in a subject. For instance, a promoter is operably linked to a coding sequence if the promoter is able to initiate or regulate the transcription or expression of a coding sequence, in which case the coding sequence should be understood as being "under the control of" the promoter. When one or more nucleotide sequences and/or elements comprised within a construct are defined herein to be "configured to be operably linked to an optional nucleotide sequence of interest", said nucleotide sequences and/or elements are understood to be configured within said construct in such a way that these nucleotide sequences and/or elements are all operably linked to said nucleotide sequence of interest once said nucleotide sequence of interest is present in said construct.

Viral Expression Construct

An expression construct carries a genome that is able to stabilize and remain episomal in a cell. Within the context of the invention, a cell may mean to encompass a cell used to make the construct or a cell wherein the construct will be administered. Alternatively a construct is capable of integrating into a cell's genome, e.g. through homologous recombination or otherwise. A particularly preferred expression construct is one wherein a nucleotide sequence encoding a FGF21 as defined herein is operably linked to a promoter as defined herein wherein said promoter is capable of directing expression of said nucleotide sequence (i.e.

coding sequence) in a cell. Preferably, said promoter directs expression of said nucleotide sequence in at least one cell of a specific organ and/or a specific tissue. Preferably, said promoter directs expression of said nucleotide sequence in at least one cell of liver, adipose tissue and/or skeletal muscle. Preferably, said promoter directs expression in at least 10%, 20%, 30%, 40%, 40%, 60%, 70%, 80%, 90%, or 100% of cells of liver, adipose tissue and/or skeletal muscle. In the context of the invention, a FGF21 to be expressed in the liver, adipose tissue or skeletal muscle refers to the preferential or predominant (at least 10% higher, at least 20% higher, at least 30% higher, at least 40% higher, at least 50% higher, at least 60% higher, at least 70% higher, at least 80% higher, at least 90% higher, at least 100% higher, at least 150% higher, at least 200% higher or more) expression of FGF21 in the liver, adipose tissue or skeletal muscle as compared to other organs or tissues. Throughout the application, where liver-specific, or adipose-specific or skeletal muscle-specific is mentioned in the context of expression, cell-type specific expression of the cell type(s) making up the liver, the adipose tissue or skeletal muscle is also envisaged, respectively.

The viral expression constructs of the invention comprise a nucleotide sequence in a form "suitable for expression in a mammal", which means that the viral expression constructs include one or more regulatory sequences, selected on the basis of the mammalian host cells to be used for expression, that is operatively linked to the nucleotide sequence to be expressed. Preferably, said mammalian host cells to be used for expression are human, murine or canine cells.

The viral expression constructs of the invention comprise a nucleotide sequence to be expressed in liver, adipose tissue and/or skeletal muscle.

As used herein, "adipose tissue" refers to tissue composed of mature adipocytes (i.e. fat cells) and a combination of small blood vessels, nerve tissue, lymph nodes and the stromal vascular fraction (SVF). The SVF is composed of endothelial cells, fibroblasts, adipocyte precursor cells (i.e. preadipocytes), and immune cells such as macrophages and T cells. In mammals, two different types of adipose tissues are traditionally distinguished: the white adipose tissue (WAT) and the brown adipose tissue (BAT). In mammals, the adipose tissue is contained in a multi-depot organ. Adipose depots include but are not limited to epididymal WAT (eWAT), inguinal WAT (iWAT), retroperitoneal WAT (rWAT), mesenteric WAT (mWAT), interscapular BAT (iBAT).

As used herein, "skeletal muscle" refers to the tissue composed of muscle fibers. A muscle fiber, also known as a myofiber, is a single multinucleated or syncitial cell that results from the fusion of many hundreds of myoblasts, some of which remain in the mature muscle as undifferentiated cells known as satellite cells. Individual muscle fibers are surrounded by a connective tissue called endomysium. Around 10 to 100 muscle fibers form fascicles, or bundles, which are themselves surrounded by another connective tissue layer called the perimysium. Finally, the skeletal muscle is formed by groups of fascicles that are surrounded also by another connective tissue layer called the epimysium. In addition to muscle fibers, skeletal muscle is also composed of numerous blood vessels and nerves. The ends of muscles converge in dense connective tissue structures, the tendons and aponeuroses that mediate attachment of muscles to the periosteum of bones or to the connective tissue of other muscles.

As used herein, "liver" refers to the tissue composed of hepatocytes. Hepatocytes represent about 50-70% of the cells in the liver. In addition to hepatocytes, the liver is composed of endothelial cells, perisinusoidal cells, oval cells, Kupffer cells and stellate cells (Ito cells). When activated by Kupffer cells, the stellate cells transform into myofibroblasts. Central veins and portal tracks (portal triads) that contain preterminal branches of the hepatic artery, the hepatic portal vein, bile ductules and lymphatic vessels are also found in the liver.

Such a preferred expression construct is said to comprise an expression cassette. An expression cassette as used herein comprises or consists of a nucleotide sequence encoding a FGF21, being operably linked to a promoter wherein said promoter is capable of directing expression of said nucleotide sequence. In an embodiment, an expression cassette as used herein comprises or consists of a nucleotide sequence encoding a FGF21, a promoter and at least one nucleotide sequence encoding a target sequence of a microRNA expressed in the liver and at least one nucleotide sequence encoding a target sequence of a microRNA expressed in the heart. In one embodiment the described expression cassettes contain nucleotide sequences encoding target sequences for a microRNA expressed in the liver and/or a microRNA expressed in the heart with perfect complementarity to their cognate microRNAs. In another embodiment, the described expression cassettes contain one or more nucleotide sequence(s) encoding microRNA binding sites with imperfect complementarity (one mismatch/five consecutive nucleotides). In yet another embodiment, the expression cassettes may contain both nucleotide sequences encoding perfect and imperfect microRNA binding sites. Expression cassettes can therefore be tailored to result in varying levels of regulation by using nucleotide sequences encoding single perfect, multiple perfect, single imperfect, multiple imperfect or a combination of perfect and imperfect target sites for microRNAs. Further, nucleotide sequence encoding target sites for different microRNAs may be used, therefore permitting a gene to be regulated by multiple microRNAs. A preferred location for the nucleotide sequence encoding a target sequence of a microRNA is the 3'UTR. However, nucleotide sequences (encoding target sequences) inserted into either a coding sequence or 5'UTR sequences may also be used.

The choice of nucleotide sequence encoding a target sequence of a microRNA is determined by the desired expression pattern. The presence of an endogenous microRNA in a cell will inhibit expression of a gene or coding sequence from an expression construct which contains a nucleotide sequence encoding a target sequence for said microRNA. For expression of the gene or coding sequence of interest to be inhibited in a given cell-type, a nucleotide sequence encoding a target sequence that is recognized by a microRNA present in that cell-type is chosen.

A viral expression construct is an expression construct which is intended to be used in gene therapy. It is designed to comprise part of a viral genome as later defined herein. Expression constructs disclosed herein could be prepared using recombinant techniques in which a nucleotide sequence encoding said FGF21 is expressed in a suitable cell, e.g., cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc.

Natl. Acad. Sci. 82:488 (describing site directed mutagenesis) and Roberts et al. (1987) Nature 328:731-734 or Wells, J. A., et al. (1985) Gene 34: 315 (describing cassette mutagenesis). Typically, a nucleic acid or nucleotide sequence encoding a FGF21 is used in an expression construct or expression vector. The phrase "expression vector" or "vector" generally refers to a nucleotide sequence that is capable of effecting expression of a gene or a coding sequence in a host compatible with such sequences. These expression vectors typically include at least suitable promoter sequences and optionally, transcription termination signals. An additional factor necessary or helpful in effecting expression can also be used as described herein. A nucleic acid or DNA or nucleotide sequence encoding a FGF21 is incorporated into a DNA construct capable of introduction into and expression in an in vitro cell culture. Specifically, a DNA construct is suitable for replication in a prokaryotic host, such as bacteria, e.g., E. coli, or can be introduced into a cultured mammalian, plant, insect, (e.g., Sf9), yeast, fungi or other eukaryotic cell lines. A DNA construct prepared for introduction into a particular host may include a replication system recognized by the host, an intended DNA segment encoding a desired polypeptide, and transcriptional and translational initiation and termination regulatory sequences operably linked to the polypeptide-encoding segment. The term "operably linked" has already been defined herein. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the tip, lac and phage promoters, tRNA promoters and glycolytic enzyme promoters are known and available (see, e.g. Sambrook and Russell, 2001, supra). An expression vector includes the replication system and transcriptional and translational regulatory sequences together with the insertion site for the polypeptide encoding segment. In most cases, the replication system is only functional in the cell that is used to make the vector (bacterial cell as E. Coli). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. S. cerevisiae, e.g., insect cells, e.g., Sf9 cells, mammalian cells, e.g., CHO cells and bacterial cells, e.g., E. coli. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal.

Viral Vector

A viral vector or a viral gene therapy vector is a vector that comprises a viral expression construct as defined above.

A viral vector or a viral gene therapy vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; *Vigna* and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an adenoviral and adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications, (Russell, 2000, J. Gen. Virol. 81: 2573-2604; Goncalves, 2005, Virol J. 2(1):43) as indicated above. AAV vectors are even more preferred since they are known to result in very stable long term expression of transgene expression (up to 9 years in dog (Niemeyer et al, Blood. 2009 Jan. 22; 113(4):797-806) and ~10 years in human (Buchlis, G. et al., Blood. 2012 Mar. 29; 119(13):3038-41). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, N Engl J Med. 2011 Dec. 22; 365(25):2357-65, Apparailly et al, Hum Gene Ther. 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and Vigna et al. (2000, J Gene Med 2000; 2: 308-16).

Other suitable gene therapy vectors include an adenovirus vector, a herpes virus vector, a polyoma virus vector or a vaccinia virus vector.

A gene therapy vector comprises a nucleotide sequence encoding a FGF21 to be expressed, whereby said nucleotide sequence is operably linked to the appropriate regulatory sequences. Such regulatory sequence will at least comprise a promoter sequence. Suitable promoters for expression of a nucleotide sequence encoding a FGF21 from a gene therapy vector include e.g. CMV promoter, viral long terminal repeat promoters (LTRs), such as those from murine moloney leukaemia virus (MMLV) rous sarcoma virus, or HTLV-1, the simian virus 40 (SV 40) early promoter, the CAG promoter, the α1-antitrypsin promoter, the mini/aP2 promoter, the mini/UCP1 promoter, the C5-12 promoter and the herpes simplex virus thymidine kinase promoter.

Several inducible promoter systems have been described that may be induced by the administration of small organic or inorganic compounds. Such inducible promoters include those controlled by heavy metals, such as the metallothionine promoter (Brinster et al. 1982 Nature 296: 39-42; Mayo et al. 1982 Cell 29: 99-108), RU-486 (a progesterone antagonist) (Wang et al. 1994 Proc. Natl. Acad. Sci. USA 91: 8180-8184), steroids (Mader and White, 1993 Proc. Natl. Acad. Sci. USA 90: 5603-5607), tetracycline (Gossen and Bujard 1992 Proc. Natl. Acad. Sci. USA 89: 5547-5551; U.S. Pat. No. 5,464,758; Furth et al. 1994 Proc. Natl. Acad. Sci. USA 91: 9302-9306; Howe et al. 1995 J. Biol. Chem. 270: 14168-14174; Resnitzky et al. 1994 Mol. Cell. Biol. 14: 1669-1679; Shockett et al. 1995 Proc. Natl. Acad. Sci. USA 92: 6522-6526) and the tTAER system that is based on the multi-chimeric transactivator composed of a tetR polypeptide, as activation domain of VP 16, and a ligand binding domain of an estrogen receptor (Yee et al., 2002, U.S. Pat. No. 6,432,705).

A gene therapy vector may optionally comprise a further nucleotide sequence coding for a further polypeptide.

A gene therapy vector is preferably formulated in a composition or pharmaceutical composition as defined herein. In this context, a composition or pharmaceutical composition may comprise a suitable pharmaceutical carrier as earlier defined herein.

Adeno-Associated Virus Vector (AAV Vector)

A preferred viral vector or a preferred gene therapy vector is an AAV vector. An AAV vector as used herein preferably comprises a recombinant AAV vector (rAAV vector). A "rAAV vector" as used herein refers to a recombinant vector comprising part of an AAV genome encapsidated in a protein shell of capsid protein derived from an AAV serotype as explained herein. Part of an AAV genome may contain the inverted terminal repeats (ITR) derived from an adeno-associated virus serotype, such as AAV1, AAV2, AAV3, AAV4, AAV5 and others. Preferred ITRs are those of AAV2 which are represented by sequences comprising or consisting of SEQ ID NO: 48 (5' ITR) and SEQ ID NO: 49 (3' ITR). The invention also preferably encompasses the use of a sequence having at least 80% (or at least 81%, 82%, 83%, 84%, 85%, 86%, 87%, 87%, 88%, 89%, 90%, 91%, 92%, 93%, 94%, 95%, 96%, 97%, 98%, 99% or 100%) identity with SEQ ID NO: 48 as 5'ITR and a sequence having at least 80% identity with SEQ ID NO: 49 as 3'ITR.

Protein shell comprised of capsid protein may be derived from an AAV serotype such as AAV1, 2, 3, 4, 5 and others. A preferred AAV capsid is an AAV1, AAV3, AAV8, AAV9 capsid. A preferred ITR is from the AAV2. A protein shell may also be named a capsid protein shell. rAAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95%, 97%, 98%, 99% or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the rAAV vector genome ITR.

A nucleic acid molecule represented by a nucleic acid sequence of choice is preferably inserted between the rAAV genome or ITR sequences as identified above, for example an expression construct comprising an expression regulatory element operably linked to a coding sequence and a 3' termination sequence. Said nucleic acid molecule may also be called a transgene.

"AAV helper functions" generally refers to the corresponding AAV functions required for rAAV replication and packaging supplied to the rAAV vector in trans. AAV helper functions complement the AAV functions which are missing in the rAAV vector, but they lack AAV ITRs (which are provided by the rAAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on an AAV helper construct. Introduction of the helper construct into the host cell can occur e.g. by transformation, transfection, or transduction prior to or concurrently with the introduction of the rAAV genome present in the rAAV vector as identified herein. The AAV helper constructs of the invention may thus be chosen such that they produce the desired combination of serotypes for the rAAV vector's capsid protein shell on the one hand and for the rAAV genome present in said rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via plasmids, as described in U.S. Pat. No. 6,531,456 incorporated herein by reference.

A "transgene" is herein defined as a gene or a coding sequence or a nucleic acid molecule (i.e. a molecule encoding a FGF21) that has been newly introduced into a cell, i.e. a gene that may be present but may normally not be expressed or expressed at an insufficient level in a cell. In this context, "insufficient" means that although said FGF21 is expressed in a cell, a condition and/or disease as defined herein could still be developed. In this case, the invention allows the over-expression of a FGF21. The transgene may comprise sequences that are native to the cell, sequences that naturally do not occur in the cell and it may comprise combinations of both. A transgene may contain sequences coding for a FGF21 and/or additional proteins as earlier identified herein that may be operably linked to appropriate regulatory sequences for expression of the sequences coding for a FGF21 in the cell. Preferably, the transgene is not integrated into the host cell's genome.

"Transduction" refers to the delivery of a FGF21 into a recipient host cell by a viral vector. For example, transduction of a target cell by a rAAV vector of the invention leads to transfer of the rAAV genome contained in that vector into the transduced cell. "Host cell" or "target cell" refers to the cell into which the DNA delivery takes place, such as the muscle cells of a subject. AAV vectors are able to transduce both dividing and non-dividing cells.

Production of an AAV Vector

The production of recombinant AAV (rAAV) for vectorizing transgenes have been described previously. See Ayuso E, et al., Curr. Gene Ther. 2010; 10:423-436, Okada T, et al., Hum. Gene Ther. 2009; 20:1013-1021, Zhang H, et al., Hum. Gene Ther. 2009; 20:922-929, and Virag T, et al., Hum. Gene Ther. 2009; 20:807-817. These protocols can be used or adapted to generate the AAV of the invention. In one embodiment, the producer cell line is transfected transiently with the polynucleotide of the invention (comprising the expression cassette flanked by ITRs) and with construct(s) that encodes rep and cap proteins and provides helper functions. In another embodiment, the cell line supplies stably the helper functions and is transfected transiently with the polynucleotide of the invention (comprising the expression cassette flanked by ITRs) and with construct(s) that encodes rep and cap proteins. In another embodiment, the cell line supplies stably the rep and cap proteins and the helper functions and is transiently transfected with the polynucleotide of the invention. In another embodiment, the cell line supplies stably the rep and cap proteins and is transfected transiently with the polynucleotide of the invention and a polynucleotide encoding the helper functions. In yet another embodiment, the cell line supplies stably the polynucleotide of the invention, the rep and cap proteins and the helper functions. Methods of making and using these and other AAV production systems have been described in the art. See Muzyczka N, et al., U.S. Pat. No. 5,139,941, Zhou X, et al., U.S. Pat. No. 5,741,683, Samulski R, et al., U.S. Pat. No. 6,057,152, Samulski R, et al., U.S. Pat. No. 6,204,059, Samulski R, et al., U.S. Pat. No. 6,268,213, Rabinowitz J, et al., U.S. Pat. No. 6,491,907, Zolotukhin S, et al., U.S. Pat. No. 6,660,514, Shenk T, et al., U.S. Pat. No. 6,951,753, Snyder R, et al., U.S. Pat. No. 7,094,604, Rabinowitz J, et al., U.S. Pat. No. 7,172,893, Monahan P, et al., U.S. Pat. No. 7,201,898, Samulski R, et al., U.S. Pat. No. 7,229,823, and Ferrari F, et al., U.S. Pat. No. 7,439,065.

The rAAV genome present in a rAAV vector comprises at least the nucleotide sequences of the inverted terminal repeat regions (ITRs) of one of the AAV serotypes (preferably the ones of serotype AAV2 as disclosed earlier herein), or nucleotide sequences substantially identical thereto or nucleotide sequences having at least 60% identity thereto, and nucleotide sequence encoding a FGF21 (under control of a suitable regulatory element) inserted between the two ITRs. A vector genome requires the use of flanking 5' and a 3' ITR sequences to allow for efficient packaging of the vector genome into the rAAV capsid.

The complete genome of several AAV serotypes and corresponding ITR has been sequenced (Chiorini et al. 1999, J. of Virology Vol. 73, No. 2, p 1309-1319). They can be either cloned or made by chemical synthesis as known in the art, using for example an oligonucleotide synthesizer as supplied e.g. by Applied Biosystems Inc. (Fosters, CA, USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the AAV sequence between the ITRs can be replaced with the desired nucleotide sequence.

Preferably, the rAAV genome as present in a rAAV vector does not comprise any nucleotide sequences encoding viral proteins, such as the rep (replication) or cap (capsid) genes of AAV. This rAAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV genome as present in said rAAV vector further comprises a promoter sequence operably linked to the nucleotide sequence encoding a FGF21. Preferred promoter sequences are promoters which confer expression in skeletal muscle cells and/or skeletal muscle, in liver cells and/or liver and in adipose cells and/or adipose tissue. Examples of such promoters include a CMV, a CAG, a mini/aP2, a mini/UCP1, a C5-12 and a hAAT promoter as earlier defined herein.

A suitable 3' untranslated sequence may also be operably linked to the nucleotide sequence encoding a FGF21. Suitable 3' untranslated regions may be those naturally associated with the nucleotide sequence or may be derived from different genes, such as for example the SV40 polyadenylation signal (SEQ ID NO: 50) and the rabbit β-globin polyadenylation signal (SEQ ID NO: 51).

Optionally, additional nucleotide sequences may be operably linked to the nucleotide sequence(s) encoding a FGF21, such as nucleotide sequences encoding signal sequences, nuclear localization signals, expression enhancers, and the like.

Codon Optimization

"Codon optimization", as used herein, refers to the processes employed to modify an existing coding sequence, or to design a coding sequence, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. For example, to suit the codon preference of mammalians, preferably of murine, canine or human expression hosts. Codon optimization also eliminates elements that potentially impact negatively RNA stability and/or translation (e. g. termination sequences, TATA boxes, splice sites, ribosomal entry sites, repetitive and/or GC rich sequences and RNA secondary structures or instability motifs).

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a viral expression construct, viral vector, composition, gene therapy composition, as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

FIGURE LEGENDS

FIGS. 1A-1H. Prevention of obesity by intra-eWAT administration of AAV9-CAG-moFGF21-dmiRT vectors in C57Bl6 mice. (FIG. 1A) Schematic representation of the AAV-CAG-moFGF21-doublemiRT vectors. The expression cassette contained the CAG promoter, a murine codon-optimized FGF21 coding sequence and four tandem repeats of the miRT122a sequence and four tandems repeats of the miRT1 sequence cloned in the 3' untranslated region of the expression cassette. ITRs from AAV2 flanked the expression cassette. The schematic representation is not to scale. CAG: chicken β-actin promoter/CMV enhancer; pA: polyA. (FIG. 1B) Expression levels of FGF21 in metabolic tissues. The expression levels of the murine codon-optimized FGF21 coding sequence were measured by RTqPCR in eWAT, iWAT, iBAT and liver of C57Bl6 mice, and normalized with Rplp0 values (n=8-11 animals/group). (FIG. 1C) Circulating levels of FGF21 (n=8-11 animals/group). (FIGS. 1D-1E) Expression levels of FGF21R1 (FIG. 1D) and β-Klotho (FIG. 1E) in metabolic tissues. The expression levels of the FGF21 receptor 1 (FGF21R1) and β-Klotho were measured by RTqPCR in eWAT, iWAT, iBAT and liver of C57Bl6 mice, and normalized with Rplp0 values (n=7 animals/group). (FIG. 1F) Body weight evolution. Body weight was measured weekly (n=8-11 animals/group). (FIG. 1G) Representative image of animals. (FIG. 1H) Weight of tissues. Weight of eWAT, iWAT, rWAT, mWAT, iBAT and liver of chow- and HFD-fed C57Bl6 mice treated intra-eWAT with AAV vectors (n=8-11 animals/group). Analyses were performed 14 weeks after intra-eWAT administration of $10^{12}$ vg of AAV9-CAG-moFGF21-doublemiRT or AAV9-CAG-null vectors. Results are expressed as the mean±SEM. ND, not detected. HFD, high fat diet. AU, arbitrary units. eWAT, epididymal white adipose tissue. iWAT, inguinal white adipose tissue. rWAT, retroperitoneal white adipose tissue. mWAT, mesenteric white adipose tissue. iBAT interscapular brown adipose tissue. *$p<0.05$ vs AAV9-CAG-null chow, $p<0.01$ vs AAV9-CAG-null chow, *$p<0.001$ vs AAV9-CAG-null chow, \$ $p<0.05$ vs AAV9-CAG-null HFD, \$\$ $p<0.01$ vs AAV9-CAG-null HFD, \$\$\$ $p<0.001$ vs AAV9-CAG-null HFD.

Figure 2A:
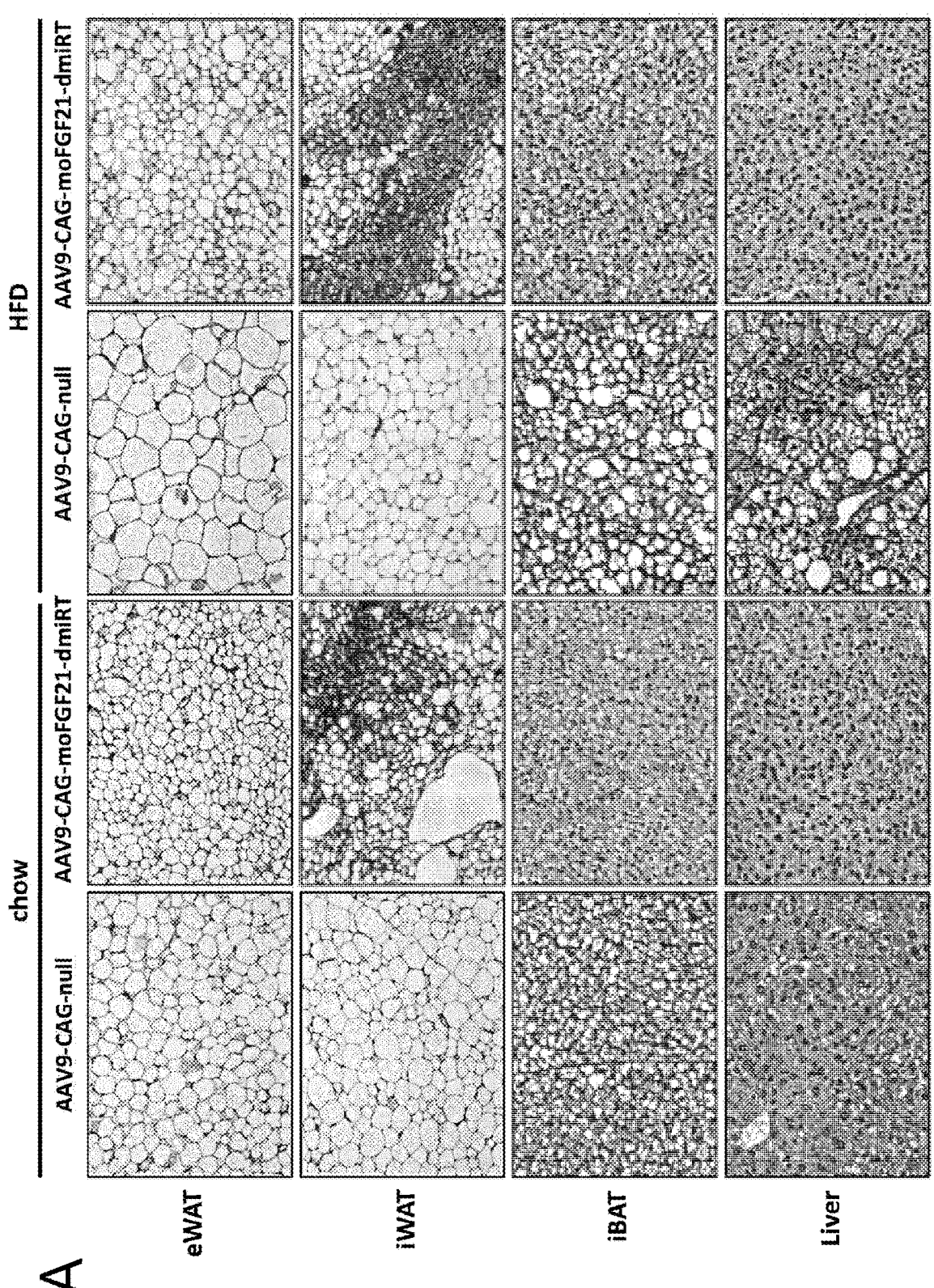
Figures 2B, 2C:
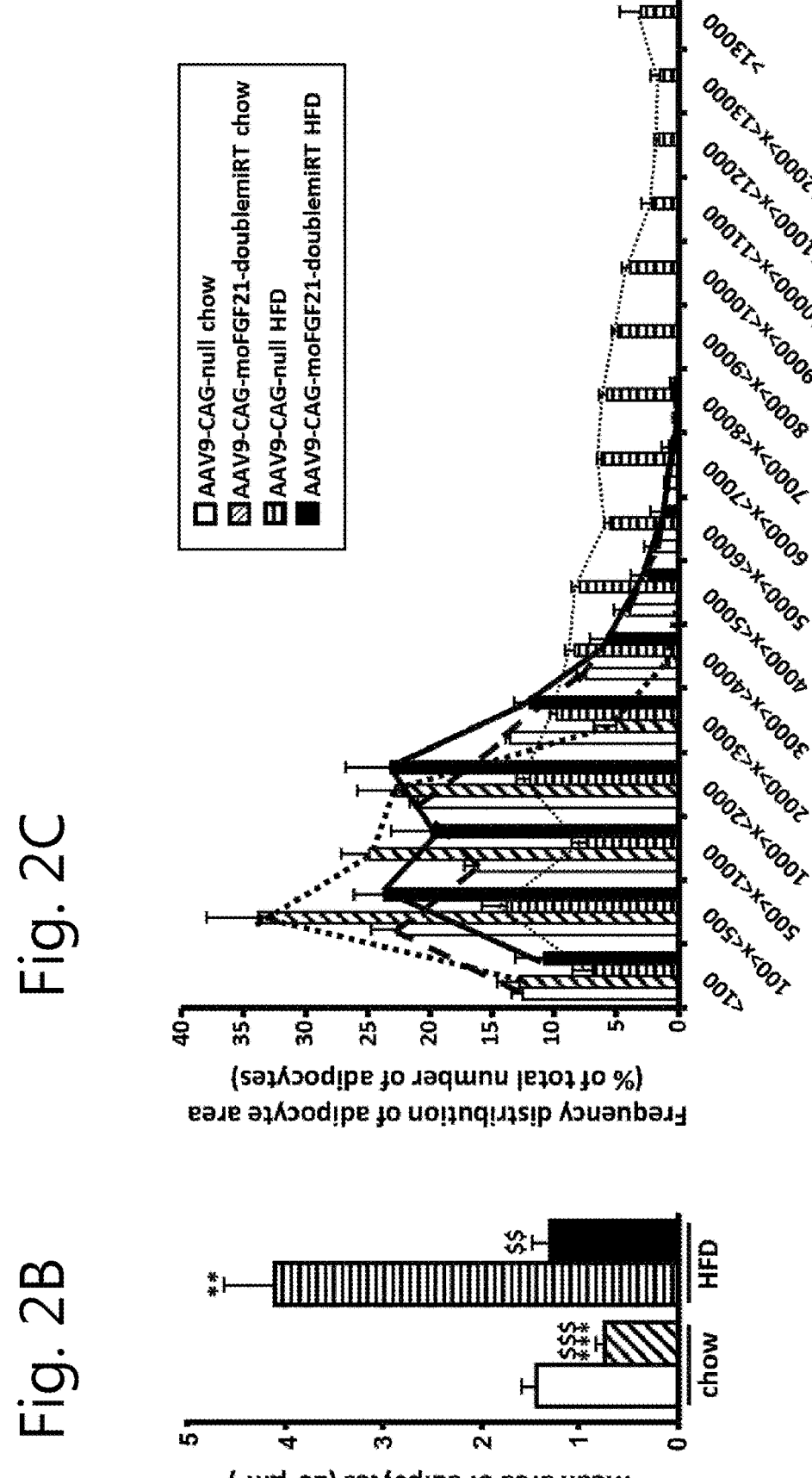

FIGS. 2A-2C. Histological analysis of adipose tissue and liver of C57Bl6 mice treated intra-eWAT with AAV9-CAG-moFGF21-doublemiRT vectors. (FIG. 2A) Representative images of sections stained with hematoxylin and eosin of epididymal white adipose tissue (eWAT), inguinal white adipose tissue (TWAT) interscapular brown adipose tissue (iBAT) and liver of chow- and HFD-fed C57Bl6 mice treated intra-eWAT with AAV9-CAG-moFGF21-doublemiRT or AAV9-CAG-null vectors. Original magnification ×100. (FIG. 2B) Mean area of white adipocytes of eWAT (n=4 animals/group). (FIG. 2C) Frequency distribution of area of white adipocytes of eWAT (n=4 animals/group). Analyses were performed 14 weeks after intra-eWAT administration of $10^{12}$ vg of AAV9-CAG-moFGF21-doublemiRT or AAV9-CAG-null vectors. Results are expressed as the mean±SEM. HFD, high fat diet. $p<0.01$ vs AAV9-CAG-null chow, *$p<0.001$ vs AAV9-CAG-null chow, \$\$ $p<0.01$ vs AAV9-CAG-null HFD, \$\$\$ $p<0.001$ vs AAV9-CAG-null HFD.

Figures 3A, 3B, 3C:
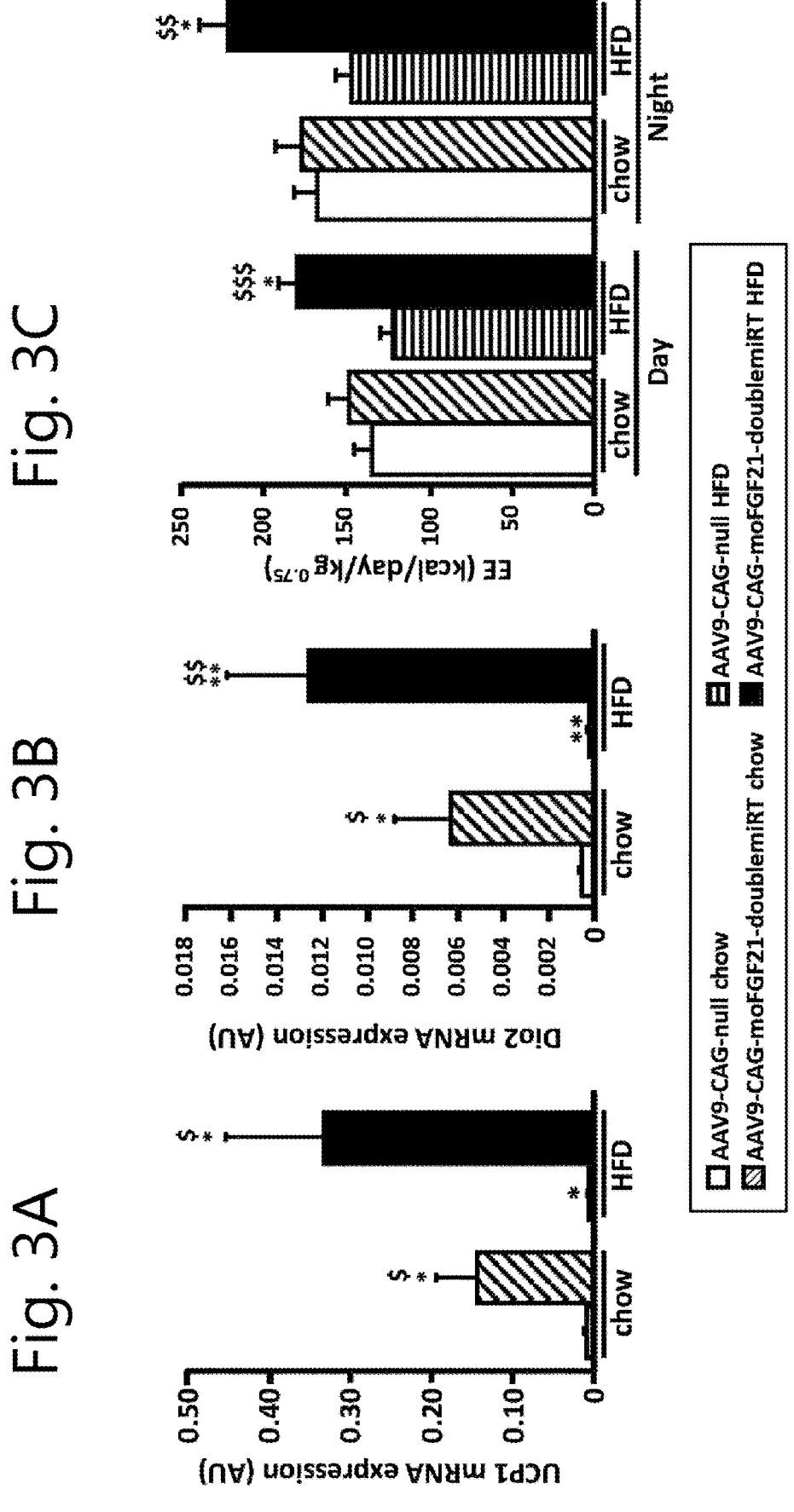

FIGS. 3A-3H. Increased energy expenditure and insulin sensitivity in C57Bl6 mice treated intra-eWAT with AAV9-CAG-moFGF21-doublemiRT vectors. (FIGS. 3A-3B) Expression levels of UCP1 (FIG. 3A) and Dio2 (FIG. 3B). The expression levels of UCP1 and Dio2 were measured by RTqPCR in iWAT and normalized with Rplp0 values (n=7 animals/group). (FIG. 3C) Energy metabolism. The energy expenditure (EE) was measured with indirect open circuit calorimeter. Oxygen consumption and carbon dioxide production were monitored simultaneously. Data were taken 9 weeks post-AAV administration during the light cycle (basal state) and dark cycle (activity phase) and adjusted for body weight (n=8-11 animals/group). (FIG. 3D) Liver triglyceride content (n=8-10 animals/group). (FIGS. 3E-3F) Serum triglyceride (FIG. 3E) and cholesterol (FIG. 3F) levels (n=8-11 animals/group). (FIG. 3G) Intraperitoneal insulin tolerance test. Mice were given an intraperitoneal injection of 0.75 U insulin/kg body weight and blood glucose levels were measured at the indicated time points (n=6-11 animals/group). The test was performed 11 weeks post-AAV administration. (FIG. 3H) Fasted insulin circulating levels. Unless otherwise indicated, analyses were performed 14 weeks after intra-eWAT administration of $10^{12}$ vg of AAV9-CAG-moFGF21-doublemiRT or AAV9-CAG-null vectors. Results are expressed as the mean±SEM. HFD, high fat diet. TG, triglycerides. Chol, cholesterol. *p<0.05 vs AAV9-CAG-null chow, p<0.01 vs AAV9-CAG-null chow, *p<0.001 vs AAV9-CAG-null chow, $ p<0.05 vs AAV9-CAG-null HFD, $$ p<0.01 vs AAV9-CAG-null HFD, $$$ p<0.001 vs AAV9-CAG-null HFD.

FIGS. 4A-4E. Reversion of obesity by intra-eWAT administration of AAV8-CAG-moFGF21-dmiRT vectors in ob/ob mice. (FIG. 4A) Expression levels of FGF21 in metabolic tissues. The expression levels of the murine codon-optimized FGF21 coding sequence were measured by RTqPCR in eWAT, iWAT, iBAT and liver of ob/ob mice, and normalized with Rplp0 values (FIG. 4B) Circulating levels of FGF21. (FIGS. 4C-4D) Body weight (FIG. 4C) and body weight gain (FIG. 4D) evolution. Body weight was measured weekly. (FIG. 4E) Weight of tissues. Weight of eWAT, iWAT, rWAT, mWAT, iBAT and liver of ob/ob mice treated intra-eWAT with AAV vectors. Analyses were performed 16 weeks after intra-eWAT administration of $10^{10}$ vg, $5\times10^{10}$ vg, $2\times10^{11}$ vg or $10^{12}$ vg of AAV8-CAG-moFGF21-doublemiRT or $10^{12}$ vg of AAV8-CAG-null vectors. Results are expressed as the mean±SEM. n=7-8 animals/group. ND, not detected. AU, arbitrary units. eWAT, epididymal white adipose tissue. iWAT, inguinal white adipose tissue. rWAT, retroperitoneal white adipose tissue. mWAT, mesenteric white adipose tissue. iBAT interscapular brown adipose tissue. *p<0.05 vs AAV8-CAG-null, p<0.01 vs AAV8-CAG-null, *p<0.001 vs AAV8-CAG-null.

Figures 5A, 5B:
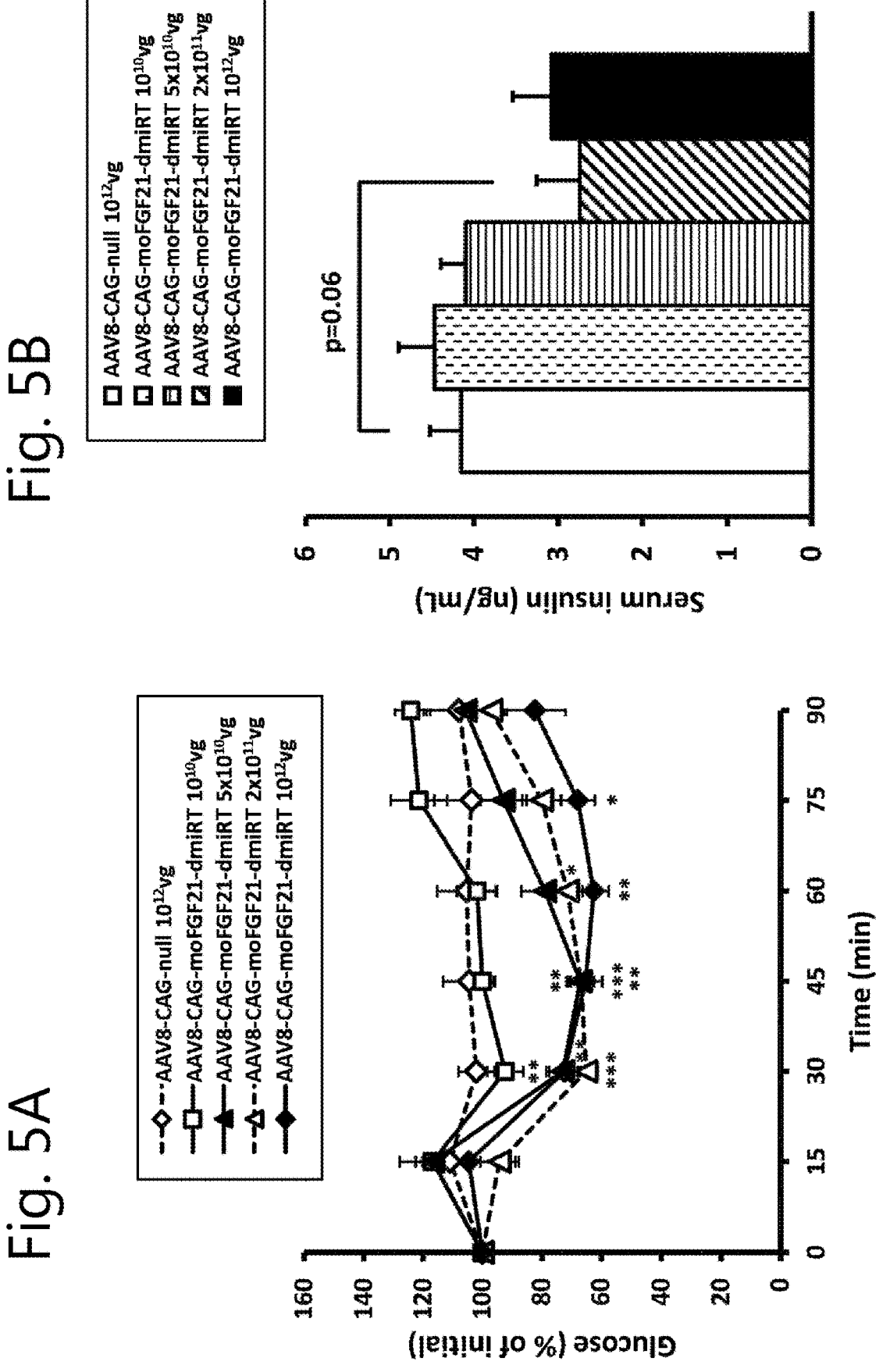

FIGS. 5A-5B. Improved insulin sensitivity in ob/ob mice treated intra-eWAT with AAV8-CAG-moFGF21-doublemiRT vectors. (FIG. 5A) Intraperitoneal insulin tolerance test. Ob/ob mice were given an intraperitoneal injection of 0.75 U insulin/kg body weight and blood glucose levels were measured at the indicated time points. The test was performed 9 weeks post-AAV administration. (FIG. 5B) Fasted insulin circulating levels 2 months post-AAV. Results are expressed as the mean±SEM, n=7-8 animals/group. *p<0.05 vs AAV8-CAG-null, p<0.01 vs AAV8-CAG-null, *p<0.001 vs AAV8-CAG-null.

FIGS. 6A-6I. Reversion of obesity and amelioration of glucose metabolism by intravenous administration of AAV8-hAAT-moFGF21-vectors in ob/ob mice. (FIG. 6A) Schematic representation of AAV8-hAAT-moFGF21 vectors. The expression cassette contained the human a1-antitrypsin (hAAT) promoter and a murine codon-optimized FGF21 coding sequence. ITRs from AAV2 flanked the expression cassette. The schematic representation is not to scale. pA: polyA. (FIG. 6B) Expression levels of FGF21. The expression levels of the murine codon-optimized FGF21 coding sequence were measured by RTqPCR in the liver of ob/ob mice, and normalized with Rplp0 values. (FIG. 6C) Circulating levels of FGF21. (FIGS. 6D-6E) Body weight (FIG. 6C) and body weight gain (FIG. 6D) evolution. Body weight was measured weekly. (FIG. 6F) Representative image of animals. (FIG. 6G) Weight of tissues. Weight of eWAT, iWAT, rWAT, mWAT, iBAT and liver of ob/ob mice treated intravenously with AAV vectors. (FIG. 6H) Intraperitoneal insulin tolerance test. Ob/ob mice were given an intraperitoneal injection of 0.75 U insulin/kg body weight and blood glucose levels were measured at the indicated time points. The test was performed 9 weeks post-AAV administration. (FIG. 6I) Fasted insulin circulating levels 3 months post-AAV. Unless otherwise indicated, analyses were performed 20 weeks after intravenous administration of $10^{11}$ vg or $5\times10^{11}$ vg of AAV8-hAAT-moFGF21 or $5\times10^{11}$ vg of AAV8-hAAT-null vectors. Results are expressed as the mean±SEM. n=9-10 animals/group. ND, not detected. AU, arbitrary units. eWAT, epididymal white adipose tissue. iWAT, inguinal white adipose tissue. rWAT, retroperitoneal white adipose tissue. mWAT, mesenteric white adipose tissue. iBAT interscapular brown adipose tissue. *p<0.05 vs AAV8-hAAT-null, p<0.01 vs AAV8-hAAT-null, *p<0.001 vs AAV8-hAAT-null.

Figure 7A:
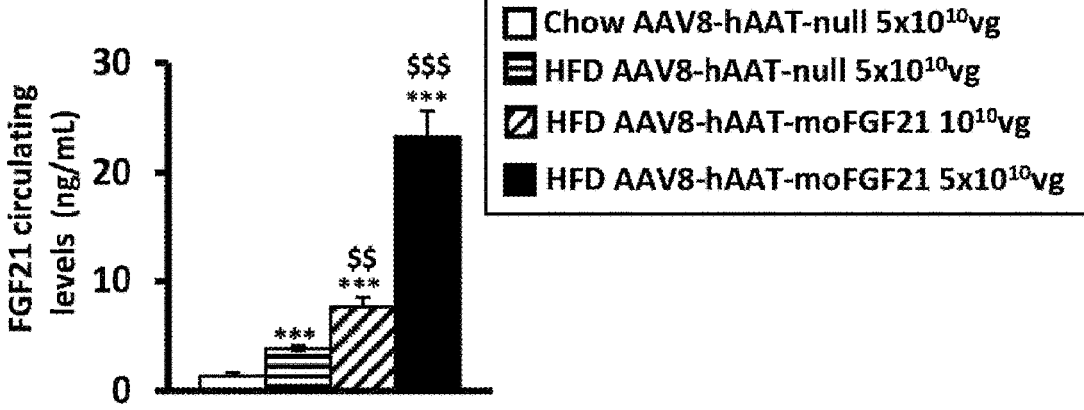
Figure 7B:
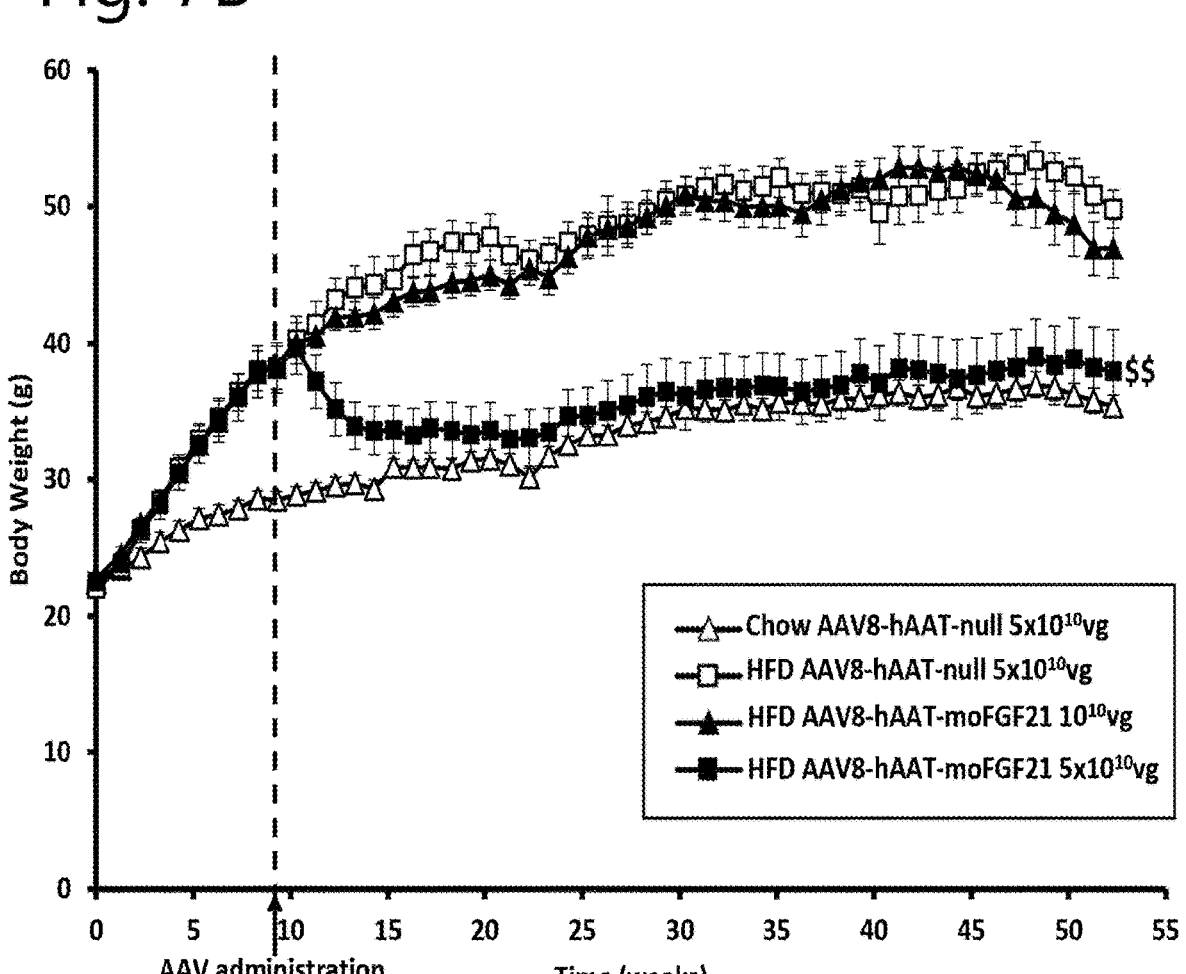
Figure 7C:
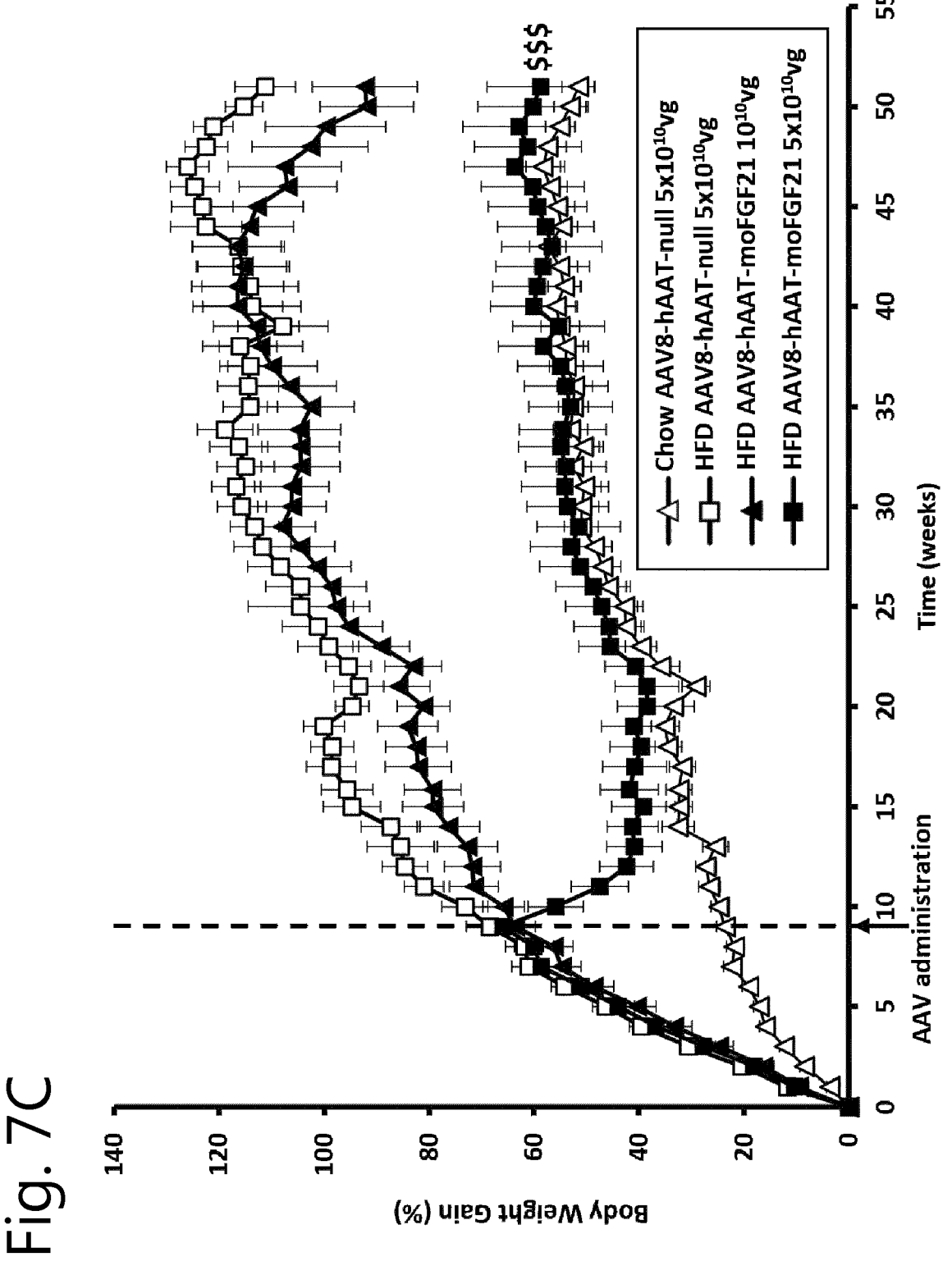

FIGS. 7A-7C. Long-term reversion of obesity by intravenous administration of AAV-hAAT-moFGF21 vectors in HFD-fed C57b16 mice. (FIG. 7A) Circulating levels of FGF21. (FIGS. 7B-7C) Body weight (FIG. 7B) and body weight gain (FIG. 7C) evolution. Body weight was measured weekly. Analyses were performed 52 weeks after intravenous administration of $10^{10}$ vg or $5\times10^{10}$ vg of AAV8-hAAT-moFGF21 or $5\times10^{10}$ vg of AAV8-hAAT-null vectors. Results are expressed as the mean±SEM, n=9-12 animals/group. ***p<0.001 vs AAV8-hAAT-null chow, $$ p<0.01 vs AAV8-hAAT-null HFD, $$$ p<0.001 vs AAV8-hAAT-null HFD.

Figure 8A:
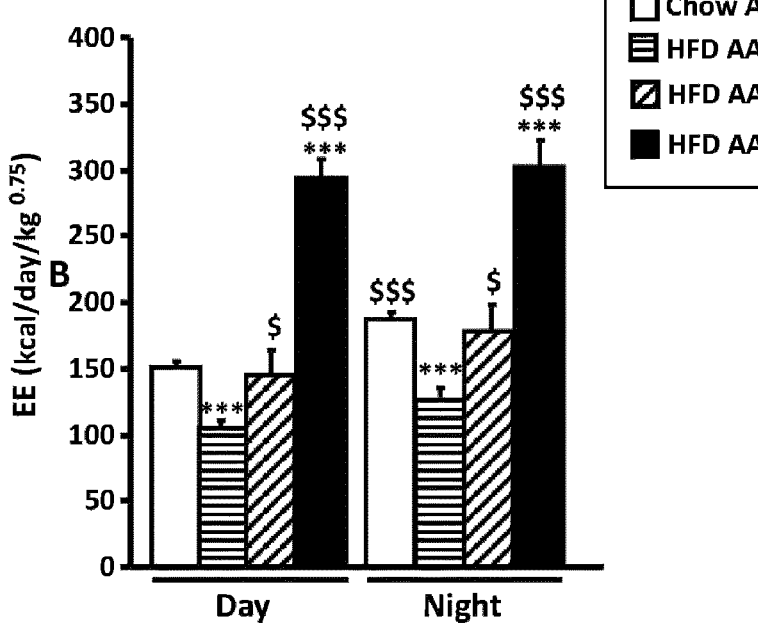
Figures 8B, 8C:
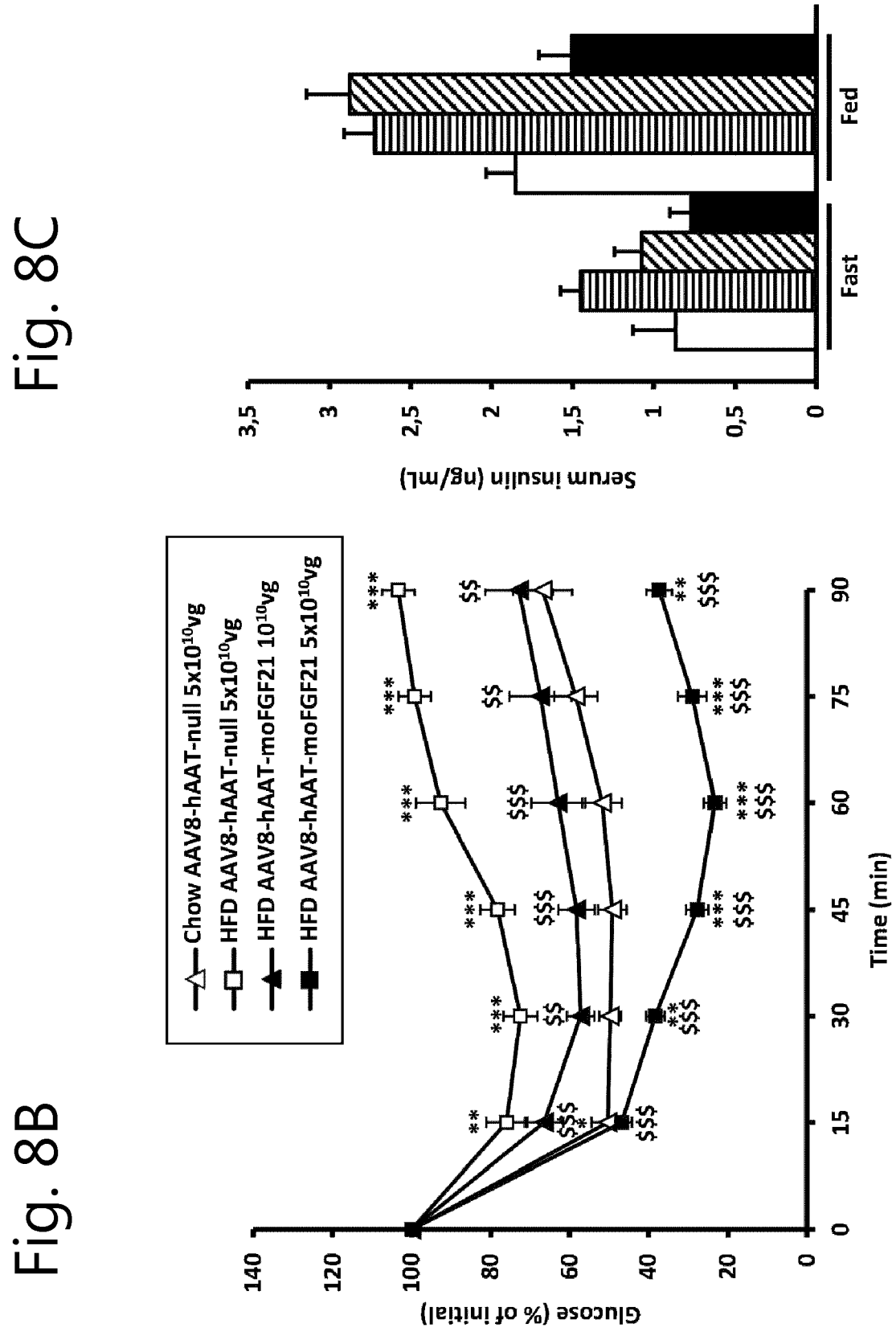

FIGS. 8A-8C. Long-term increased energy expenditure and insulin sensitivity by intravenous administration of AAV-hAAT-moFGF21 vectors in HFD-fed C57Bl6 mice. (FIG. 8A) Energy metabolism. The energy expenditure (EE) was measured with indirect open circuit calorimeter. Oxygen consumption and carbon dioxide production were monitored simultaneously. Data were taken 4 weeks post-AAV administration during the light cycle (basal state) and dark cycle (activity phase) and adjusted for body weight. (FIG. 8B) Intraperitoneal insulin tolerance test. C57Bl6 mice were given an intraperitoneal injection of 0.75 U insulin/kg body weight and blood glucose levels were measured at the indicated time points. The test was performed 7 weeks post-AAV administration. (FIG. 8C) Fasted and fed insulin circulating levels. Results are expressed as the mean±SEM, n=9-12 animals/group. HFD, high fat diet. *p<0.05 vs AAV8-hAAT-null chow, p<0.01 vs AAV8-hAAT-null chow, *p<0.001 vs AAV8-hAAT-null chow, $ p<0.05 vs AAV8-hAAT-null HFD, $$ p<0.01 vs AAV8-hAAT-null HFD, $$$ p<0.001 vs AAV8-hAAT-null HFD.

Figure 9A:
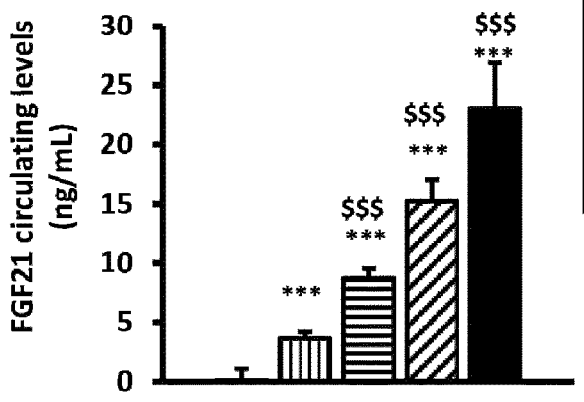
Figure 9B:
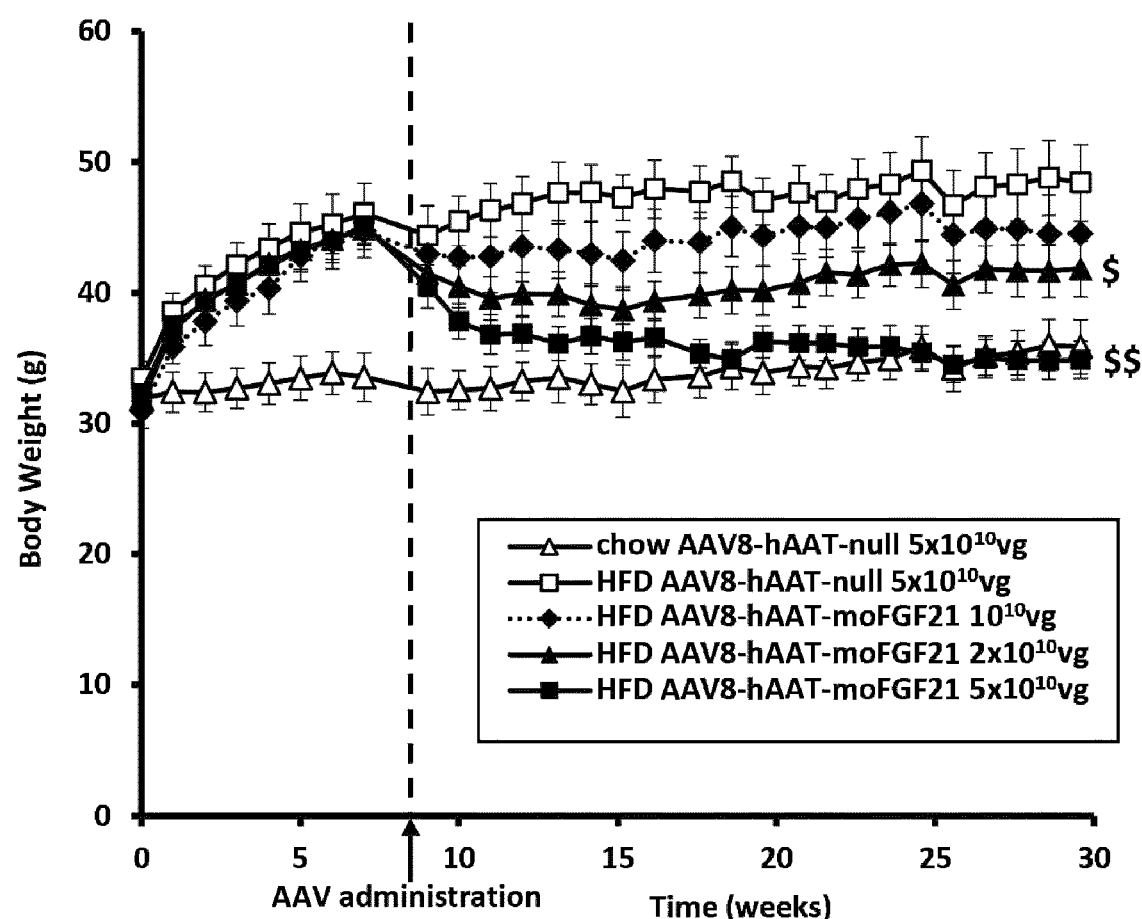
Figure 9C:
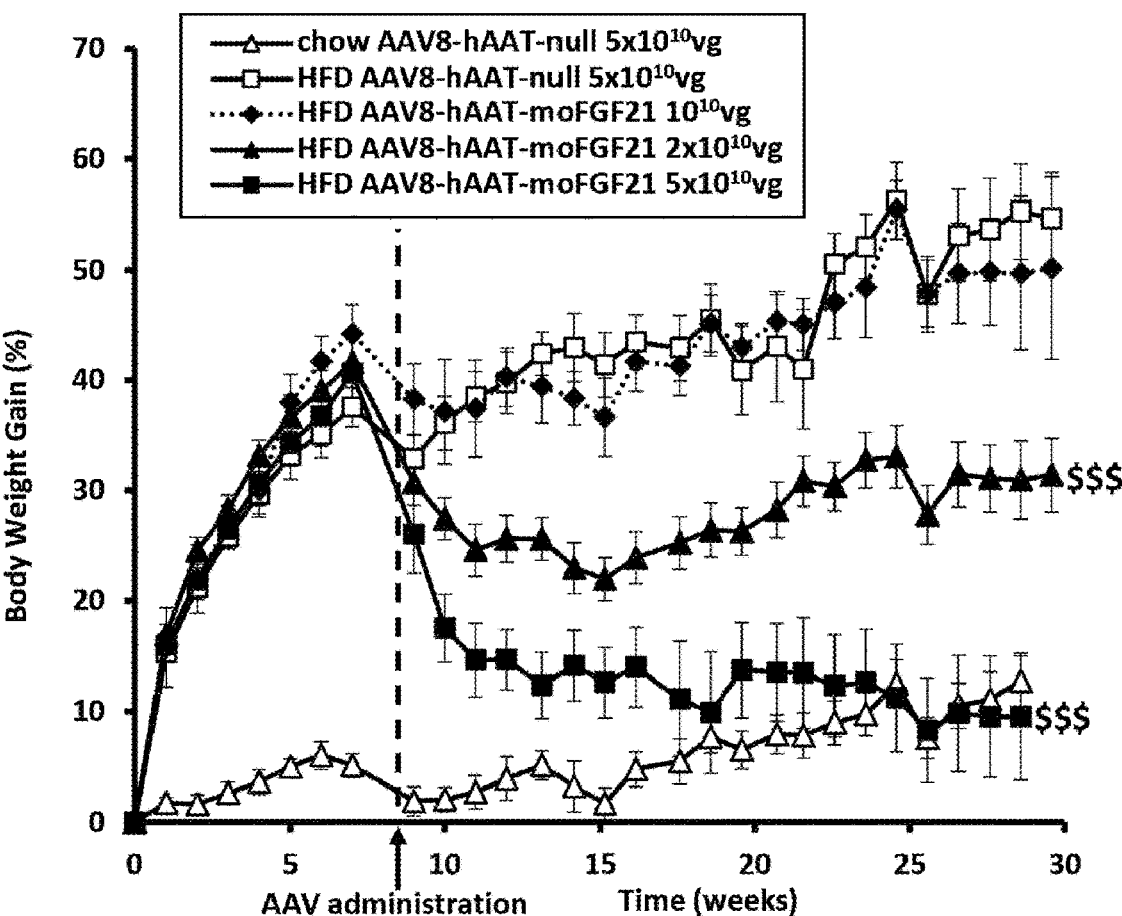

FIGS. 9A-9C. Reversion of obesity by intravenous administration of AAV-hAAT-moFGF21 vectors in old HFD-fed mice. (FIG. 9A) Circulating levels of FGF21. (FIGS. 9B-9C) Body weight (FIG. 9B) and body weight gain (FIG. 9C) evolution. Body weight was measured weekly. Analysis were performed 21 weeks after intravenous administration of $10^{10}$ vg, $2\times10^{10}$ vg or $5\times10^{10}$ vg of AAV8-hAAT-moFGF21 or $5\times10^{10}$ vg of AAV8-hAAT-null vectors. Results are expressed as the mean±SEM, n=7-8 animals/group. HFD, high fat diet. ***p<0.05 vs AAV8-hAAT-null chow, $ p<0.05 vs AAV8-hAAT-null HFD, $$ p<0.01 vs AAV8-hAAT-null HFD. $$$ p<0.001 vs AAV8-hAAT-null HFD.

Figure 10A:
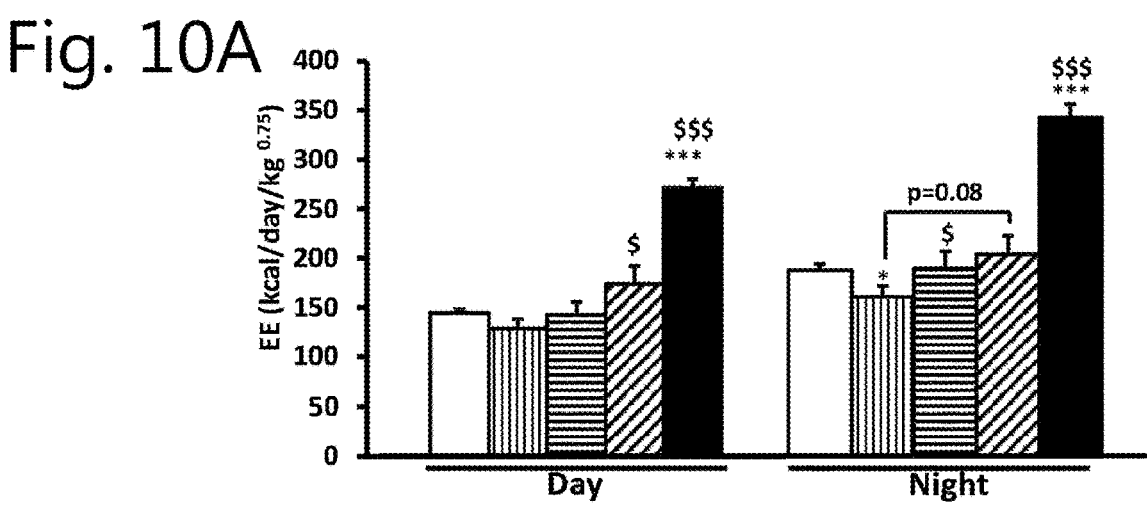
Figures 10B, 10C:
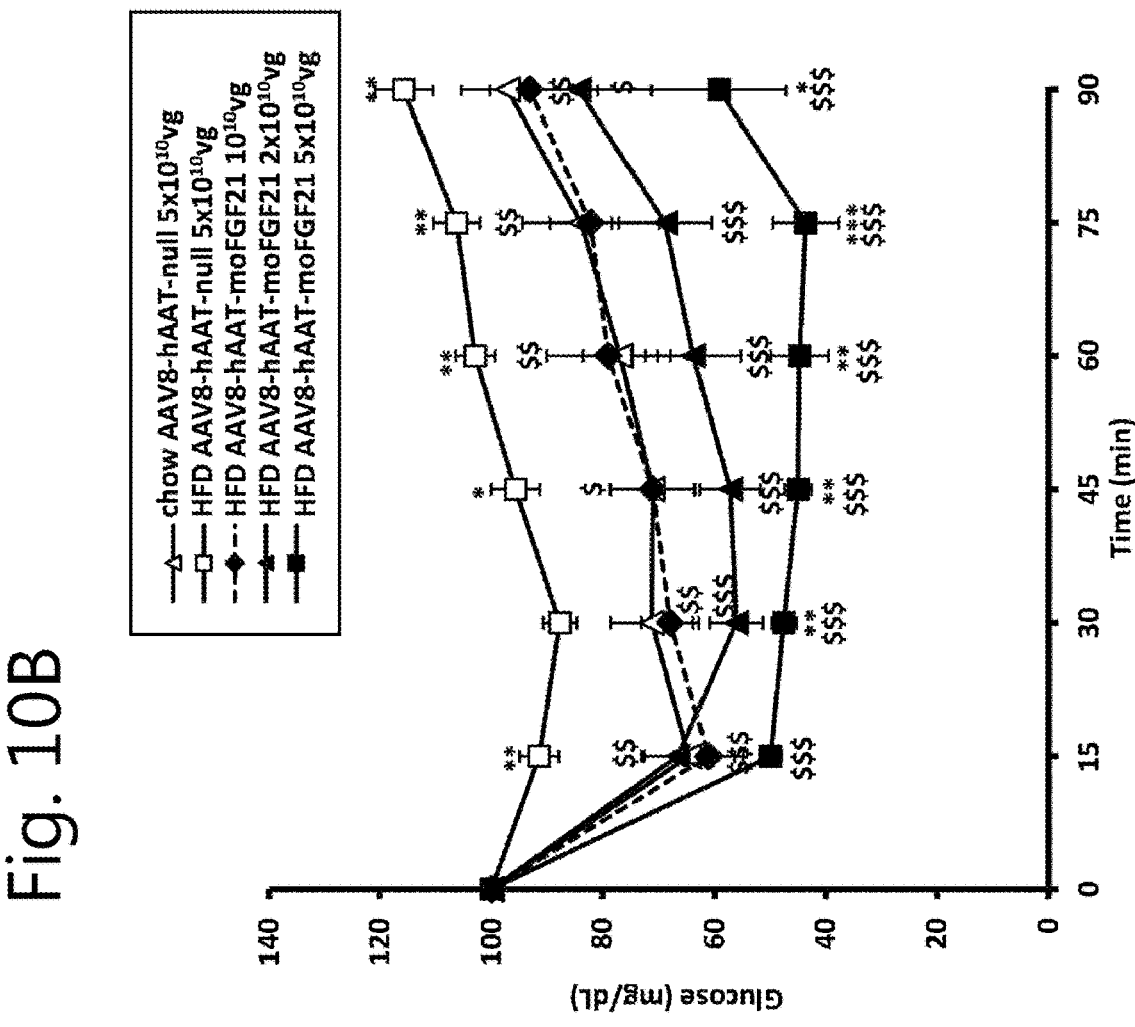

FIGS. 10A-10C. Increased energy expenditure and insulin sensitivity by intravenous administration of AAV-hAAT-moFGF21 vectors in old HFD-fed mice. (FIG. 10A) Energy metabolism. The energy expenditure (EE) was measured with indirect open circuit calorimeter. Oxygen consumption and carbon dioxide production were monitored simultaneously. Data were taken 6 weeks post-AAV administration during the light cycle (basal state) and dark cycle (activity phase) and adjusted for body weight. (FIG. 10B) Intraperitoneal insulin tolerance test. Old C57Bl6 mice were given an intraperitoneal injection of 0.75 U insulin/kg body weight and blood glucose levels were measured at the indicated time points. The test was performed 9 weeks post-AAV administration. (FIG. 10C) Fasted and fed insulin circulating levels. Results are expressed as the mean±SEM, n=7-8 animals/group. HFD, high fat diet. p<0.01 vs AAV8-hAAT-null chow, *p<0.001 vs AAV8-hAAT-null chow, $ p<0.05 vs AAV8-hAAT-null HFD, $$ p<0.01 vs AAV8-hAAT-null HFD, $$$ p<0.001 vs AAV8-hAAT-null HFD.

FIGS. 11A-11D. Body weight loss by intramuscular administration of AAV-CMV-moFGF21 vectors in C57Bl6 mice. (FIG. 11A) Schematic representation of the AAV-CMV-moFGF21 vectors. The expression cassette contained the cytomegalovirus (CMV) promoter and a murine codon-optimized FGF21 coding sequence. ITRs from AAV2 flanked the expression cassette. The schematic representation is not to scale. pA: polyA. (FIG. 11B) Circulating FGF21 levels. (FIGS. 11C-11D) Body weight (FIG. 11C) and body weight gain (FIG. 11D) evolution. Body weight was measured weekly. Results are expressed as the mean±SEM. n=6-7 animals/group. *p<0.05 vs AAV1-CMV-null, **p<0.01 vs AAV1-CMV-null. FGF21 labels in the figure refer to moFGF21 in accordance with this Figure legend.

Figure 12:
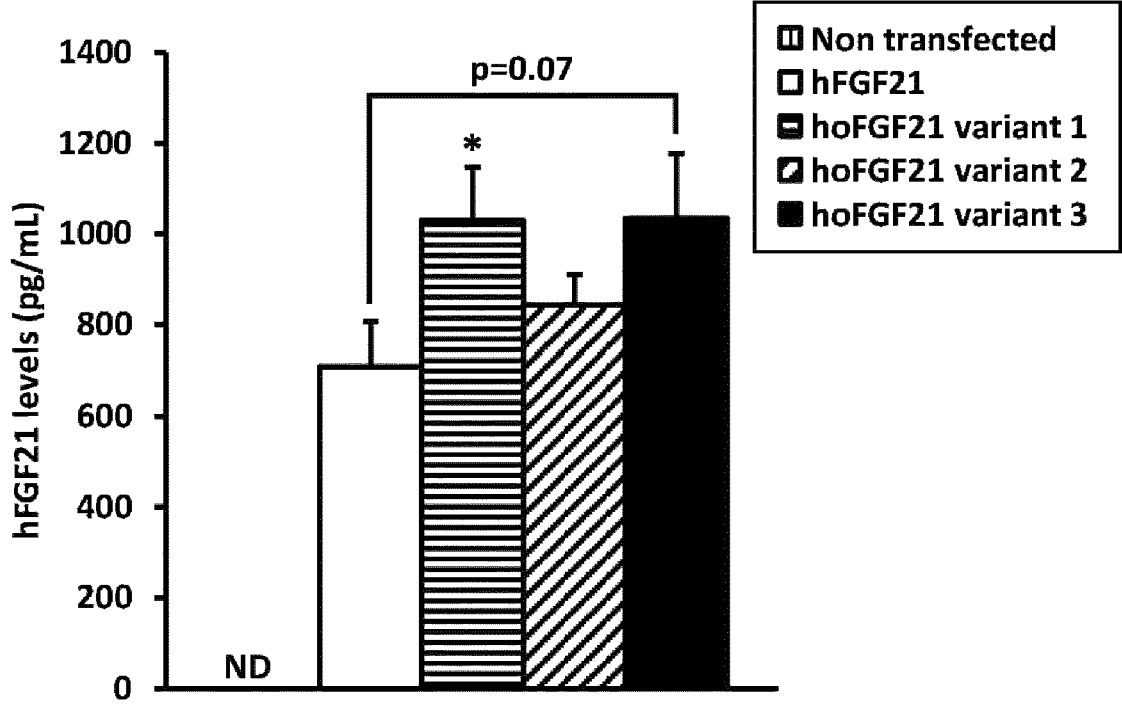

FIG. 12. Increased FGF21 protein production by codon-optimization of nucleotide sequences encoding human FGF21. (A) Levels of hFGF21 protein in the culture media of BEK293 cells transfected with wild-type hFGF21 or three different versions of codon-optimized human FGF21 sequences. Results are expressed as the mean±SEM. n=3 wells/group. ND, non detected. *p<0.05 vs Non-transfected cells.

FIGS. 13A-13D. Intra-eWAT administration of AAV8-CAG-moFGF21-dmiRT vectors in ob/ob mice.

Figure 13A:
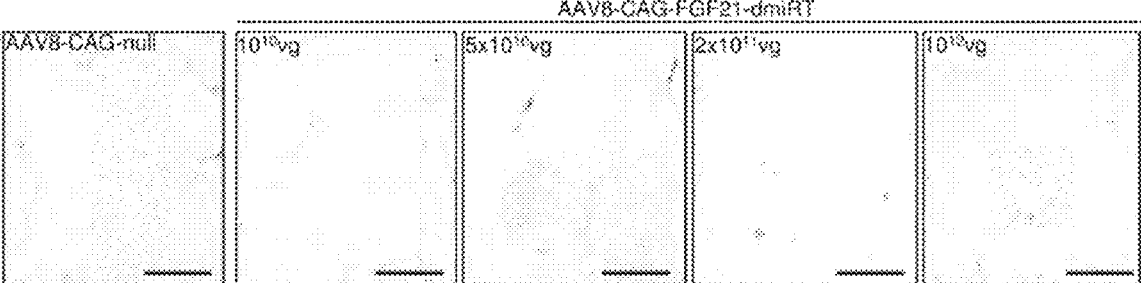
Figure 13B:
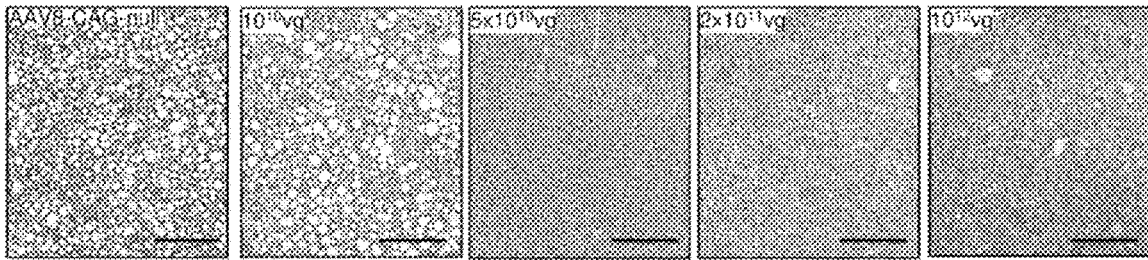

FIGS. 13A, 13B Representative images of the hematoxylin-eosin staining of (FIG. 13A) eWAT and (FIG. 13B) liver tissue sections obtained from ob/ob animals injected intra-eWAT either null or FGF21-encoding AAV8 vectors at all doses tested. Scale bars: 100 μm for eWAT and 200 μm for liver.

Figure 13C:
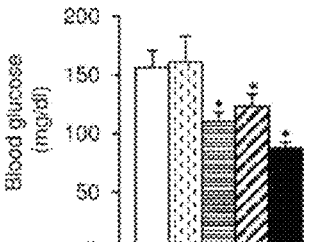

FIG. 13C Glycemia in the fed state.

Figure 13D:
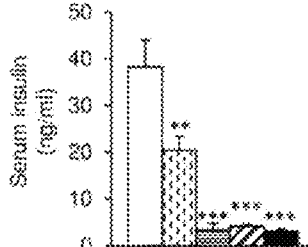

FIG. 13D Insulinemia in the fed state 3 months post-AAV. FGF21 labels in the figure refer to moFGF21.

Data information: All values are expressed as mean±SEM. In (FIGS. 13A, 13B) n=6-9 animals/group. In (FIGS. 13C-13D) n=4-8 animals/group. In (I) n=6-8 animals/group. *P<0.05, P<0.01 and *P<0.001 versus the Null-injected group.

FIGS. 14A-14F. Impact of FGF21 gene transfer to the eWAT of ob/ob mice.

FIG. 14A Serum adiponectin levels in 25-week-old ob/ob animals injected intra-eWAT at 11 weeks of age with either AAV8-CAG-null vectors or AAV8-CAG-moFGF21-dmiRT vectors at 4 different doses ($1\times10^{10}$, $5\times10^{10}$, $2\times10^{11}$, $1\times10^{12}$ vg/mouse).

FIG. 14B Quantification by qRT-PCR of the expression of the macrophage marker F4/80 the same groups of animals as in (FIG. 14A).

FIG. 14C Representative images of the immunostaining of eWAT sections from ob/ob mice that received AAV8-CAG-moFGF21-dmiRT vectors for the macrophage-specific marker Mac2. n=4-8/group. Scale bars: 200 μm.

FIG. 14D Weight of the liver in all intra-eWAT treatment groups.

FIGS. 14E, 14F Hepatic triglyceride and cholesterol content in the fed stated in the same cohorts as in (FIG. 14A)

FGF21 labels in the figure refer to moFGF21 in accordance with this Figure legend. Data information: All values are expressed as mean±SEM. In (FIGS. 14A, 14B, 14D) n=4-8 animals/group. *P<0.05, <001 and *P<0.001 versus null-injected ob/ob group.

FIGS. 15A-15E. Reduced obesity and improved insulin sensitivity in ob/ob mice treated with AAV8-hAAT-moFGF21 vectors.

FIG. 15A Representative images of the hematoxylin-eosin staining of eWAT tissue sections obtained from ob/ob animals injected with either null or FGF21-encoding AAV vectors at $1\times10^{11}$ or $5\times10^{11}$ vg/mouse.

FIG. 15B Serum adiponectin levels in all groups.

FIG. 15C Representative images of the hematoxylin-eosin staining of liver tissue sections obtained from ob/ob animals injected with either null or FGF21-encoding AAV vectors at $1\times10^{11}$ or $5\times10^{11}$ vg/mouse.

FIG. 15D Fed blood glucose levels.

FIG. 15E Fed serum Insulin levels 5 months post-AAV.

FGF21 labels in the figure refer to moFGF21 in accordance with this Figure legend. Data information: All data represent the mean±SEM. In (FIGS. 15A-15C, 15E) n=9-10 animals/group. *P<0.05, P<001 and *P<0.001 versus null-injected ob/ob group.

FIGS. 16A-16G. Effects of FGF21 liver gene transfer on ob/ob mice.

FIG. 16A Immunohistochemistry for the macrophage-specific marker Mac2 in eWAT sections from ob/ob mice that received AAV8-hAAT-moFGF21 vectors. Scale bars: 500 μm.

FIGS. 16B, 16C Quantification by qRT-PCR of the expression of the markers of inflammation F4/80 (FIG. 16B) and TNF-α (FIG. 16C) in the same cohorts of mice.

FIGS. 16D, 16E Weight (FIG. 16D) and representative images of the liver (FIG. 16E) obtained from animals belonging to the same experimental groups as in (FIG. 16A).

FIGS. 16F, 16G Hepatic triglyceride and cholesterol content in the fed state in the same cohorts as in (FIG. 16A)

FGF21 labels in the figure refer to moFGF21 in accordance with this Figure legend.

Data information: All values are expressed as mean±SEM. In (FIGS. 16B, 16D-16F) n=9-10 animals/group. *P<0.05, <001 and *P<0.001 versus null-injected ob/ob group.

FIGS. 17A-17G. AAV8-hAAT-moFGF21 treatment increases the expression of genes involved in glucose uptake and thermogenesis in adipose tissue of ob/ob mice.

Figure 17A:
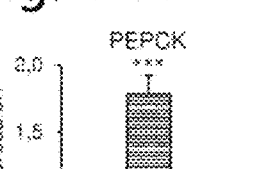
Figure 17B:
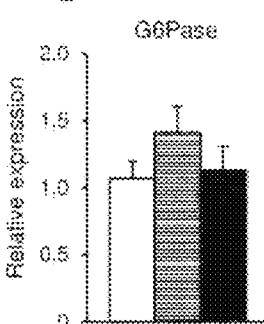
Figure 17C:
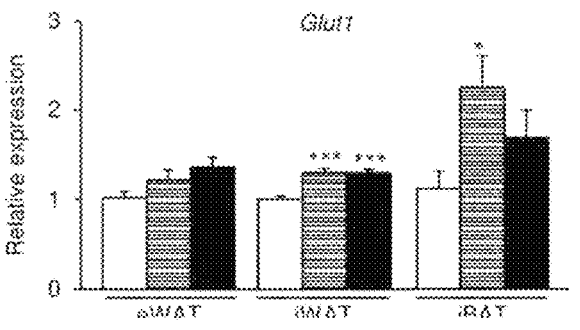

FIGS. 17A, 17B Quantification by qRT-PCR of liver PEPCK and G6Pase expression in ob/ob mice injected at 2 months of age with either AAV8-hAAT-null vectors or AAV8-hAAT-moFGF21 vectors.

FIGS. 17C-17F Quantification by qRT-PCR of GLUT1 (FIG. 17C), GLUT4 (FIG. 17D), HKI (FIG. 17E) and HKII (FIG. 17F) expression in eWAT, TWAT and iBAT in the same animals as in (FIG. 17A)

Figure 17D:
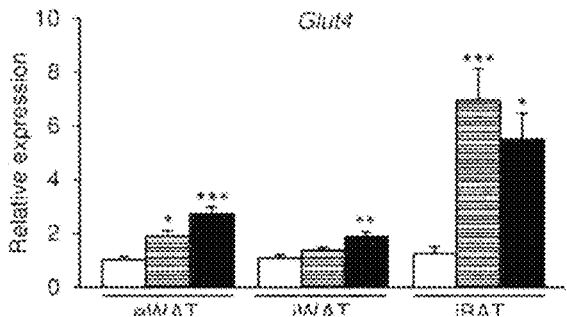
Figure 17E:
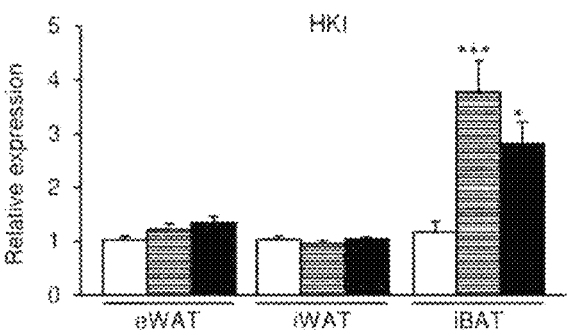
Figure 17F:
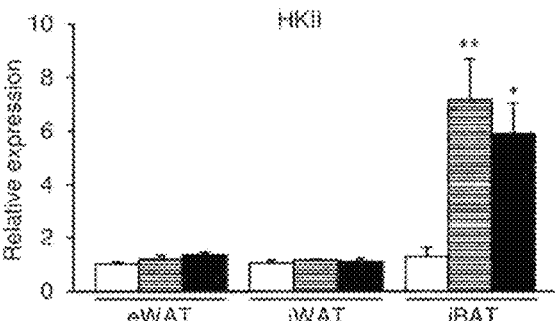
Figure 17G:
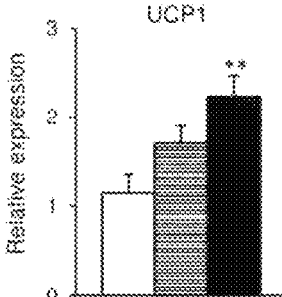

FIG. 17G Relative expression of UCP1 in iBAT in the same cohorts as in (FIG. 17A).

FGF21 labels in the figure refer to moFGF21 in accordance with this Figure legend.

Data information: All values are expressed as mean±SEM. In (FIGS. 17A-17G) n=9-10 animals/group. *P<0.05, P<001 and *P<0.001 versus null-injected ob/ob group.

Figure 18A:
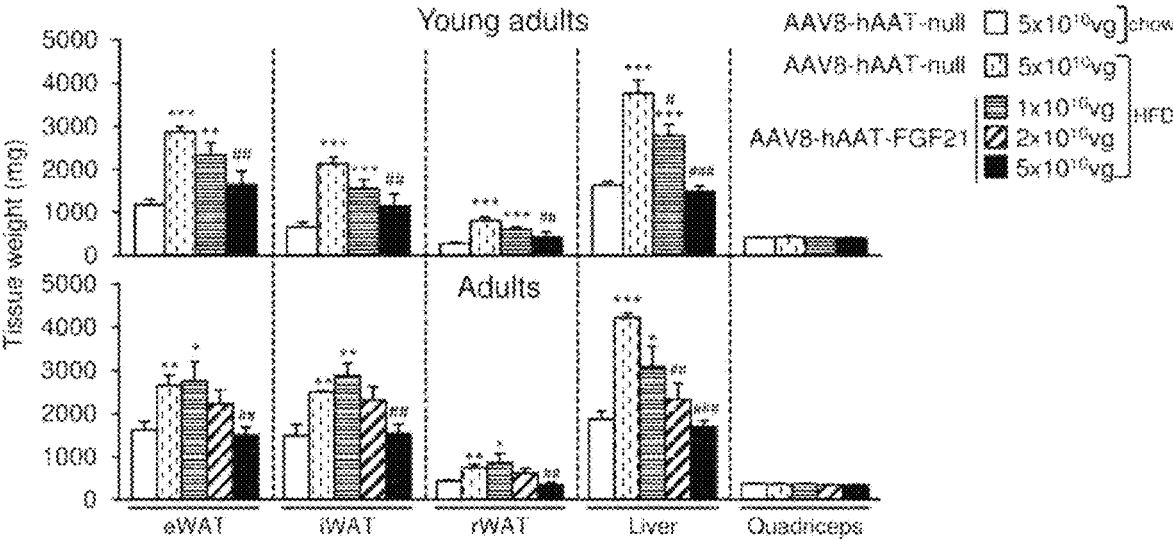
Figure 18B:
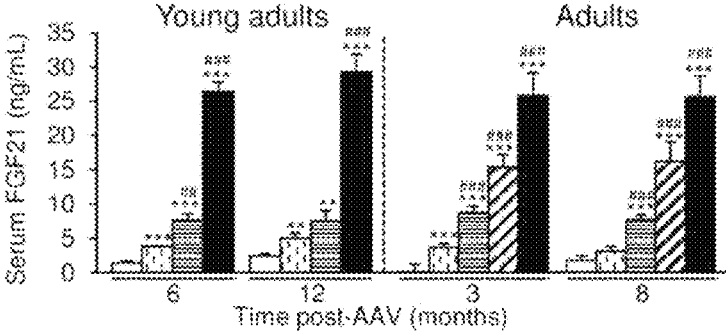

FIGS. 18A-18B. AAV8-mediated liver gene transfer of FGF21 counteracts HFD-induced obesity.

FIG. 18A Weight of the epididymal (eWAT), inguinal (iWAT) and retroperitoneal (rWAT) white adipose tissue depots, the liver and the quadriceps obtained from mice treated with AAV8-hAAT-moFGF21 vectors as young adults (top panel) or as adults (bottom panel).

FIG. 18B Circulating levels of FGF21 at different time-points after vector administration.

FGF21 labels in the figure refer to moFGF21 in accordance with this Figure legend.

Data information: All values are expressed as mean±SEM. In (FIGS. 18A-18B) n=7-10 animals/group. *P<0.05, P<0.01 and *P<0.001 versus the chow-fed Null-injected group. #P<0.05, ##P<0.01 and ####P<0.001 versus the HFD-fed Null-injected group. HFD, High-fat diet.

FIGS. 19A-19E. FGF21 gene transfer to the liver counteracts HFD-induced obesity.

FIGS. 19A, 19B Representative images of animals belonging to all experimental groups of the studies performed in young adults (FIG. 19A) or in adults (FIG. 19B).

FIG. 19C Representative images of the epididymal white adipose (eWAT) pad obtained at sacrifice from animals treated with several doses of AAV8-hAAT-moFGF21 as young adults (left) or adults (right).

FIG. 19D Representative images of the liver obtained from animals treated as young adults (left) or adults (right).

FIG. 19E AAV-derived FGF21 expression in the liver of animals treated as young adults or adults. The qPCR was performed with primers that specifically detected the codon-optimized murine FGF21 (coFGF21) coding sequence.

FGF21 labels in the figure refer to moFGF21 in accordance with this Figure legend.

Data information: All values are expressed as mean±SEM. In (FIG. 19E) n=7-10 animals/group. HFD, High-fat diet. ND, non-detected.

FIGS. 20A-20E. AAV8-hAAT-moFGF21-mediated increased energy expenditure and decreased fat accumulation in iBAT and TWAT.

Figure 20A:
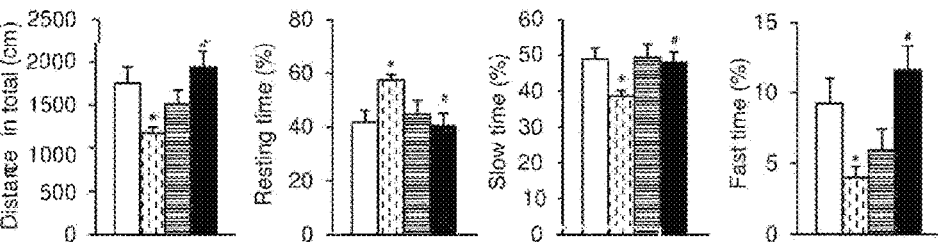

FIG. 20A Assessment of the locomotor activity through the Open field test in animals that had been subjected to HFD-feeding since ~2 months of age and were treated with either null or FGF21-encoding vectors 2 months later (young adults).

Figure 20B:
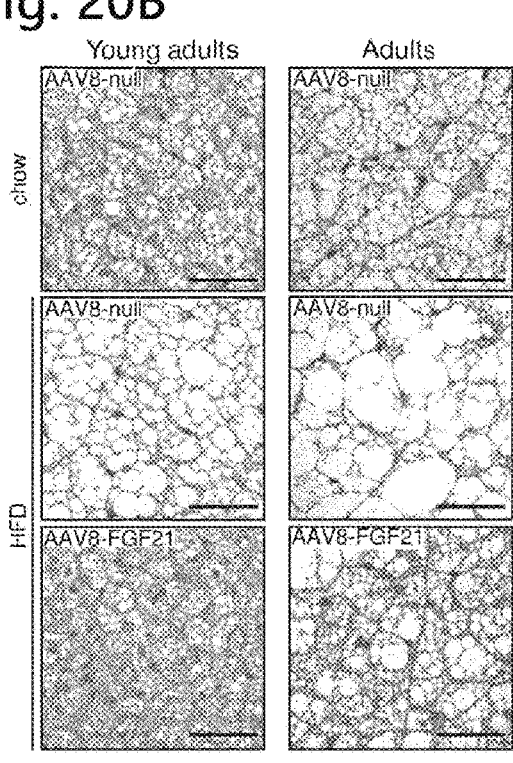

FIG. 20B Hematoxylin-eosin staining of iBAT tissue sections obtained from animals treated as young adults (left) or adults (right).

Figure 20D:
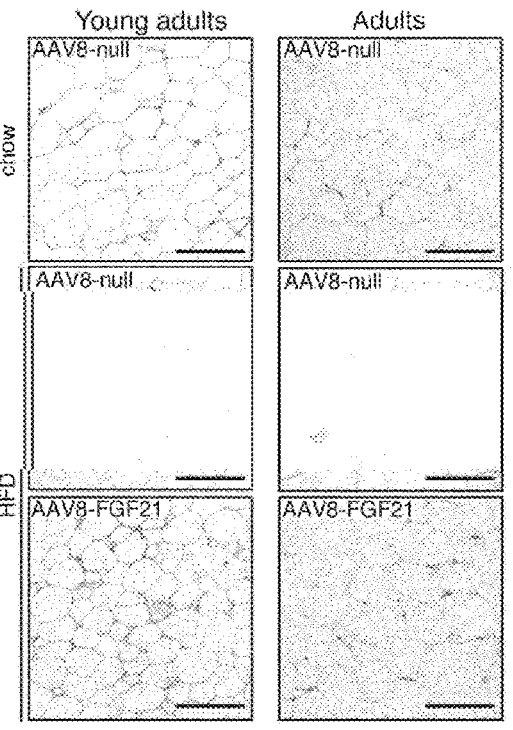
Figure 20C:
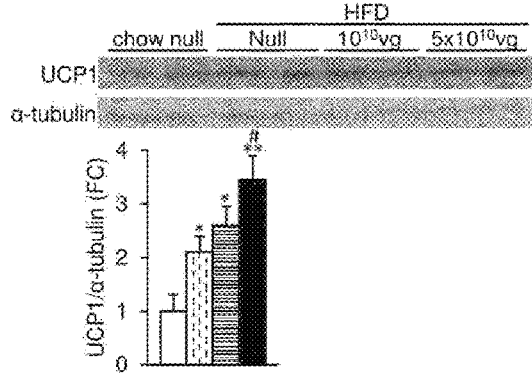

FIG. 20C Western-blot analysis of UCP1 content in iBAT from the same cohort of animals as in (FIG. 20A). A representative immunoblot is shown (left). The histogram depicts the densitometric analysis of two different immunoblots (right).

FIG. 20D Hematoxylin-eosin staining of TWAT tissue sections obtained from animals treated as young adults (left) or adults (right).

Figure 20E:
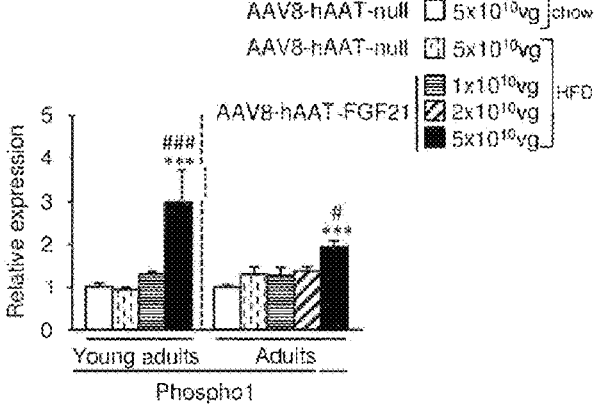

FIG. 20E Quantification by qRT-PCR of the expression of Phosphol in TWAT in the groups of animals that initiated the HFD feeding and received FGF21 vectors as young adults or adults.

FGF21 labels in the figure refer to moFGF21 in accordance with this Figure legend.

Data information: All values are expressed as mean±SEM. In (FIGS. 20A-20C) n=7-10 animals/group. In (FIG. 20E) n=4 animals/group. In (G) n=7-10 animals/group. *P<0.05, P<001 and *P<0.001 versus the chow-fed Null-injected group. #P<0.05 and ####P<0.001 versus the HFD-fed Null-injected group. HFD, High-fat diet.

FIGS. 21A-21C. Energy expenditure 10 months after gene transfer to the liver.

FIG. 21A Energy expenditure was measured 10 months after AAV8-hAAT-null or AAV8-hAAT-moFGF21 vector delivery in the cohort of animals that initiated HFD-feeding at 2 months of age. Data were taken during the light and dark cycles.

FIG. 21B Western-blot analysis of UCP1 content in TWAT from the same cohort of animals. A representative immunoblot is shown (left). The graph shows the densitometric analysis of two different immunoblots (right).

FIG. 21C Relative expression of Serca2b and RyR2 in the TWAT of the groups of animals that initiated the HFD feeding and received FGF21 vectors as young adults or adults FGF21 labels in the figure refer to moFGF21 in accordance with this Figure legend.

Data information: All values are expressed as mean±SEM. In (FIG. 21A) n=7-10 animals/group. In (FIG. 21B) n=4 animals/group. In (FIG. 21C) n=7-10 animals/group. *P<0.05, P<0.01 and *P<0.001 versus the chow-fed Null-injected group. ####P<0.001 versus the HFD-fed Null-injected group. HFD, High-fat diet.

FIGS. 22A-22D. AAV8-hAAT-moFGF21-mediated reversal of islet hyperplasia.

FIG. 22A Fasted glucagon levels in the group of animals that initiated the HFD feeding and received FGF21 vectors as young adults.

FIG. 22B β-cell mass in the group of animals that initiated the HFD feeding and received FGF21 vectors as adults.

FIG. 22C Representative images of the immunostaining against insulin in pancreas sections from animals that received 5×10^10 vg/mouse of AAV8-hAAT-moFGF21 as adults. Scale bars: 400 μm. Inset scale bars: 100 μm.

FIG. 22D Representative images of the double immunostaining against insulin (dark grey) and glucagon (light grey) in pancreas sections from animals that received 5×10^10 vg/mouse of AAV8-hAAT-moFGF21 as young adults (upper panel) or adults (lower panel). Scale bars: 100 μm.

FGF21 labels in the figure refer to moFGF21 in accordance with this Figure legend.

Data information: All values are expressed as mean±SEM. In (FIGS. 22A-22C) n=7-10 animals/group. In (FIG. 22D) n=4-5 animals/group. *P<0.05, P<001 and *P<0.001 versus the chow-fed Null-injected group. #P<0.05, ##P<0.01 and ####P<0.001 versus the HFD-fed Null-injected group. HFD, High-fat diet.

Figures 23A, 23B:
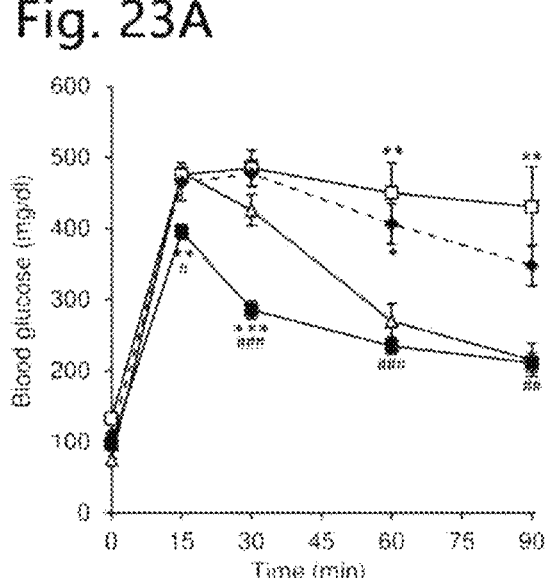

FIGS. 23A-23B. Treatment with AAV8-hAAT-moFGF21 improves glucose tolerance.

FIG. 23A Glucose tolerance was studied in the group of mice that initiated the HFD feeding and received FGF21 vectors as young adults after an intraperitoneal injection of glucose (2 g/kg body weight).

FIG. 23B Serum insulin levels during the glucose tolerance test shown in (FIG. 23A).

Data information: All data represent the mean mean±SEM. In (FIGS. 23A-23B) n=7-10 animals/group. *P<0.05, P<0.01 and *P<0.001 versus the chow-fed Null-injected group. #P<0.05, ##P<0.01 and ####P<0.001 versus the HFD-fed Null-injected group. HFD, High-fat diet.

FIGS. 24A-24H. Reversal of WAT hypertrophy and inflammation by AAV8-hAAT-moFGF21 treatment.

FIG. 24A Representative images of the hematoxylin-eosin staining of the eWAT from animals fed a chow or a HFD and administered with either AAV8-hAAT-null or 5×10^10 vg/mouse AAV8-hAAT-moFGF21 vectors as young adults (left panels) or adults (right panels). While HFD-fed, null-injected mice had larger adipocytes, HFD-fed, FGF21-treated animals had adipocytes of reduced size. Scale bars: 100 μm.

FIG. 24B Morphometric analysis of the area of WAT adipocytes in animals treated as young adults or as adults.

FIGS. 24C, 24D Circulating levels of adiponectin (FIG. 24C) and leptin (FIG. 24D).

FIG. 24E Immunohistochemistry for the macrophage-specific marker Mac2 in eWAT sections from animals that received 5×10^10 vg/mouse AAV8-hAAT-moFGF21 as adults. The micrographs illustrate the presence of crown-like structures (arrows and inset) in the eWAT of HFD-fed, null-injected animals but no in the eWAT of HFD-fed, FGF21-treated mice. Scale bars: 200 μm and 50 μm (inset).

FIGS. 24F-24H Quantification by qRT-PCR of the expression of the markers of inflammation F4/80 (FIG. 24F), IL 1-β (FIG. 24G) and TNF-α (FIG. 24H) in the group of animals that initiated the HFD feeding and received FGF21 vectors as adults.

FGF21 labels in the figure refer to moFGF21 in accordance with this Figure legend.

Data information: All values are expressed as mean±SEM. In (FIG. 24B) n=4 animals/group. In (FIGS. 24F-24H) n=7-10 animals/group. *P<0.05, P<0.01 and *P<0.001 versus the chow-fed Null-injected group. #P<0.05, ##P<0.01 and ###P<0.001 versus the HFD-fed Null-injected group. HFD, High-fat diet.

FIGS. 25A-25E. Adipocyte size and inflammation in AAV8-hAAT-moFGF21-treated animals.

FIG. 25A Frequency distribution of adipocyte area in the groups of animals that initiated the chow or HFD feeding and received either AAV8-hAAT-null or 5×10^10 vg/mouse AAV8-hAAT-moFGF21 vectors as young adults (top graph) or adults (bottom graph).

FIG. 25B Mac2 immunohistochemistry in eWAT of animals in which the study was initiated as young adults. The crown-like structures formed by infiltrating macrophages in the eWAT of HFD-fed, null-injected mice are indicated by arrows. Scale bars: 200 μm and 50 μm (inset).

FIGS. 25C-25E Relative expression by qRT-PCR of the markers of inflammation F4/80, CD68 and TNF-α in the same cohort of animals as in (FIG. 25B).

FGF21 labels in the figure refer to moFGF21 in accordance with this Figure legend.

Data information: All values are expressed as mean±SEM. In (FIG. 25A) n=4 animals/group. In (FIGS. 25C-25E) n=7-10 animals/group. ***P<0.001 versus the chow-fed Null-injected group. ###P<0.001 versus the HFD-fed Null-injected group. HFD, High-fat diet.

FIGS. 26A-26D. Treatment with FGF21-encoding vectors reverses hepatic steatosis and inflammation.

Figure 26A:
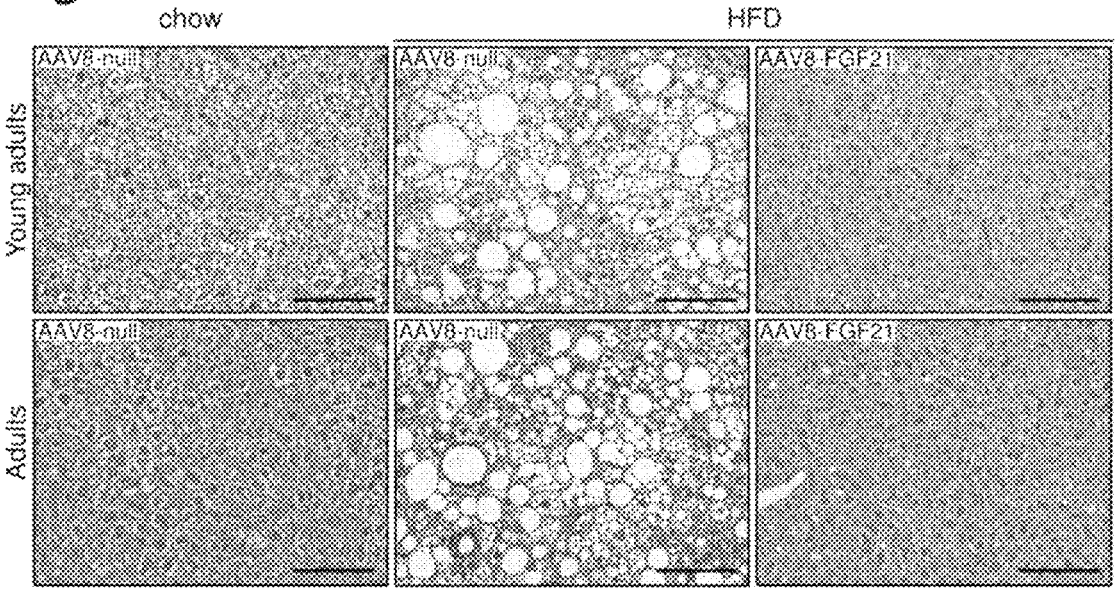

FIG. 26A Representative images of the hematoxylin-eosin staining of liver sections obtained from animals fed a chow or a HFD and administered with either AAV8-hAAT-null or 5×10^10 vg/mouse AAV8-hAAT-moFGF21 vectors. HFD clearly induced the deposition of lipid droplets in the liver, and this was reverted by AAV8-hAAT-moFGF21 treatment both in young adults and in adults. Scale bars: 100 μm.

Figures 26B, 26C:
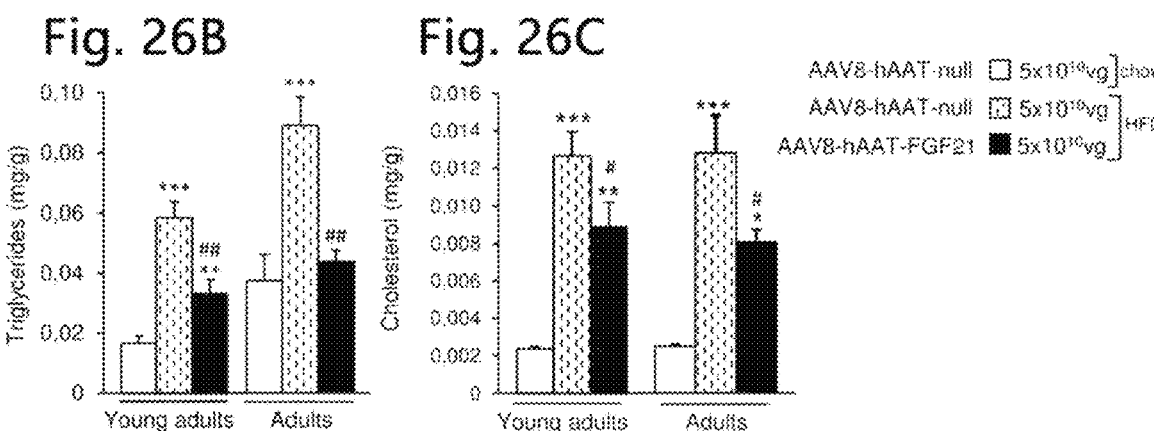

FIGS. 26B, 26C Fed hepatic triglyceride and cholesterol content in the same cohorts of animals.

Figure 26D:
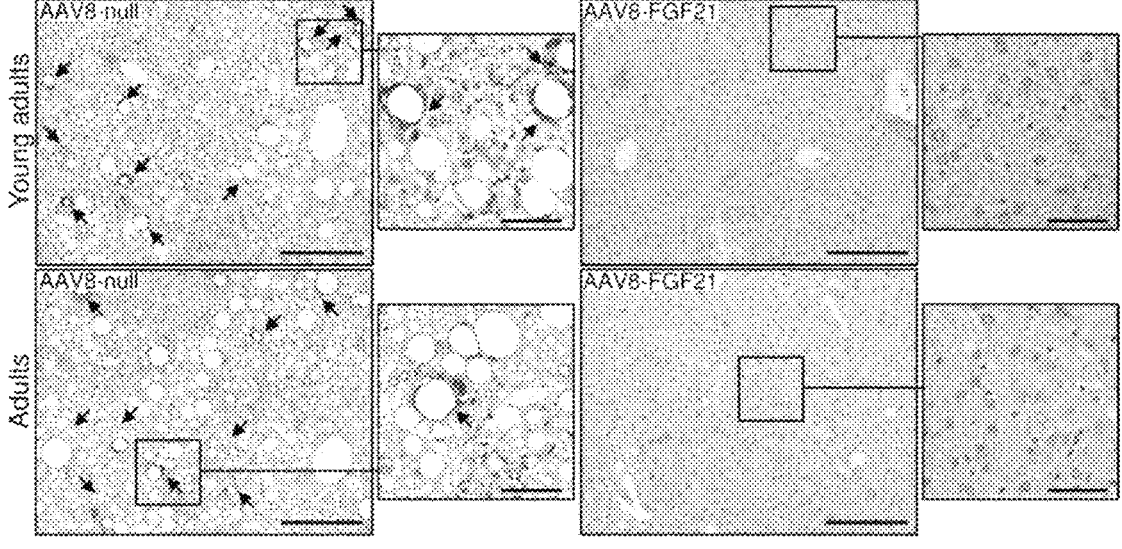

FIG. 26D Immunostaining for the macrophage-specific marker Mac-2 of liver sections from animals fed a HFD that received either AAV8-hAAT-null or 5×10^10 vg/mouse AAV8-hAAT-moFGF21 vectors. Arrows indicate the presence of crown-like structures. Scale bars: 200 μm and 50 μm (inset).

FGF21 labels in the figure refer to moFGF21 in accordance with this Figure legend.

Data information: All values are expressed as mean±SEM. In (FIGS. 26B-26C) n=7-10 animals/group. P<001 and *P<0.001 versus the chow-fed Null-injected group. ##P<0.01 versus the HFD-fed Null-injected group. HFD, High-fat diet.

Figure 27:
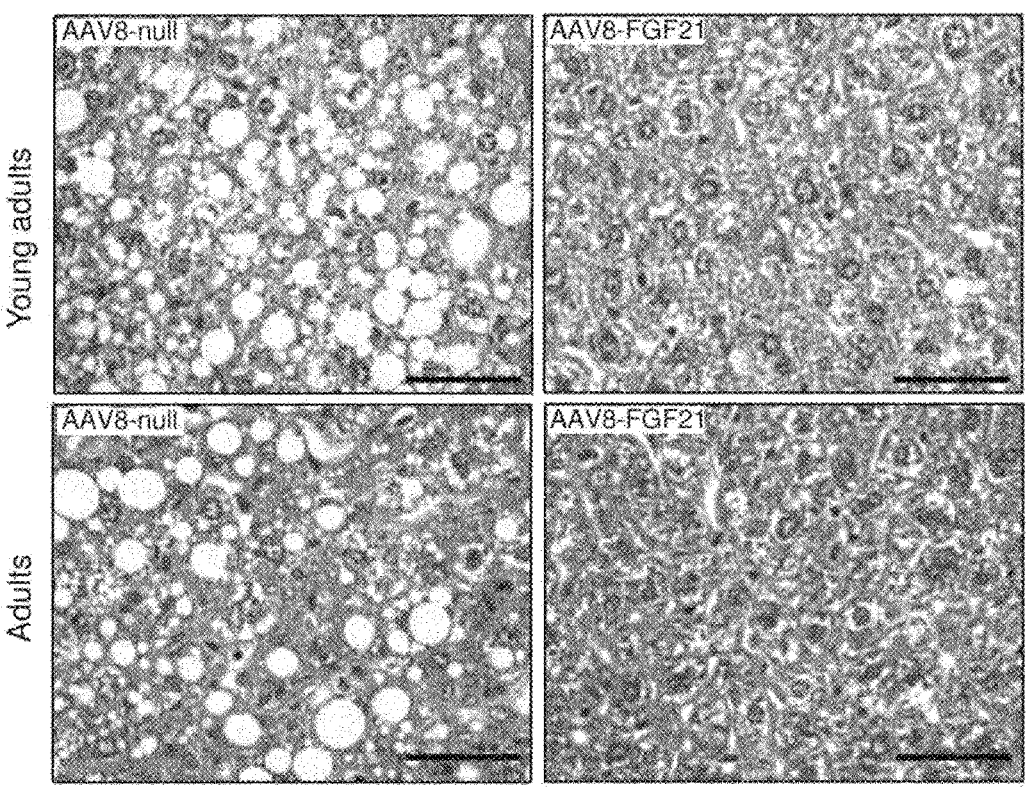

FIG. 27. AAV8-hAAT-moFGF21-mediated amelioration of liver fibrosis.

Analysis of hepatic fibrosis through Masson's trichrome staining in animals fed a HFD that received 5×10^10 vg/mouse of either AAV8-hAAT-null or AAV8-hAAT-moFGF21 vectors. AAV8-hAAT-moFGF21 treatment (right panels) markedly decreased the detection of collagen fibers that were readily detectable (in blue) in animals treated with the null vector (left panels). Scale bars: 50 μm. FGF21 labels in the figure refer to moFGF21 in accordance with this Figure legend.

Figure 28A:
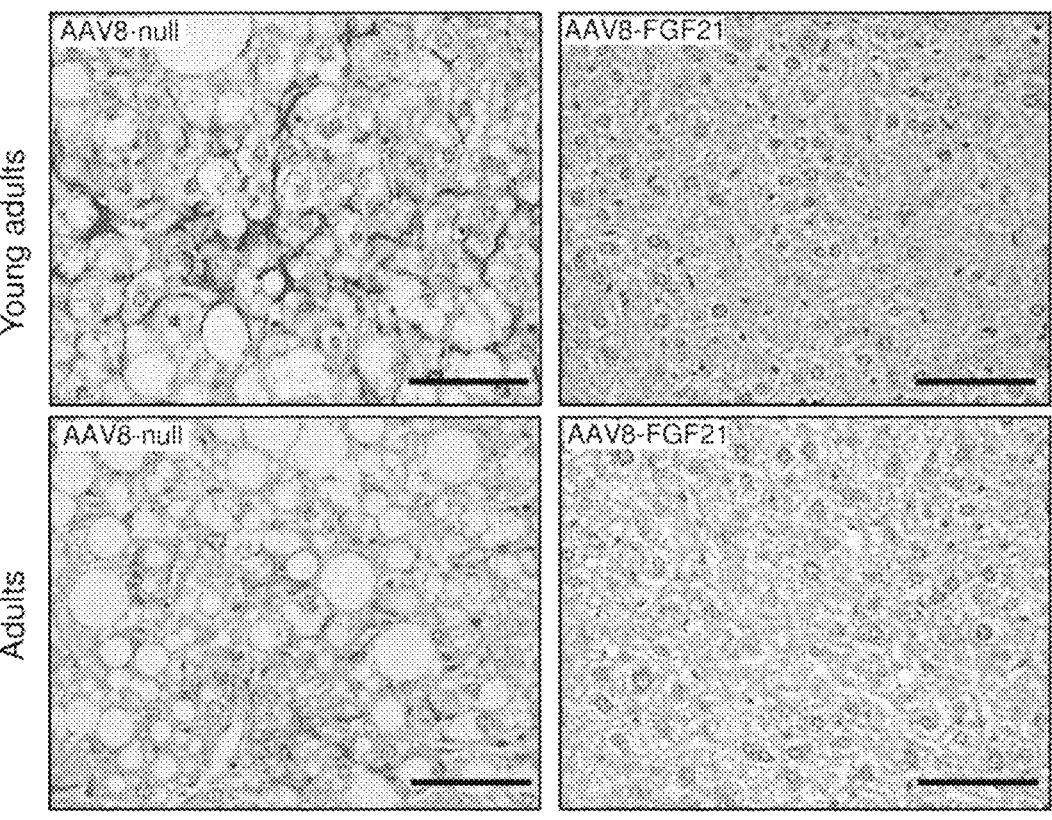

FIGS. 28A-28C. AAV8-hAAT-moFGF21 treatment improves liver fibrosis.

FIG. 28A Analysis of hepatic fibrosis through PicroSirius staining in animals fed a HFD that received 5×10^10 vg/mouse of either AAV8-hAAT-null or AAV8-hAAT-moFGF21 vectors. AAV8-hAAT-moFGF21 treatment (right panels) markedly decreased the detection of collagen fibers that were readily detectable (in black) in animals treated with the null vector (left panels). Scale bars: 50 μm.

FIGS. 28B, 28C Quantification by qRT-PCR of the expression of collagen 1 in the liver in the group of animals that initiated the HFD feeding and received FGF21 vectors as young adults (FIG. 28B) or adults (FIG. 28C).

FGF21 labels in the figure refer to moFGF21 in accordance with this Figure legend.

Data information: All values are expressed as mean±SEM. In (FIGS. 28B-28C) n=7-10 animals/group. *P<0.05, P<0.01 and *P<0.001 versus the chow-fed Null-injected group. #P<0.05 and ###P<0.001 versus the HFD-fed Null-injected group. HFD, High-fat diet.

FIGS. 29A-29Q. No bone abnormalities were observed in AAV8-hAAT-moFGF21-treated animals. The long-term effects of FGF21 gene transfer on bones were studied by comparison of HFD-fed mice treated with the highest dose (5×10^10 vg/mouse) of AAV8-hAAT-moFGF21 vectors as young adults or adults with null-injected, chow or HFD-fed animals.

FIG. 29A Total naso-anal length.

FIG. 29B Tibial length.

FIGS. 29C-29O Micro-computed tomography (μCT) analysis of the epiphysis (FIGS. 29C-29J) and the diaphysis (FIGS. 29K-29O) of tibiae obtained at the time of sacrifice, i.e. when animals were 18 months of age, from HFD-fed mice administered with either null or FGF21-encoding AAV vectors.

FIGS. 29P, 29Q Circulating IGFBP1 (FIG. 29P) and IGF1 (FIG. 29Q) levels measured by ELISA.

FGF21 labels in the figure refer to moFGF21 in accordance with this Figure legend.

Data information: All data represent the mean±SEM. In (FIGS. 29A, 29P-29Q) n=7-10 animals/group. In (FIGS. 29B-29O) n=4 animals/group. P<0.01 and *P<0.001 versus the chow-fed Null-injected group. HFD, High-fat diet; BMD, bone mineral density; BMC, bone mineral content; BV, bone volume; BV/TV, bone volume/tissue volume ratio; BS/BV, bone surface/bone volume ratio; Tb.N, trabecular number; Tb.Th, trabecular thickness; Tb.Sp, trabecular separation.

Figure 30:
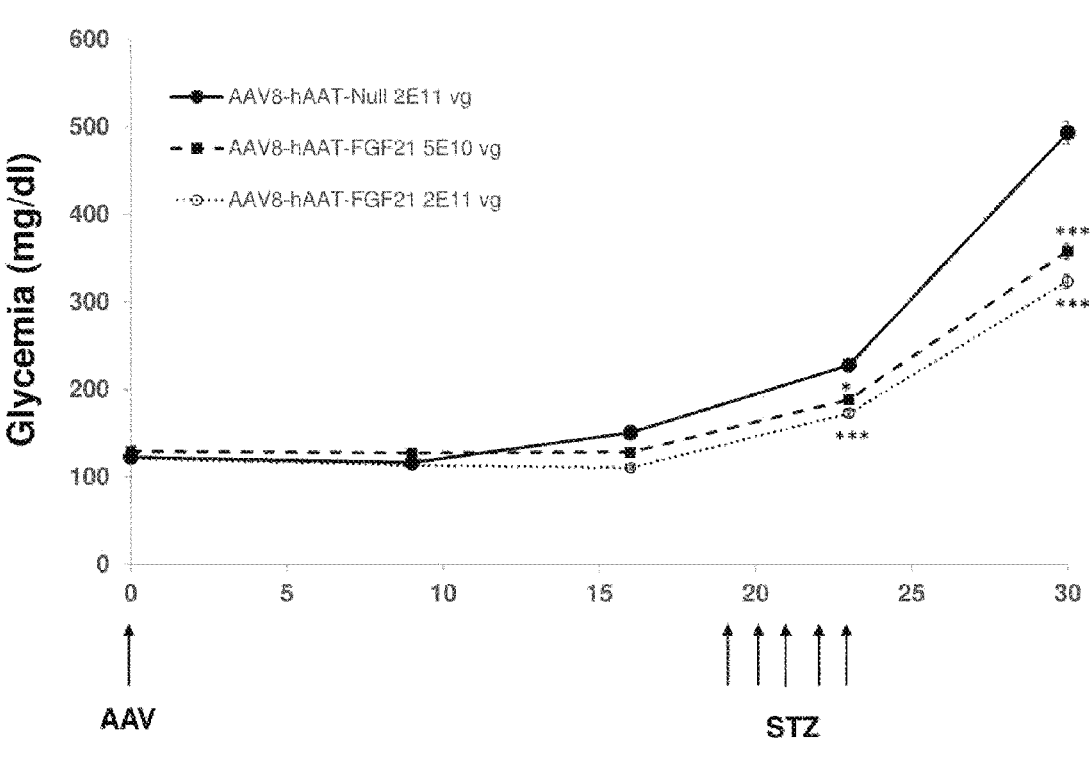

FIG. 30. Analysis of glycaemic profiles in C57Bl6 mice treated with AAV8-hAAT-moFGF21 vectors. Blood glucose levels were evaluated under fed conditions. AAV, IV administration of $5 \times 10^{10}$ vg or $2 \times 10^{11}$ vg of AAV8-hAAT-moFGF21 (n=13 and 15, respectively) or $2 \times 10^{11}$ vg of AAV8-null vectors (n=15). STZ, treatment with streptozotocin ($5 \times 50$ mg/kg). Results shown are means+SEM. *p<0.05; ***p<0.001 vs AAV8-hAAT-Null. FGF21 labels in the figure refer to moFGF21 in accordance with this Figure legend.

FIGS. 31A-31H. Gene transfer of FGF21 to the skeletal muscle of healthy animals.

FIG. 31A Circulating levels of FGF21 measured 40 weeks after injection of $3 \times 10^{11}$ vg/mouse of either AAV1-CMV-Null or AAV1-CMV-moFGF21 vectors to the skeletal muscle of healthy animals fed a chow diet.

FIG. 31B AAV-derived FGF21 expression in the muscles and liver of healthy animals injected intramuscularly with AAV1-CMV-Null or AAV1-CMV-moFGF21 vectors.

FIG. 31C Evolution of the body weight in the 40-week follow-up period.

FIG. 31D Wet tissue weight of different muscles, adipose pads and liver.

FIGS. 31E, 31F Hepatic triglyceride and cholesterol content in the fed state.

FIG. 31G Fed serum insulin levels.

FIG. 31H Insulin sensitivity assessed through intraperitoneal injection of insulin (0.75 units/kg body weight) and represented as percentage of initial blood glucose.

FGF21 labels in the figure refer to moFGF21 in accordance with this Figure legend.

Data information: All values are expressed as mean±SEM. In (FIGS. 31A-31H) n=5-7 animals/group. *P<0.05, P<0.01 and *P<0.001 versus the Null-injected group.

FIGS. 32A-32F. AAV1-mediated skeletal muscle gene transfer of FGF21 counteracts HFD-induced obesity and insulin resistance.

FIGS. 32A, 32B Evolution of body weight (FIG. 32A) and body weight gain (FIG. 32B) in animals treated with AAV1-CMV-moFGF21. C57Bl6 mice were fed a HFD for ~12 weeks and then administered with $3 \times 10^{11}$ vg/mouse of AAV1-CMV-moFGF21 vectors. Control obese mice and control chow-fed mice received $3 \times 10^{11}$ vg of AAV1-CMV-null.

FIG. 32C Circulating levels of FGF21 at different time-points after vector administration.

FIGS. 32D, 32E Fasted blood glucose (FIG. 32D) and fed serum insulin (FIG. 32E) levels in the same groups of animals as in (FIGS. 32A, 32B).

FIG. 32F Insulin sensitivity was determined in all experimental groups after an intraperitoneal injection of insulin (0.75 units/kg body weight). Results were calculated as the percentage of initial blood glucose levels.

FGF21 labels in the figure refer to moFGF21 in accordance with this Figure legend.

Data information: All values are expressed as mean±SEM. In (FIGS. 32A-32F) HFD-fed mice n=10 animals/group; chow-fed mice n=5 animals/group. ***P<0.001 versus the HFD-fed null-injected group.

Figure 33:
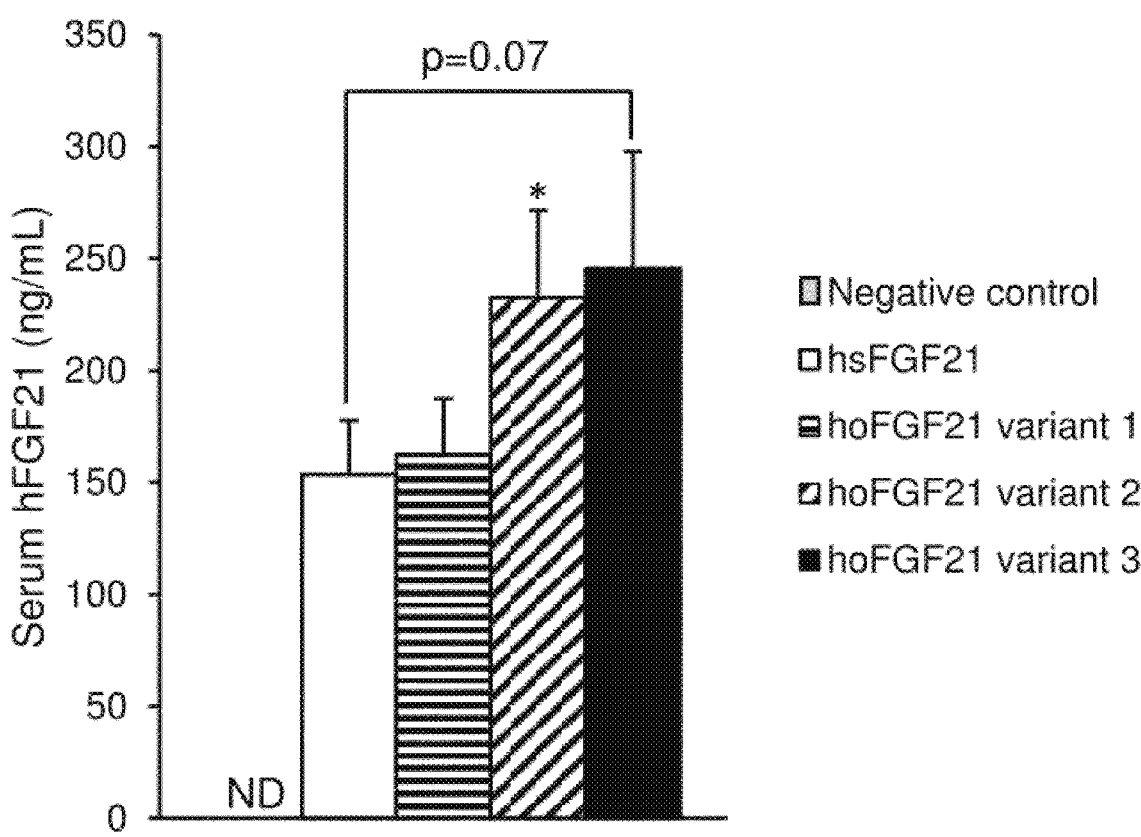

FIG. 33. In vivo increased FGF21 circulating levels by codon-optimization of nucleotide sequences encoding human FGF21. Circulating levels of hFGF21 in C57Bl6 mice administered hydrodynamically with plasmids encoding wild-type hFGF21 or three different variants of codon-optimized human FGF21 sequences. Results are expressed as the mean±SEM. n=9-10 mice/group. ND, non detected. Negative control, untreated mice. *p<0.05 vs Non-treated mice.

Figures 34A, 34B, 34C, 34D, 34E:
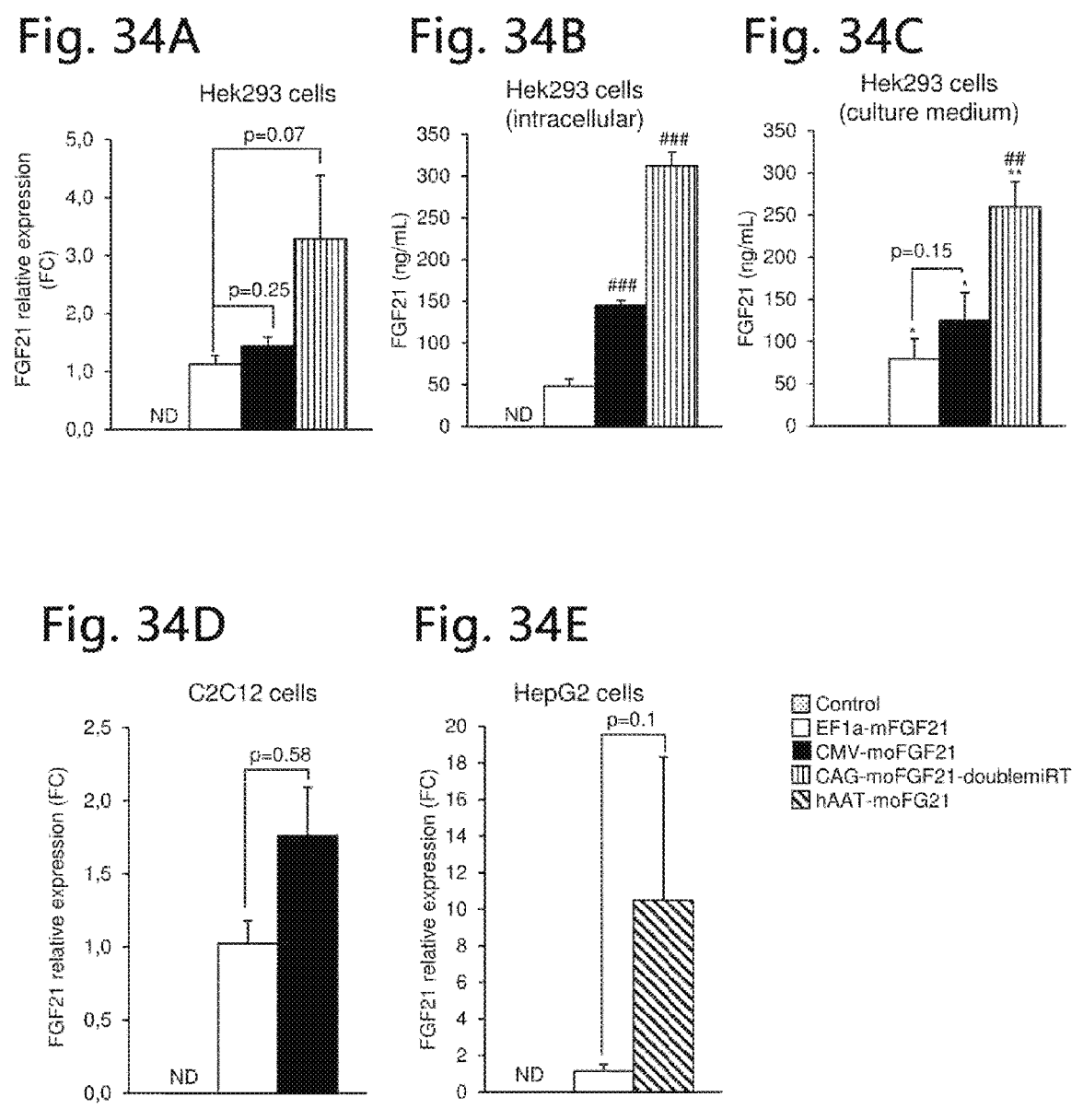

FIGS. 34A-34E. In vitro increased FGF21 expression levels by hAAT-moFGF21, CAG-moFGF21-doublemiRT and CMV-moFGF21 expression cassettes. (FIG. 34A) Expression levels of FGF21 in HEK293 cells transfected with plasmids encoding the WT murine FGF21 coding sequence under the control of the EF1a promoter (EF1a-mFGF21) or a codon-optimized murine FGF21 coding sequence under the control of the CMV promoter (CMV-moFGF21) or of the CAG promoter in conjunction with four tandem repeats of the miRT122a sequence and four tandems repeats of the miRT1 sequence (CAG-moFGF21-doublemiRT). (FIGS. 34B and 34C) Intracellular FGF21 protein content (FIG. 34B) and FGF21 protein levels in the culture medium (FIG. 34C) in the same cells as in (FIG. 34A). (FIG. 34D) Expression levels of FGF21 in C2C12 cells transfected with plasmids encoding the WT murine FGF21 coding sequence under the control of the EF1a promoter (EF1a-mFGF21) or a codon-optimized murine FGF21 coding sequence under the control of the CMV promoter (CMV-moFGF21). (FIG. 34E) Expression levels of FGF21 in HepG2 cells transfected with plasmids encoding the WT murine FGF21 coding sequence under the control of the EF1a promoter (EF1a-mFGF21) or a codon-optimized murine FGF21 coding sequence under the control of the hAAT promoter (hAAT-moFGF21). The qPCR was performed with primers that detected both the wt and the codon-optimized FGF21 coding sequences. Results are expressed as the mean±SEM. n=3 wells/group. ND, non detected. *p<0.05 vs control. ###p<0.001 vs EF1a-mFGF21.

Figures 35A, 35B:
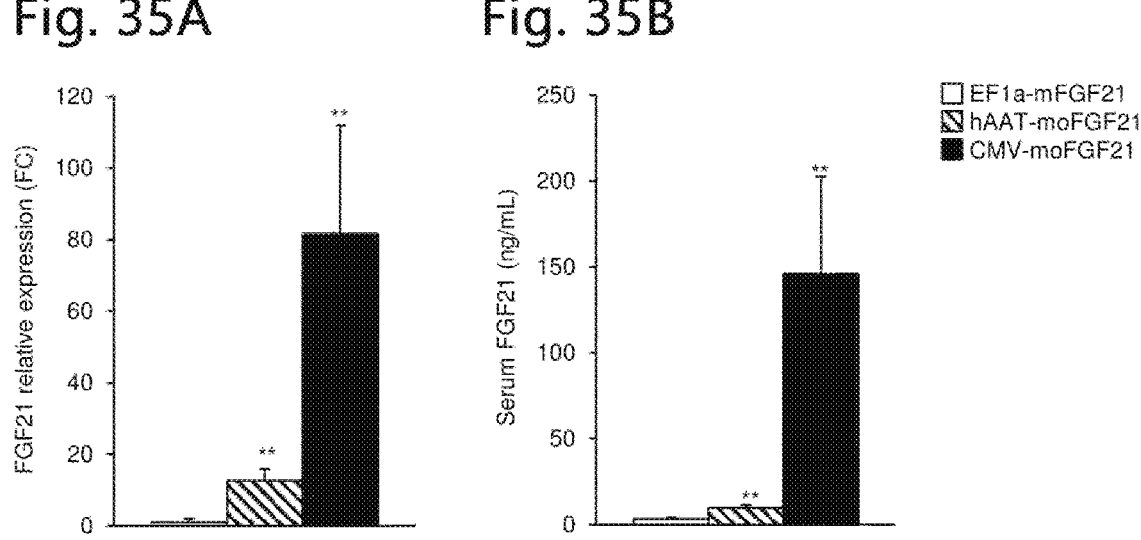

FIGS. 35A-35B. In vivo increased hepatic FGF21 expression and FGF21 circulating levels by hAAT-moFGF21 and CMV-moFGF21 expression cassettes. (FIG. 35A) Expression levels of FGF21 in the liver of C57Bl6 mice hydrodynamically administered with plasmids encoding the WT murine FGF21 coding sequence under the control of the elongation factor 1a (EF1a) promoter (EF1a-mFGF21) or a codon-optimized murine FGF21 coding sequence under the control of the CMV promoter (CMV-moFGF21) or the hAAT promoter (hAAT-moFGF21). The qPCR was performed with primers that detected both the wt and the codon-optimized FGF21 coding sequences. (FIG. 35B) FGF21 circulating levels in the same cohorts as in (FIG. 35A). Results are expressed as the mean±SEM. n=5 mice/group. **p<0.01 vs. EF1a-mFGF21

Figure 36A:
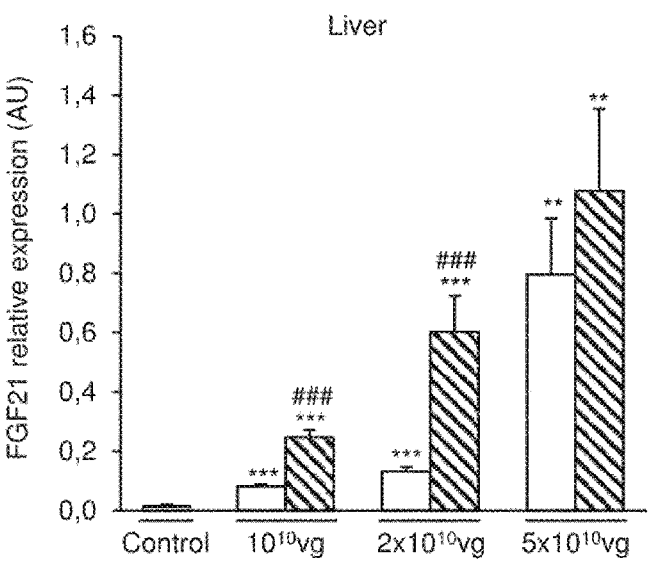
Figure 36B:
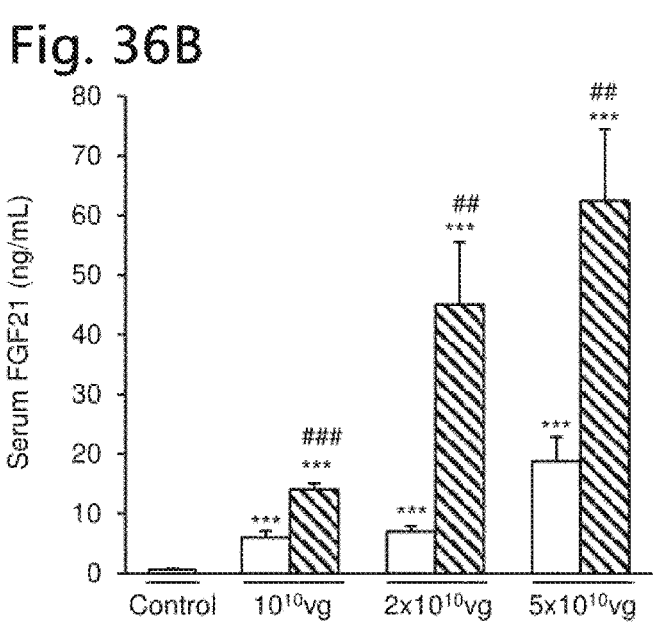

FIGS. 36A-36B. In vivo increased hepatic FGF21 expression and FGF21 circulating levels by AAV8-hAAT-moFGF21. (FIG. 36A) Expression levels of FGF21 in the liver of C57Bl6 mice intravenously administered with $1 \times 10^{10}$ vg, $2 \times 10^{10}$ vg or $5 \times 10^{10}$ vg of AAV8 vectors encoding the WT murine FGF21 coding sequence under the control of the elongation factor 1a (EF1a) promoter (AAV8-EF1a-mFGF21) or a codon-optimized murine FGF21 coding sequence under the control of the hAAT promoter (AAV8-hAAT-moFGF21). The qPCR was performed with primers that detected both the wt and the codon-optimized FGF21 coding sequences. (FIG. 36B) FGF21 circulating levels in the same cohorts as in (FIG. 36A). Analyses were performed two weeks post-AAV. Results are expressed as the mean±SEM. n=4-5 mice/group. Control, untreated mice. p<0.01 and *p<0.001 vs. control. ##p<0.01 and ###p<0.001 vs. AAV8-EF1a-mFGF21

Figure 37A:
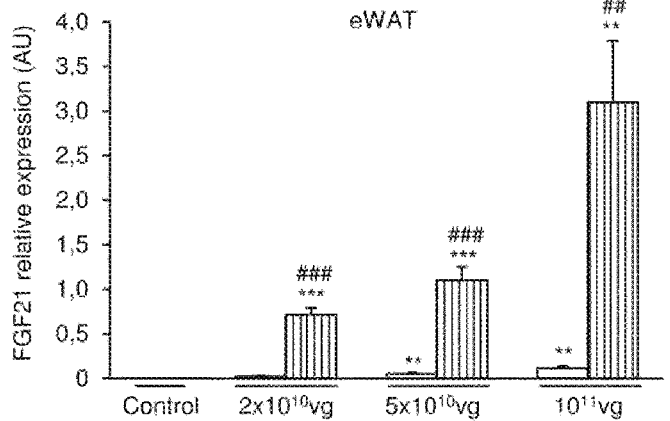
Figure 37B:
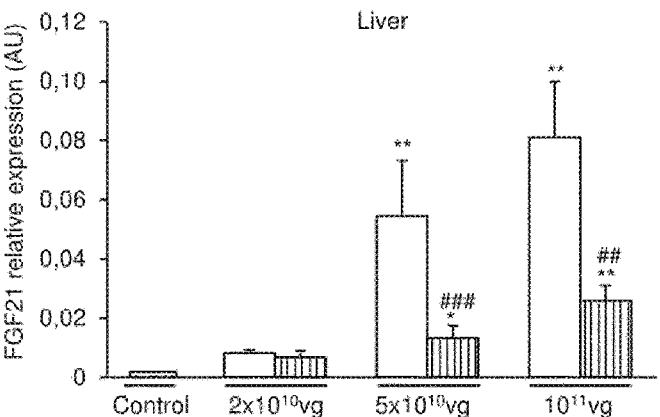

FIGS. 37A-37B. In vivo increased adipose FGF21 expression by AAV8-CAG-moFGF21-dmiRT. (FIGS. 37A-37B)

Expression levels of FGF21 in the eWAT (FIG. 37A) or the liver (FIG. 37B) of C57Bl6 mice administered intra-eWAT with $2\times10^{10}$ vg, $5\times10^{10}$ vg or $1\times10^{11}$ vg of either AAV8 vectors encoding the WT murine FGF21 coding sequence under the control of the elongation factor 1a (EF1a) promoter (AAV8-EF1a-mFGF21) or AAV8 vectors encoding a codon-optimized murine FGF21 coding sequence under the control of the CAG promoter in conjunction with four tandem repeats of the miRT122a sequence and four tandems repeats of the miRT1 sequence (AAV8-CAG-moFGF21-doublemiRT). The qPCR was performed with primers that detected both the wt and the codon-optimized FGF21 coding sequences. Analyses were performed two weeks post-AAV. Results are expressed as the mean±SEM. n=4-5 mice/group. Control, untreated mice. eWAT, epidydimal white adipose tissue. *p<0.05, p<0.01 and FIGS. 38A-38B. In vivo increased FGF21 expression in the skeletal muscle by AAV1-CMV-moFGF21. (FIGS. 38A-38B) Expression levels of FGF21 in the quadriceps (FIG. 38A) or the liver (FIG. 38**B) of C57Bl6 mice administered intramuscularly with $5\times10^{10}$ vg, $1\times10^{11}$ vg or $3\times10^{11}$ vg of either AAV8 vectors encoding the WT murine FGF21 coding sequence under the control of the elongation factor 1a (EF1a) promoter (AAV8-EF1a-mFGF21) or AAV1 vectors encoding a codon-optimized murine FGF21 coding sequence under the control of the CMV promoter (AAV1-CMV-FGF21). The qPCR was performed with primers that detected both the wt and the codon-optimized FGF21 coding sequences. Analyses were performed two weeks post-AAV. Results are expressed as the mean±SEM. n=4-5 mice/group. Control, untreated mice. *p<0.05, p<0.01 and *p<0.001 vs. control. #p<0.05, ##p<0.01 and ###p<0.001 vs. AAV8-EF1a-mFGF21.

EXAMPLES

General Procedures to the Examples
Subject Characteristics

Male C57Bl/6J mice and B6.V-Lep$^{ob}$/OlaHsd (ob/ob) mice were used. Mice were fed ad libitum with a standard diet (2018S Teklad Global Diets®, Harlan Labs., Inc., Madison, WI, US) or a high fat diet (TD.88137 Harlan Teklad Madison, WI, US) and kept under a light-dark cycle of 12 h (lights on at 8:00 a.m.) and stable temperature (22° C.±2). For tissue sampling, mice were anesthetized by means of inhalational anesthetic isoflurane (IsoFlo®, Abbott Laboratories, Abbott Park, IL, US) and decapitated. Tissues of interest were excised and kept at −80° C. or with formalin until analysis. All experimental procedures were approved by the Ethics Committee for Animal and Human Experimentation of the Universitat Autónoma de Barcelona.
Recombinant AAV Vectors Single-stranded AAV vectors of serotype 1, 8 or 9 were produced by triple transfection of HEK293 cells according to standard methods (Ayuso, E. et al, 2010. Curr Gene Ther. 10(6):423-36). Cells were cultured in 10 roller bottles (850 cm², flat; Corning™, Sigma-Aldrich Co., Saint Louis, MO, US) in DMEM 10% FBS to 80% confluence and co-transfected by calcium phosphate method with a plasmid carrying the expression cassette flanked by the AAV2 ITRs, a helper plasmid carrying the AAV2 rep gene and the AAV of serotypes 1, 8 or 9 cap gene, and a plasmid carrying the adenovirus helper functions. Transgenes used were: murine, canine or human codon-optimized or wt FGF21 coding-sequence driven by 1) the cytomegalovirus (CMV) early enhancer/chicken beta actin (CAG) promoter with the addition of four tandem repeats of the miRT122a sequence (5'CAAACACCATTGTCACACTCCA3') (SEQ ID NO:12) and four tandems repeats of the miRT1 sequence (5'TTA-CATACTTCTTTACATTCCA3') (SEQ ID NO:13) cloned in the 3' untranslated region of the expression cassette; 2) the CMV promoter; or 3) the human al-antitrypsin promoter (hAAT). Noncoding plasmids carrying the CAG, hAAT or CMV promoters were used to produce null vectors. AAV were purified with an optimized method based on a polyethylene glycol precipitation step and two consecutive cesium chloride (CsCl) gradients. This second-generation CsCl-based protocol reduced empty AAV capsids and DNA and protein impurities dramatically (Ayuso, E. et al., 2010. Curr Gene Ther. 10(6):423-36). Purified AAV vectors were dialyzed against PBS, filtered and stored at −80° C. Titers of viral genomes were determined by quantitative PCR following the protocol described for the AAV2 reference standard material using linearized plasmid DNA as standard curve (Lock M, et al., Hum. Gene Ther. 2010; 21:1273-1285). The vectors were constructed according to molecular biology techniques well known in the art.
In Vivo Intra-eWAT Administration of AAV Vectors Mice were anesthetized with an intraperitoneal injection of ketamine (100 mg/kg) and xylazine (10 mg/kg). A laparotomy was performed in order to expose the epididymal white adipose tissue. AAV vectors were resuspended in PBS with 0.001% Pluronic® F68 (Gibco) and injected directly into the epididymal fat pad. Each epididymal fat pad was injected twice with 50 μL of the AAV solution (one injection close to the testicle and the other one in the middle of the fat pad). The abdomen was rinsed with sterile saline solution and closed with a two-layer approach.
Systemic Administration of AAV Vectors The appropriate amount of the AAV solution was diluted in 200 μL of PBS with 0.001% Pluronic® and was manually injected into the lateral tail vein without exerting pressure at the moment of delivery. Before the injection, the animals were put under a 250 W infrared heat lamp (Philips NV, Amsterdam, NL) for a few minutes to dilate the blood vessels and facilitate viewing and easier access to the tail vein. A plastic restrainer (Harvard Apparatus, Holliston, MA, US) was used to secure the animal for injection. No anesthesia was used since an appropriate restraining device was employed. A 30-gauge needle was utilized to inject the animals.
Intramuscular Administration of AAV Vectors Mice were anesthetized with an intraperitoneal injection of ketamine (100 mg/kg) and xylazine (10 mg/kg). Hind limbs were shaved and vectors were administered by intramuscular injection in a total volume of 180 μl divided into six injection sites distributed in the quadriceps, gastrocnemius, and tibialis cranealis of each hind limb.
Immunohistochemical and Morphometric Analysis Tissues were fixed for 24 h in formalin (Panreac Quimica), embedded in paraffin, and sectioned. Tissue samples were stained with hematoxylin-eosin. Adipocyte area was determined in 12 hematoxylin/eosin WAT images per animal taken at 10× with the Nikon Eclipse E800 microscope (Nikon, Tokyo, Japan) connected to a video-camera with a monitor with an image analysis software (analySIS 3.0; Soft Imaging System, Center Valley, PA, EEUU) and each adipocyte area was quantified in μm². Mean adipocyte area was calculated for each experimental group and distribution of adipocytes according to size categories was represented in a histogram. Four animals per group were used and at least 250 adipocytes per animal were analyzed.

Immunohistochemistry

Tissues were fixed for 12-24 h in 10% formalin, embedded in paraffin and sectioned. Sections were incubated overnight at 4° C. with rat anti-Mac2 (1:50; CL8942AP; Cedarlane), guinea pig anti-insulin (1:100; I-8510; Sigma-Aldrich) or rabbit anti-glucagon (1:100; 219-01; Signet Labs). Biotinylated rabbit anti-rat (1:300; E0467; Dako), goat anti-rabbit IgG (Alexa Fluor 568-conjugated) (1:200; A11011; ThermoFisher), goat anti-guinea pig IgG (Alexa Fluor 488-conjugated) (1:300; A11073; ThermoFisher) or rabbit anti-guinea pig coupled to peroxidase (1:300; P0141; Dako) were used as secondary antibodies. The ABC peroxidase kit (Pierce) was used for immunodetection, and sections were counterstained in Mayer's hematoxylin. Hoechst (B2261; Sigma-Aldrich) was used for nuclear counterstaining of fluorescent specimens. PicroSirius Red staining and Masson's trichrome staining were used to evaluate fibrosis. The percentage of β-cell area in the pancreas was analyzed in two insulin-stained sections 200 μm apart, by dividing the area of all insulin+ cells in one section by the total pancreas area of that section. β-cell mass was calculated by multiplying pancreas weight by percentage of β-cell area, as previously described (Jimenez et al, 2011).

RNA Analysis

Total RNA was obtained from adipose depots or liver by using QIAzol Lysis Reagent (Qiagen NV, Venlo, NL) or Tripure isolation reagent (Roche Diagnostics Corp., Indianapolis, IN, US), respectively, and RNeasy Lipid Tissue Minikit (Qiagen NV, Venlo, NL). In order to eliminate the residual viral genomes, total RNA was treated with DNAseI (Qiagen NV, Venlo, NL). For RT-PCR, 1 μg of RNA samples was reverse-transcribed using Transcriptor First Strand cDNA Synthesis Kit (04379012001, Roche, California, USA). Real-time quantitative PCR was performed in a SmartCyclerII® (Cepheid, Sunnyvale, USA) using EXPRESS SYBRGreen qPCR supermix (Invitrogen™, Life Technologies Corp., Carslbad, CA, US). Data was normalized with Rplp0 values and analyzed as previously described (Pfaffl, M., Nucleic Acids Res. 2001; 29(9):e45).

Hormone and Metabolite Assays

Blood glucose levels were measured with a Glucometer Elite™ analyzer (Bayer, Leverkusen, Germany). Circulating levels of FGF21 were determined by quantitative sandwich enzyme immunoassay Mouse/Rat FGF-21 ELISA kit (MF2100, R&Dsystems, Abingdon, UK). Serum insulin concentrations were determined by Rat Insulin ELISA sandwich assay (90010, Crystal Chem INC. Downers Grove, IL 60515, USA). To extract lipids from tissue, frozen samples of approximately 100 mg were weighted and homogenized in 15 ml chloroform:methanol (2:1). Lipid and aqeuous phases were then separated by adding 3 ml of $H_2SO_4$ 0.05% and keeping them overnight at 4° C. Once the phases were separated, the aqueous superior phase was eliminated using a Pasteur pipet and 1 ml of the inferior lipid phase was recuperated in a glass tube. 1 ml of a chloroform and Triton X-100 at 1% solution was added to the glass tube and it was incubated at 90° C. in a bath, to evaporate the chloroform. By the use of the chloroform and Triton X-100 mix, any remaining aqeuous particle was eliminated from the lipid phase. After the evaporation, chloroform was rinsed to the walls of the tube to concentrate the sample and, it was warmed again at 90° C. to evaporate the chloroform. Once the sediment was completely dry and concentrated, it was resuspended by the addition of 500 μl of H20 miliQ at 37° C. The amount of triglycerides was finally determined using the commercial product GPO-PAP (Roche Diagnostics, Basel, Switzerland). Serum triglycerides and cholesterol were quantified spectrophotometrically using an enzymatic assay kit (Horiba-ABX, Montpellier, France). All biochemical parameters were determined using Pentra 400 Analyzer (Horiba-ABX).

Glycemia was determined using a Glucometer Elite™ (Bayer). Glucagon levels were measured using a glucagon Radioimmunoassay (#GL-32K, EMD Millipore). Adiponectin, leptin, IGFBP1 and IGF1 were determined using the Mouse Adiponectin ELISA kit (80569, Crystal Chem), the Mouse Leptin ELISA kit (90030, Crystal Chem), the IGFBP1 (Mouse) ELISA kit (KA3054, Abnova) and the m/r IGF-I-ELISA kit (E25, Mediagnost), respectively.

Insulin Tolerance Tests

For insulin tolerance tests, insulin (0.75 IU/kg body wt; Humulin Regular; Eli Lilly, Indianapolis, IN) was injected intraperitoneally into awake fed mice. Glucose concentration was determined in blood samples obtained from the tail vein at the indicated time points after the insulin injection.

Glucose Tolerance Test

Awake mice were fasted overnight (16 h) and administered with an intraperitoneal injection of glucose (2 g/kg body weight). Glycemia was measured in tail vein blood samples at the indicated time points. Venous blood was collected from tail vein in tubes (Microvette® CB 300, SARSTEDT) at the same time points and immediately centrifuged to separate serum, which was used to measure insulin levels.

Oximetry

An indirect open circuit calorimeter (Oxylet, Panlab, Cornelia, Spain) was used to monitor oxygen consumption, carbon dioxide production in eight metabolic chambers simultaneously. Mice were individualized and acclimated to the metabolic chambers for 24 h, and data were collected every 15 min for 3 min in each cage for other 24 h. Data were taken from the light and dark cycle and adjusted for body weight. To calculate energy expenditure the Metabolism software provided by the manufacturer was used.

Transfection of HEK293, C2C12 and HepG2 Cells

Cells were cultured in a 24-well plate and transfected with 0.8 μg of DNA per well using Lipofectamine 2000 following the manufacturer's instructions (Thermo Fisher Scientific).

Bone Analysis

Bone volume and architecture were evaluated by μCT. Mouse tibiae were fixed in neutral buffered formalin (10%) and scanned using the eXplore Locus CT scanner (General Electric) at 27-micron resolution. Trabeculae were analyzed in 1 mm3 of proximal tibial epiphysis and 1.8 mm3 of cortical tibial diaphysis in 4 mice/group. Bone parameters were calculated with the MicroView 3D Image Viewer & Analysis Tool. The length of the tibia was measured from the intercondilar eminence to the medial malleolus.

Western Blot Analysis iWAT and iBAT were homogenized in QIAzol Lysis Reagent (Qiagen) and the protein fraction was isolated from the organic phase following the manufacturer's instructions. Proteins were separated by 12% SDS-PAGE, and analyzed by immunoblotting with rabbit polyclonal anti-UCP1 (ab10983; Abcam) and rabbit polyclonal anti-α-tubulin (ab4074; Abcam) antibodies. Detection was performed using ECL Plus detection reagent (Amersham Biosciences).

Open Field Test

The open field test was performed between 9:00 am and 1:00 pm as previously reported (Haurigot et al, 2013). Briefly, animals were placed in the center of a brightly lit chamber (41×41×30 cm) crossed by 2 bundles of photobeams (LE 8811; Panlab) that detect horizontal and vertical movements. Motor and exploratory activities were evaluated during the first 6 minutes. The total distance covered was evaluated using a video tracking system (SMART Junior; Panlab).

Statistical Analysis

All values are expressed as mean±SEM. Differences between groups were compared by Student's t-test. Differences were considered significant at $p<0.05$.

EXAMPLES

Example 1. Prevention of Obesity and Diabetes by Intra-eWAT Administration of AAV-CAG-moFGF21-dmiRT Vectors in C57Bl6 Mice We evaluated the therapeutic potential of the AAV-mediated genetic engineering of adipose tissue with FGF21 to prevent obesity and diabetes in 8-week-old male C57Bl6. Intra-eWAT (eWAT: epididymal white adipose tissue) administration of $10^{12}$ viral genomes (vg) of AAV9 vectors encoding a murine codon-optimized FGF21 coding sequence under the control of the CAG ubiquitous promoter which included target sites of miR122 and miR1 (AAV9-CAG-moFGF21-doublemiRT) (FIG. 1A) mediated adipose-specific overexpression of FGF21 (FIG. 1B) as well as high secretion of the protein into the bloodstream (FIG. 1C). AAV9-CAG-moFGF21-doublemiRT-treated mice also showed overexpression of the FGF21 receptor1 (FGF21R1) in eWAT (FIG. 1D) and β-Klotho (a FGF21 co-receptor) in adipose tissue and liver (FIG. 1E) in comparison with AAV9-CAG-null vectors (vectors that retain equal infectivity but do not encode any transgene). The CAG-moFGF21-doublemiRT construct is comprised in SEQ ID NO: 32 and the CAG-null construct is comprised in SEQ ID NO:31.

Figure 1F:
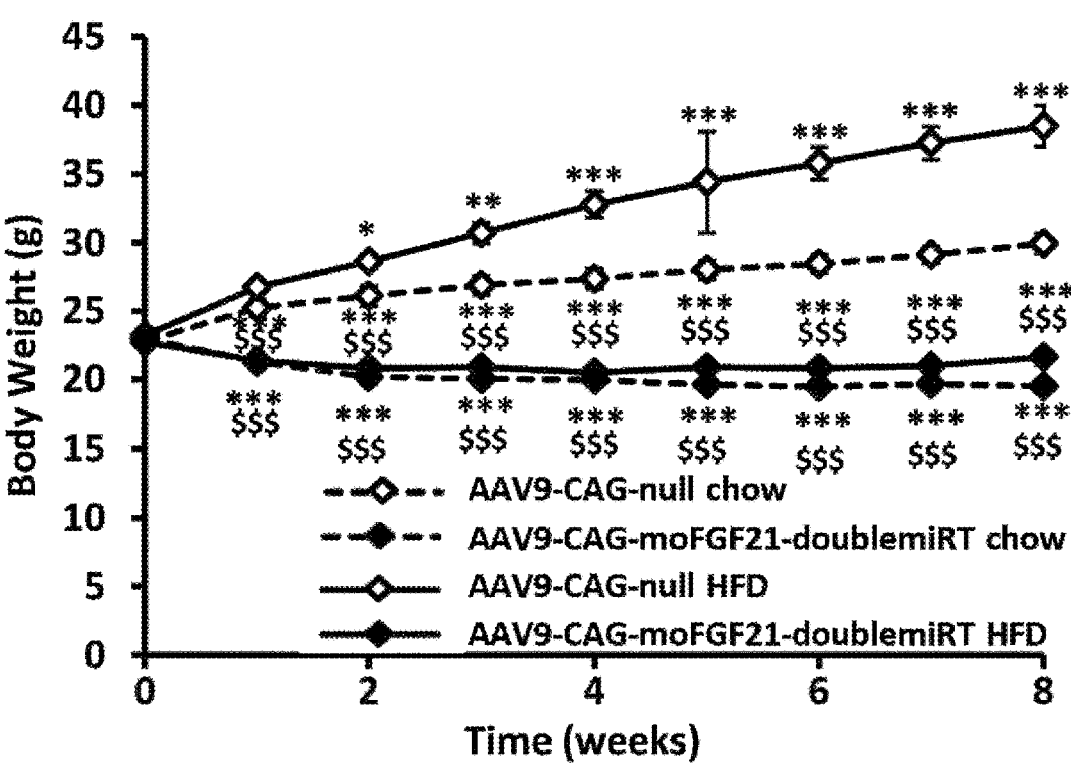
Figure 1G:
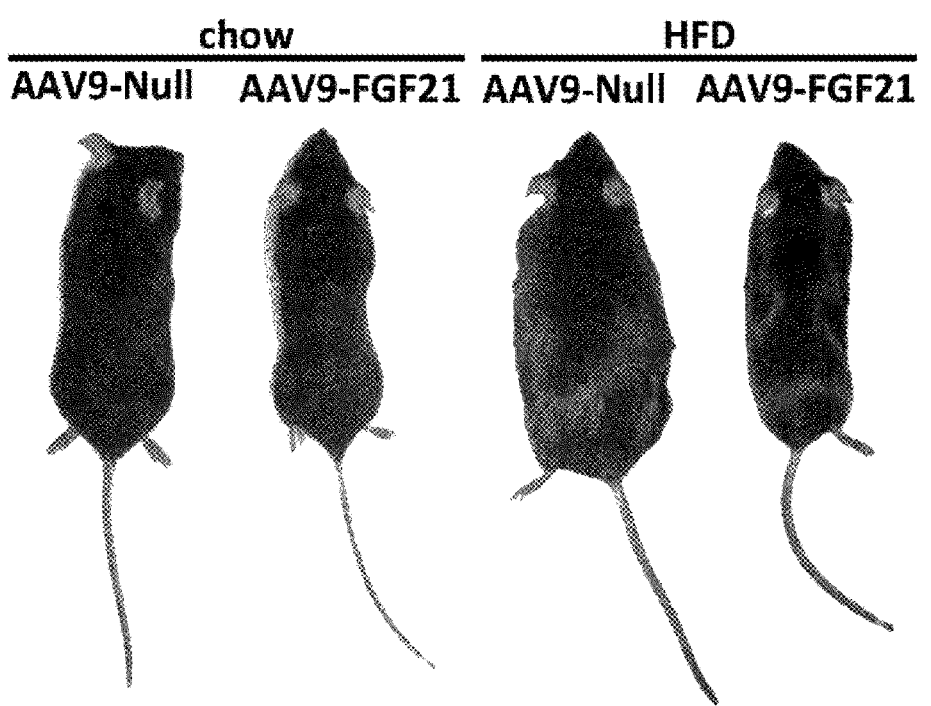
Figure 1H:
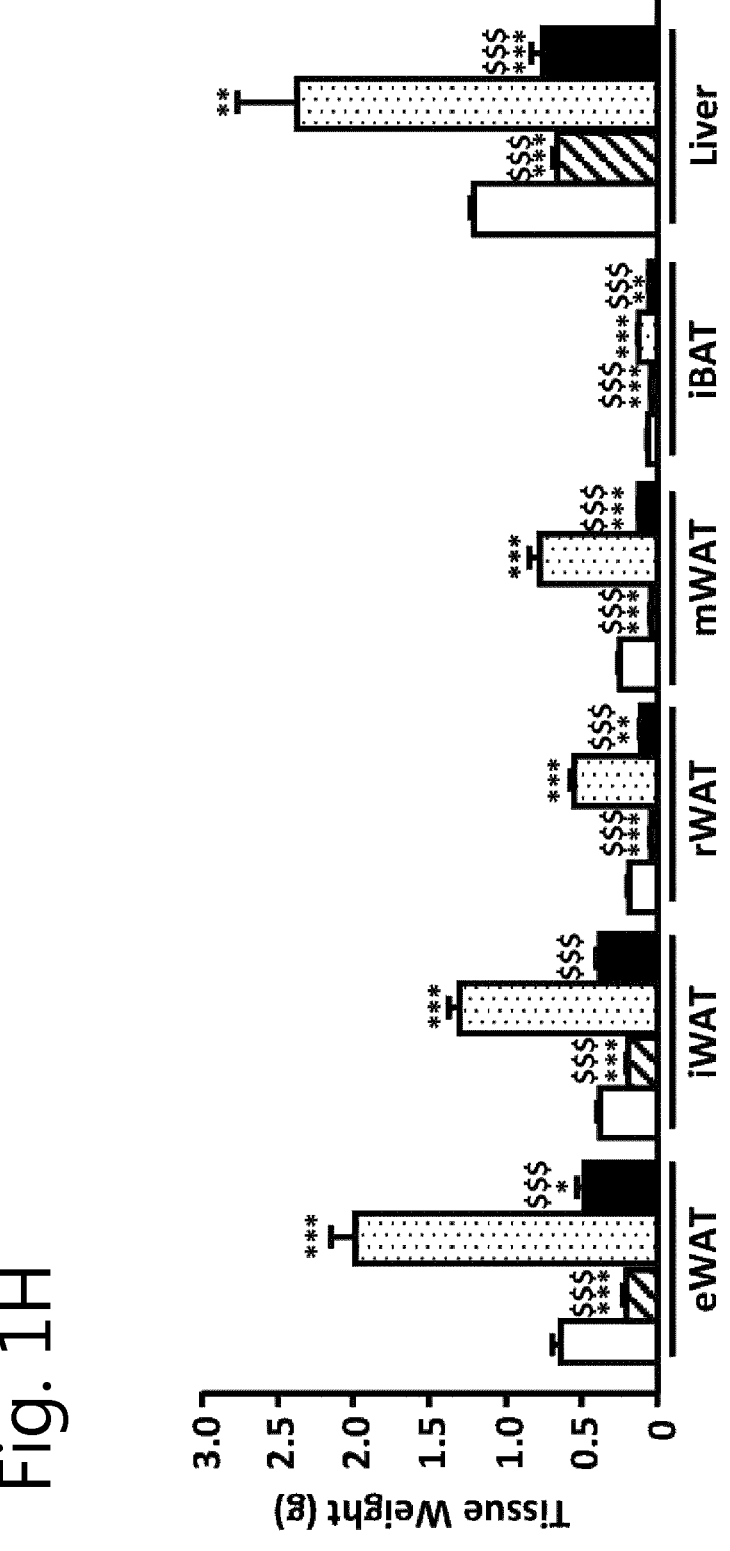

Following AAV-mediated gene transfer of FGF21 to eWAT, mice fed a chow diet showed loss of body weight (FIGS. 1F and 1G). When challenged with a high fat diet (HFD), animals overexpressing FGF21 in adipose tissue remained lean for the duration of the experiment whereas AAV9-CAG-null treated mice became progressively obese (FIGS. 1F and 1G). According to their lower body weight, both chow- and HFD-fed AAV9-CAG-moFGF21-doublemiRT-treated mice showed decreased weight of adipose depots and liver (FIG. 1H).

Histological analysis of white adipose tissue by hematoxylin-eosin staining revealed decreased white adipocyte size in eWAT and iWAT (iWAT: inguinal white adipose tissue) and multiple multilocular adipocytes in iWAT, suggesting that browning of this depot had occurred (FIG. 2A). Morphometric analysis further confirmed decreased mean area of white adipocytes in AAV9-CAG-moFGF21-doublemiRT-treated mice (FIG. 2B). The frequency distribution of the area of white adipocytes was also different between groups. Both chow- and HFD-fed AAV9-CAG-moFGF21-doublemiRT-treated mice presented increased number of small adipocytes and fewer big adipocytes (FIG. 2C). Noticeably, the frequency distribution of the area of white adipocytes in HFD-fed AAV9-CAG-moFGF21-doublemiRT-treated mice was almost identical to that of chow-fed AAV9-CAG-null-treated animals (FIG. 2C). Therefore, the HFD-induced hypertrophy of adipocytes observed in AAV9-CAG-null-treated mice was blocked in mice overexpressing FGF21. Overexpression of UCP1 and Dio2 in iWAT (FIGS. 3A and 3B) further confirmed browning of iWAT in chow- and HFD-fed AAV9-CAG-moFGF21-doublemiRT-treated mice.

Histologic analysis of iBAT (iBAT: interscapular brown adipose tissue) showed lower lipid accumulation in this depot in chow- and HFD-fed AAV9-CAG-moFGF21-doublemiRT-treated mice in comparison with AAV9-CAG-null mice (FIG. 2A). According to this result and to browning of iWAT, energy expenditure (FIG. 3C) of HFD-fed AAV9-CAG-moFGF21-doublemiRT-treated mice during the light and dark cycles was higher than that of HFD-fed AAV9-CAG-null mice. Altogether, these data suggest that AAV9-CAG-moFGF21-doublemiRT-treated mice have increased thermogenic activity.

Figures 3D, 3E, 3F:
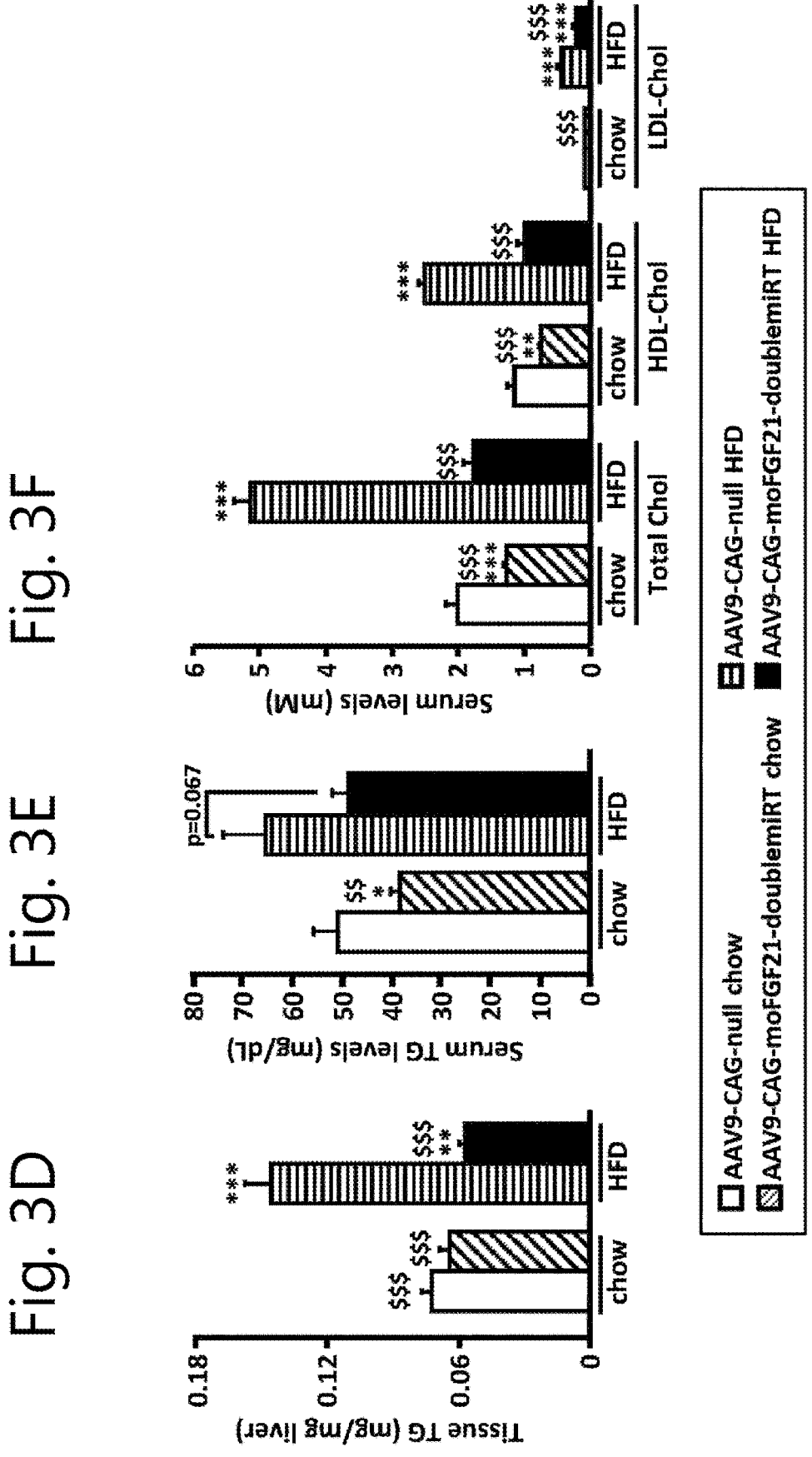
Figure 3G:
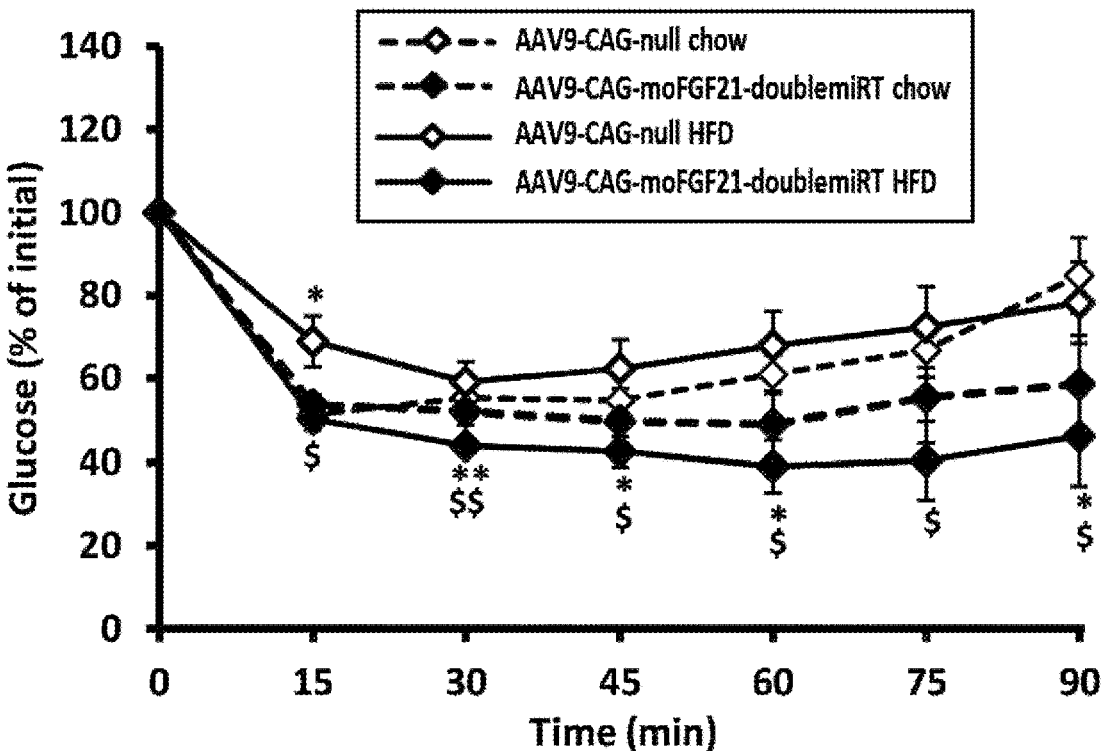

Liver histologic sections showed decreased lipid accumulation in hepatocytes of mice overexpressing FGF21 compared with AAV9-CAG-null-treated mice both under chow or HFD (FIG. 2A). Accordingly, HFD-fed AAV9-CAG-moFGF21-doublemiRT-treated mice normalized their hepatic content of tryglycerides (TG) (FIG. 3D). In parallel, circulating levels of TG, total cholesterol, HDL-cholesterol and LDL-cholesterol were normalized in HFD-fed mice overexpressing FGF21 (FIGS. 3E and 3F).

Figure 3H:
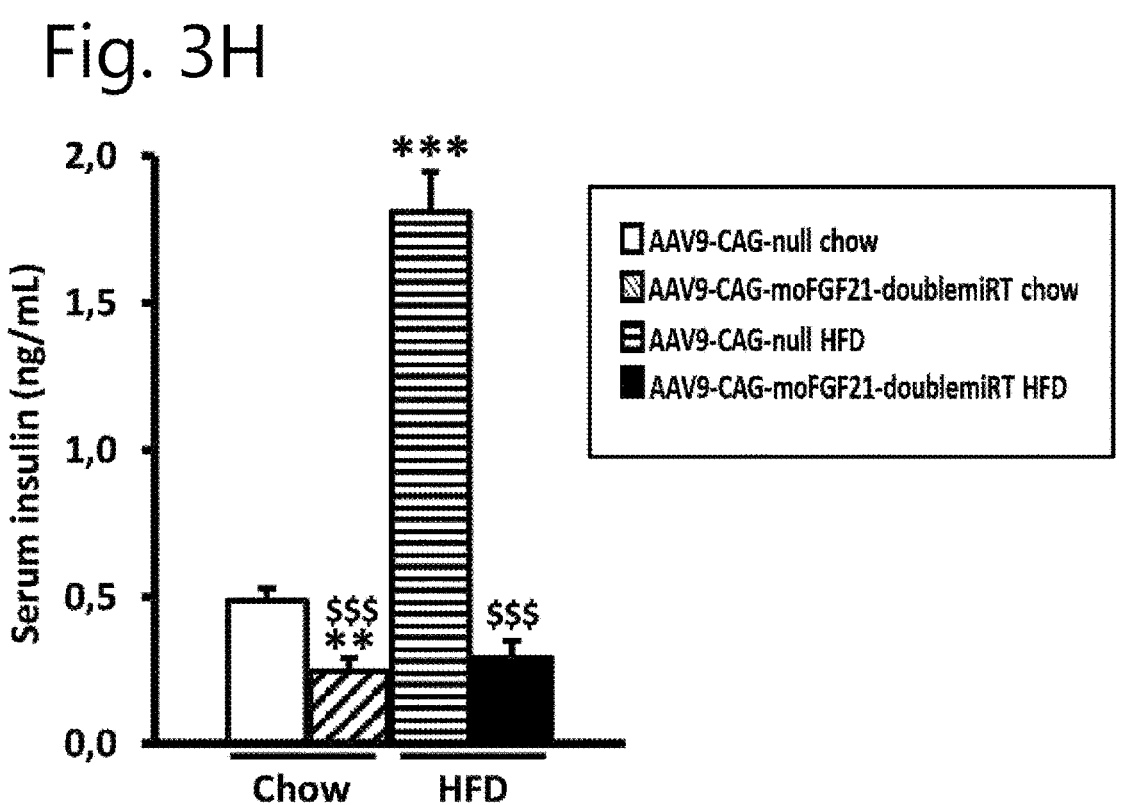

HFD-fed mice overexpressing FGF21 were more insulin sensitive than HFD-fed AAV9-null treated mice (FIG. 3G) and both chow- and HFD-fed AAV9-CAG-moFGF21-doublemiRT-treated mice showed decreased insulin circulating levels in comparison with their AAV9-CAG-null treated counterparts (FIG. 3H).

Example 2. Reversion of Obesity and Improvement of Glucose Metabolism by Intra-eWAT Administration of AAV-CAG-moFGF21-dmiRT Vectors in Ob/Ob Mice We evaluated the anti-diabetic and anti-obesogenic therapeutic potential of the AAV-mediated genetic engineering of adipose tissue with FGF21 in 11-week-old male ob/ob mice, which have defective leptin signalling and are a widely used genetic model of obesity and diabetes. To this end, a dose-response study was performed. Ob/ob mice were administered locally into the eWAT with four different doses ($10^{10}$ vg, $5\times10^{10}$ vg, $2\times10^{11}$ vg or $10^{12}$ vg) of AAV8-CAG-moFGF21-doublemiRT vectors (FIG. 1A). As control, ob/ob animals were administered intra-eWAT with $10^{12}$ vg of AAV8-CAG-null vectors.

Figures 4A, 4B:
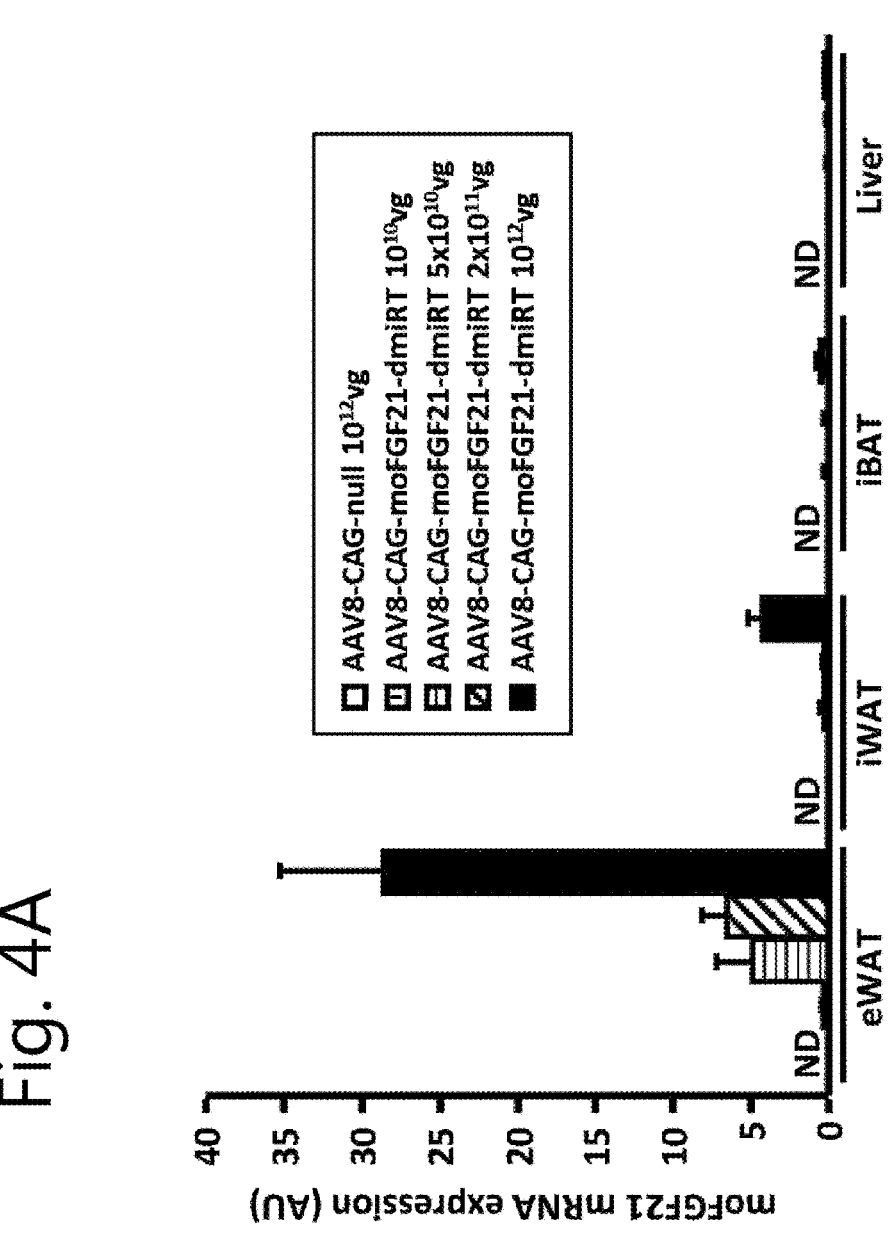
Figures 4C, 4D:
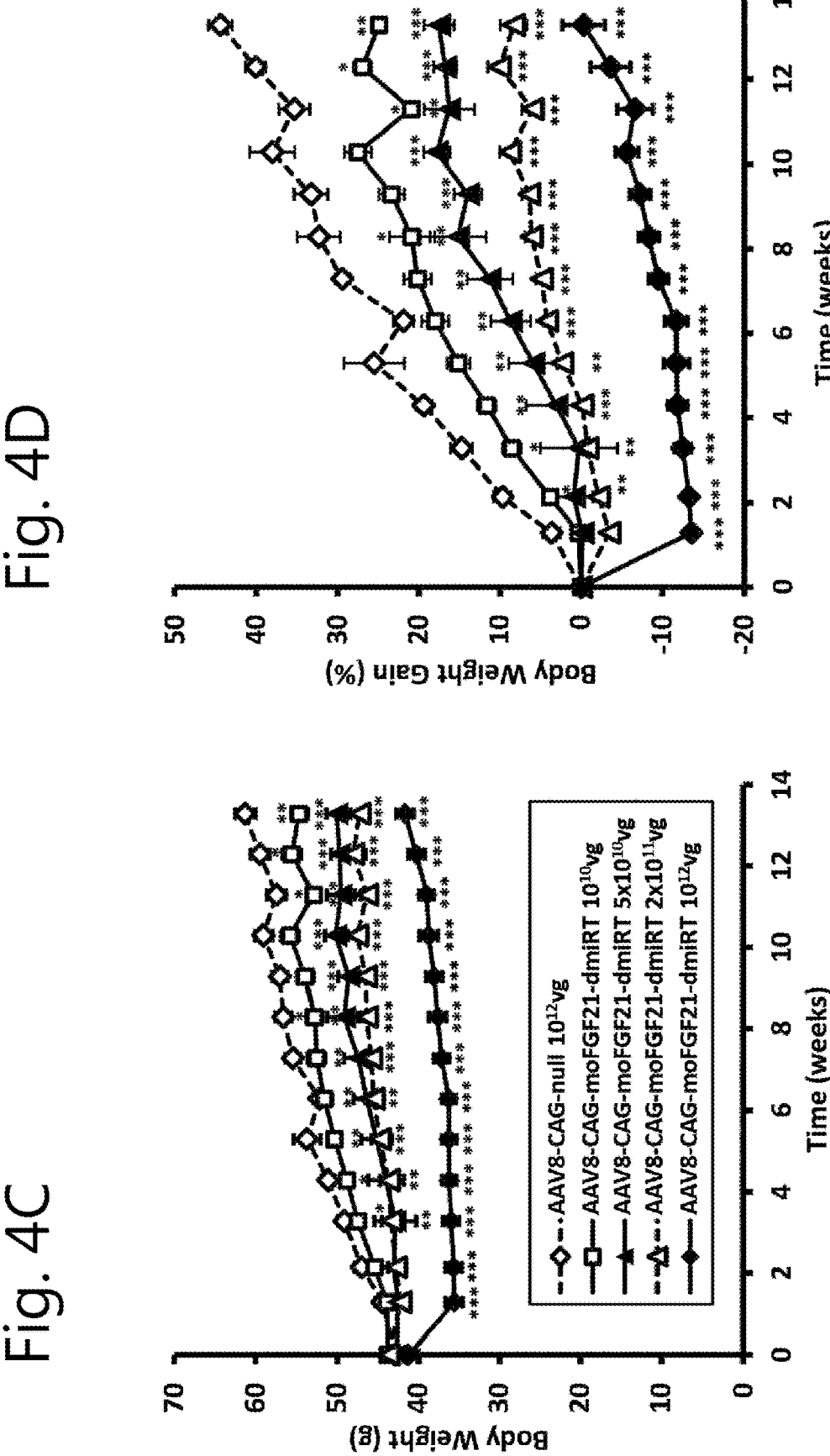
Figure 4E:
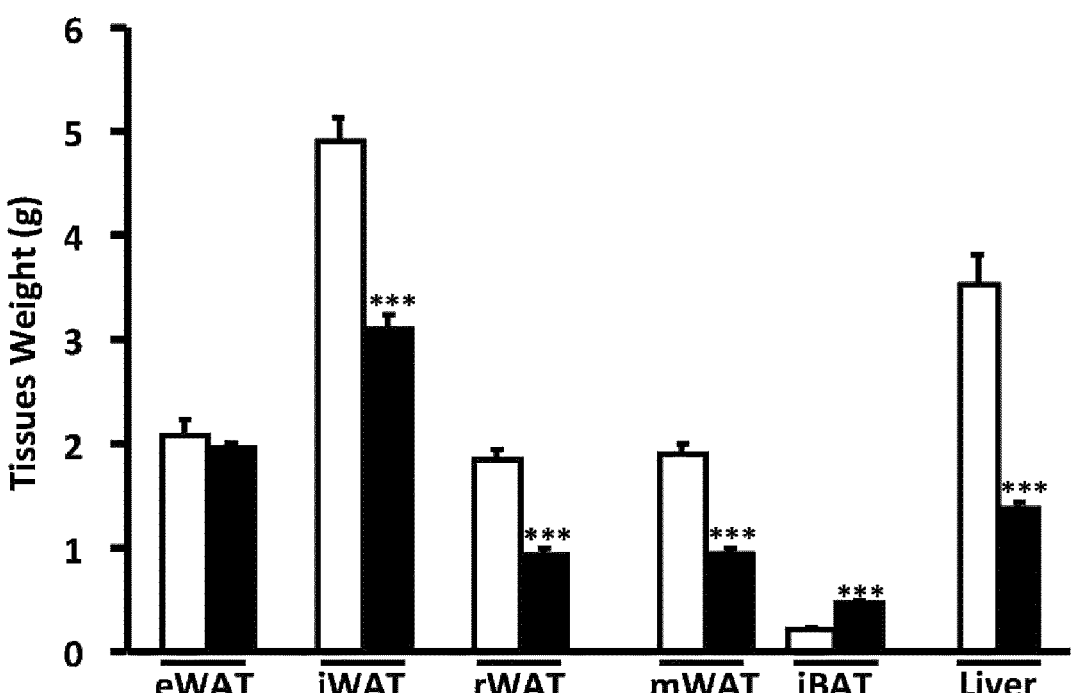

Intra-eWAT administration of AAV8-CAG-moFGF21-doublemiRT vectors mediated specific overexpression of FGF21 in white adipose tissue as well as high secretion of the protein into the bloodstream in a dose-dependent manner (FIGS. 4A and 4B). Specifically, the dose of $10^{12}$ vg of AAV8-CAG-moFGF21-doublemiRT vectors mediated a very robust overexpression of FGF21 in eWAT and iWAT (FIG. 4A) and achieved the highest circulating FGF21 levels (FIG. 4B). In contrast, the lowest dose administered, $10^{10}$ vg of AAV8-CAG-moFGF21-doublemiRT vectors, only produced a very modest overexpression of FGF21 in eWAT (FIG. 4A) and animals treated with this dose showed no differences in the serum FGF21 levels in comparison with AAV8-CAG-null treated animals (FIG. 4B), probably because FGF21 acted in a paracrine-autocrine manner. Accordingly, whereas AAV8-CAG-null-treated animals progressively increased their body weight, animals treated with AAV8-CAG-moFGF21-doublemiRT vectors showed decreased body weight gain proportional to the dose of vectors administered (FIGS. 4C and 4D). Noticeably, animals treated with $10^{12}$ vg of AAV8-CAG-moFGF21-doublemiRT vectors lost approximately 15% of weight during the first two weeks after AAV administration and afterwards increased their body weight until they reached the initial body weight (FIGS. 4C and 4D). Thus, animals administered intra-eWAT with $10^{12}$ vg of AAV8-CAG-moFGF21-doublemiRT vectors showed a 40% difference in total body weight in comparison with AAV8-CAG-null-treated animals at the end of the experiment (FIG. 4D). In agreement, animals treated with $10^{12}$ vg of AAV8-CAG-moFGF21-doublemiRT vectors showed marked decreased adiposity and a 60% reduction of the weight of the liver (FIG. 4E). iBAT weight was increased in this cohort of mice (FIG. 4E), probably due to increased thermogenic activity.

Animals treated with $5 \times 10^{10}$ vg, $2 \times 10^{11}$ vg or $10^{12}$ vg of AAV8-CAG-moFGF21-doublemiRT vectors presented improved insulin sensitivity in comparison with AAV8-CAG-null-treated mice (FIG. 5A). Animals treated with $2 \times 10^{11}$ vg or $10^{12}$ vg of AAV8-CAG-moFGF21-doublemiRT vectors also showed lower insulin circulating levels than ob/ob mice treated with AAV8-CAG-null vectors (FIG. 5B).

Example 3. Reversion of Obesity and Improvement of Glucose Metabolism by Intravenous Administration of AAV-hAAT-moFGF21 Vectors in Ob/Ob Mice We also evaluated the anti-diabetic and anti-obesogenic effects mediated by the increased circulating levels of FGF21 by means of AAV-mediated genetic engineering of the liver in 8-week-old male ob/ob mice. Ob/ob mice were administered intravenously (IV) with $10^{11}$ vg or $5 \times 10^{11}$ vg of AAV8 vectors encoding a murine codon-optimized FGF21 coding sequence under the control of the liver-specific human al-antitrypsin (hAAT) promoter (AAV8-hAAT-moFGF21) (FIG. 6A). As control, ob/ob animals were administered IV with $5 \times 10^{11}$ vg of AAV8-hAAT-null vectors. The hAAT-moFGF21 construct is comprised in SEQ ID NO: 34 and the hAAT-null construct is comprised in SEQ ID NO:33.

Figure 6D:
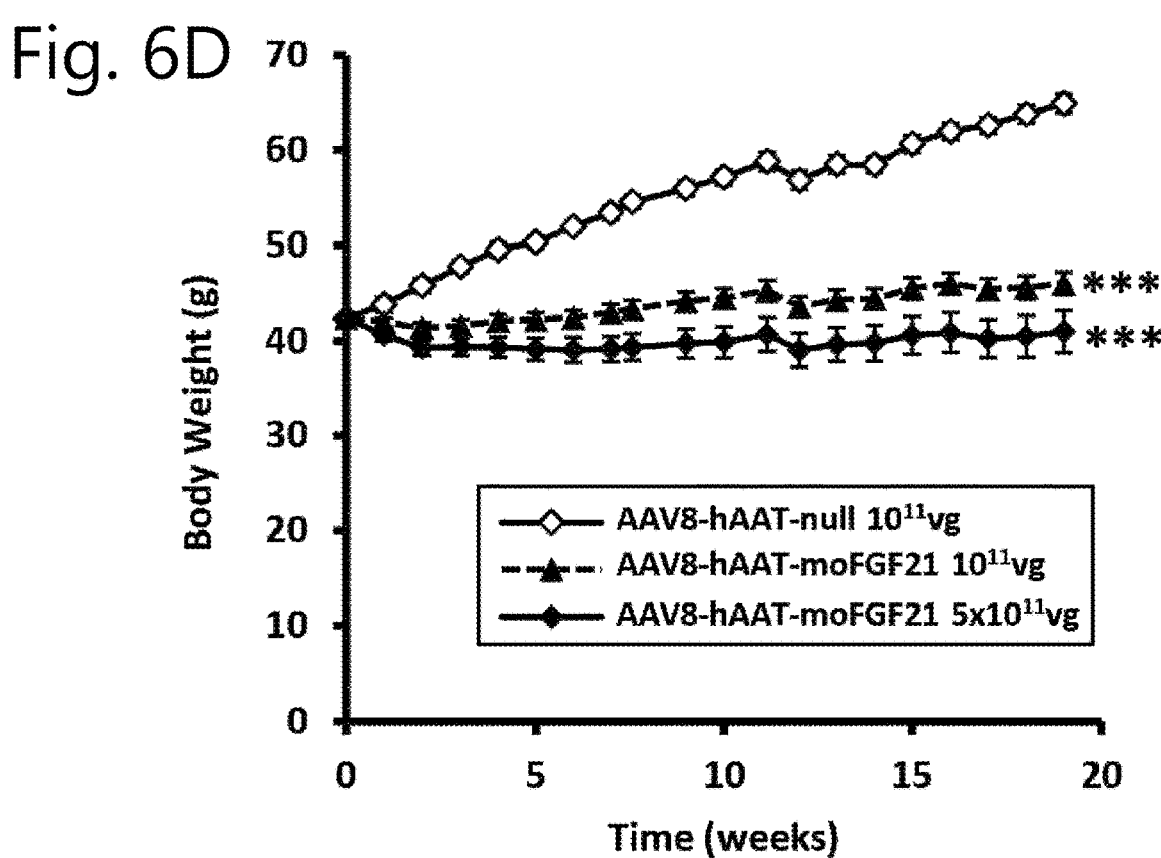
Figure 6E:
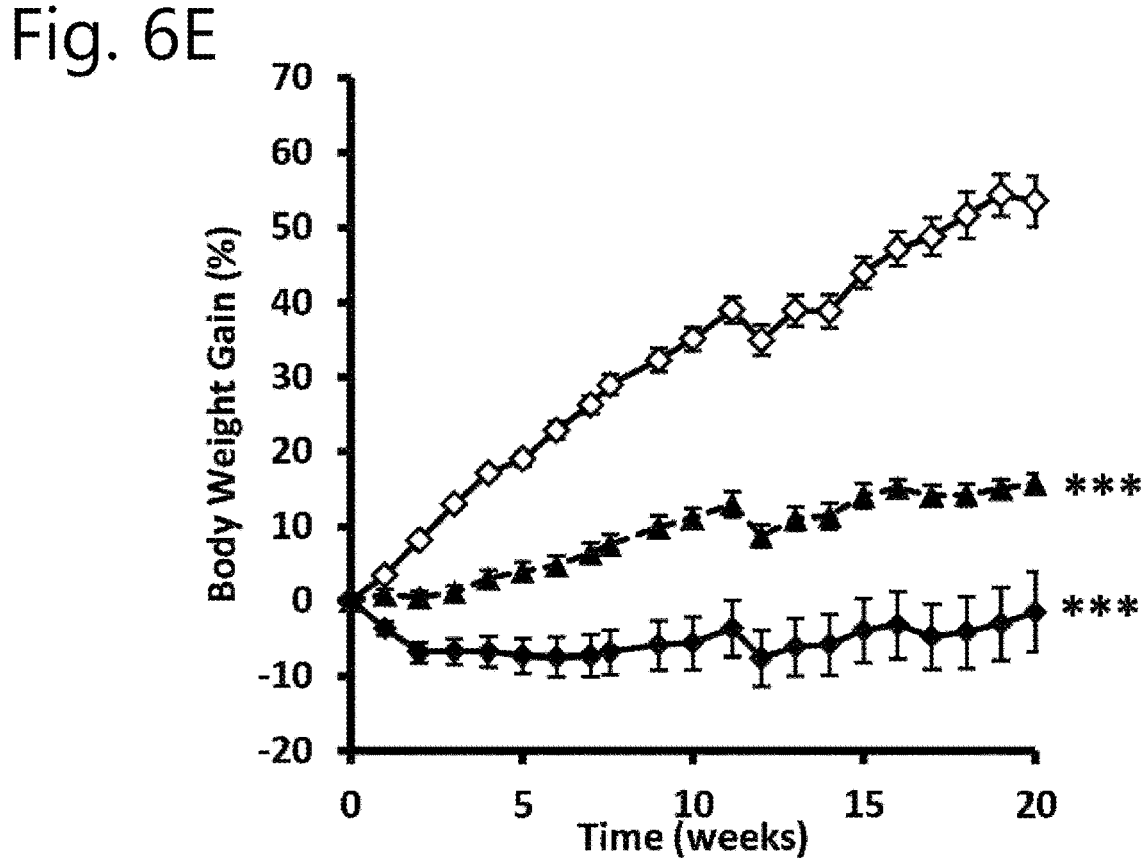
Figure 6F:
Figure 6G:
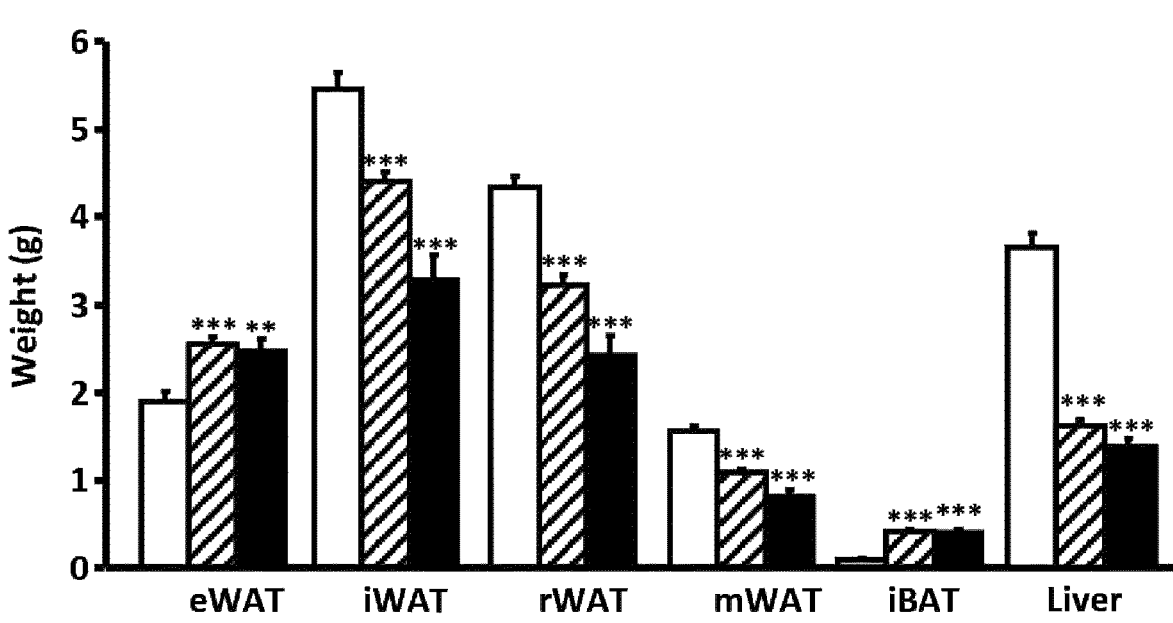

Intravenous administration of AAV8-hAAT-moFGF21 vectors mediated specific overexpression of FGF21 in the liver as well as high secretion of the protein into the bloodstream in a dose-dependent manner (FIGS. 6B and 6C). Specifically, the dose of $5 \times 10^{11}$ vg of AAV8-hAAT-moFGF21 vectors mediated a very robust overexpression of FGF21 in the liver (FIG. 6B) and achieved the highest circulating FGF21 levels (FIG. 6C). The body weight of animals treated with this dose of AAV8-hAAT-moFGF21 vectors decreased approximately 7% during the two first weeks after AAV administration and afterwards slightly increased whereas AAV8-hAAT-null-treated mice progressively put on weight (FIGS. 6D, 6E and 6F). Mice administered with $10^{11}$ vg of AAV8-hAAT-moFGF21 vectors gained markedly much less weight than AAV8-hAAT-null-treated animals (FIGS. 6D, 6E and 6F). Specifically, AAV8-hAAT-null animals showed a 50% increase in their body weight at the end of the experiment in comparison with the 10% weight gain of animals treated with $10^{11}$ vg of AAV8-hAAT-moFGF21 vectors (FIG. 6E). According to their lower body weight, animals overexpressing FGF21 in the liver showed significant decreased adiposity, particularly in those animals treated with the highest dose of vectors, and approximately a 60% reduction of the liver weight (FIG. 6G). iBAT weight was similarly increased in both groups of AAV8-hAAT-moFGF21-treated mice (FIG. 6G), probably due to higher thermogenic activity in these animals in comparison with mice administered with AAV8-hAAT-null vectors.

Figure 6H:
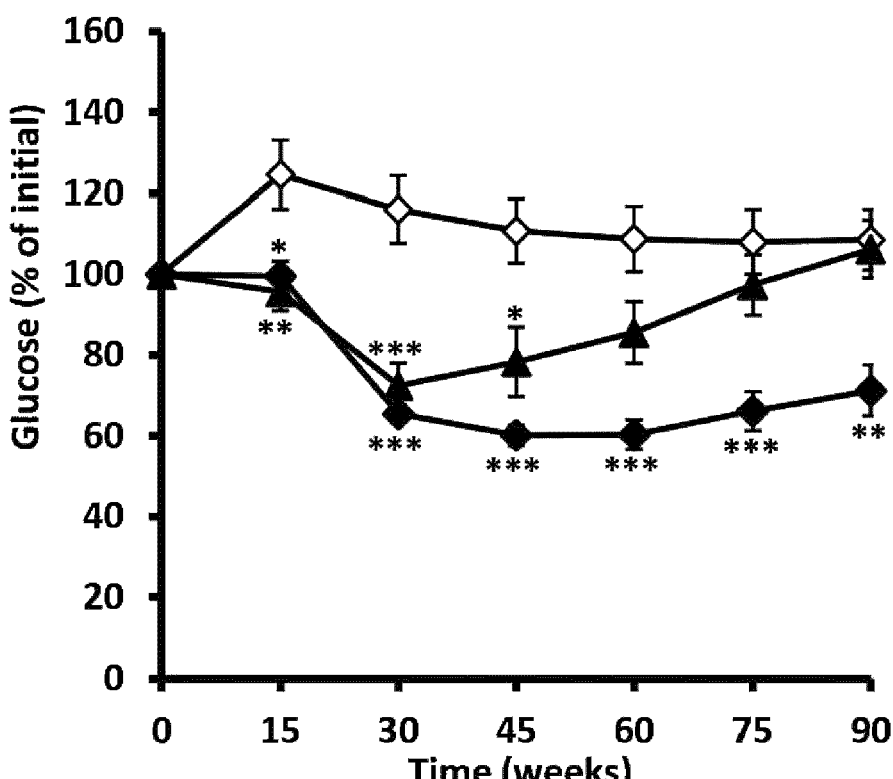
Figure 6I:
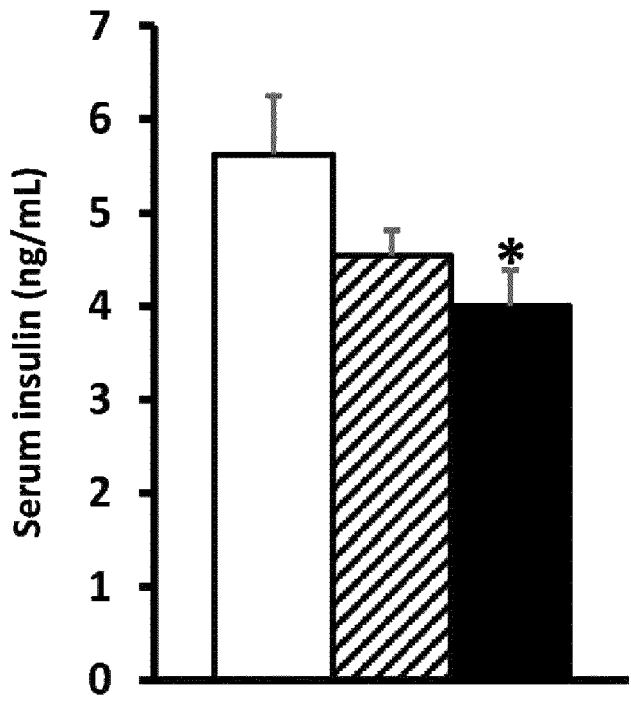

Animals treated with AAV8-hAAT-moFGF21 vectors showed improved insulin sensitivity and decreased insulin circulating levels in comparison with AAV8-hAAT-null-treated mice (FIGS. 6H and 6I)

Example 4. Long-Term Reversion of Obesity and Diabetes by Intravenous Administration of AAV-hAAT-moFGF21 Vectors in HFD-Fed Mice We also evaluated the anti-diabetic and anti-obesogenic effects mediated by the increased circulating levels of FGF21 by means of AAV-mediated genetic engineering of the liver in obese C57Bl6 mice. Nine-week-old male C57Bl6 mice (young adults) were fed a HFD for 9 weeks and then administered IV with $10^{10}$ vg or $5 \times 10^{10}$ vg of AAV8-hAAT-moFGF21 vectors (FIG. 6A). After AAV administration, AAV8-hAAT-moFGF21-treated mice were maintained on HFD for 52 weeks. As controls, $5 \times 10^{10}$ vg of AAV8-hAAT-null were administered IV to chow- and HFD-fed C57Bl6 mice. These two latter cohorts of mice were maintained either on chow diet or HFD thereafter.

Intravenous administration of AAV8-hAAT-moFGF21 vectors in HFD-fed mice mediated high secretion of FGF21 into the bloodstream in a dose-dependent manner (FIG. 7A). No differences in body weight were observed between HFD-fed AAV8-null-treated mice and HFD-fed animals administered with $10^{10}$ vg of AAV8-hAAT-moFGF21 vectors (FIGS. 7B and 7C). However, HFD-fed animals treated with $5 \times 10^{10}$ vg of AAV8-hAAT-moFGF21 vectors initially lost 20% of body weight after AAV administration and then progressively gained weight similarly to chow-fed AAV8-hAAT-null-treated mice (FIGS. 7B and 7C). Noticeably, from week 9 after AAV administration onwards no statistical significant differences were observed in the total body weight and body weight gain between HFD-fed animals administered with $5 \times 10^{10}$ vg of AAV8-hAAT-moFGF21 vectors and chow-fed AAV8-hAAT-null-treated mice (FIGS. 7B and 7C).

The energy expenditure of HFD-fed mice treated with $5 \times 10^{10}$ vg of AAV8-hAAT-moFGF21 vectors during the light and dark cycles was higher than that of chow- and HFD-fed AAV8-hAAT-null mice (FIG. 8A). No differences in energy expenditure were observed among chow- and HFD-fed AAV8-hAAT-null-treated animals and mice administered with $10^{10}$ vg of AAV8-hAAT-moFGF21 vectors (FIG. 8A). Altogether, these data suggest that mice treated with $5 \times 10^{10}$ vg of AAV8-hAAT-moFGF21 have increased thermogenic activity.

Animals treated with $10^{10}$ vg of AAV8-hAAT-moFGF21 vectors presented improved insulin sensitivity in comparison with HFD-fed mice administered with AAV8-hAAT-null vectors and their insulin sensitivity was similar to that of chow-fed mice treated with AAV8-hAAT-null vectors (FIG. 8B). Noticeably, animals administered with $5 \times 10^{10}$ vg of AAV8-hAAT-moFGF21 vectors presented improved insulin sensitivity in comparison with chow-fed mice administered with AAV8-hAAT-null vectors and showed normalized insulin circulating levels (FIGS. 8B and 8C).

Example 5. Reversion of Obesity and Diabetes by Intravenous Administration of AAV-hAAT-moFGF21 Vectors in Old HFD-Fed Mice We also evaluated the anti-diabetic and anti-obesogenic effects of FGF21 in obese old (adults) C57Bl6 mice. Seven and a half-month-old male C57Bl6 mice were fed a HFD for 8 weeks and then administered IV with $10^{10}$ vg, $2\times10^{10}$ vg or $5\times10^{10}$ vg of AAV8-hAAT-moFGF21 vectors (FIG. 6A). After AAV administration, AAV8-hAAT-moFGF21-treated mice were maintained on HFD for 22 weeks. As controls, $5\times10^{10}$ vg of AAV8-hAAT-null were administered IV to chow- and HFD-fed old C57Bl6 mice. These two latter cohorts of mice were maintained either on chow diet or HFD thereafter. Intravenous administration of AAV8-hAAT-moFGF21 vectors in old HFD-fed mice mediated high secretion of FGF21 into the bloodstream in a dose-dependent manner (FIG. 9A).

No differences in body weight were observed between HFD-fed AAV8-null-treated mice and HFD-fed animals administered with $10^{10}$ vg of AAV8-hAAT-moFGF21 vectors (FIGS. 9B and 9C). However, HFD-fed animals treated with either $2\times10^{10}$ vg or $5\times10^{10}$ vg of AAV8-hAAT-moFGF21 vectors initially lost 15 and 20%, respectively, of body weight after AAV administration (FIGS. 9B and 9C). Thereafter, animals treated with $2\times10^{10}$ vg of AAV8-hAAT-moFGF21 vectors progressively gained weight similarly to chow-fed AAV8-hAAT-null-treated mice whereas no significant changes in body weight of animals treated with $5\times10^{10}$ vg of AAV8-hAAT-moFGF21 vectors were observed (FIGS. 9B and 9C). Noticeably from week 3 after AAV administration onwards no statistical significant differences were observed in the total body weight and body weight gain between HFD-fed animals administered with $5\times10^{10}$ vg of AAV8-hAAT-moFGF21 vectors and chow-fed AAV8-hAAT-null-treated mice (FIGS. 9B and 9C).

The energy expenditure of HFD-fed mice treated with $5\times10^{10}$ vg of AAV8-hAAT-moFGF21 vectors during the light and dark cycles was higher than that of chow- and HFD-fed AAV8-hAAT-null mice (FIG. 10A). Animals treated with $2\times10^{10}$ vg of AAV8-hAAT-moFGF21 vectors showed increased energy expenditure during the light cycle and a tendency to increase energy expenditure during the dark cycle (FIG. 10A). Animals treated with $10^{10}$ vg of AAV8-hAAT-moFGF21 vectors showed increased energy expenditure during the dark cycle (FIG. 10A). No differences were observed among chow- and HFD-fed AAV8-hAAT-null-treated animals and mice administered with $10^{10}$ vg of AAV8-hAAT-moFGF21 vectors (FIG. 10A). Altogether, these data suggest that old mice treated with AAV8-hAAT-moFGF21 have increased thermogenic activity.

Animals treated with $10^{10}$ vg or $2\times10^{10}$ vg of AAV8-hAAT-moFGF21 vectors presented improved insulin sensitivity in comparison with HFD-fed mice administered with AAV8-hAAT-null vectors and their insulin sensitivity was similar to that of chow-fed mice treated with AAV8-hAAT-null vectors (FIG. 10B). Noticeably, animals administered with $5\times10^{10}$ vg of AAV8-hAAT-moFGF21 vectors presented improved insulin sensitivity in comparison with chow-fed mice administered with AAV8-hAAT-null vectors (FIG. 10A). Animals treated with $10^{10}$ vg, $2\times10^{10}$ vg or $5\times10^{10}$ vg of AAV8-hAAT-moFGF21 vectors showed lower fasted and fed insulin circulating levels than HFD-fed AAV8-hAAT-null-treated mice (FIG. 10C). Noticeably, no differences in fed insulin circulating levels were observed between old animals administered IV with $2\times10^{10}$ vg or $5\times10^{10}$ vg of AAV8-hAAT-moFGF21 vectors and chow-fed AAV8-hAAT-null-treated mice (FIG. 1C).

Example 6. Evaluation of Weight Loss by Intramuscular Administration of AAV-CMV-moFGF21 Vectors in C57Bl6 Mice We also evaluated the therapeutic potential of increasing FGF21 circulating levels by the AAV-mediated genetic engineering of skeletal muscle in C57Bl6 mice. In order to target the skeletal muscle, the CMV promoter and the AAV1 serotype were selected. Although the CMV promoter is an ubiquitous promoter, its concomitant use together with the AAV1 capsids enables to very efficiently target the skeletal muscle without transducing the liver, as previously published (Mas et al., Diabetes 2006; Callejas et al., Diabetes 2013).

A dose of $3\times10^{11}$ vg of AAV1 vectors encoding a murine codon-optimized FGF21 coding sequence under the control of the ubiquitous CMV promoter (AAV1-CMV-moFGF21) (FIG. 11A) were administered by intramuscular injection in the quadriceps, gastrocnemius, and tibialis cranealis of each hind limb ($5\times10^{10}$ vg/muscle) of 6 to 12-week-old male C57BL6 mice. As control, age-matched C57Bl6 animals were administered intramuscularly in the same muscles with $3\times10^{11}$ vg of AAV1-CMV-null vectors ($5\times10^{10}$ vg/muscle). The CMV-moFGF21 construct is comprised in SEQ ID NO: 36 and the CMV-null construct is comprised in SEQ ID NO:35.

Intramuscular administration of AAV1-CMV-moFGF21 vectors mediated high secretion of FGF21 into the bloodstream (FIG. 11B). Animals treated with AAV1-CMV-moFGF21 vectors showed decreased body weight and body weight gain in comparison with AAV1-CMV-null-treated mice (FIGS. 11C and 11D).

Example 7. Increased Protein Production by Codon-Optimized Human FGF21 Nucleotide Sequences To evaluate if codon-optimization was able to mediate increased FGF21 protein production, HEK293 cells were transfected with plasmids encoding three different codon-optimized human FGF21 nucleotide sequences (SEQ ID NO's: 40-42). As control, non-transfected cells and cells transduced with wild-type hFGF21 coding sequence were used. Expression of the three codon-optimized human FGF21 sequences and the WT human FGF21 sequence was under the control of the hAAT promoter (SEQ ID NO:47). Cells transduced with either codon-optimized human FGF21 version 1 or 3 were able to secrete higher human FGF21 levels into the culture media in comparison with wild-type or codon-optimized FGF21 variant 2 (FIG. 12), thus demonstrating increased FGF21 protein production by codon-optimization of variants 1 and 3.

Example 8. Reversion of Obesity and Diabetes in Mice by Administration of AAV Vectors Encoding Human FGF21 (In Vivo Experiment Proving the Activity of FGF21)

HFD-fed mice are treated with AAV vectors encoding human FGF21. As controls, the same dose of AAV-null vectors is administered to chow- and HFD-fed mice.

To evaluate the capacity of human FGF21 to induce browning of WAT and thermogenic activity of BAT, to increase energy expenditure and to improve glucose and energy metabolism, the following tests are performed:

- measurement of body weight and food and liquid intake weekly
- measurement of body temperature
- measurement of energy expenditure and respiratory quotient by indirect calorimetry
- measurement of glycemia
- evaluation of whole-body glucose disposal by intraperitoneal glucose tolerance test evaluation of insulin sensitivity by intraperitoneal insulin tolerance test analyses in tissue and serum samples, including examination of the level of overexpression of human FGF21 in the targeted tissue and into the bloodstream morphological and histological analysis.

determination of circulating levels of hormones and cytokines determination of serum metabolic parameters, such as free fatty acids, glycerol, triglycerides, cholesterol and ketone bodies evaluation of browning capacity by examination of the presence of beige adipocytes in the inguinal fat pad by immunohistochemistry, and gene expression of classic white, brown and beige adipocyte markers

Example 9: In Vitro Assay for Assessing FGF21 Activity

FGF21 is expected to increase glucose uptake and GLUT1 expression in 3T3-L1 cells (Kharitonenkov, A. et al., 2005. *J Clin. Invest* 115:1627-1635).

Example 10. Reversion of Obesity and Improvement of Glucose Metabolism by Intra-eWAT Administration of AAV8-CAG-moFGF21-dmiRT Vectors in Ob/Ob Mice: Further Observations We further evaluated the anti-diabetic and anti-obesogenic therapeutic potential of the AAV-mediated genetic engineering of adipose tissue with FGF21 in ob/ob mice (see Example 2).

Ob/ob mice that received intra-eWAT injections of AAV8-CAG-moFGF21-dmirT vectors showed a reduction in the size of white adipocytes of the epididymal pad (FIG. 13A). Circulating adiponectin levels also increased with dose (FIG. 14A). eWAT inflammation, evaluated through Mac2 staining, was also reduced as a function of the dose of vector, as did the expression of the macrophage marker F4/80 (FIGS. 14B and C). The liver of ob/ob mice injected with null vectors or the lowest dose of AAV8-CAG-moFGF21-dmirT showed accumulation of lipid droplets in hepatocytes (FIG. 13B). The administration of doses of 5×10^10 vg/mouse or higher of FGF21-encoding vectors completely prevented the development of hepatic steatosis (FIG. 13B), which correlated with the weight of the organ (FIG. 14D) and its total triglyceride and cholesterol content (FIGS. 14E and F). Further evidence that the dose of 5×10^10 vg/mouse represented a threshold for therapeutic efficacy came from the analysis of glycemia and insulinemia. While the dose of 1×10^10 vg/mouse did not modify the levels of blood glucose in the fed state and only partially reduced insulin levels, doses of 5×10^10 vg/mouse and higher completely normalized glycemia and insulinemia (FIGS. 13C and D). Altogether, this example confirms the therapeutic potential of overexpressing FGF21 in adipose tissue.

Example 11. Reversion of Obesity and Improvement of Glucose Metabolism by Intravenous Administration of AAV8-hAAT-moFGF21 Vectors in Ob/Ob Mice: Further Observations We further evaluated the anti-diabetic and anti-obesogenic therapeutic potential of intravenous administration of AAV8-hAAT-moFGF21 vectors in ob/ob mice (see Example 3).

In agreement with their lower body weight, ob/ob animals overexpressing FGF21 in the liver showed significantly decreased size of white adipocytes, particularly those animals treated with 5×10^11 vg (FIG. 15A). This was parallel with a dose-dependent increase in circulating adiponectin levels (FIG. 15B) and decreased WAT inflammation, as evidenced by decreased staining for Mac2 and expression of F4/80 and TNF-α in eWAT (FIG. 16A-C). Noticeably, ob/ob mice treated with 5×10^11 vg showed a remarkable reduction in "crown-like" structures in eWAT (FIG. 16A).

While 7-month-old ob/ob mice showed marked hepatic steatosis, the liver of FGF21-treated ob/ob mice did not show accumulation of lipids in hepatocytes (FIG. 15C). This agreed with a 60% reduction in the weight of this organ (FIGS. 16D and E) as well as with a marked reduction in the total liver triglyceride and cholesterol content (FIGS. 16F and G) in ob/ob mice receiving therapeutic vectors. Ob/ob animals treated with both doses of AAV8-hAAT-moFGF21 also showed decreased fed glycemia, and their insulinemia in the fed state was reduced by ~70% (FIGS. 15D and E).

We evaluated whether the decrease in circulating glucose levels observed in ob/ob mice after AAV8-hAAT-moFGF21 treatment resulted from suppression of hepatic gluconeogenesis by measuring the expression by qPCR of phosphoenolpyruvate carboxykinase (PEPCK) and glucose-6-phosphatase (G6Pase). No changes in the expression of these enzymes were observed in the liver of AAV8-hAAT-moFGF21-treated ob/ob mice, except for the animals treated with 1×10^11 vg of AAV8-hAAT-moFGF21 that showed increased PEPCK expression (FIGS. 17A and B). These results suggested that AAV-mediated long-term expression of FGF21 in the liver, and the subsequent increase of circulating FGF21, did not lower glucose by inhibiting hepatic glucose production.

The glucose-lowering effects of FGF21 have also been attributed to increased glucose uptake by adipocytes and enhanced energy expenditure (Xu J. et al., 2009. *AJP Endocrinol. Metab.* 297:E1105-E1114; Ding X. et al., 2012. *Cell Metab.* 16:387-393; Camacho R. C. et al., 2013. *Eur. J. Pharmacol.* 715:41-45; Emanuelli B. et al., 2014. *Clin. Invest.* 124:515-527; Kharitonenkov A. et al., 2005. *Endocrinology* 148: 774-781; Hondares E. et al., 2010. *Cell Metab.* 11:206-212; Samms R. J. et al., 2015. *Cell Rep.* 11:991-999). Thus, we assessed in different pads of adipose tissue (iWAT, eWAT and iBAT) the expression of key components of the glucose uptake machinery by qPCR, such as the glucose transporters Glut1 and Glut4, the glucose phosphorylating enzymes hexokinase I and II (HKI and HKI), and UCP1 in the case of iBAT. In AAV8-FGF21 treated ob/ob mice, the expression of Glut1 was increased in iWAT and iBAT (FIG. 17C), and that of Glut4 was increased in eWAT, iWAT and iBAT (FIG. 17D). HKI and HKII were upregulated only in iBAT (FIGS. 17E and F). Moreover, UCP1 expression was increased in the iBAT of ob/ob mice treated with the high dose of AAV8-hAAT-moFGF21 vectors (FIG. 17G). Altogether, these results suggest that the long-term amelioration of glycemia observed in ob/ob mice following treatment with AAV8-hAAT-moFGF21 vectors probably results from increased glucose uptake by white and brown adipocytes and enhanced thermogenesis in iBAT.

Example 12. Long-Term Reversion of Obesity and Diabetes by Intravenous Administration of AAV8-hAAT-moFGF21 Vectors in HFD-Fed Mice and HFD-Fed Old Mice: Decreased Tissue Weight and Stable Expression Up to 1 Year Representative images of animals belonging to all experimental groups of the studies performed in young adults or in adults (see Examples 4 and 5) are shown in FIG. 19A-B. The reversion of obesity by AAV8-hAAT-moFGF21 treatment was parallel to a dose-dependent decrease in the weight of the main white adipose tissue (WAT) depots, such as the epididymal (eWAT), inguinal (iWAT) and retroperitoneal (rWAT) fat pads, both in animals treated as young adults or as adults (FIG. 18A and FIG. 19C). The HFD-induced increase in the weight of the liver was completely normalized by FGF21 gene transfer at the highest doses of vector used, whereas the weight of the quadriceps was unchanged by the diet or AAV delivery (FIG. 18A and FIG. 19D).

AAV8-hAAT-moFGF21-treated mice of both ages showed specific overexpression of codon-optimized FGF21 in the liver (FIG. 19E), which resulted in secretion of FGF21 into the bloodstream in a dose-dependent manner in both groups of mice, with levels remaining stable for up to 1 year after a single administration of the vector (FIG. 18B).

Example 13. Long-Term Reversion of Obesity and Diabetes by Intravenous Administration of AAV8-hAAT-moFGF21 Vectors in HFD-Fed Mice and HFD-Fed Old Mice: Increased Locomotor Activity and Investigating the Thermogenic Mechanism Increased energy expenditure (see Examples 4 and 5) was also seen in animals treated as young adults 10 months after AAV8-hAAT-moFGF21 delivery (FIG. 21A).

This observation was in agreement with AAV8-hAAT-moFGF21-mediated effects on locomotor activity. In contrast to the hypoactivity observed in the open field test in the animals fed a HFD that received AAV8-null vectors, mice treated with $5\times10^{10}$ vg AAV8-hAAT-moFGF21 as young adults showed the same degree of spontaneous locomotor activity than chow-fed, null-injected animals. As shown in FIG. 20A, 1 year after AAV8-hAAT-moFGF21 delivery, treated animals travelled more distance, rested less time, and spent more time doing slow and fast movements than untreated HFD-fed controls.

Given that changes in energy expenditure may reflect changes in thermogenesis, we evaluated the degree of activation of the brown adipose tissue (BAT). Both mice treated as young adults or adults with $5\times10^{10}$ vg AAV8-hAAT-moFGF21 showed decreased lipid deposition in iBAT (FIG. 20B). The content of UCP1 protein in BAT was increased in a dose-dependent manner in mice treated with AAV8-hAAT-moFGF21 vectors as young adults (FIG. 20C), consistent with an increase in non-shivering thermogenesis induced by FGF21 gene transfer to the liver.

The browning of the subcutaneous WAT, characterized by the appearance of beige adipocytes, is also associated with increases in energy expenditure (Harms & Seale, 2013). To evaluate if browning was accountable for the enhancement of energy expenditure observed following AAV8-hAAT-moFGF21 treatment, histological evaluation of iWAT was performed. In agreement with the decreased weight of this pad (FIG. 18A), the adipocytes of HFD-fed AAV8-hAAT-moFGF21-treated animals were smaller than those of HFD-fed null-injected animals (FIG. 20D). Treatment with AAV8-hAAT-moFGF21 vectors, nevertheless, did not result in increased detection of multilocular beige adipocytes in iWAT at any of the doses tested, either in animals treated as young adults or adults (FIG. 20D). Accordingly, there were no statistically significant differences in the levels of UCP1 protein in iWAT between the HFD-fed groups (FIG. 21B).

The creatine-driven substrate cycle and sarco/endoplasmic reticulum Ca2+-ATPase 2b (Serca2b)-mediated calcium cycling can increase thermogenesis in iWAT independently of UCP1 (Kazak L. et al., 2015. Cell 163:643-655; Ikeda K. et al., 2017. Nat. Med. 23:1454-1465). Higher levels of expression of phosphatase orphan 1 (Phosphol), an enzyme involved in the creatine-driven substrate cycle, were observed in iWAT of HFD-fed mice treated with $5\times10^{10}$ vg of AAV8-hAAT-moFGF21 when compared with age-matched, chow- and HFD-fed control groups (FIG. 20E), suggesting that the activity of the creatine-driven cycle was probably increased as a result of FGF21 gene transfer. Regarding the calcium cycling-dependent thermogenic mechanism, no differences in the expression levels of Serca2b were detected in the iWAT of animals treated with AAV8-hAAT-moFGF21 vectors when compared with chow- or HFD-fed null-treated animals (FIG. 21C). On the other hand, the iWAT expression of ryanodine receptor 2 (RyR2), another enzyme involved in the same cycle, was increased by HFD-feeding in both null- and AAV8-hAAT-moFGF21-treated mice (FIG. 21C). Altogether, these results suggest that the calcium cycling-dependent thermogenic mechanism is not involved in the improvement of whole-body energy homeostasis observed after AAV-FGF21 treatment.

Example 14. Long-Term Reversion of Obesity and Diabetes by Intravenous Administration of AAV8-hAAT-moFGF21 Vectors in HFD-Fed Mice and HFD-Fed Old Mice: Glucagon Levels, Islet Hyperplasia and Glucose Tolerance Moreover, HFD-fed animals treated as young adults with AAV8-hAAT-moFGF21 vectors showed decreased circulating levels of glucagon compared with HFD-fed null-treated mice (FIG. 22A).

While AAV8-null-treated mice developed islet hyperplasia as a consequence of HFD feeding, the β-cell mass of animals treated with AAV8-hAAT-FGF21 vectors (at the doses of $2\times10^{10}$ or $5\times10^{10}$ vg/mouse) was similar to that of control mice fed a chow diet (FIGS. 22B and C). Double immunostaining for insulin and glucagon of pancreatic sections from HFD-fed AAV8-hAAT-moFGF21-treated mice showed normal distribution of α and β cells in the islets of these animals, with localization of glucagon-expressing cells in the periphery of the islet and of insulin-expressing cells in the core (FIG. 22D).

To evaluate glucose tolerance in FGF21-treated mice, an intraperitoneal glucose tolerance test (GTT) (2 g glucose/kg bw) was performed 10 weeks after AAV administration. HFD-fed animals injected with either null or FGF21-encoding vectors at a dose of $1\times10^{10}$ vg/mouse were glucose intolerant and showed markedly increased circulating levels of insulin during the GTT (FIGS. 23A and B). In contrast, animals treated with $5\times10^{10}$ vg/mouse of AAV8-hAAT-moFGF21 showed improved glucose clearance when compared to chow-fed control mice (FIG. 23A). Insulin levels were indistinguishable between these two experimental groups (FIG. 23B). These results further confirmed improved insulin sensitivity in HFD-fed mice treated with $5\times10^{10}$ vg/mouse of AAV8-hAAT-moFGF21.

Example 15. Reversion of HFD-Associated WAT Hypertrophy and Inflammation by Intravenous Administration of AAV8-hAAT-moFGF21 Vectors HFD-feeding induces an increase in the size of WAT adipocytes (Sattar N. & Gill J. M. R., 2014. BMC Med. 12:123). Administration of FGF21-encoding vectors counteracted this increase (FIG. 24A). Morphometric analysis of WAT revealed that the area of white adipocytes of animals treated as young adults with $1\times10^{10}$ or $5\times10^{10}$ vg of vector, and of mice treated as adults with $2\times10^{10}$ or $5\times10^{10}$ vg of vector was similar to that of animals fed a chow diet (FIG. 24B). In both groups of FGF21-treated animals, there was a redistribution of the size of adipocytes, with a greater proportion of smaller adipocytes (FIG. 25A). In agreement with the decrease in adiposity and reversal of WAT hypertrophy, adiponectin and leptin levels were also normalized in animals treated with highest doses of AAV8-hAAT-moFGF21 vectors, irrespective of the age of initiation of the treatment (FIGS. 24C and D).

Obesity also causes the inflammation of WAT (Hafer G. R. et al., 2008. Eur. Heart J. 29:2959-2571). Thus, we analyzed inflammation in this tissue through immunostaining for the macrophage-specific marker Mac2 and the expression of pro-inflammatory molecules. While HFD-fed mice showed increased presence of macrophages, revealed as "crown-like" structures, in the eWAT, animals treated as young adults or adults with $5\times10^{10}$ vg AAV8-hAAT-moFGF2l had no sign of macrophage infiltration (FIG. 24E and FIG. 25B). This was parallel to the normalization in the expression of the macrophage markers F480 and CD68 and of the pro-inflammatory cytokines TNF$\alpha$ and IL-1$\beta$ (FIG. 24F-H and FIG. 25C-E), indicating that FGF21 expression counteracted the inflammation of WAT associated to obesity.

Example 16. Reversal of Hepatic Steatosis, Inflammation and Fibrosis by Intravenous Administration of AAV8-hAAT-moFGF21 Vectors Histological analysis of the liver showed that all null-treated animals fed a HFD had marked hepatic steatosis at the time of sacrifice (FIG. 26A-D). In contrast, HFD-fed mice receiving $5\times10^{10}$ vg AAV8-hAAT-moFGF21 as young adults or as adults evidenced reversal of this pathological deposition of lipids (FIG. 26A). These histological findings were parallel to a marked reduction in the total liver triglyceride and cholesterol content of $5\times10^{10}$ vg AAV8-hAAT-moFGF21-treated animals (FIGS. 26B and C). In addition, animals fed a HFD and treated with $5\times10^{10}$ vg AAV8-hAAT-moFGF21 vectors when young adults or adults showed no sign of hepatic inflammation, as evidenced by the lack of staining for Mac2, which revealed increased presence of macrophages in the livers of null-treated HFD-fed mice (FIG. 26D). Finally, FGF21 gene transfer to the liver reversed hepatic fibrosis. While collagen fibers were readily detectable following PicroSirius Red staining or Masson's trichrome staining of liver sections from animals fed a HFD and injected with control null vectors, they were undetectable in the livers of AAV8-hAAT-moFGF21 treated mice (FIG. 28A and FIG. 27). These mice also showed markedly reduced hepatic expression of collagen 1 (FIGS. 28B and C). Altogether these findings indicated that AAV8-hAAT-moFGF21 treatment protected from the development of HFD-induced non-alcoholic steatohepatitis (NASH).

Example 17. Long-Term Safety of Liver-Directed AAV-FGF21 Treatment

Pharmacological treatment with FGF21 or transgenic overexpression have been associated with perturbation of bone homeostasis through increased bone resorption, which could cause bone loss (Wei W. et al., 2012. Proc. Natl. Acad. Sci. 109:3143-3148; Wang X. et al., 2015. Cell Metab. 22:811-824; Charoenphandhu N. et al., 2017. J. Bone Miner. Metab. 35:142-149; Talukdar S. et al., 2016. Cell Metab.

23:427-440; Kim A. M. et al., 2017. Diabetes, Obes. Metab). Given the therapeutic potential of AAV8-hAAT-moFGF21 for the treatment of obesity and diabetes, we evaluated the long-term effects of gene transfer on the bones of the animals treated with the highest dose of vector. At the time of sacrifice (~16.5 months of age), the naso-anal length and the tibial length were normal in the animals that were administered with AAV8-hAAT-moFGF21 vectors at 9 or 29 weeks of age (FIGS. 29A and B). We then examined bone structure by micro-computed tomography ($\mu$CT). Analysis of the proximal epiphysis of the tibia revealed no significant differences in the trabecular and cortical bone of mice fed a HFD and administered with $5\times10^{10}$ vg AAV8-hAAT-moFGF21 in comparison with age-matched mice treated with null vectors. Specifically, no differences were documented in the bone mineral density (BMD) (FIG. 29C), bone mineral content (BMC) (FIG. 29D), bone volume (BV) (FIG. 29E), bone volume/tissue volume ratio (BV/TV) (FIG. 29F), bone surface/bone volume ratio (BS/BV) (FIG. 29G), trabecular number (Tb.N) (FIG. 29H), trabecular thickness (Tb.Th) (FIG. 29I) or trabecular separation (Tb.Sp) (FIG. 29J). Similarly, the analysis of the compact bone at the tibial diaphysis showed no differences in the BMC, BMD, BV, BV/TV or BS/BV between the HFD-fed null-injected or FGF21-treated groups (FIG. 29K-O).

The pathological effects of FGF21 have been reported to be mediated, at least in part, by increased production of Insulin-like Growth Factor Binding Protein 1 (IGFPB1) by the liver (Wang X. et al., 2015. Cell Metab. 22:811-824). In agreement with the lack of bone alterations, high-dose AAV8-hAAT-moFGF21 treatment did not lead to an increase in the levels of circulating IGFBP1 protein in animals treated 12 (young adults) or 6 (adults) months earlier when compared to null-injected HFD-fed mice (FIG. 29P). Circulating IGF1 levels were also normal in all experimental groups (FIG. 29Q). Altogether these results support the safety for bone tissue of AAV-mediated FGF21 gene transfer to the liver.

Example 18. Prevention of HFD-Induced Liver Tumours by Intravenous Administration of AAV8-hAAT-moFGF21 Vectors Long-term feeding (>60 weeks) with a HFD has been associated with increased incidence of liver neoplasms in C57BL/6J mice (Hill-Baskin A. E. et al., 2009. Hum. Mol. Genet. 18:2975-2988; Nakagawa H., 2015. World J. Hepatol. 7:2110). In our study in animals that initiated the HFD as young adults and maintained it for 60 weeks we found liver tumours in 66.7% (6/9) of animals injected with null-vectors. Animals treated with AAV8-hAAT-moFGF21 vectors were protected from HFD-induced development of liver neoplasms: 0% (0/8) of animals treated with the $5\times10^{10}$ vg of FGF21-encoding vectors showed tumours, and the incidence was 40% (4/10) in the cohort treated with the lowest dose ($1\times10^{10}$ vg). None (0/11) of the chow-fed mice developed tumours in the same period of time (Table 1).

TABLE 1

| Liver tumour incidence in young adults. | | |
| --- | --- | --- |
| Group | Hepatocarcinoma | Hepatocarcinoma (%) |
| Chow AAV8-null | 0/11 | 0% |
| HFD AAV8-null | 6/9 | 66.7% |

TABLE 1-continued

Liver tumour incidence in young adults.

| Group | Hepatocarcinoma | Hepatocarcinoma (%) |
| --- | --- | --- |
| HFD AAV8-FGF21 ($1 \times 10^{10}$ vg/mouse) | 4/10 | 40% |
| HFD AAV8-FGF21 ($5 \times 10^{10}$ vg/mouse) | 0/8 | 0% |

Example 19. Amelioration of STZ-Induced Hyperglycemia by Liver-Specific AAV8-Mediated FGF21 Overexpression Material and Methods Animals We used 9-week-old male C57bl6 mice. Mice had free access to a standard diet and were kept under a 12 h light-dark cycle (lights on at 08:00 hours). For diabetes induction, mice received five intraperitoneal injections, on consecutive days, of streptozotocin (50 mg/kg) dissolved in 0.1 mol/l citrate buffer (pH 4.5). Blood glucose levels were assessed using an analyser (Glucometer Elite; Bayer, Leverkusen, Germany). Animal care and experimental procedures were approved by the Ethics Committee in Animal and Human Experimentation of the Universitat Autonoma de Barcelona.

In Vivo Administration of AAV Vectors

For systemic administration, AAV vectors were diluted in 200 μl of 0.001% F68 Pluronic® (Gibco) in PBS and injected via the tail vein.

Results

In order to test the protective potential against type 1 diabetes of AAV-derived FGF21, $5 \times 10^{10}$ vg or $2 \times 10^{11}$ vg of AAV8 vectors encoding a codon-optimized murine FGF21 coding sequence under the control of the hAAT promoter (AAV8-hAAT-moFGF21) were administered IV to male 9-week-old C57Bl6 mice. Control mice received $2 \times 10^{11}$ vg of AAV8-hAAT-Null vectors. Two weeks post-AAV administration, all animals were treated with streptozotocin (STZ) (5 doses of 50 mg/kg; 1 dose per day) to trigger the diabetic process.

Analysis of the blood glucose levels revealed that animals treated with AAV8 vectors encoding moFGF21 displayed lower circulating glucose levels than C57Bl6 mice treated with AAV8-hAAT-Null vectors (FIG. 30).

Example 20. Extension of Healthy Lifespan by Intramuscular Administration of AAV-CMV-moFGF21 Vectors in C57Bl6 Mice Due to the Prevention of Weight Gain and Insulin Resistance Associated with Aging Skeletal muscle (Skm) is a readily accessible tissue and has been used to produce secretable therapeutic proteins (Haurigot V. et al., 2010. J. Clin. Invest. 123:3254-3271; Callejas D. et al., 2013. Diabetes 62:1718-1729; Jaen M. L. et al., 2017. Mol. Ther. Methods Clin. Dev. 6:1-7). To explore if the Skm could represent a viable source of circulating FGF21, AAV vectors of serotype 1, which show a high tropism for Skm (Chao L. et al., 2000. J. Clin. Invest. 106: 1221-1228; Wu Z. et al., 2006. J. Virol. 80:9093-9103; Lisowski L. et al., 2015. Curr. Opin. Pharmacol. 24:59-67), carrying murine optimized FGF21 under the control of the CMV promoter were used (AAV1-CMV-moFGF21). Vectors were injected at a dose of $5 \times 10^{10}$ vg/muscle to the quadriceps, gastrocnemius and tibialis cranialis of both legs (total dose, $3 \times 10^{11}$ vg/mouse) of 8-week-old C57Bl6 mice. Control animals were injected with AAV1-CM V-Null vectors at the same dose. The use of healthy mice fed a standard diet further allowed us to evaluate the long-term safety of FGF21 gene therapy.

Eleven-month-old animals injected with FGF21-encoding vectors at 8 weeks of age showed a marked increase in circulating FGF21 (FIG. 31A), which was parallel to high levels of expression of vector-derived FGF21 in the 3 injected muscles (FIG. 31B). In agreement with previous reports, this combination of vector serotype, promoter and route of administration did not lead to expression of the transgene in the liver (FIG. 31B).

At the end of the ~10-month follow-up period, mice injected intramuscularly with AAV1-CMV-moFGF21 maintained the body weight they had at the initiation of the study and were ~38% slimmer than controls, which steady increased their weight as animals aged (FIG. 31C). While the weight of the muscles was barely affected by FGF21 gene transfer, the weight of the white and brown depots as well as the liver were considerably reduced (FIG. 31D). Indeed, the weight of the WAT pads analysed was reduced by >50% (FIG. 31D). Moreover, mice treated with AAV1-CMV-moFGF21 showed a marked reduction in the hepatic total triglyceride content (FIG. 31E). No changes in hepatic cholesterol levels were observed (FIG. 31F). As opposed to null-injected animals, animals treated with AAV1-CMV-moFGF21 showed normoglycemia (data not shown) and reduced insulinemia when they were approximately 1-year-old (FIG. 31G). Accordingly, FGF21-treated mice showed markedly improved insulin sensitivity at the end of the study (FIG. 31H). Altogether, this study demonstrates that administration of AAV vectors that leads to therapeutically-relevant levels of circulating FGF21 is safe in the long-term in healthy, and may be used to reverse the increase in body weight and insulin resistance associated to aging.

Example 21. Reversion of Obesity and Diabetes by Intramuscular Administration of AAV1-CMV-moFGF21 Vectors in HFD-Fed C57Bl6 Mice We next evaluated whether im administration of AAV1-CMV-moFGF21 vectors was also able to reverse obesity and insulin resistance. To this end, two-month-old C57Bl6 mice were fed either a chow or a HFD for 12 weeks. During these first 3 months of follow-up, while the weight of chow-fed animals increased by 20%, animals fed a HFD became obese (95% body weight gain) (FIGS. 32A and B). Vectors were then injected at a dose of $5 \times 10^{10}$ vg/muscle to the quadriceps, gastrocnemius and tibialis cranialis of both legs (total dose, $3 \times 10^{11}$ vg/mouse) of obese C57Bl6 mice. As controls, another cohort of obese mice and the cohort of chow-fed mice received $3 \times 10^{11}$ vg of non-coding null vectors (AAV1-CMV-null). Following AAV delivery, mice were maintained on chow or HFD feeding. Animals treated with AAV1-CMV-moFGF21 experienced progressive loss of body weight (FIGS. 32A and B). The reversion of obesity by AAV1-CMV-FGF21 treatment was parallel to an increase in the circulating levels of FGF21 (FIG. 32C).

Null-treated mice fed a HFD showed normal fed glycemia (FIG. 32D), but were hyperinsulinemic (FIG. 32E), suggesting that these mice had developed insulin resistance. In contrast, HFD-fed mice treated with AAV1-CMV-moFGF21 were, by the end of the study, normoglycemic and normoinsulinemic (FIGS. 32D and E). Moreover, animals administered with AAV1-CMV-moFGF21 showed greater insulin sensitivity than their HFD-fed controls (FIG. 32F).

Example 22. Increased FGF21 Circulating Levels by Codon-Optimized Human FGF21 Nucleotide Sequences To evaluate if codon-optimization was able to mediate increased FGF21 circulating levels, 8-week-old male C57Bl6 mice were hydrodynamically injected with plasmids encoding three different codon-optimized human FGF21 nucleotide sequences (SEQ ID NO's: 40-42) under the control of the hAAT promoter. As control, non-treated mice and mice hydrodynamically injected with a plasmid encoding wild-type hFGF21 coding sequence under the control of the hAAT promoter were used.

Material and Methods

In vivo delivery of plasmids into mice by hydrodynamic tail vein injection Plasmid DNA was diluted in saline in a volume (ml) equal to ~10% of the animals' average body weight (grams) and was manually injected into the lateral tail vein in less tan 5 seconds. Before the injection, the animals were put under a 250 W infrared heat lamp (Philips) for a few minutes to dilate the blood vessels and facilitate viewing and easier access to the tail vein. A plastic restrainer (Harvard Apparatus) was used to secure the animal for injection. No anaesthesia was used as it is not necessary so long as an appropriate restraining device is employed. We used 26G 3/8 in. gauge hypodermic needles (BD), the largest feasible needle gauge that fit snugly into the access vein, to inject the animals.

Results

Mice treated with either codon-optimized human FGF21 version 2 or 3 were able to secrete higher human FGF21 levels into the circulation in comparison with wild-type or codon-optimized FGF21 variant 1 (FIG. 33, thus demonstrating increased FGF21 protein production by codon-optimization of variants 2 and 3.

Example 23. In Vitro and In Vivo Increased FGF21 Expression and Protein Production Levels by hAAT-moFGF21, CAG-moFGF21-doublemiRT and CMV-moFGF21 Expression Cassettes Material and Methods In vivo delivery of plasmids into mice by hydrodynamic tail vein injection Plasmid DNA was diluted in saline in a volume (ml) equal to −10% of the animals' average body weight (grams) and was manually injected into the lateral tail vein in less tan 5 seconds. Before the injection, the animals were put under a 250 W infrared heat lamp (Philips) for a few minutes to dilate the blood vessels and facilitate viewing and easier access to the tail vein. A plastic restrainer (Harvard Apparatus) was used to secure the animal for injection. No anaesthesia was used as it is not necessary so long as an appropriate restraining device is employed. We used 26 G ⅜ in. gauge hypodermic needles (BD), the largest feasible needle gauge that fit snugly into the access vein, to inject the animals.

Results

In Vitro

HEK293 cells were transfected with plasmids encoding the WT murine FGF21 coding sequence under the control of the elongation factor 1a (EF1a) promoter (EF1a-mFGF21) (Zhang et al., EBioMedicine 15 (2017) 173-183) (SEQ ID NO:57) or a codon-optimized murine FGF21 coding sequence under the control of the CMV promoter (CMV-moFGF21) or the CAG promoter in conjunction with four tandem repeats of the miRT122a sequence and four tandems repeats of the miRT1 sequence (CAG-moFGF21-doublemiRT). As control, non-transfected cells were used. HEK293 cells transduced with CAG-moFGF21-doublemiRT expressed higher levels of FGF21 in comparison with cells transduced with EF1a-mFGF21 or non-transduced cells (FIG. 34A). Moreover, HEK293 cells transduced with CAG-moFGF21-doublemiRT also showed higher intracellular FGF21 protein content and higher FGF21 protein levels in the culture medium (FIGS. 34B and C). Although HEK293 cells transduced with EF1a-mFGF21 or CMV-moFGF21 expressed similar levels of FGF21 (FIG. 34A), HEK293 cells transduced with CMV-moFGF21 showed higher intracellular FGF21 protein content and higher FGF21 protein levels in the culture medium (FIGS. 34B and C).

C2C12 cells were transfected with plasmids encoding the WT murine FGF21 coding sequence under the control of the EF1a promoter (EF1a-mFGF21) (Zhang et al., EBioMedicine 15 (2017) 173-183) or a codon-optimized murine FGF21 coding sequence under the control of the CMV promoter (CMV-moFGF21). As control, non-transfected cells were used. C2C12 cells transduced with CMV-moFGF21 expressed higher levels of FGF21 in comparison with cells transduced with EF1a-mFGF21 or non-transduced cells (FIG. 34D).

HepG2 cells were transfected with plasmids encoding the WT murine FGF21 coding sequence under the control of the EF1a promoter (EF1a-mFGF21) (Zhang et al., EBioMedicine 15 (2017) 173-183) or a codon-optimized murine FGF21 coding sequence under the control of the hAAT promoter (hAAT-moFGF21). As control, non-transfected cells were used. HepG2 cells transduced with hAAT-moFGF21 expressed higher levels of FGF21 in comparison with cells transduced with EF1a-mFGF21 or non-transduced cells (FIG. 34E).

In Vivo 8-week-old male C57Bl6 mice were hydrodynamically administered with 5 µg of plasmids encoding the WT murine FGF21 coding sequence under the control of the elongation factor 1a (EF1a) promoter (EF1a-mFGF21) (Zhang et al., EBioMedicine 15 (2017) 173-183) or a codon-optimized murine FGF21 coding sequence under the control of the CMV promoter (CMV-moFGF21) or the hAAT promoter (hAAT-moFGF21). Analysis of FGF21 expression levels in the liver 24 h post-administration of plasmids revealed that animals treated with hAAT-moFGF21 or CMV-moFGF21 expressed much higher levels of FGF21 than animals receiving EF1a-mFGF21 (FIG. 35A). In addition, animals treated with hAAT-moFGF21 or CMV-moFGF21 showed higher FGF21 circulating levels than animals receiving EF1a-mFGF21 (FIG. 35B).

Example 24. In Vivo Increased FGF21 Expression in Target Tissues and FGF21 Circulating Levels by AAV8-hAAT-moFGF21, AAV8-CAG-moFGF21-doublemiRT and AAV1-CMC-moFGF21 in Comparison with AAV8-Ef1a-mFGF21

Hepatic Expression

Male C57Bl6 mice were intravenously administered with $1\times10^{10}$ vg, $2\times10^{10}$ vg or $5\times10^{10}$ vg of AAV8 vectors encoding the WT murine FGF21 coding sequence under the control of the elongation factor 1a (EF1a) promoter (AAV8-EF1a-mFGF21) or a codon-optimized murine FGF21 cod-
ing sequence under the control of the liver-specific hAAT
promoter (AAV8-hAAT-moFGF21). Two weeks post-AAV
administration, animals treated with AAV8-hAAT-
moFGF21 showed both higher expression levels of FGF21
in the liver and higher FGF21 circulating levels than animals
treated with AAV8-EF1a-mFGF21, irrespective of the dose
of vector (FIGS. 36A and B).
Adipose Expression
    Male C57Bl6 mice were administered intra-eWAT with
$2\times10^{10}$ vg, $5\times10^{10}$ vg or $1\times10^{11}$ vg of either AAV8 vectors
encoding the WT murine FGF21 coding sequence under the
control of the elongation factor 1a (EF1a) promoter (AAV8-
EF1a-mFGF21) or AAV8 vectors encoding a codon-opti-
mized murine FGF21 coding sequence under the control of
the CAG promoter in conjunction with four tandem repeats
of the miRT122a sequence and four tandems repeats of the
miRT1 sequence (AAV8-CAG-moFGF21-doublemiRT).
Two weeks post-AAV administration, animals treated with
AAV8-CAG-moFGF21-doublemiRT showed higher expres-
sion levels of FGF21 in WAT than animals administered
with AAV8-EF1a-mFGF21 (FIG. 37A). Moreover, animals

Figure 38A:
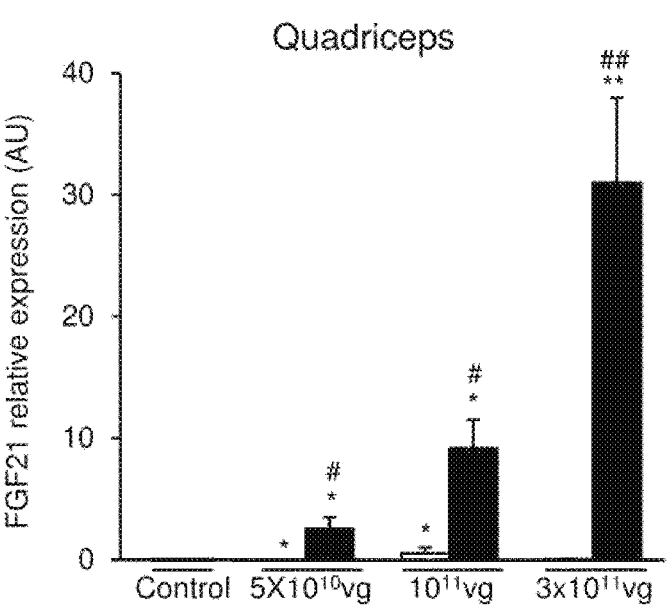
Figure 38B:
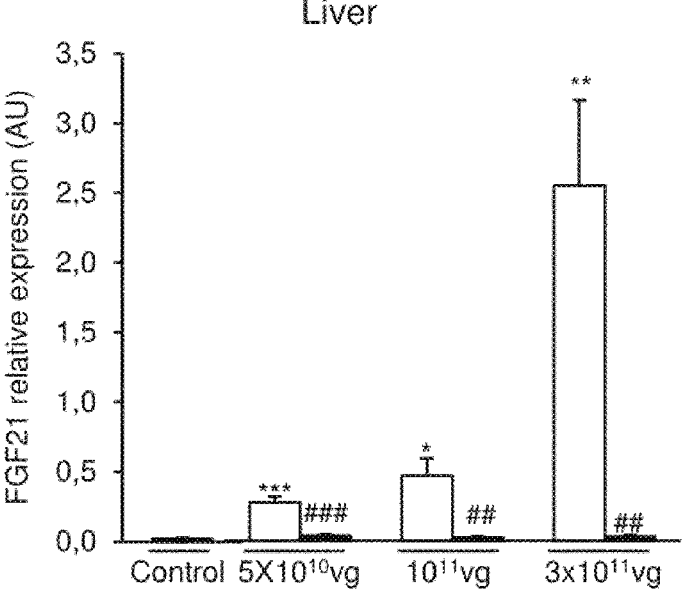

66 treated with AAV8-CAG-moFGF21-doublemiRT showed
much lower expression of FGF21 in the liver than animals
administered with AAV8-EF1a-mFGF21 (FIG. 37B), dem-
onstrating that intra-eWAT administration of AAV8-CAG-
moFGF21-doublemiRT vectors efficiently precluded trans-
gene expression in off-target tissues.
Skeletal Muscle Expression
    Male C57Bl6 mice were administered intramuscularly
with $5\times10^{10}$ vg, $1\times10^{11}$ vg or $3\times10^{11}$ vg of either AAV8
vectors encoding the WT murine FGF21 coding sequence
under the control of the elongation factor 1a (EF1a) pro-
moter (AAV8-EF1a-mFGF21) or AAV1 vectors encoding a
codon-optimized murine FGF21 coding sequence under the
control of the CMV promoter (AAV1-CMV-FGF21). Two
weeks post-AAV administration, animals treated with
AAV1-CMV-FGF21 showed much higher expression levels
of FGF21 in skeletal muscle than animals administered with
AAV8-EF1a-mFGF21 (FIG. 38A). Moreover, animals
treated with AAV8-EF1a-mFGF21 showed high expression
of FGF21 in the liver whereas intramuscular administration
of AAV1-CMV-FGF21 vectors efficiently precluded hepatic
transgene expression (FIG. 38B).

| | SEQUENCES |
|---|---|
| SEQ ID NO: | Type of sequence |
| 1 | Amino acid sequence of *homo sapiens* FGF21 |
| 2 | Amino acid sequence of *mus musculus* FGF21 |
| 3 | Amino acid sequence of *canis lupus familiaris* FGF21 |
| 4 | Nucleotide sequence of *homo sapiens* FGF21 |
| 5 | Codon optimized nucleotide sequence of *homo sapiens* FGF21-variant 1 |
| 6 | Codon optimized nucleotide sequence of *homo sapiens* FGF21-variant 2 |
| 7 | Codon optimized nucleotide sequence of *homo sapiens* FGF21-variant 3 |
| 8 | Nucleotide sequence of *mus musculus* FGF21 |
| 9 | Codon optimized nucleotide sequence of *mus musculus* FGF21 |
| 10 | Nucleotide sequence of *canis lupus familiaris* FGF21 |
| 11 | Codon optimized nucleotide sequence of *canis lupus familiaris* FGF21 |
| 12 | Nucleotide sequence encoding miRT122a |
| 13 | Nucleotide sequence encoding miRT1 |
| 14 | Nucleotide sequence encoding miRT152 |
| 15 | Nucleotide sequence encoding miRT199a-5p |
| 16 | Nucleotide sequence encoding miRT199a-3p |
| 17 | Nucleotide sequence encoding miRT215 |
| 18 | Nucleotide sequence encoding miRT192 |
| 19 | Nucleotide sequence encoding miRT148a |
| 20 | Nucleotide sequence encoding miRT194 |
| 21 | Nucleotide sequence encoding miRT124 |
| 22 | Nucleotide sequence encoding miRT216 |

| SEQUENCES |
|---|
| 23 Nucleotide sequence encoding miRT125 |
| 24 Nucleotide sequence encoding miRT133a |
| 25 Nucleotide sequence encoding miRT206 |
| 26 Nucleotide sequence encoding miRT130 |
| 27 Nucleotide sequence encoding miRT99 |
| 28 Nucleotide sequence encoding miRT208-5p |
| 29 Nucleotide sequence encoding miRT208a-3p |
| 30 Nucleotide sequence encoding miRT499-5p |
| 31 Construct A |
| 32 Construct B |
| 33 Construct C |
| 34 Construct D |
| 35 Construct E |
| 36 Construct F |
| 37 Construct G |
| 38 Construct H |
| 39 Construct I |
| 40 Construct J |
| 41 Construct K |
| 42 Construct L |
| 43 Nucleotide sequence of chimeric intron composed of introns from human β-globin and immunoglobulin heavy chain genes |
| 44 Nucleotide sequence of CAG promoter |
| 45 Nucleotide sequence of CMV promoter |
| 46 Nucleotide sequence of CMV enhancer |
| 47 Nucleotide sequence of hAAT promoter |
| 48 Truncated AAV2 5'ITR |
| 49 Truncated AAV2 3'ITR |
| 50 SV40 polyadenylation signal |
| 51 Rabbit β-Globin polyadenylation signal |
| 52 CMV promoter and CMV enhancer sequence |
| 53 Hepatocyte control region (HCR) enhancer from apolipoprotein E |
| 54 mini/aP2 promoter |
| 55 mini/UCP1 promoter |
| 56 C5-12 promoter |
| 57 pAAV-EF1a-mmFGF21-pA |

Amino acid sequence of *homo sapiens* FGF21

(SEQ ID NO: 1)

MDSDETGFEHSGLWVSVLAGLLLGACQAHPIPDSSPLLQFGGQVRQRYLYTDD

AQQTEAHLEIREDGTVGGAADQSPESLLQLKALKPGVIQILGVKTSRFLCQRPD

-continued

| SEQUENCES |
|---|

GALYGSLHFDPEACSFRELLLEDGYNVYQSEAHGLPLHLPGNKSPHRDPAPRG

PARFLPLPGLPPALPEPPGILAPQPPDVGSSDPLSMVGPSQGRSPSYAS

Nuleotide sequence of *homo sapiens* FGF21

(SEQ ID NO: 4)

ATGGACTCGGACGAGACCGGGTTCGAGCACTCAGGACTGTGGGTTTCTGTG

CTGGCTGGTCTTCTGCTGGGAGCCTGCCAGGCACACCCCATCCCTGACTCCA

GTCCTCTCCTGCAATTCGGGGGCCAAGTCCGGCAGCGGTACCTCTACACAG

ATGATGCCCAGCAGACAGAAGCCCACCTGGAGATCAGGGAGGATGGGACG

GTGGGGGGCGCTGCTGACCAGAGCCCCGAAAGTCTCCTGCAGCTGAAAGCC

TTGAAGCCGGGAGTTATTCAAATCTTGGGAGTCAAGACATCCAGGTTCCTG

TGCCAGCGGCCAGATGGGGCCCTGTATGGATCGCTCCACTTTGACCCTGAG

GCCTGCAGCTTCCGGGAGCTGCTTCTTGAGGACGGATACAATGTTTACCAG

TCCGAAGCCCACGGCCTCCCGCTGCACCTGCCAGGGAACAAGTCCCCACAC

CGGGACCCTGCACCCCGAGGACCAGCTCGCTTCCTGCCACTACCAGGCCTG

CCCCCCGCACTCCCGGAGCCACCCGGAATCCTGGCCCCCCAGCCCCCCGAT

GTGGGCTCCTCGGACCCTCTGAGCATGGTGGGACCTTCCCAGGGCCGAAGC

CCCAGCTACGCTTCCTGA

Codon optimized nucleotide sequence of *homo sapiens* FGF21-variant 1

(SEQ ID NO: 5)

ATGGATTCTGATGAGACAGGCTTCGAGCACAGCGGCCTGTGGGTTTCAGTT

CTGGCTGGACTGCTGCTGGGAGCCTGTCAGGCACACCCTATTCCAGATAGC

AGCCCTCTGCTGCAGTTCGGCGGACAAGTGCGGCAGAGATACCTGTACACC

GACGACGCCCAGCAGACAGAAGCCCACCTGGAAATCAGAGAGGATGGCAC

AGTTGGCGGAGCCGCCGATCAGTCTCCTGAATCTCTGCTCCAGCTGAAGGC

CCTGAAGCCTGGCGTGATCCAGATCCTGGGCGTGAAAACCAGCCGGTTCCT

GTGCCAAAGACCTGACGGCGCCCTGTATGGCAGCCTGCACTTTGATCCTGA

GGCCTGCAGCTTCAGAGAGCTGCTGCTTGAGGACGGCTACAACGTGTACCA

GTCTGAGGCCCATGGCCTGCCTCTGCATCTGCCTGGAAACAAGAGCCCTCA

CAGAGATCCCGCTCCTAGAGGCCCTGCCAGATTTCTGCCTCTTCCTGGATTG

CCTCCTGCTCTGCCAGAGCCTCCTGGAATTCTGGCTCCTCAGCCTCCTGATG

TGGGCAGCTCTGATCCTCTGAGCATGGTCGGACCTAGCCAGGGCAGATCTC

CTAGCTACGCCTCTTGA

Codon optimized nucleotide sequence of *homo sapiens* FGF21-variant 2

(SEQ ID NO: 6)

ATGGACAGCGATGAAACCGGGTTCGAGCACAGCGGTCTGTGGGTGTCCGTG

CTGGCCGGACTGCTCCTGGGAGCCTGTCAGGCGCACCCCATCCCTGACTCC

TCGCCGCTGCTGCAATTCGGCGGACAAGTCCGCCAGAGATACCTGTACACC

GACGACGCCCAGCAGACCGAAGCCCACCTGGAAATTCGGGAGGACGGGAC

TGTGGGAGGCGCTGCAGATCAGTCACCCGAGTCCCTCCTCCAACTGAAGGC

CTTGAAGCCCGGCGTGATTCAGATCCTGGGCGTGAAAACTTCCCGCTTCCTT

TGCCAACGGCCGGATGGAGCTCTGTACGGATCCCTGCACTTCGACCCCGAA

GCCTGCTCATTCCGCGAGCTGCTCCTTGAGGACGGCTATAACGTGTACCAG

| SEQUENCES |
| --- |

TCTGAGGCCCATGGACTCCCCCTGCATCTGCCCGGCAACAAGTCCCCTCAC

CGGGATCCTGCCCCAAGAGGCCCAGCTCGGTTTCTGCCTCTGCCGGGACTG

CCTCCAGCGTTGCCCGAACCCCCTGGTATCCTGGCCCCGCAACCACCTGAC

GTCGGTTCGTCGGACCCGCTGAGCATGGTCGGTCCGAGCCAGGGAAGGTCC

CCGTCCTACGCATCCTGA

Codon optimized nucleotide sequence of *homo sapiens* FGF21-variant 3

(SEQ ID NO: 7)

ATGGATTCCGACGAAACTGGATTTGAACATTCAGGGCTGTGGGTCTCTGTG

CTGGCTGGACTGCTGCTGGGGGCTTGTCAGGCTCACCCCATCCCTGACAGC

TCCCCTCTGCTGCAGTTCGGAGGACAGGTGCGGCAGAGATACCTGTATACC

GACGATGCCCAGCAGACAGAGGCACACCTGGAGATCAGGGAGGACGGAAC

CGTGGGAGGAGCAGCCGATCAGTCTCCCGAGAGCCTGCTGCAGCTGAAGG

CCCTGAAGCCTGGCGTGATCCAGATCCTGGGCGTGAAGACATCTCGGTTTC

TGTGCCAGCGGCCCGACGGCGCCCTGTACGGCTCCCTGCACTTCGATCCCG

AGGCCTGTTCTTTTAGGGAGCTGCTGCTGGAGGACGGCTACAACGTGTATC

AGAGCGAGGCACACGGCCTGCCACTGCACCTGCCTGGCAATAAGTCCCCTC

ACCGCGATCCAGCACCCAGGGGCCCAGCACGCTTCCTGCCTCTGCCAGGCC

TGCCCCCTGCCCTGCCAGAGCCACCCGGCATCCTGGCCCCCCAGCCTCCAG

ATGTGGGCTCCAGCGATCCTCTGTCAATGGTGGGGCCAAGTCAGGGGCGGA

GTCCTTCATACGCATCATAA

Nucleotide sequence encoding miRT122a (target sequence of microRNA 122a)

(SEQ ID NO: 12)

5' CAAACACCATTGTCACACTCCA 3'

Nucleotide sequence encoding miRT1 (target sequence of microRNA 1)

(SEQ ID NO: 13)

5' TTACATACTTCTTTACATTCCA 3'

Nucleotide sequence encoding miRT152 (target sequence of microRNA 152)

(SEQ ID NO: 14)

5' CCAAGTTCTGTCATGCACTGA 3'

Nucleotide sequence encoding miRT199a-5p (target sequence of microRNA 199a)

(SEQ ID NO: 15)

5' GAACAGGTAGTCTGAACACTGGG 3'

Nucleotide sequence encoding miRT199a-3p (target sequence of microRNA 199a)

(SEQ ID NO: 16)

5' TAACCAATGTGCAGACTACTGT 3'

Nucleotide sequence encoding miRT215 (target sequence of microRNA 215)

(SEQ ID NO: 17)

5' GTCTGTCAATTCATAGGTCAT 3'

Nucleotide sequence encoding miRT192 (target sequence of microRNA 192)

(SEQ ID NO: 18)

5' GGCTGTCAATTCATAGGTCAG 3'

Nucleotide sequence encoding miRT148a (target sequence of microRNA 148a)

(SEQ ID NO: 19)

5' ACAAAGTTCTGTAGTGCACTGA 3'

Nucleotide sequence encoding miRT194 (target sequence of microRNA 194)

(SEQ ID NO: 20)

5' TCCACATGGAGTTGCTGTTACA 3'

-continued

| SEQUENCES |
| --- |

Nucleotide sequence encoding miRT124 (target sequence of microRNA 124)

(SEQ ID NO: 21)

5' GGCATTCACCGCGTGCCTTA 3'

Nucleotide sequence encoding miRT216 (target sequence of microRNA 216)

(SEQ ID NO: 22)

5' TCACAGTTGCCAGCTGAGATTA 3'

Nucleotide sequence encoding miRT125 (target sequence of microRNA 125)

(SEQ ID NO: 23)

5' TCACAGGTTAAAGGGTCTCAGGGA 3'

Nucleotide sequence encoding miRT133a (target sequence of microRNA 133a)

(SEQ ID NO: 24)

5' CAGCTGGTTGAAGGGGACCAAA 3'

Nucleotide sequence encoding miRT206 (target sequence of microRNA 206)

(SEQ ID NO: 25)

5' CCACACACTTCCTTACATTCCA 3'

Nucleotide sequence encoding miRT130 (target sequence of microRNA 130)

(SEQ ID NO: 26)

5' ATGCCCTTTTAACATTGCACTG 3'

Nucleotide sequence encoding miRT99 (target sequence of microRNA 99)

(SEQ ID NO: 27)

5' CACAAGATCGGATCTACGGGTT 3'

Nucleotide sequence encoding miRT208-5p (target sequence of microRNA 208a)

(SEQ ID NO: 28)

5' GTATAACCCGGGCCAAAAGCTC 3'

Nucleotide sequence encoding miRT208a-3p (target sequence of microRNA 208a)

(SEQ ID NO: 29)

5' ACAAGCTTTTTGCTCGTCTTAT 3'

Nucleotide sequence encoding miRT499-5p (target sequence of heart-specific
microRNA 499)

(SEQ ID NO: 30)

5' AAACATCACTGCAAGTCTTAA 3'

Nucleotide sequence of CAG promoter (SEQ ID NO: 44)

GACATTGATTATTGACTAGTTATTAATAGTAATCAATTACGGGGTCATTAGT

TCATAGCCCATATATGGAGTTCCGCGTTACATAACTTACGGTAAATGGCCC

GCCTGGCTGACCGCCCAACGACCCCCGCCCATTGACGTCAATAATGACGTA

TGTTCCCATAGTAACGCCAATAGGGACTTTCCATTGACGTCAATGGGTGGA

GTATTTACGGTAAACTGCCCACTTGGCAGTACATCAAGTGTATCATATGCC

AAGTACGCCCCCTATTGACGTCAATGACGGTAAATGGCCCGCCTGGCATTA

TGCCCAGTACATGACCTTATGGGACTTTCCTACTTGGCAGTACATCTACGTA

TTAGTCATCGCTATTACCATGGTCGAGGTGAGCCCCACGTTCTGCTTCACTC

TCCCCATCTCCCCCCCCTCCCCACCCCCAATTTTGTATTTATTTATTTTTTAA

TTATTTTGTGCAGCGATGGGGGCGGGGGGGGGGGGGGGGCGCGCGCCAGG

CGGGGCGGGGCGGGGCGAGGGGCGGGGCGGGGCGAGGCGGAGAGGTGCG

GCGGCAGCCAATCAGAGCGGCGCGCTCCGAAAGTTTCCTTTTATGGCGAGG

CGGCGGCGGCGGCGGCCCTATAAAAAGCGAAGCGCGCGGCGGGCGGGAGT

CGCTGCGTTGCCTTCGCCCCGTGCCCCGCTCCGCGCCGCCTCGCGCCGCCCG

CCCCGGCTCTGACTGACCGCGTTACTCCCACAGGTGAGCGGGCGGGACGGC

CCTTCTCCTCCGGGCTGTAATTAGCGCTTGGTTTAATGACGGCTTGTTTCTTT

TCTGTGGCTGCGTGAAAGCCTTGAGGGGCTCCGGGAGGGCCCTTTGTGCGG

-continued

| SEQUENCES |
| --- |

GGGGAGCGGCTCGGGGGGTGCGTGCGTGTGTGTGCGTGGGGAGCGCCG

CGTGCGGCTCCGCGCTGCCCGGCGGCTGTGAGCGCTGCGGGCGCGGCGCGG

GGCTTTGTGCGCTCCGCAGTGTGCGCGAGGGGAGCGCGGCCGGGGGCGGT

GCCCCGCGGTGCGGGGGGCTGCGAGGGGAACAAAGGCTGCGTGCGGGGTG

TGTGCGTGGGGGGGTGAGCAGGGGGTGTGGGCGCGTCGGTCGGGCTGCAA

CCCCCCCTGCACCCCCCTCCCCGAGTTGCTGAGCACGGCCCGGCTTCGGGT

GCGGGGCTCCGTACGGGGCGTGGCGCGGGGCTCGCCGTGCCGGGCGGGGG

GTGGCGGCAGGTGGGGGTGCCGGGCGGGGCGGGGCCGCCTCGGGCCGGGG

AGGGCTCGGGGGAGGGGCGCGGCGGCCCCCGGAGCGCCGGCGGCTGTCGA

GGCGCGGCGAGCCGCAGCCATTGCCTTTTATGGTAATCGTGCGAGAGGGCG

CAGGGACTTCCTTTGTCCCAAATCTGTGCGGAGCCGAAATCTGGGAGGCGC

CGCCGCACCCCCTCTAGCGGGCGCGGGGCGAAGCGGTGCGGCGCCGGCAG

GAAGGAAATGGGCGGGGAGGGCCTTCGTGCGTCGCCGCGCGCCGCCGTCCCCT

TCTCCCTCTCCAGCCTCGGGGCTGTCCGCGGGGGGACGGCTGCCTTCGGGG

GGGACGGGGCAGGGCGGGGTTCGGCTTCTGGCGTGTGACCGGCGGCTCTAG

AGCCTCTGCTAACCATGTTCATGCCTTCTTCTTTTTCCTACAG

Nucleotide sequence of CMV promoter (SEQ ID NO: 45)

GTGATGCGGTTTTGGCAGTACACCAATGGGCGTGGATAGCGGTTTGACTCA

CGGGGATTTCCAAGTCTCCACCCCATTGACGTCAATGGGAGTTTGTTTTGGC

ACCAAAATCAACGGGACTTTCCAAAATGTCGTAACAACTGCGATCGCCCGC

CCCGTTGACGCAAATGGGCGGTAGGCGTGTACGGTGGGAGGTCTATATAAG

CAGAGCT

Nucleotide sequence of CMV enhancer (SEQ ID NO: 46)

GGCATTGATTATTGACTAGTTATTAATAGTAATCAATTACGGGGTCATTAGT

TCATAGCCCATATATGGAGTTCCGCGTTACATAACTTACGGTAAATGGCCC

GCCTGGCTGACCGCCCAACGACCCCCGCCCATTGACGTCAATAATGACGTA

TGTTCCCATAGTAACGCCAATAGGGACTTTCCATTGACGTCAATGGGTGGA

GTATTTACGGTAAACTGCCCACTTGGCAGTACATCAAGTGTATCATATGCC

AAGTCCGCCCCCTATTGACGTCAATGACGGTAAATGGCCCGCCTGGCATTA

TGCCCAGTACATGACCTTACGGGACTTTCCTACTTGGCAGTACATCTACGTA

TTAGTCATCGCTATTACCATG

Nucleotide sequence of hAAT promoter (SEQ ID NO: 47)

GATCTTGCTACCAGTGGAACAGCCACTAAGGATTCTGCAGTGAGAGCAGAG

GGCCAGCTAAGTGGTACTCTCCCAGAGACTGTCTGACTCACGCCACCCCCT

CCACCTTGGACACAGGACGCTGTGGTTTCTGAGCCAGGTACAATGACTCCT

TTCGGTAAGTGCAGTGGAAGCTGTACACTGCCCAGGCAAAGCGTCCGGGCA

GCGTAGGCGGGCGACTCAGATCCCAGCCAGTGGACTTAGCCCCTGTTTGCT

CCTCCGATAACTGGGGTGACCTTGGTTAATATTCACCAGCAGCCTCCCCCGT

TGCCCCTCTGGATCCACTGCTTAAATACGGACGAGGACAGGGCCCTGTCTC

| SEQUENCES |
| --- |

CTCAGCTTCAGGCACCACCACTGACCTGGGACAGTGAAT

Truncated AAV2 5'ITR (SEQ ID NO: 48)

GCGCGCTC GCTCGCTCAC TGAGGCCGCC CGGGCAAAGC

CCGGGCGTCG GGCGACCTTT GGTCGCCCGG CCTCAGTGAG

CGAGCGAGCG

CGCAGAGAGG GAGTGGCCAA CTCCATCACT AGGGGTTCCT

Truncated AAV2 3'ITR (SEQ ID NO: 49)

AGGAACCCCT AGTGATGGAG TTGGCCACTC CCTCTCTGCG

CGCTCGCTCG CTCACTGAGG CCGGGCGACC AAAGGTCGCC

CGACGCCCGG GCTTTGCCCG GCGGCCTCA GTGAGCGAGC GAGCGCGC

SV40 polyadenylation signal (SEQ ID NO: 50)

TAAGATACATTGATGAGTTTGGACAAACCACAACTAGAATGCAGTGAAAA

AAATGCTTTATTTGTGAAATTTGTGATGCTATTGCTTTATTTGTAACCATTAT

AAGCTGCAATAAACAAGTT

Rabbit β-Globin polyadenylation signal (SEQ ID NO: 51)

GATCTTTTTCCCTCTGCCAAAAATTATGGGGACATCATGAAGCCCCTTGAGC

ATCTGACTTCTGGCTAATAAAGGAAATTTATTTTCATTGCAATAGTGTGTTG

GAATTTTTTGTGTCTCTCACTCGGAAGGACATATGGGAGGGCAAATCATTT

AAAACATCAGAATGAGTATTTGGTTTAGAGTTTGGCAACATATGCCCATAT

GCTGGCTGCCATGAACAAAGGTTGGCTATAAAGAGGTCATCAGTATATGAA

ACAGCCCCCTGCTGTCCATTCCTTATTCCATAGAAAAGCCTTGACTTGAGGT

TAGATTTTTTTTATATTTTGTTTTGTGTTATTTTTTTCTTTAACATCCCTAAAA

TTTTCCTTACATGTTTTACTAGCCAGATTTTTCCTCCTCTCCTGACTACTCCC

AGTCATAGCTGTCCCTCTTCTCTTATGGAGATC

CMV promoter and CMV enhancer sequence (SEQ ID NO: 52)

GGCATTGATTATTGACTAGTTATTAATAGTAATCAATTACGGGGTCATTAGT

TCATAGCCCATATATGGAGTTCCGCGTTACATAACTTACGGTAAATGGCCC

GCCTGGCTGACCGCCCAACGACCCCCGCCCATTGACGTCAATAATGACGTA

TGTTCCCATAGTAACGCCAATAGGGACTTTCCATTGACGTCAATGGGTGGA

GTATTTACGGTAAACTGCCCACTTGGCAGTACATCAAGTGTATCATATGCC

AAGTCCGCCCCCTATTGACGTCAATGACGGTAAATGGCCCGCCTGGCATTA

TGCCCAGTACATGACCTTACGGGACTTTCCTACTTGGCAGTACATCTACGTA

TTAGTCATCGCTATTACCATGGTGATGCGGTTTTGGCAGTACACCAATGGGC

GTGGATAGCGGTTTGACTCACGGGGATTTCCAAGTCTCCACCCCATTGACG

TCAATGGGAGTTTGTTTTGGCACCAAAATCAACGGGACTTTCCAAAATGTC

GTAACAACTGCGATCGCCCGCCCCGTTGACGCAAATGGGCGGTAGGCGTGT

ACGGTGGGAGGTCTATATAAGCAGAGCT

-continued

| SEQUENCES |
| --- |

Hepatocyte control region (HCR) enhancer from apolipoprotein E (SEQ ID NO: 53)

CAGAGAGGTCTCTGACCTCTGCCCCAGCTCCAAGGTCAGCAGGCAGGGAGG

GCTGTGTGTTTGCTGTTTGCTGCTTGCAATGTTTGCCCATTTTAGGGACATG

AGTAGGCTGAAGTTTGTTCAGTGTGGACTTCAGAGGCAGCACACAAACAGC miniaP2 promoter (SEQ ID NO: 54)

GATTA

ACCCGCCATG CTACTTATCT ACTCGACATT GATTATTGAC TAGGGGAATT

CCAGCAGGAA TCAGGTAGCT GGAGAATCGC ACAGAGCCAT

GCGATTCTTG

GCAAGCCATG CGACAAAGGC AGAAATGCAC ATTTCACCCA

GAGAGAAGGG

ATTGATGTCA GCAGGAAGTC ACCACCCAGA GAGCAAATGG

AGTTCCCAGA

TGCCTGACAT TTGCCTTCTT ACTGGATCAG AGTTCACTAG TGGAAGTGTC

ACAGCCCAAA CACTCCCCCA AAGCTCAGCC CTTCCTTGCC TTGTAACAAT

CAAGCCGCTC CTGGATGAAC TGCTCCGCCC TCTGTCTCTT TGGCAGGGTT

GGAGCCCACT GTGGCCTGAG CGACTTCTAT GGCTCCCTTT TCTGTGATTT

TCATGGTTTC TGAGCTCTTT TCCCCCGCTT TATGATTTTC TCTTTTTGTC

TCTCTCTTGC TAAACCTCCT TCGTATATAT GCCCTCTCAG GTTTCATTTC

TGAATCATCT ACTGTGAACT ATTCCCATTG TTTGCCAGAA GCCCCCTGGT

TCTTCCTTCT AGACACCAGG CAAGGGGCAG GAGGTAAGAG

GCAGGAGTCC

ATAAAACAGC CCTGAGAGCC TGCTGGGTCA GTGCCTGCTG TCAGAA miniUCP1 promoter (SEQ ID NO: 55)

GACGTCACAG TGGGTCAGTC ACCCTTGATC ACACTGCACC AGTCTTCACC

TTTCCACGCT TCCTGCCAGA GCATGAATCA GGCTCTCTGG GGATACCGGC

CTCACCCCTA CTGAGGCAAA CTTTCTCCCA CTTCTCAGAG GCTCTGAGGG

CAGCAAGGTC AGCCCTTTCT TTGGAATCTA GAACCACTCC CTGTCTTGAG

CTGACATCAC AGGGCAGGCA GATGCAGCAG GGAAGGGCCT

GGGACTGGGA

CGTTCATCCT ACAAGAAAGC TGTGGAACTT TTCAGCAACA TCTCAGAAAT

CAGATCGCAC TTATTCAAAG GAGCCAGGCC CTGCTCTGCG CCCTGGTGGA

GGCTCCTCAT GTGAAGAGTG ACAAAAGGCA CCATGTTGTG

GATACGGGGC

GAAGCCCCTC CGGTGTGTCC TCCAGGCATC ATCAGGAACT

AGTGCCAAAG

CAGAGGTGCT GGCCAGGGCT TTGGGAGTGA CGCGCGTCTG

GGAGGCTTGT

-continued

| SEQUENCES |
|---|

GCGCCCAGGG CACGCCCCTG CCGATTCCCA CTAGCAGGTC

TTGGGGGACC

TGGGCCGGCT CTGCCCCTCC TCCAGCAATC GGGCTATAAA GCTCTTCCAA

GTCAGGGCGC AGAAGTGCCG GGCGATCCGG GCTTAAAGAG

CGAGAGGAAG

GGACGCTCAC CTTTGAGCTC CTCCACAAAT AGCCCTGGTG GCTGCCACAG

AAGTTCGAAG TTGAGAGTTC GG

C5-12 promoter (SEQ ID NO: 56)

CGGCCGTCCG CCTTCGGCAC CATCCTCACG ACACCCAAAT ATGGCGACGG

GTGAGGAATG

GTGGGGAGTT ATTTTTAGAG CGGTGAGGAA GGTGGGCAGG

CAGCAGGTGT TGGCGCTCTA

AAAATAACTC CCGGGAGTTA TTTTTAGAGC GGAGGAATGG

TGGACACCCA AATATGGCGA

CGGTTCCTCA CCCGTCGCCA TATTTGGGTG TCCGCCCTCG GCCGGGGCCG

CATTCCTGGG

GGCCGGGCGG TGCTCCCGCC CGCCTCGATA AAAGGCTCCG

GGGCCGGCGG CGGCCCACGA

GCTACCCGGA GGAGCGGGAG GCGCCA pAAV-EF1a-mmFGF21-pA (SEQ ID NO: 57)

CCTGCAGGCAGCTGCGCGCTCGCTCGCTCACTGAGGCCGCCCGGGCAAAGC

CCGGGCGTCGGGCGACCTTTGGTCGCCCGGCCTCAGTGAGCGAGCGAGCGC

GCAGAGAGGGAGTGGCCAACTCCATCACTAGGGGTTCCTGCGGCCGCGGCT

CCGGTGCCCGTCAGTGGGCAGAGCGCACATCGCCCACAGTCCCCGAGAAGT

TGGGGGGAGGGGTCGGCAATTGAACCGGTGCCTAGAGAAGGTGGCGCGGG

GTAAACTGGGAAAGTGATGTCGTGTACTGGCTCCGCCTTTTTCCCGAGGGT

GGGGGAGAACCGTATATAAGTGCAGTAGTCGCCGTGAACGTTCTTTTTCGC

AACGGGTTTGCCGCCAGAACACAGGTAAGTGCCGTGTGTGGTTCCCGCGGG

CCTGGCCTCTTTACGGGTTATGGCCCTTGCGTGCCTTGAATTACTTCCACTG

GCTGCAGTACGTGATTCTTGATCCCGAGCTTCGGGTTGGAAGTGGGTGGGA

GAGTTCGAGGCCTTGCGCTTAAGGAGCCCCTTCGCCTCGTGCTTGAGTTGA

GGCCTGGCCTGGGCGCTGGGGCCGCCGCGTGCGAATCTGGTGGCACCTTCG

CGCCTGTCTCGCTGCTTTCGATAAGTCTCTAGCCATTTAAAATTTTTGATGA

CCTGCTGCGACGCTTTTTTTCTGGCAAGATAGTCTTGTAAATGCGGGCCAAG

ATCTGCACACTGGTATTTCGGTTTTTGGGGCCGCGGGCGGCGACGGGGCCC

GTGCGTCCCAGCGCACATGTTCGGCGAGGCGGGGCCTGCGAGCGCGGCCAC

CGAGAATCGGACGGGGGTAGTCTCAAGCTGGCCGGCCTGCTCTGGTGCCTG

GCCTCGCGCCGCCGTGTATCGCCCCGCCCTGGGCGGCAAGGCTGGCCCGGT

CGGCACCAGTTGCGTGAGCGGAAAGATGGCCGCTTCCCGGCCCTGCTGCAG

-continued

| SEQUENCES |
| --- |

GGAGCTCAAAATGGAGGACGCGGCGCTCGGGAGAGCGGGCGGGTGAGTCA

CCCACACAAAGGAAAAGGGCCTTTCCGTCCTCAGCCGTCGCTTCATGTGAC

TCCACGGAGTACCGGGCGCCGTCCAGGCACCTCGATTAGTTCTCGAGCTTTT

GGAGTACGTCGTCTTTAGGTTGGGGGGAGGGGTTTTATGCGATGGAGTTTC

CCCACACTGAGTGGGTGGAGACTGAAGTTAGGCCAGCTTGGCACTTGATGT

AATTCTCCTTGGAATTTGCCCTTTTTGAGTTTGGATCTTGGTTCATTCTCAAG

CCTCAGACAGTGGTTCAAAGTTTTTTTCTTCCATTTCAGGTGTCGTGAGGAA

TTTCGACTGCTAGCACGCGTGATATCAATGGAATGGATGAGATCTAGAGTT

GGGACCCTGGGACTGTGGGTCCGACTGCTGCTGGCTGTCTTCCTGCTGGGG

GTCTACCAAGCATACCCCATCCCTGACTCCAGCCCCCTCCTCCAGTTTGGGG

GTCAAGTCCGGCAGAGGTACCTCTACACAGATGACGACCAAGACACTGAA

GCCCACCTGGAGATCAGGGAGGATGGAACAGTGGTAGGCGCAGCACACCG

CAGTCCAGAAAGTCTCCTGGAGCTCAAAGCCTTGAAGCCAGGGGTCATTCA

AATCCTGGGTGTCAAAGCCTCTAGGTTTCTTTGCCAACAGCCAGATGGAGC

TCTCTATGGATCGCCTCACTTTGATCCTGAGGCCTGCAGCTTCAGAGAACTG

CTGCTGGAGGACGGTTACAATGTGTACCAGTCTGAAGCCCATGGCCTGCCC

CTGCGTCTGCCTCAGAAGGACTCCCCAAACCAGGATGCAACATCCTGGGGA

CCTGTGCGCTTCCTGCCCATGCCAGGCCTGCTCCACGAGCCCCAAGACCAA

GCAGGATTCCTGCCCCCAGAGCCCCCAGATGTGGGCTCCTCTGACCCCCTG

AGCATGGTAGAGCCTTTACAGGGCCGAAGCCCCAGCTATGCGTCCTGAGAT

ATCAAAGAATTCTAAGCTTGTCGACGAATGCAATTGTTGTTAATTAATTGTT

AACTTGTTTATTGCAGCTTATAATGGTTACAAATAAAGCAATAGCATCACA

AATTTCACAAATAAAGCATTTTTTTCACTGCATTCTAGTTGTGGTTTGTCCA

AACTCATCAATGTATCTTAGTCGAGTTAATTAACGGCGGCCGCAGGAACCC

CTAGTGATGGAGTTGGCCACTCCCTCTCTGCGCGCTCGCTCGCTCACTGAGG

CCGGGCGACCAAAGGTCGCCCGACGCCCGGGCTTTGCCCGGGCGGCCTCAG

TGAGCGAGCGAGCGCGCAGCTGCCTGCAGGGGCGCCTGATGCGGTATTTTC

TCCTTACGCATCTGTGCGGTATTTCACACCGCATACGTCAAAGCAACCATA

GTACGCGCCCTGTAGCGGCGCATTAAGCGCGGCGGGTGTGGTGGTTACGCG

CAGCGTGACCGCTACACTTGCCAGCGCCCTAGCGCCCGCTCCTTTCGCTTTC

TTCCCTTCCTTTCTCGCCACGTTCGCCGGCTTTCCCCGTCAAGCTCTAAATCG

GGGGCTCCCTTTAGGGTTCCGATTTAGTGCTTTACGGCACCTCGACCCCAAA

AAACTTGATTTGGGTGATGGTTCACGTAGTGGGCCATCGCCCTGATAGACG

GTTTTTCGCCCTTTGACGTTGGAGTCCACGTTCTTTAATAGTGGACTCTTGTT

CCAAACTGGAACAACACTCAACCCTATCTCGGGCTATTCTTTTGATTTATAA

GGGATTTTGCCGATTTCGGCCTATTGGTTAAAAAATGAGCTGATTTAACAA

AAATTTAACGCGAATTTTAACAAAATATTAACGTTTACAATTTTATGGTGCA

CTCTCAGTACAATCTGCTCTGATGCCGCATAGTTAAGCCAGCCCCGACACC

-continued

| SEQUENCES |
| --- |

CGCCAACACCCGCTGACGCGCCCTGACGGGCTTGTCTGCTCCCGGCATCCG

CTTACAGACAAGCTGTGACCGTCTCCGGGAGCTGCATGTGTCAGAGGTTTT

CACCGTCATCACCGAAACGCGCGAGACGAAAGGGCCTCGTGATACGCCTAT

TTTTATAGGTTAATGTCATGATAATAATGGTTTCTTAGACGTCAGGTGGCAC

TTTTCGGGGAAATGTGCGCGGAACCCCTATTTGTTTATTTTTCTAAATACAT

TCAAATATGTATCCGCTCATGAGACAATAACCCTGATAAATGCTTCAATAA

TATTGAAAAAGGAAGAGTATGAGTATTCAACATTTCCGTGTCGCCCTTATTC

CCTTTTTTGCGGCATTTTGCCTTCCTGTTTTTGCTCACCCAGAAACGCTGGTG

AAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACG

TTTTCCAATGATGAGCACTTTTAAAGTTCTGCTATGTGGCGCGGTATTATCC

CGTATTGACGCCGGGCAAGAGCAACTCGGTCGCCGCATACACTATTCTCAG

AATGACTTGGTTGAGTACTCACCAGTCACAGAAAAGCATCTTACGGATGGC

ATGACAGTAAGAGAATTATGCAGTGCTGCCATAACCATGAGTGATAACACT

GCGGCCAACTTACTTCTGACAACGATCGGAGGACCGAAGGAGCTAACCGCT

TTTTTGCACAACATGGGGGATCATGTAACTCGCCTTGATCGTTGGGAACCG

GAGCTGAATGAAGCCATACCAAACGACGAGCGTGACACCACGATGCCTGT

AGCAATGGCAACAACGTTGCGCAAACTATTAACTGGCGAACTACTTACTCT

AGCTTCCCGGCAACAATTAATAGACTGGATGGAGGCGGATAAAGTTGCAG

GACCACTTCTGCGCTCGGCCCTTCCGGCTGGCTGGTTTATTGCTGATAAATC

TGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAAC

TATGGATGAACGAAATAGACAGATCGCTGAGATAGGTGCCTCACTGATTAA

GCATTGGTAACTGTCAGACCAAGTTTACTCATATATACTTTAGATTGATTTA

AAACTTCATTTTTAATTTAAAAGGATCTAGGTGAAGATCCTTTTTGATAATC

TCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCG

GATCAAGAGCTACCAACTCTTTTTCCGAAGGTAACTGGCTTCAGCAGAGCG

CAGATACCAAATACTGTCCTTCTAGTGTAGCCGTAGTTAGGCCACCACTTCA

AGAACTCTGTAGCACCGCCTACATACCTCGCTCTGCTAATCCTGTTACCAGT

GGCTGCTGCCAGTGGCGATAAGTCGTGTCTTACCGGGTTGGACTCAAGACG

ATAGTTACCGGATAAGGCGCAGCGGTCGGGCTGAACGGGGGGTTCGTGCA

CACAGCCCAGCTTGGAGCGAACGACCTACACCGAACTGAGATACCTACAGC

GTGAGCTATGAGAAAGCGCCACGCTTCCCGAAGGGAGAAAGGCGGACAGG

TATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGA

CTTGAGCGTCGATTTTTGTGATGCTCGTCAGGGGGGCGGAGCCTATGGAAA

-continued

| SEQUENCES |
| --- |

AACGCCAGCAACGCGGCCTTTTTACGGTTCCTGGCCTTTTGCTGGCCTTTTG

CTCACATGT

Elongation factor 1 alpha promoter: from 150 to 1327 (1178 bp)

*Mus musculus* FGF21: from 1359 to 1991 (633 bp)

SEQ ID NO: 57 also contains the truncated AAV2 5' and 3' ITR and the SV40 polyA
(already included in sequence listing, SEQ ID NO: 48, 49 and 50)

---

The invention claimed is:

1. A method for preventing and/or treating a metabolic disorder selected from non-alcoholic steatohepatitis (NASH), non-alcoholic fatty liver disease (NAFLD), diabetes and/or obesity comprising intramuscularly administering to a subject in need thereof a recombinant adeno-associated virus (rAAV) vector comprising a vector genome and an AAV 1 serotype capsid, the vector genome comprising an inverted terminal repeat (ITR) and a viral expression construct comprising a nucleotide sequence operably linked to a ubiquitous promoter, wherein the nucleotide sequence encodes a polypeptide comprising a full-length Fibroblast growth factor 21 (FGF21) protein which is expressed in skeletal muscle of the subject at an efficacious amount to prevent and/or treat at least one symptom of the metabolic disorder.

2. The method of claim 1, wherein the ubiquitous promoter comprises a cytomegalovirus (CMV) promoter or a CAG promoter.

3. The method of claim 1, wherein the nucleotide sequence encoding the FGF21 is selected from the group consisting of a nucleotide sequence having at least 95% sequence identity with the nucleotide sequence of SEQ ID NO: 5, 6, or 7.

4. The method of claim 1, wherein the metabolic disorder is diabetes and/or obesity.

5. The method of claim 1, wherein the metabolic disorder is NASH.

6. The method of claim 1, wherein the ubiquitous promoter comprises a cytomegalovirus (CMV) promoter.

7. The method of claim 1, wherein the ubiquitous promoter comprises a CAG promoter.

8. The method of claim 1, wherein the viral expression construct further comprises a polyadenylation signal and/or an enhancer sequence.

9. The method of claim 1, wherein the expression cassette is flanked by a 5' ITR and a 3' ITR.

10. The method of claim 1, wherein the FGF21 comprises the amino acid sequence of SEQ ID NO: 1.

11. The method of claim 1, wherein the nucleotide sequence encoding the FGF21 comprises a sequence selected from SEQ ID NO: 5, 6, or 7.

12. The method of claim 1, wherein the nucleotide sequence encoding the FGF21 comprises the sequence of SEQ ID NO: 5.

13. The method of claim 1, wherein the nucleotide sequence encoding the FGF21 comprises the sequence of SEQ ID NO: 6.

14. The method of claim 1, wherein the nucleotide sequence encoding the FGF21 comprises the sequence of SEQ ID NO: 7.

15. The method of claim 1, wherein the metabolic disorder is diabetes.

16. The method of claim 1, wherein the metabolic disorder is non-alcoholic fatty liver disease (NAFLD).

* * * * *

SEQUENCE LISTING

Sequence total quantity: 57
SEQ ID NO: 1                    moltype = AA   length = 209
FEATURE                         Location/Qualifiers
source                          1..209
                                mol_type = protein
                                organism = Homo sapiens
SEQUENCE: 1
MDSDETGFEH SGLWVSVLAG LLLGACQAHP IPDSSPLLQF GGQVRQRYLY TDDAQQTEAH  60
LEIREDGTVG GAADQSPESL LQLKALKPGV IQILGVKTSR FLCQRPDGAL YGSLHFDPEA  120
CSFRELLLED GYNVYQSEAH GLPLHLPGNK SPHRDPAPRG PARFLPLPGL PPALPEPPGI  180
LAPQPPDVGS SDPLSMVGPS QGRSPSYAS                                     209

SEQ ID NO: 2                    moltype = AA   length = 210
FEATURE                         Location/Qualifiers
source                          1..210
                                mol_type = protein
                                organism = Mus musculus
SEQUENCE: 2
MEWMRSRVGT LGLWVRLLLA VFLLGVYQAY PIPDSSPLLQ FGGQVRQRYL YTDDDQDTEA  60
HLEIREDGTV VGAAHRSPES LLELKALKPG VIQILGVKAS RFLCQQPDGA LYGSPHFDPE  120
ACSFRELLLE DGYNVYQSEA HGLPLRLPQK DSPNQDATSW GPVRFLPMPG LLHEPQDQAG  180
FLPPEPPDVG SSDPLSMVEP LQGRSPSYAS                                    210

SEQ ID NO: 3                    moltype = AA   length = 209
FEATURE                         Location/Qualifiers
source                          1..209
                                mol_type = protein
                                note = Canis lupus familiaris
                                organism = Canis lupus
SEQUENCE: 3
MGWAEAGFEH LGLWVPVLAV LLLEACRAHP IPDSSPLLQF GGQVRQRYLY TDDAQETEAH  60
LEIRADGTVV GAARQSPESL LELKALKPGV IQILGVKTSR FLCQGPDGTL YGSLHFDPVA  120
CSFRELLLED GYNIYHSETL GLPLRLRPHN SAYRDLAPRG PARFLPLPGL LPAPPEPPGI  180
LAPEPPDVGS SDPLSMVGPS QGRSPSYAS                                     209

SEQ ID NO: 4                    moltype = DNA   length = 630
FEATURE                         Location/Qualifiers
source                          1..630
                                mol_type = other DNA
                                organism = Homo sapiens
SEQUENCE: 4
atggactcgg acgagaccgg gttcgagcac tcaggactgt gggtttctgt gctggctggt  60
cttctgctgg gagcctgcca ggcacacccc atccctgact ccagtcctct cctgcaattc  120
gggggccaag tccggcagcg gtacctctac acagatgatg cccagcgac agaagcccac  180
ctggagatca gggaggatgg gacggtgggg ggcgctgctg accagagccc cgaaagtctc  240
ctgcagctga aagccttgaa gccgggagtt attcaaatct tgggagtcaa gacatccagg  300
ttcctgtgcc agcggccaga tggggccctg tatggatcgc tccactttga ccctgaggcc  360
tgcagcttcc gggagctgct tcttgaggac ggatacaatg tttaccagtc cgaagcccac  420
ggcctcccgc tgcacctgcc agggaacaag tccccacacc gggaccctgc accccgagga  480
ccagctcgct tcctgccact accaggcctg ccccccgcac tcccggagcc accccggaatc  540
ctggccccc agcccccga tgtgggctcc tcggaccctc tgagcatggt gggaccttcc  600
cagggccgaa gccccagcta cgcttcctga                                    630

SEQ ID NO: 5                    moltype = DNA   length = 630
FEATURE                         Location/Qualifiers
misc_feature                    1..630
                                note = Codon optimized Homo sapiens FGF21 - variant 1
source                          1..630
                                mol_type = other DNA
                                organism = synthetic construct

```
SEQUENCE: 5
atggattctg atgagacagg cttcgagcac agcggcctgt gggtttcagt tctggctgga   60
ctgctgctgg gagcctgtca ggcacaccct attccagata gcagccctct gctgcagttc   120
ggcggacaag tgcggcagag atacctgtac accgacgacg cccagcagac agaagcccac   180
ctggaaatca gagaggatgg cacagttggc ggagccgccg atcagtctcc tgaatctctg   240
ctccagctga aggccctgaa gcctggcgtg atccagatcc tgggcgtgaa aaccagccgg   300
ttcctgtgcc aaagacctga cggcgccctg tatggcagcc tgcactttga tcctgaggcc   360
tgcagcttca gagagctgct gcttgaggac ggctacaacg tgtaccagtc tgaggcccat   420
ggcctgcctc tgcatctgcc tggaaacaag agccctcaca gagatcccgc tcctagaggc   480
cctgccagat ttctgcctct tcctggattg cctcctgctc tgccagagcc tcctggaatt   540
ctggctcctc agcctcctga tgtgggcagc tctgatcctc tgagcatggt cggacctagc   600
caggggcagat ctcctagcta cgcctcttga                                     630

SEQ ID NO: 6          moltype = DNA   length = 630
FEATURE               Location/Qualifiers
misc_feature          1..630
                      note = Codon optimized Homo sapiens FGF21 - variant 2
source                1..630
                      mol_type = other DNA
                      organism = synthetic construct
SEQUENCE: 6
atggacagcg atgaaaccgg gttcgagcac agcggtctgt gggtgtccgt gctggccgga   60
ctgctcctgg gagcctgtca ggcgcacccc atccctgact cctcgccgct gctgcaattc   120
ggcggacaag tccgccagag atacctgtac accgacgacg cccagcagac cgaagcccac   180
ctggaaattc gggaggacgg gactgtggga ggcgctgcag atcagtcacc cgagtccctc   240
ctccaactga aggccttgaa gcccggcgtg attcagatcc tgggcgtgaa aacttcccgc   300
ttcctttgcc aacggccgga tggagctctg tacggatccc tgcacttcga ccccgaagcc   360
tgctcattcc gcgagctgct ccttgaggac ggctataacg tgtaccagtc tgaggcccat   420
ggactccccc tgcatctgcc cggcaacaag tcccctcacc gggatcctgc cccaagaggc   480
ccagctcggt ttctgcctct gccgggactg cctccagcgt gcccgaacc ccctggtatc   540
ctggccccgc aaccacctga cgtcggttcg tcggacccgc tgagcatggt cggtccgagc   600
caggggaggt cccgtccta cgcatcctga                                       630

SEQ ID NO: 7          moltype = DNA   length = 630
FEATURE               Location/Qualifiers
misc_feature          1..630
                      note = Codon optimized Homo sapiens FGF21 - variant 3
source                1..630
                      mol_type = other DNA
                      organism = synthetic construct
SEQUENCE: 7
atggattccg acgaaactgg atttgaacat tcagggctgt gggtctctgt gctggctgga   60
ctgctgctgg gggcttgtca ggctcacccc atccctgaca gctccctct gctgcagttc   120
ggaggacagg tgcggcagag atacctgtat accgacgatg cccagcgac agaggcacac   180
ctggagatca gggaggacgg aaccgtggga ggagcagccg atcagtctcc cgagagcctg   240
ctgcagctga aggccctgaa gcctggcgtg atccagatcc tgggcgtgaa gacatctcgg   300
tttctgtgcc agcggcccga cggcgccctg tacggctcc tgcacttcga tcccgaggcc   360
tgttctttta gggagctgct gctggaggac ggctacaacg tgtatcagag cgaggcacac   420
ggcctgccac tgcacctgcc tggcaataag tcccctcacc gcgatccagc acccaggggc   480
ccagcacgct tctgcctct gccaggcctg cccctgccc tgccagagcc acccggcatc   540
ctggcccccc agcctccaga tgtgggctcc agcgatcctc tgtcaatggt ggggccaagt   600
caggggcgga gtccttcata cgcatcataa                                     630

SEQ ID NO: 8          moltype = DNA   length = 633
FEATURE               Location/Qualifiers
source                1..633
                      mol_type = other DNA
                      organism = Mus musculus
SEQUENCE: 8
atggaatgga tgagatctag agttgggacc ctgggactgt gggtccgact gctgctggct   60
gtcttcctgc tgggggtcta ccaagcatac cccatccctg actccagccc cctcctccag   120
tttgggggtc aagtccggca gaggtacctc tacacagatg acgaccaaga cactgaagcc   180
cacctggaga tcagggagga tggaacagtg gtaggcgcag cacaccgcag tccagaaagt   240
ctcctggaga tcaaagcctt gaagccaggg gtcattcaaa tcctgggtgt caaagcctct   300
aggtttcttt gccaacagcc agatggagct ctctatggat cgcctcactt tgatcctgag   360
gcctgcagct tcagagaact gctgctggag gacggttaca atgtgtacca gtctgaagcc   420
catggcctgc cctgcgtct gcctcagaag gactccccaa accaggatgc aacatcctgg   480
ggacctgtgc gcttcctgcc catgccaggc ctgctccacg agcccaaga ccaagcagga   540
ttcctgcccc cagagccccc agatgtgggc tcctctgacc ccctgagcat ggtagagcct   600
ttacagggcc gaagccccag ctatgcgtcc tga                                 633

SEQ ID NO: 9          moltype = DNA   length = 633
FEATURE               Location/Qualifiers
misc_feature          1..633
                      note = Codon optimized Mus musculus FGF21
source                1..633
                      mol_type = other DNA
                      organism = synthetic construct
SEQUENCE: 9
```

-continued

```
atggaatgga tgagaagcag agtgggcacc ctgggcctgt gggtgcgact gctgctggct    60
gtgtttctgc tgggcgtgta ccaggcctac cccatccctg actctagccc cctgctgcag   120
tttggcggac aagtgcggca gagatacctg tacaccgacg acgaccagga caccgaggcc   180
cacctggaaa tccgcgagga tggcacagtc gtgggcgctg ctcacagaag ccctgagagc   240
ctgctggaac tgaaggccct gaagcccggc gtgatccaga tcctgggcgt gaaggccagc   300
agattcctgt gccagcagcc tgacggcgcc ctgtacggct ctcctcactt cgatcctgag   360
gcctgcagct tcagagagct gctgctggag gacggctaca acgtgtacca gtctgaggcc   420
cacggcctgc ccctgagact gcctcagaag gacagcccta accaggacgc cacaagctgg   480
ggacctgtgc ggttcctgcc tatgcctgga ctgctgcacg agccccagga tcaggctggc   540
tttctgcctc ctgagcctcc agacgtgggc agcagcgacc ctctgagcat ggtggaacct   600
ctgcagggca gaagccccag ctacgcctct tga                               633
```

SEQ ID NO: 10         moltype = DNA   length = 629
FEATURE               Location/Qualifiers
source                1..629
                      mol_type = other DNA
                      note = Canis lupus familiaris
                      organism = Canis lupus
SEQUENCE: 10

```
atgggctggg ccgaggccgg gttcgagcac ctgggactgt gggtccctgt gctggctgtg    60
cttttgctgt aagcctgccg ggcacatccg atccctgact ccagcccct cctacaattt    120
ggaggtcaag ttcgacagcg gtacctctac accgacgatg cccaggagac agaggcccac   180
ctagagatca gggccgatgg cacagggtgg gggctgcccg ccagagccct gaaagtctcc   240
tggagctgaa agccctaaag ccaggggtca ttcaaatctt gggagtcaaa acatccaggt   300
tcctgtgcca gggcccagat gggacactat atggctcgct ccatttcgac cctgtggcct   360
gcagtttccg agaactgctt cttgaggatg ggtacaacat taccactcc gagacccttg   420
gtctcccgct tcgcctgcgc ccccacaact ccgcataccg ggacttggca ccccgcgggc   480
ctgcccgctt cctgccactg ccaggcctgc ttccagcacc cccagagcct ccagggatcc   540
tggccccgga gcctcctgac gtgggctcct cggaccctct gagcatggtg gggccttcac   600
agggccggag tcccagctat gcttcctaa                                    629
```

SEQ ID NO: 11         moltype = DNA   length = 630
FEATURE               Location/Qualifiers
misc_feature          1..630
                      note = Codon optimized Canis lupus familiaris FGF21
source                1..630
                      mol_type = other DNA
                      organism = synthetic construct
SEQUENCE: 11

```
atgggatggg ctgaggctgg attcgaacac ctgggactct gggtgcccgt cctggccgtg    60
ctgctcctgg aggcttgcag ggctcatccc atccctgaca gctccccact cctgcagttt   120
ggaggacagg tgaggcagcg gtacctgtat accgacgatg cccaggagac agaagctcac   180
ctggaaattc gggctgatgg aacagtggtc ggagctgccc gacagtcccc agagtctctc   240
ctggaactga aggccctcaa acccggagtg atccagattc tgggcgtcaa gacttctaga   300
ttcctgtgcc agggaccaga cggcaccctg tacggcagcc tgcatttcga tcctgtggcc   360
tgttcctttc gagagctcct gctcgaagac ggctacaaca tctatcactc tgagaccctg   420
ggactcccac tgcgactcag acctcataat agtgcctatc gagatctggc tcccaggggc   480
ccagctaggt ttctgccact ccccggactg ctccctgctc cacctgagcc acccggcatt   540
ctggctccag aacctccaga cgtgggctct agtgatccac tgagtatggt cggcccctca   600
caggggaggt cacctagcta cgccagctga                                   630
```

SEQ ID NO: 12         moltype = DNA   length = 22
FEATURE               Location/Qualifiers
misc_feature          1..22
                      note = Nucleotide sequence encoding miRT122a
source                1..22
                      mol_type = other DNA
                      organism = synthetic construct
SEQUENCE: 12

```
caaacaccat tgtcacactc ca                                            22
```

SEQ ID NO: 13         moltype = DNA   length = 22
FEATURE               Location/Qualifiers
misc_feature          1..22
                      note = Nucleotide sequence encoding miRT1
source                1..22
                      mol_type = other DNA
                      organism = synthetic construct
SEQUENCE: 13

```
ttacatactt ctttacattc ca                                            22
```

SEQ ID NO: 14         moltype = DNA   length = 21
FEATURE               Location/Qualifiers
misc_feature          1..21
                      note = Nucleotide sequence encoding miRT152
source                1..21
                      mol_type = other DNA
                      organism = synthetic construct
SEQUENCE: 14

-continued

```
ccaagttctg tcatgcactg a                                              21

SEQ ID NO: 15          moltype = DNA   length = 23
FEATURE                Location/Qualifiers
misc_feature           1..23
                       note = Nucleotide sequence encoding miRT199a-5p
source                 1..23
                       mol_type = other DNA
                       organism = synthetic construct
SEQUENCE: 15
gaacaggtag tctgaacact ggg                                            23

SEQ ID NO: 16          moltype = DNA   length = 22
FEATURE                Location/Qualifiers
misc_feature           1..22
                       note = Nucleotide sequence encoding miRT199a-3p
source                 1..22
                       mol_type = other DNA
                       organism = synthetic construct
SEQUENCE: 16
taaccaatgt gcagactact gt                                             22

SEQ ID NO: 17          moltype = DNA   length = 21
FEATURE                Location/Qualifiers
misc_feature           1..21
                       note = Nucleotide sequence encoding miRT215
source                 1..21
                       mol_type = other DNA
                       organism = synthetic construct
SEQUENCE: 17
gtctgtcaat tcataggtca t                                              21

SEQ ID NO: 18          moltype = DNA   length = 21
FEATURE                Location/Qualifiers
misc_feature           1..21
                       note = Nucleotide sequence encoding miRT192
source                 1..21
                       mol_type = other DNA
                       organism = synthetic construct
SEQUENCE: 18
ggctgtcaat tcataggtca g                                              21

SEQ ID NO: 19          moltype = DNA   length = 22
FEATURE                Location/Qualifiers
misc_feature           1..22
                       note = Nucleotide sequence encoding miRT148a
source                 1..22
                       mol_type = other DNA
                       organism = synthetic construct
SEQUENCE: 19
acaaagttct gtagtgcact ga                                             22

SEQ ID NO: 20          moltype = DNA   length = 22
FEATURE                Location/Qualifiers
misc_feature           1..22
                       note = Nucleotide sequence encoding miRT194
source                 1..22
                       mol_type = other DNA
                       organism = synthetic construct
SEQUENCE: 20
tccacatgga gttgctgtta ca                                             22

SEQ ID NO: 21          moltype = DNA   length = 20
FEATURE                Location/Qualifiers
misc_feature           1..20
                       note = Nucleotide sequence encoding miRT124
source                 1..20
                       mol_type = other DNA
                       organism = synthetic construct
SEQUENCE: 21
ggcattcacc gcgtgcctta                                                20

SEQ ID NO: 22          moltype = DNA   length = 22
FEATURE                Location/Qualifiers
misc_feature           1..22
                       note = Nucleotide sequence encoding miRT216
source                 1..22
                       mol_type = other DNA
                       organism = synthetic construct
```

-continued

```
SEQUENCE: 22
tcacagttgc cagctgagat ta                                            22

SEQ ID NO: 23           moltype = DNA  length = 24
FEATURE                 Location/Qualifiers
misc_feature            1..24
                        note = Nucleotide sequence encoding miRT125
source                  1..24
                        mol_type = other DNA
                        organism = synthetic construct
SEQUENCE: 23
tcacaggtta aagggtctca ggga                                          24

SEQ ID NO: 24           moltype = DNA  length = 22
FEATURE                 Location/Qualifiers
misc_feature            1..22
                        note = Nucleotide sequence encoding miRT133a
source                  1..22
                        mol_type = other DNA
                        organism = synthetic construct
SEQUENCE: 24
cagctggttg aagggggacca aa                                           22

SEQ ID NO: 25           moltype = DNA  length = 22
FEATURE                 Location/Qualifiers
misc_feature            1..22
                        note = Nucleotide sequence encoding miRT206
source                  1..22
                        mol_type = other DNA
                        organism = synthetic construct
SEQUENCE: 25
ccacacactt ccttacattc ca                                            22

SEQ ID NO: 26           moltype = DNA  length = 22
FEATURE                 Location/Qualifiers
misc_feature            1..22
                        note = Nucleotide sequence encoding miRT130
source                  1..22
                        mol_type = other DNA
                        organism = synthetic construct
SEQUENCE: 26
atgccctttt aacattgcac tg                                            22

SEQ ID NO: 27           moltype = DNA  length = 22
FEATURE                 Location/Qualifiers
misc_feature            1..22
                        note = Nucleotide sequence encoding miRT99
source                  1..22
                        mol_type = other DNA
                        organism = synthetic construct
SEQUENCE: 27
cacaagatcg gatctacggg tt                                            22

SEQ ID NO: 28           moltype = DNA  length = 22
FEATURE                 Location/Qualifiers
misc_feature            1..22
                        note = Nucleotide sequence encoding miRT208a-5p
source                  1..22
                        mol_type = other DNA
                        organism = synthetic construct
SEQUENCE: 28
gtataacccg ggccaaaagc tc                                            22

SEQ ID NO: 29           moltype = DNA  length = 22
FEATURE                 Location/Qualifiers
misc_feature            1..22
                        note = Nucleotide sequence encoding miRT208a-3p
source                  1..22
                        mol_type = other DNA
                        organism = synthetic construct
SEQUENCE: 29
acaagctttt tgctcgtctt at                                            22

SEQ ID NO: 30           moltype = DNA  length = 21
FEATURE                 Location/Qualifiers
misc_feature            1..21
                        note = Nucleotide sequence encoding miRT499-5p
source                  1..21
                        mol_type = other DNA
```

-continued

```
                              organism = synthetic construct
SEQUENCE: 30
aaacatcact gcaagtctta a                                           21

SEQ ID NO: 31             moltype = DNA  length = 6343
FEATURE                   Location/Qualifiers
misc_feature              1..6343
                          note = pAAV-CAG-null
source                    1..6343
                          mol_type = other DNA
                          organism = synthetic construct
SEQUENCE: 31
aattcgagct cggtacccgg gaatcaattc actcctcagg tgcaggctgc ctatcagaag   60
gtggtggctg gtgtggccaa tgccctggct cacaaatacc actgagatct ttttccctct  120
gccaaaaatt atggggacat catgaagccc cttgagcatc tgacttctgg ctaataaagg  180
aaatttattt tcattgcaat agtgtgttgg aattttttgt gtctctcact cggaaggaca  240
tatgggaggg caaatcattt aaaacatcag aatgagtatt tggtttagag tttggcaaca  300
tatgcccata tgctggctgc catgaacaaa ggttggctat aaagaggtca tcagtatatg  360
aaacagcccc ctgctgtcca ttccttattc catagaaaag ccttgacttg aggttagatt  420
ttttttatat tttgttttgt gttattttt tctttaacat ccctaaaatt ttccttacat  480
gttttactag ccagattttt cctcctctcc tgactactcc cagtcatagc tgtccctctt  540
ctcttatgga gatccctcga cctgcagccc aagctgtaga taagtagcat ggcgggttaa  600
tcattaacta caaggaaccc ctagtgatgg agttggccac tccctctctg cgcgctcgct  660
cgctcactga ggccgggcga ccaaaggtcg cccgacgccc gggctttgcc cggcggcct  720
cagtgagcga gcgagcgcgc agctgcatta atgaatcggc caacgcgcgg ggagaggcgg  780
tttgcgtatt gggcgctctt ccgcttcctc gctcactgac tcgctgcgct cggtcgttcg  840
gctgcggcga gcggtatcag ctcactcaaa ggcggtaata cggttatcca cagaatcagg  900
ggataacgca ggaaagaaca tgtgagcaaa aggccagcaa aaggccagga accgtaaaaa  960
ggccgcgttg ctggcgtttt tccataggct ccgcccccct gacgagcatc acaaaaatcg 1020
acgctcaagt cagaggtggc gaaacccgac aggactataa agataccagg cgtttccccc 1080
tggaagctcc ctcgtgcgct ctcctgttcc gaccctgccg cttaccggat acctgtccgc 1140
ctttctccct tcgggaagcg tggcgctttc tcatagctca cgctgtaggt atctcagttc 1200
ggtgtaggtc gttcgctcca agctgggctg tgtgcacgaa ccccccgttc agcccgaccg 1260
ctgcgcctta tccggtaact atcgtcttga gtccaacccg gtaagacacg acttatcgcc 1320
actggcagca gccactggta acaggattag cagagcgagg tatgtaggcg gtgctacaga 1380
gttcttgaag tggtggccta actacggcta cactagaaga acagtatttg gtatctgcgc 1440
tctgctgaag ccagttacct tcggaaaaag agttggtagc tcttgatccg gcaaacaaac 1500
caccgctggt agcggtggtt tttttgtttg caagcagcag attacgcgca gaaaaaaagg 1560
atctcaagaa gatcctttga tcttttctac ggggtctgac gctcagtgga acgaaaactc 1620
acgttaaggg attttggtca tgagattatc aaaaaggatc ttcacctaga tccttttaaa 1680
ttaaaaatga agttttaaat caatctaaag tatatatgag taaacttggt ctgacagtta 1740
ccaatgctta atcagtgagg cacctatctc agcgatctgt ctatttcgtt catccatagt 1800
tgcctgactc cccgtcgtgt agataactac gatacgggag ggcttaccat ctggccccag 1860
tgctgcaatg ataccgcgag acccacgctc accggctcca gatttatcag caataaacca 1920
gccagccgga agggccgagc gcagaagtgg tcctgcaact ttatccgcct ccatccagtc 1980
tattaattgt tgccgggaag ctagagtaag tagttcgcca gttaatagtt tgcgcaacgt 2040
tgttgccatt gctacaggca tcgtggtgtc acgctcgtcg tttggtatgg cttcattcag 2100
ctccggttcc caacgatcaa ggcgagttac atgatccccc atgttgtgca aaaaagcggt 2160
tagctccttc ggtcctccga tcgttgtcag aagtaagttg gccgcagtgt tatcactcat 2220
ggttatggca gcactgcata attctcttac tgtcatgcca tccgtaagat gcttttctgt 2280
gactggtgag tactcaacca agtcattctg agaatagtgt atgcggcgac cgagttgctc 2340
ttgcccggcg tcaatacggg ataataccgc gccacatagc agaactttaa aagtgctcat 2400
cattggaaaa cgttcttcgg ggcgaaaact ctcaaggatc ttaccgctgt tgagatccag 2460
ttcgatgtaa cccactcgtg cacccaactg atcttcagca tcttttactt tcaccagcgt 2520
ttctgggtga gcaaaaacag gaaggcaaaa tgccgcaaaa aagggaataa gggcgacacg 2580
gaaatgttga atactcatac tcttcctttt tcaatattat tgaagcattt atcagggtta 2640
ttgtctcatg agcggataca tatttgaatg tatttagaaa aataaacaaa tagggggttcc 2700
gcgcacattt ccccgaaaag tgccacctga cgtctaagaa accattatta tcatgacatt 2760
aacctataaa aataggcgta tcacgaggcc ctttcgtctc gcgcgtttcg gtgatgacgg 2820
tgaaaacctc tgacacatgc agctcccgga gacggtcaca gcttgtctgt aagcggatgc 2880
cgggagcaga caagcccgtc agggcgcgtc agcgggtgtt ggcgggtgtc ggggctggct 2940
taactatgcg gcatcagagc agattgtact gagagtgcac catatgcggt gtgaaatacc 3000
gcacagatgc gtaaggagaa aataccgcat caggcgattc aacatccaa taaatcatac 3060
aggcaaggca agaattagc aaaattaagc aataaagcct cagagcataa agctaaatcg 3120
gttgtaccaa aaacattatg accctgtaat acttttgcgg gagaagcctt tatttcaacg 3180
caaggataaa aattttttaga accctcatat attttaaatg caatgcctga gtaatgtgta 3240
ggtaaagatt caaacgggtg agaaaggccg gagacagtca aatcaccatc aatatgatat 3300
tcaaccgttc tagctgataa attcatgccg gagagggtg ctatttttga gaggtctcta 3360
caaaggctat caggtcattg cctgagagtc tggagcaaac aagagaatcg atgaacggta 3420
atcgtaaaac tagcatgtca atcatatgta ccccggttga taatcagaaa agccccaaaa 3480
acaggaagat tgtataagca aatatttaaa ttgtaagcgt taatattttg ttaaaattcg 3540
cgttaaattt ttgttaaatc agctcatttt ttaaccaata ggccgaaatc ggcaaaatcc 3600
cttataaatc aaaagaatag accgagatag ggttgagtgt tgttccagtt tggaacaaga 3660
gtccactatt aaagaacgtg gactccaacg tcaaagggcg aaaaaccgtc tatcagggcg 3720
atggcccact acgtgaacca tcaccctaat caagtttttt ggggtcgagg tgccgtaaag 3780
cactaaatcg gaaccctaaa gggagccccc gatttagagc ttgacgggga agccggcgca 3840
acgtggcgag aaaggaaggg aagaaagcga aaggagcggg cgctagggcg ctggcaagtg 3900
tagcggtcac gctgcgcgta accaccacac ccgccgcgct taatgcgccg ctacagggcg 3960
cgtactatgg ttgctttgac gagcacgtat aacgtgcttt cctcgttaga atcagagcgg 4020
```

```
gagctaaaca ggaggccgat taaagggatt ttagacagga acggtacgcc agaatcctga  4080
gaagtgtttt tataatcagt gaggccaccg agtaaaagag tctgtccatc acgcaaatta  4140
accgttgtcg caatacttct ttgattagta ataacatcac ttgcctgagt agaagaactc  4200
aaactatcgg ccttgctggt aatatccaga acaatattac cgccagccat tgcaacggaa  4260
tcgccattcg ccattcaggc tgcgcaactg ttgggaaggg cgatcggtgc gggcctcttc  4320
gctattacgc cagctgcgcg ctcgctcgct cactgaggcc gcccgggcaa agccggggcg  4380
tcgggcgacc tttggtcgcc cggcctcagt gagcgagcga gcgcgcagag agggagtggc  4440
caactccatc actaggggtt ccttgtagtt aatgattaac cgccatgct acttatctac  4500
tcgacattga ttattgacta gttattaata gtaatcaatt acggggtcat tagttcatag  4560
cccatatatg gagttccgcg ttacataact tacggtaaat ggcccgcctg gctgaccgcc  4620
caacgacccc cgcccattga cgtcaataat gacgtatgtt cccatagtaa cgccaatagg  4680
gactttccat tgacgtcaat gggtggagta tttacggtaa actgcccact ggcagtaca  4740
tcaagtgtat catatgccaa gtacgccccc tattgacgtc aatgacggta aatggcccgc  4800
ctggcattat gcccagtaca tgaccttatg ggactttcct acttggcagt acatctacgt  4860
attagtcatc gctattacca tggtcgaggt gagccccacg ttctgcttca ctctccccat  4920
ctccccccc tccccacccc caattttgta tttatttatt ttttaattat tttgtgcagc  4980
gatgggggcg ggggggggg ggggcgcgc gccaggcggg gcggggcggg gcgagggggcg  5040
gggcgggggcg aggcggagag gtgcggcggc agccaatcag agccgcgcgc tccgaaagtt  5100
tcctttatg gcgaggcggc ggcggcggcg gccctataaa aagcgaagcg cgcggcgggc  5160
gggagtcgct gcgttgcctt cgccccgtgc cccgctccgc cgccgcctcg cgccgcccgc  5220
cccggctctg actaccgcg ttactcccac aggtgagcgg gcgggacggc ccttctcctc  5280
cgggctgtaa ttagcgcttg gtttaatgac ggcttgtttc ttttctgtgg ctgcgtgaaa  5340
gccttgaggg gctccgggag ggccctttgt gcggggggag cggctcgggg ggtgcgtgcg  5400
tgtgtgtgtg cgtggggagc gccgcgtgcg gctccgcgct gcccggcggc tgtgagcgct  5460
gcgggcgcg cgcggggctt tgtgcgctcc gcagtgtgcg cgaggggagc gcggccgggg  5520
gcggtgcccc gcggtgacaa gggggctgcg aggggaacaa aggctgcgtg cggggtgtgt  5580
gcgtggggggg gtgagcaggg gggtgtgggcg cgtcggtcgg gctgcaaccc cccctgcacc  5640
cccctccccg agttgctgag cacggcccgg cttcgggtgc ggggctccgt acggggcgtg  5700
gcgcgggggct cgccgtgccg ggcggggggt ggcggcaggt gggggtgccg ggcggggcgg  5760
ggccgcctcg ggccgggggag ggctcggggg aggggcgggg cgccccccgg agcgccgggcg  5820
gctgtcgagg cgcggcgagc cgcagccatt gccttttatg gtaatcgtgc gagagggcgc  5880
agggacttcc tttgtcccaa atctgtgcgg agccgaaatc tgggaggcgc cgccgcaccc  5940
cctctagcgg gcgcggggcg aagcggtgcg gcgccggcag gaaggaaatg ggcggggagg  6000
gccttcgtgc gtcgccgcgc cgccgtcccc ttctccctct ccagcctcgg ggctgtccgc  6060
gggggacgg ctgccttcgg gggggacggg gcagggcggg gttcggcttc tggcgtgtga  6120
ccggcggctc tagagcctct gctaaccatg ttcatgcctt cttctttttc ctacagctcc  6180
tgggcaacgt gctggttatt gtgctgtctc atcattttgg caaagaattg attaattcga  6240
gcgaacgcgt cgagtcgctc ggtacgattt aaattgaatt ggcctcgagc gcaagcttga  6300
gctagctcga tatcggccta ggctggatcc gcgcggccgc aag              6343
```

```
SEQ ID NO: 32              moltype = DNA   length = 7319
FEATURE                    Location/Qualifiers
misc_feature               1..7319
                           note = pAAV-CAG-moFGF21-dmiRT
source                     1..7319
                           mol_type = other DNA
                           organism = synthetic construct
SEQUENCE: 32
agtgagcgag cgagcgcgca gctgcattaa tgaatcggcc aacgcgcggg gagaggcggt  60
ttgcgtattg ggcgctcttc cgcttcctcg ctcactgact cgctgcgctc ggtcgttcgg  120
ctgcggcgag cggtatcagc tcactcaaag gcggtaatac ggttatccac agaatcaggg  180
gataacgcag gaaagaacat gtgagcaaaa ggccagcaaa aggccaggaa ccgtaaaaag  240
gccgcgttgc tggcgttttt ccataggctc cgcccccctg acgagcatca caaaaatcga  300
cgctcaagtc agaggtggcg aaacccgaca ggactataaa gataccaggc gtttccccct  360
ggaagctccc tcgtgcgctc tcctgttccg accctgccgc ttaccggata cctgtccgcc  420
tttctccctt cgggaagcgt ggcgctttct catagctcac gctgtaggta tctcagttcg  480
gtgtaggtcg ttcgctccaa gctgggctgt gtgcacgaac cccccgttca gcccgaccgc  540
tgcgccttat ccggtaacta tcgtcttgag tccaacccgg taagacacga cttatcgcca  600
ctggcagcag ccactggtaa caggattagc agagcgaggt atgtaggcgg tgctacagag  660
ttcttgaagt ggtggcctaa ctacggctac actagaagaa cagtatttgg tatctgcgct  720
ctgctgaagc cagttacctt cggaaaaaga gttggtagct cttgatccgg caaacaaacc  780
accgctggta gcggtggttt ttttgtttgc aagcagcaga ttacgcgcag aaaaaaagga  840
tctcaagaag atcctttgat cttttctacg gggtctgacg ctcagtggaa cgaaaactca  900
cgttaaggga ttttggtcat gagattatca aaaaggatct tcacctagat ccttttaaat  960
taaaaatgaa gttttaaatc aatctaaagt atatatgagt aaacttggtc tgacagttac  1020
caatgcttaa tcagtgaggc acctatctca gcgatctgtc tatttcgttc atccatagtt  1080
gcctgactcc ccgtcgtgta gataactacg atacgggagg gcttaccatc tggccccagt  1140
gctgcaatga taccgcgaga cccacgctca ccggctccag atttatcagc aataaaccag  1200
ccagccggaa gggccgagcg cagaagtggt cctgcaactt tatccgcctc catccagtct  1260
attaattgtt gccgggaagc tagagtaagt agttcgccag ttaatagttt gcgcaacgtt  1320
gttgccattg ctacaggcat cgtggtgtca cgctcgtcgt ttggtatggc ttcattcagc  1380
tccggttccc aacgatcaag gcgagttaca tgatccccca tgttgtgcaa aaaagcggtt  1440
agctccttcg gtcctccgat cgttgtcaga agtaagttgg ccgcagtgtt atcactcatg  1500
gttatggcag cactgcataa ttctcttact gtcatgccat ccgtaagatg cttttctgtg  1560
actggtgagt actcaaccaa gtcattctga atagtgta tgcggcgacc gagttgctct  1620
tgcccggcgt caatacggga taataccgcg ccacatagca gaactttaaa agtgctcatc  1680
attggaaaac gttcttcggg gcgaaaactc tcaaggatct taccgctgtt gagatccagt  1740
tcgatgtaac ccactcgtgc acccaactga tcttcagcat ctttttactt caccagcgtt  1800
tctgggtgag caaaaacagg aaggcaaaat gccgcaaaaa agggaataag ggcgacacgg  1860
```

-continued

```
aaatgttgaa tactcatact cttccttttt caatattatt gaagcattta tcagggttat  1920
tgtctcatga gcggatacat atttgaatgt atttagaaaa ataaacaaat aggggttccg  1980
cgcacatttc cccgaaaagt gccacctgac gtctaagaaa ccattattat catgacatta  2040
acctataaaa ataggcgtat cacgaggccc tttcgtctcg cgcgtttcgg tgatgacggt  2100
gaaaacctct gacacatgca gctcccggag acggtcacag cttgtctgta agcggatgcc  2160
gggagcagac aagcccgtca gggcgcgtca gcgggtgttg gcgggtgtcg gggctggctt  2220
aactatgcgg catcagagca gattgtactg agagtgcacc atatgcggtg tgaaataccg  2280
cacagatgcg taaggagaaa ataccgcatc aggcgattcc aacatccaat aaatcataca  2340
ggcaaggcaa agaattagca aaattaagca ataaagcctc agagcataaa gctaaatcgg  2400
ttgtaccaaa aacattatga ccctgtaata cttttgcggg agaagccttt atttcaacgc  2460
aaggataaaa attttttagaa ccctcatata ttttaaatgc aatgcctgag taatgtgtag  2520
gtaaagattc aaacgggtga gaaaggccgg agacagtcaa atcaccatca atatgatatt  2580
caaccgttct agctgataaa ttcatgccgg agagggtagc tattttttgag aggtctctac  2640
aaaggctatc aggtcattgc ctgagagtct ggagcaaaca agagaatcga tgaacggtaa  2700
tcgtaaaact agcatgtcaa tcatatgtac cccggttgat aatcagaaaa gccccaaaaa  2760
caggaagatt gtataagcaa atatttaaat tgtaagcgtt aatattttgt taaaattcgc  2820
gttaaatttt tgttaaatca gctcattttt taaccaatag gccgaaatcg gcaaaatccc  2880
ttataaatca aaagaataga ccgagatagg gttgagtgtt gttccagttt ggaacaagag  2940
tccactatta aagaacgtgg actccaacgt caaagggcga aaaaccgtct atcagggcga  3000
tggcccacta cgtgaaccat caccctaatc aagtttttg gggtcgaggt gccgtaaagc  3060
actaaatcgg aaccctaaag ggagcccccg atttagagct tgacggggaa agccggcgaa  3120
cgtggcgaga aaggaaggga agaaagcgaa aggagcggtc gctagggcgc tggcaagtgt  3180
agcggtcacg ctgcgcgtaa ccaccacacc cgccgcgctt aatgcgccgc tacagggcgc  3240
gtactatggt tgctttgacg agcacgtata acgtgctttc ctcgttagaa tcagagcggg  3300
agctaaacag gaggccgatt aaaggggattt tagacaggaa cggtacgcca gaatcctgag  3360
aagtgttttt ataatcagtg aggccaccga gtaaaagagt ctgtccatca cgcaaattaa  3420
ccgttgtcgc aatacttctt tgattagtaa taacatcact tgcctgagta gaagaactca  3480
aactatcggc cttgctggta atatccagaa caatattacc gccagccatt gcaacggaat  3540
cgccattcgc cattcaggct gcgcaactgt tgggaagggc gatcggtgcg ggcctcttcc  3600
actgaggccc agctgcgcgc tcgctcgctc actgaggccg cccgggcaaa gcccgggcgt  3660
cgggcgacct ttggtcgccc ggcctcagtg agcgagcgag cgcgcagaga gggagtggcc  3720
aactccatca ctaggggttc cttgtagtta atgattaacc cgccatgcta cttatctact  3780
cgacattgat tattgactag ttattaatag taatcaatta cggggtcatt agttcatagc  3840
ccatatatgg agttccgcgt tacataactt acggtaaatg gcccgcctgg ctgaccgccc  3900
aacgaccccc gcccattgac gtcaataatg acgtatgttc ccatagtaac gccaataggg  3960
actttccatt gacgtcaatg ggtggagtat ttacggtaaa ctgcccactt ggcagtacat  4020
caagtgtatc atatgccaag tacgccccct attgacgtca atgacggtaa atggcccgcc  4080
tggcattatg cccagtacat gaccttatgg gactttccta cttggcagta catctacgta  4140
ttagtcatcg ctattaccat ggtcgaggtg agccccacgt tctgcttcac tctccccatc  4200
tcccccccct ccccacccc aattttgtat ttatttattt tttaattatt ttgtgcagcag  4260
atgggggcgg gggggggggg ggggcgcgcg ccaggcgggg cggggcgggg cgagggggcgg  4320
ggcgggggcga ggcggagagg tgcggcggca gccaatcaga gcggcgcgct ccgaaagttt  4380
ccttttatgg cgaggcggcg gcggcggcgg ccctataaaa gcggaagcgc gcggcggggcg  4440
ggagtcgctg cgttgccttc gccccgtgcc ccgctccgcg ccgcctcgcg ccgcccgccc  4500
cggctctgac tgaccgcgtt actcccacag gtgagcgggc gggacggccc ttctcctccg  4560
ggctgtaatt agcgcttggt ttaatgacgg cttgtttctt ttctgtggct gcgtgaaagc  4620
cttgaggggc tccgggaggg cctttgtgc ggggggaacgc gctcggggggg tgcgtgcgtg  4680
tgtgtgtgcg tggggagcgc cgcgtgcggc tccgcgctgc ccggcggctg tgagcgctgc  4740
gggcgcggcg cggggctttg tgcgctccgc agtgtgcgcg aggggagcgc ggccggggggc  4800
ggtgccccgc ggtgcggggg gctgcgaggg gaacaaaggc tgcgtgcggg gtgtgtgcgt  4860
gggggggtga gcagggggtg tgggcgcgtc ggtcgggctg caaccccccc tgcacccccc  4920
tccccgagtt gctgagcacg gcccggcttc gggtgcgggg ctccgtacgg ggcgtggcgc  4980
ggggctcgcc gtgccgggcg gggggtggcg gcaggtgggg gtgccgggcg gggcgggggcc  5040
gcctcgggcc ggggagggct cggggagggg gcgcggcggc ccccgagcg ccggcggctg  5100
tcgagcgcg gcgagccgca gccattgcct tttatggtaa tcgtgcgaga gggcgcaggg  5160
acttcctttg tcccaaatct gtgcggagcc gaaatctggg aggcgccgcc gcaccccctc  5220
tagcgggcgc ggggcgaagc ggtgcggcgc cggcaggaag gaaatggggcg gggagggcct  5280
tcgtgcgtcg ccgcgccgcc gtcccttct ccctctccag cctcggggct gtccgcgggg  5340
ggacggctgc cttcgggggg gacggggcag ggcgggggttc ggcttctggc gtgtgaccgg  5400
cggctctaga gcctctgcta accatgttca tgccttcttc tttttcctac agctcctggg  5460
caacgtgctg gttattgtgc tgtctcatca ttttggcaaa gaattgatta attcgagcga  5520
acgcgtgag tcgctcggta cgatttaaat tgaattggcc tcgagcgcaa gcttgagcta  5580
gcgccaccat ggaatggatg agaagcagag tgggcaccct gggcctgtgg gtgcgactgc  5640
tgctggctgt gtttctgctg ggcgtgtacc aggcctaccc catccctgac tctagccccat  5700
tgctcagtt tggcggacaa gtgcggcaga gataccgta caccgacgac gaccaggaca  5760
ccgaggccca cctggaaatc cgcgaggatg gcacagtcgt gggcgctgct cacagaagcc  5820
ctgagagcct gctggaactg aaggcccga agccggcgt gatccagatc ctgggcgtga  5880
aggccagcag attcctgtgc cagcagcctg acggcgcct gtacggctct cctcacttcg  5940
atcctgagc ctgcagcttc agagagctgc tgctggaaga ggctacaac gtgtaccagt  6000
ctgaggccca cggcctgccc ctgagactgc tcagaagga cagccctaac caggacgcca  6060
caagctgggg acctgtgcgg ttcctgccta tgcctggact gctgcacgag ccccaggatc  6120
aggctggctt tctgcctcct gagcctccag acgtgggcag cagcgaccct ctgagcatgg  6180
tggaacctct gcagggcaga agcccagct acgcctcttg agaatgcggg cccggtaccc  6240
ccgacgcggc cgctaattct agatcgcgaa caaacaccat tgtcacactc cagtatacac  6300
aaacaccatt gtcacactcc agatatcaca aacaccattg tcacactcca aggcgaacaa  6360
acaccattgt cacactccaa ggctattcta gatcgcgaat acatacttc tttacattcc  6420
agtatacatt acatacttct ttacattcca gatatcatta catacttctt tacattccaa  6480
ggcgaattac atacttcttt acattccaag gctacctgag gcccgggggt acctcttaat  6540
taactggcct catgggcctt ccgctcactg cccgctttcc agtcgggaaa cctgtcgtgc  6600
```

```
cagtcaggtg caggctgcct atcagaaggt ggtggctggt gtggccaatg ccctggctca    6660
caaataccac tgagatcttt ttccctctgc caaaaattat ggggacatca tgaagccect    6720
tgagcatctg acttctggct aataaaggaa atttattttc attgcaatag tgtgttggaa    6780
tttttttgtgt ctctcactcg gaaggacata tgggagggca aatcatttaa aacatcagaa   6840
tgagtatttg gtttagagtt tggcaacata tgcccatatg ctggctgcca tgaacaaagg    6900
ttggctataa agaggtcatc agtatatgaa acagccccct gctgtccatt ccttattcca    6960
tagaaaagcc ttgacttgag gttagatttt ttttatattt tgtttgtgt tattttttc      7020
tttaacatcc ctaaaatttt ccttacatgt tttactagcc agatttttcc tcctctcctg    7080
actactccca gtcatagctg tccctcttct cttatggaga tccctcgacc tgcagcccaa    7140
gctgtagata agtagcatgg cgggttaatc attaactaca aggaaccoct agtgatggag    7200
ttggccactc cctctctgcg cgctcgctcg ctcactgagg ccgggcgacc aaaggtcgcc    7260
cgacgcccgg gctttgcccg ggcggcctca gtgagcgagc gagcgcgcag ctggcgtaa     7319
```

```
SEQ ID NO: 33            moltype = DNA   length = 5678
FEATURE                  Location/Qualifiers
misc_feature             1..5678
                         note = pGG2-hAAT-null
source                   1..5678
                         mol_type = other DNA
                         organism = synthetic construct SEQUENCE: 33
cagcagctgc gcgctcgctc gctcactgag gccgcccggg caaagcccgg gcgtcgggcg    60
acctttggtc gcccggcctc agtgagcgag cgagcgcgca gagagggagt ggccaactcc    120
atcactaggg gttccttgta gttaatgatt aacccgccat gctacttatc tacgtagcca    180
tgctctagac atggctcgac agatctgata tcatcgatga attcgagctc ggtacccggc    240
cgcagattta ggtgacacta tagaatatgc atcactagta agcttgcgaa ttccagtcta    300
cagagaggtc tctgacctct gccccagctc caaggtcagc aggcagggag ggctgtgtgt    360
ttgctgtttg ctgcttgcaa tgtttgccca ttttagggac atgagtaggc tgaagtttgt    420
tcagtgtgga cttcagaggc agcacacaaa cagcaagctt gcgaattcca gtctacagag    480
aggtctctga cctctgcccc agctccaagg tcagcaggca ggggctg tgtgtttgct       540
gtttgctgct tgcaatgttt gcccatttta gggacatgag taggctgaag tttgttcagt    600
gtggacttca gaggcagcac acaaacagca agcttgcgaa ttccagtcta cagagaggtc    660
tctgacctct gccccagctc caaggtcagc aggcagggag ggctgtgtgt ttgctgtttg    720
ctgcttgcaa tgtttgccca ttttagggac atgagtaggc tgaagtttgt tcagtgtgga    780
cttcagaggc agcacacaaa cagcaagctt gctctcagac tggaattcgt cgacgagctc    840
cctatagtga gtcgtattag aggccgactg acccggtacc cggggatctt gctaccagtg    900
gaacagccac taaggattct gcagtgagag cagagggcca gctaagtggt actctcccag    960
agactgtctg actcacgcca cccctccac cttggacaca ggacgctgtg gtttctgagc      1020
caggtacaat gactcctttc ggtaagtgca gtggaagctg tacactgccc aggcaaagcg    1080
tccgggcagc gtaggcgggc gactcagatc ccagccagtg gacttagccc ctgtttgctc    1140
ctccgataac tggggtgacc ttggttaata ttcaccagca gcctcccccg ttgcccctct    1200
ggatccactg cttaaaatacg gacgaggaca gggccctgtc tcctcagctt caggcaccac   1260
cactgacctg ggacagtgaa tgtcccctg atctgcggcc gtgactctct taaggtagcc    1320
ttgcagaagt tggtcgtgag gcactgggca ggtaagtatc aaggttacaa gacaggttta    1380
aggagaccaa tagaaactgg gcttgtcgag acagagaaga ctcttgcgtt tctgataggc     1440
acctattggt cttactgaca tccactttgc ctttctctcc acaggtgtcc actcccagtt    1500
caattacagc tcttaaggct agagtactta atacgactca ctataggcta gcctcgacct    1560
cgagacgcgt gatatcggat cccggccggc ggccgcttcc ctttagtgag ggttaatgct    1620
tcgagcagac atgataagat acattgatga gtttggacaa accacaacta gaatgcagtg    1680
aaaaaaatgc tttatttgtg aaatttgtga tgctattgct ttatttgtaa ccattataag    1740
ctgcaataaa caagttaaca acaacaattg cattcatttt atgtttcagg ttcaggggga    1800
gatgtgggag gttttttaaa gcaagtaaaa cctctacaaa tgtggtaaaa tccgataagg    1860
gactagagca tggctacgta gataagtagc atggcgggtt aatcattaac tacaaggaac    1920
ccctagtgat ggagttggcc actccctctc tgcgcgctcg ctcgctcact gaggccgggc    1980
gaccaaaggt cgcccgacgc ccgggctttg cccgggcggc ctcagtgagc gagcgagcg     2040
gccagctggc gtaatagcga gaggcccgc accgatcgcc cttcccaaca gttgcgcagc     2100
ctgaatggcg aatggaattc cagacgattg agcgtcaaaa tgtaggtatt tccatgagcg    2160
tttttccgtt gcaatggctg gcggtaatat tgttctggat attaccagca aggccgatag    2220
tttgagttct tctactcagg caagtgatgt tattactaat caaagaagta ttgcgacaac    2280
ggttaatttg cgtgatggac agactctttt actcggtggc ctcactgatt ataaaaacac    2340
ttctcaggat tctggcgtac cgttcctgtc taaaatccct ttaatcggcc tcctgtttag    2400
ctcccgctct gattctaacg aggaaagcac gttatacgtg ctcgtcaaag caaccatagt    2460
acgcgccctg tagcggcgca ttaagcgcgg cgggtgtggt ggttacgcgc agcgtgaccg    2520
ctacacttgc cagcgcccta gcgcccgctc cttttcgctt cttcccttcc tttctcgcca    2580
cgttcgccgg ctttccccgt caagctctaa atcggggggc tccctttaggg ttccgattta   2640
gtgctttacg gcacctcgac cccaaaaaac ttgattaggg tgatggttca cgtagtgggc    2700
catcgcccta atagacggtt tttcgccctt tgacgttgga gtccacgttc tttaatagtg    2760
gactcttgtt ccaaactgga caacactca accctatctc ggtctattct tttgatttat     2820
aagggatttt gccgatttcg gcctattggt taaaaaatga gctgatttaa caaaaattta    2880
acgcgaattt taacaaaata ttaacgtcta caatttaaat atttgcttat acaatcttcc    2940
tgttttgggg gcttttctga ttatcaaccg gggtacatat gattgacatg ctagttttac    3000
gattaccgtt catcgattct cttgtttgct ccagactctc aggcaatgac ctgatagcct    3060
ttgtagagac ctctcaaaaa tagctaccct ctccggcatg aatttatcag ctagaacggt    3120
tgaatatcat attgatggtg atttgactgt ctccggcctt tctcacccgt ttgaatcttt    3180
acctacacat tactcaggca ttgcatttaa aatatatgag ggttctaaaa atttttatcc    3240
ttgcgttgaa ataaaggctt ctcccgcaaa agtattacag ggtcataatg tttttggtac     3300
aaccgattta gctttatgct ctgaggcttt attgcttaat tttgctaatt ctttgccttg    3360
cctgtatgat ttattggatg ttggaatcgc ctgatgcggt attttctcct tacgcatctg    3420
tgcggtattt cacaccgcat atggtgcact ctcagtacaa tctgctctga tgccgcatag    3480
```

-continued

```
ttaagccagc cccgacaccc gccaacaccc gctgacgcgc cctgacgggc ttgtctgctc  3540
ccggcatccg cttacagaca agctgtgacc gtctccggga gctgcatgtg tcagaggttt  3600
tcaccgtcat caccgaaacg cgcgagacga aagggcctcg tgatacgcct atttttatag  3660
gttaatgtca tgataataat ggtttcttag acgtcaggtg gcacttttcg gggaaatgtg  3720
cgcggaaccc ctatttgttt attttctaa atacattcaa atatgtatcc gctcatgaga  3780
caataaccct gataaatgct tcaataatat tgaaaaagga agagtatgag tattcaacat  3840
ttccgtgtcg cccttattcc cttttttgcg gcattttgcc ttcctgtttt tgctcaccca  3900
gaaacgctgg tgaaagtaaa agatgctgaa gatcagttgg gtgcacgagt gggttacatc  3960
gaactggatc tcaacagcgg taagatcctt gagagttttc gccccgaaga acgttttcca  4020
atgatgagca cttttaaagt tctgctatgt ggcgcggtat tatcccgtat tgacgccgga  4080
caagagcaac tcggtcgccg catacactat tctcagaatg acttggttga gtactcacca  4140
gtcacagaaa agcatcttac ggatggcatg acagtaagag aattatgcag tgctgccata  4200
accatgagtg ataacactgc ggccaactta cttctgacaa cgatcggagg accgaaggag  4260
ctaaccgctt ttttgcacaa catgggggat catgtaactc gccttgatcg ttgggaaccg  4320
gagctgaatg aagccatacc aaacgacgag cgtgacacca cgatgcctgt agcaatggca  4380
acaacgttgc gcaaactatt aactggcgaa ctacttactc tagcttcccg gcaacaatta  4440
atagactgga tggaggcgga taaagttgca ggaccacttg tgcgctcggc ccttccggct  4500
ggctggttta ttgctgataa atctggagcc ggtgagcgtg ggtctcgcgg tatcattgca  4560
gcactgggc cagatggtaa gccctcccgt atcgtagtta tctacacgac ggggagtcag  4620
gcaactatgg atgaacgaaa tagacagatc gctgagatag gtgcctcact gattaagcat  4680
tggtaactgt cagaccaagt ttactcatat atactttaga ttgatttaaa acttcatttt  4740
taatttaaaa ggatctaggt gaagatcctt tttgataatc tcatgaccaa aatcccttaa  4800
cgtgagtttt cgttccactg agcgtcagac cccgtagaaa agatcaaagg atcttcttga  4860
gatcctttt ttctgcgcgt aatctgctgc ttgcaaacaa aaaaaccacc gctaccagcg  4920
gtggtttgtt tgccggatca agagctacca actctttttc cgaaggtaac tggcttcagc  4980
agagcgcaga taccaaatac tgtccttcta gtgtagccgt agttaggcca ccacttcaag  5040
aactctgtag caccgcctac atacctcgct ctgctaatcc tgttaccagt ggctgctgcc  5100
agtggcgata agtcgtgtct taccgggttg gactcaagac gatagttacc ggataaggcg  5160
cagcggtcgg gctgaacggg gggttcgtgc acacagccca gcttggagcg aacgacctac  5220
accgaactga gatacctaca gcgtgagcta tgagaaagcg ccacgcttcc cgaagggaga  5280
aaggcggaca ggtatccggt aagcggcagg gtcggaacag gagagcgcac gagggagctt  5340
ccaggggaa acgcctggta tctttatagt cctgtcgggt ttcgccacct ctgacttgag  5400
cgtcgatttt tgtgatgctc gtcaggggg cggagcctat ggaaaaacgc cagcaacgcg  5460
gcctttttac ggttcctggc cttttgctgg ccttttgctc acatgttctt tcctgcgtta  5520
tccctgatt ctgtggataa ccgtattacc gcctttgagt gagctgatac cgctcgccgc  5580
agccgaacga ccgagcgcag cgagtcagtg agcgaggaag cggaagagcg cccaatacgc  5640
aaaccgcctc tccccgcgcg ttggccgatt cattaatg                         5678
```

```
SEQ ID NO: 34              moltype = DNA  length = 6363
FEATURE                    Location/Qualifiers
misc_feature              1..6363
                          note = pGG2-hAAT-moFGF21
source                    1..6363
                          mol_type = other DNA
                          organism = synthetic construct
SEQUENCE: 34
cgcgtgatat cggatcccgg ccggcggccg cttcccttta gtgagggtta atgcttcgag  60
cagacatgat aagatacatt gatgagtttg gacaaaccac aactagaatg cagtgaaaaa  120
aatgctttat ttgtgaaatt tgtgatgcta ttgcttatt tgtaaccatt ataagctgca  180
ataaacaagt taacaacaac aattgcattc attttatgtt tcaggttcag ggggagatgt  240
gggaggtttt ttaaagcaag taaaacctct acaaatgtgg taaaatccga taagggacta  300
gagcatggct acgtgataa gtagcatggc gggttaatca ttaactacaa ggaacccta  360
gtgatggagt tggccactcc ctctctgcgc gctcgctcgc tcactgaggc cgggcgacca  420
aaggtcgccc gacgcccggg ctttgcccgg cggcctcag tgagcgagcg agcgcgccag  480
ctggcgtaat agcgaagagg cccgcaccga tcgcccttcc caacagttgc gcagcctgaa  540
tggcgaatgg aattccagac gattgagcgt caaaatgtag gtatttccat gagcgttttt  600
ccgttgcaat ggctggcggt aatattgttc tggatattac cagcaaggcc gatagtttga  660
gttcttctac tcaggcaagt gatgttatta ctaatcaaag aagtattgcg acaacggtta  720
atttgcgtga tggacagact cttttactcg gtggcctcac tgattataaa aacacttctc  780
aggattctgg cgtaccgttc ctgtctaaaa tccctttaat cggcctcctg tttagctccc  840
gctctgattc taacgaggaa agcacgttat acgtgctcgt caaagcaacc atagtacgcg  900
ccctgtagcg gcgcattaag cgcggcgggt gtggtggtta cgcgcagcgt gaccgctaca  960
cttgccagcg ccctagcgcc cgctcctttc gctttcttcc cttcctttct cgccacgttc  1020
gccggctttc cccgtcaagc tctaaatcgg gggctccctt tagggttccg atttagtgct  1080
ttacggcacc tcgaccccaa aaaacttgat tagggtgatg gttcacgtag tgggccatcg  1140
ccctgataga cggtttttcg ccctttgacg ttggagtcca cgttctttaa tagtggactc  1200
ttgttccaaa ctggaacaac actcaaccct atctcggtct attcttttga tttataaggg  1260
attttgccga tttcggccta ttggttaaaa aatgagctga tttaacaaaa atttaacgcg  1320
aattttaaca aaatattaac gtctacaatt taaatattg cttatacaat cttcctgttt  1380
ttggggcttt tctgattatc aaccggggta catatgattg acatgctagt tttacgatta  1440
ccgttcatcg attctcttgt ttgctccaga ctctcaggca atgacctgat agcctttgta  1500
gagacctctc aaaaatagct accctctccg gcatgaattt atcagctaga acggttgaat  1560
atcatattga tggtgatttg actgtctccg gcctttctca cccgtttgaa tctttaccta  1620
cacattactc aggcattgca tttaaaatat atgagggttc taaaaatttt tatccttgcg  1680
ttgaaataaa ggcttctccc gcaaaagtat tacagggtca taatgttttt ggtacaaccg  1740
atttagcttt atgctctgag gctttattgc ttaattttgc taattctttg ccttgcctgt  1800
atgatttatt ggatgttgga atcgcctgat gcggtatttt ctccttacgc atctgtgcgg  1860
tatttcacac cgcatatggt gcactctcag tacaatctgc tctgatgccg catagttaag  1920
ccagcccga cacccgccaa cacccgctga cgcgccctga cgggcttgtc tgctcccggc  1980
```

```
atccgcttac agacaagctg tgaccgtctc cgggagctgc atgtgtcaga ggttttcacc  2040
gtcatcaccg aaacgcgcga gacgaaaggg cctcgtgata cgcctatttt tataggttaa  2100
tgtcatgata ataatggttt cttagacgtc aggtggcact tttcggggaa atgtgcgcgg  2160
aacccctatt tgtttatttt tctaaataca ttcaaatatg tatccgctca tgagacaata  2220
accctgataa atgcttcaat aatattgaaa aaggaagagt atgagtattc aacatttccg  2280
tgtcgccctt attccctttt ttgcggcatt ttgccttcct gttttttgctc acccagaaac  2340
gctggtgaaa gtaaaagatg ctgaagatca gttgggtgca cgagtgggtt acatcgaact  2400
ggatctcaac agcggtaaga tccttgagag ttttcgcccc gaagaacgtt ttccaatgat  2460
gagcactttt aaagttctgc tatgtggcgc ggtattatcc cgtattgacg ccgggcaaga  2520
gcaactcggt cgccgcatac actattctca gaatgacttg gttgagtact caccagtcac  2580
agaaaagcat cttacggatg gcatgacagt aagagaatta tgcagtgctg ccataaccat  2640
gagtgataac actgcggcca acttacttct gacaacgatc ggaggaccga aggagctaac  2700
cgcttttttg cacaacatgg gggatcatgt aactcgcctt gatcgttggg aaccggagct  2760
gaatgaagcc ataccaaacg acgagcgtga caccacgatg cctgtagcaa tggcaacaac  2820
gttgcgcaaa ctattaactg gcgaactact tactctagct tcccggcaac aattaataga  2880
ctggatggag gcggataaag ttgcaggacc acttctgcgc tcggcccttc cggctggctg  2940
gtttattgct gataaatctg gagccggtga gcgtgggtct cgcggtatca ttgcagcact  3000
ggggccagat ggtaagccct cccgtatcgt agttatctac acgacgggga gtcaggcaac  3060
tatggatgaa cgaaatagac agatcgctga gataggtgcc tcactgatta agcattggta  3120
actgtcagac caagtttact catatatact ttagattgat ttaaaacttc atttttaatt  3180
taaaaggatc taggtgaaga tcctttttga taatctcatg accaaaatcc cttaacgtga  3240
gttttcgttc cactgagcgt cagaccccgt agaaaagatc aaaggatctt cttgagatcc  3300
tttttttctg cgcgtaatct gctgcttgca aacaaaaaaa ccaccgctac cagcggtggt  3360
ttgtttgccg gatcaagagc taccaactct ttttccgaag gtaactggct tcagcagagc  3420
gcagatacca aatactgtcc ttctagtgta gccgtagtta ggccaccact tcaagaactc  3480
tgtagcaccg cctacatacc tcgctctgct aatcctgtta ccagtggctg ctgccagtgg  3540
cgataagtcg tgtcttaccg ggttggactc aagacgatag ttaccggata aggcgcagcg  3600
gtcgggctga acggggggtt cgtgcacaca gcccagcttg gagcgaacga cctacaccga  3660
actgagatac ctacagcgtg agctatgaga aagcgccacg cttcccgaag ggagaaaggc  3720
ggacaggtat ccggtaagcg gcagggtcgg aacaggagag cgcacgaggg agcttccagg  3780
gggaaacgcc tggtatcttt atagtcctgt cgggtttcgc cacctctgac ttgagcgtcg  3840
atttttgtga tgctcgtcag ggggggcggag cctatggaaa aacgccagca acgcggcctt  3900
tttacggttc ctggcctttt gctggccttt tgctcacatg ttctttcctg cgttatcccc  3960
tgattctgtg gataaccgta ttaccgcctt tgagtgagct gataccgctc gccgcagccg  4020
aacgaccgag cgcagcgagt cagtgagcga ggaagcggaa gagcgcccaa tacgcaaacc  4080
gcctctcccc gcgcgttggc cgattcatta atgcagcagc tgcgcgctcg ctcgctcact  4140
gaggccgccc gggcaaagcc cgggcgtcgg gcgacctttg tcgcccggc ctcagtgagc  4200
gagcgagcgc gcagagaggg agtggccaac tccatcacta ggggttcctt gtagttaatg  4260
attaacccgc catgctactt atctacgtag ccatgctcta cagactggcc tacagatctg  4320
atatcatcga tgaattcgag ctcggtaccc ggccgcagat ttaggtgaca ctatagaata  4380
tgcatcacta gtaagcttgc gaattccagt ctacagagag gtctctgacc tctgccccag  4440
ctccaaggtc agcaggcagg gagggctgtg tgtttgctgt ttgctgcttg caatgtttgc  4500
ccattttagg acatgagta ggctgaagtt tgttcagtgt tgttcagtga ggcagcacac  4560
aaacagcaag cttgcgaatt ccagtctaca gagaggtctc tgacctctgc cccagctcca  4620
aggtcagcag gcagggaggg ctgtgtgttt gctgtttgct gcttgcaatg tttgcccatt  4680
ttagggacat gagtaggctg aagtttgttc agtgtggact tcagaggcag cacacaaaca  4740
gcaagcttgc gaattccagt ctacagagag gtctctgacc tctgccccag ctccaaggtc  4800
agcaggcagg gagggctgtg tgtttgctgt ttgctgcttg caatgtttgc ccattttagg  4860
gacatgagta ggctgaagtt tgttcagtgt ggacttcaga ggcagcacac aaacagcaag  4920
ctttgctcta gactggaatt cgtcgacgag ctccctatag tgagtcgtat tagaggccga  4980
ctgaccggt acccggggat cttgctacca gtggaacagc cactaaggat tctgcagtga  5040
gagcagaggg ccagctaagt ggtactctcc cagagactgt ctgactcacg ccacccctc  5100
caccttggac acaggacgct gtggtttctg agccaggtac aatgactcct ttcggtaagt  5160
gcagtggaag ctgtacactg cccaggcaaa gcgtccgggc agcgtaggcg ggcgactcag  5220
atcccagcca gtggacttag cccctgtttg ctcctccgat aactggggtg accttggtta  5280
atattcacca gcagcctccc ccgttgccc tctggatcca ctgcttaaat acggacgagg  5340
acagggccct gtctcctcag cttcaggcac caccactgac ctgggacagt gaatgtcccc  5400
ctgatctgcg gccgtgactc tcttaaggta gccttgcaga agttggtcgt gaggcactgg  5460
gcaggtaagt atcaaggtta caagacaggt ttaaggagac caatagaaac tgggcttgtc  5520
gagacagaga agactcttgc gtttctgata ggcacctatt ggtcttactg acatccactt  5580
tgcctttctc tccacaggtg tccactccca gttcaattac agctcttaag gctagagtac  5640
ttaatacgac tcactatagg ctagcctcga cctcgagcgc aagcttgagc tagcgccacc  5700
atggaatgga tgagaagcag agtgggcacc ctgggcctgt gggtgcgact gctgctggct  5760
gtgtttctgc tgggcgtgta ccaggcctac cccatccctg actctagccc cctgcctcag  5820
tttggcggac aagtgcggca gagatacctg tacaccgacg acgaccagga caccgaggcc  5880
cacctggaaa tccgcgagga tggcacagtc gtgggcgctg ctcacagaag ccctgagagc  5940
ctgctggaac tgaaggccct gaagcccggc gtgatccaga tcctgggcgt gaaggccagc  6000
agattcctgt gccagcagcc tgacggcgcc ctgtacggct ctcctcactt cgatcctgag  6060
gcctgcagct tcagagagct gctgctggag gacggctaca acgtgtacca gtctgaggcc  6120
cacggcctgc ccctgagact gcctcagaag acagcccta accaggacgc cacaagctgg  6180
ggacctgtgc ggttcctgcc tatgcctgga ctgctgcacg agcccaggga tcaggctggc  6240
tttctgcctc ctgagcctcc agacgtgggc agcagcgacc tctgagcat ggtggaacct  6300
ctgcagggca gaagccccag ctacgcctct tgagaatgcg ggcccggtac ccccgacgcg  6360
gcc                                                                6363
```

SEQ ID NO: 35          moltype = DNA   length = 4403
FEATURE                Location/Qualifiers
misc_feature           1..4403
                       note = pAAV-CMV-null

```
source                1..4403
                      mol_type = other DNA
                      organism = synthetic construct
SEQUENCE: 35
cgacggtacc agcgctgtcg aggccgcttc gagcagacat gataagatac attgatgagt   60
ttggacaaac cacaactaga atgcagtgaa aaaaatgctt tatttgtgaa atttgtgatg  120
ctattgcttt atttgtaacc attataagct gcaataaaca agttaacaac aacaattgca  180
ttcattttat gtttcaggtt caggggggaga tgtgggaggg ttttttaaagc aagtaaaacc  240
tctacaaatg tggtaaaatc gattaggatc ttcctagagc atggctacct agacatggct  300
cgacagatca gcgctcatgc tctggaagat ctcgatttaa atgcggccgc aggaacccct  360
agtgatggag ttggccactc cctctctgcg cgctcgctcg ctcactgagg ccgggcgacc  420
aaaggtcgcc cgacgcccgg gctttgcccg ggcggcctca gtgagcgagc gagcgcgcag  480
ctgcctgcag gggcgcctga tgcggtattt tctccttacg catctgtgcg gtatttcaca  540
ccgcatacgt caaagcaacc atagtacgcg ccctgtagcg gcgcattaag cgcggcgggt  600
gtggtggtta cgcgcagcgt gaccgctaca cttgccagcg ccctagcgcc cgctcctttc  660
gctttcttcc cttcctttct cgccacgttc gccggctttc cccgtcaagc tctaaatcgg  720
gggctccctt tagggttccg atttagtgct ttacggcacc tcgaccccaa aaaacttgat  780
ttgggtgatg gttcacgtag tgggccatcg ccctgataga cggtttttcg ccctttgacg  840
ttggagtcca cgttctttaa tagtggactc ttgttccaaa ctggaacaac actcaaccct  900
atctcgggct attctttga tttataaggg attttgccga tttcggccta ttggttaaaa  960
aatgagctga tttaacaaaa atttaacgcg aattttaaca aaatattaac gtttacaatt 1020
ttatggtgca ctctcagtac aatctgctct gatgccgcat agttaagcca gccccgacac 1080
ccgccaacac ccgctgacgc gccctgacgg gcttgtctgc tcccggcatc cgcttacaga 1140
caagctgtga ccgtctccgg gagctgcatg tgtcagaggt tttcaccgtc atcaccgaaa 1200
cgcgcgagac gaaagggcct cgtgatacgc ctatttttat aggttaatgt catgataata 1260
atggtttctt agacgtcagg tggcactttt cggggaaatg tgcgcggaac ccctatttgt 1320
ttatttttct aaatacattc aaatatgtat ccgctcatga gacaataacc ctgataaatg 1380
cttcaataat attgaaaaag gaagagtatg agtattcaac atttccgtgt cgcccttatt 1440
cccttttttg cggcatttttg ccttcctgtt tttgctcacc cagaaacgct ggtgaaagta 1500
aaagatgctg aagatcagtt gggtgcacga gtgggttaca tcgaactgga tctcaacagc 1560
ggtaagatcc ttgagagttt tcgccccgaa gaacgttttc caatgatgag cacttttaaa 1620
gttctgctat gtggcgcggt attatcccgt attgacgccg gcaagagca actcggtcgc 1680
cgcatacact attctcagaa tgacttggtt gagtactcac cagtcacaga aaagcatctt 1740
acggatggca tgacagtaag agaattatgc agtgctgcca taaccatgag tgataacact 1800
gcggccaact tacttctgac aacgatcgga ggaccgaagg agctaaccgc tttttttgcac 1860
aacatggggg atcatgtaac tcgccttgat cgttgggaac cggagctgaa tgaagccata 1920
ccaaacgacg agcgtgacac cacgatgcct gtagcaatgg caacaacgtt gcgcaaacta 1980
ttaactggcg aactacttac tctagcttcc cggcaacaat taatagactg gatggaggcg 2040
gataaagttg caggaccact tctgcgctcg gcccttccgg ctggctggtt tattgctgat 2100
aaatctggag ccggtgagcg tgggtctcgc ggtatcattg cagcactggg gccagatggt 2160
aagccctccc gtatcgtagt tatctacacg acggggagtc aggcaactat ggatgaacga 2220
aatagacaga tcgctgagat aggtgcctca ctgattaagc attggtaact gtcagaccaa 2280
gtttactcat atatacttta gattggattta aaacttcatt tttaatttaa aaggatctag 2340
gtgaagatcc tttttgataa tctcatgacc aaaatccctt aacgtgagtt ttcgttccac 2400
tgagcgtcag accccgtaga aaagatcaaa ggatcttctt gagatccttt ttttctgcgc 2460
gtaatctgct gcttgcaaac aaaaaaacca ccgctaccag cggtggtttg tttgccggat 2520
caagagctac caactctttt tccgaaggta actggcttca gcagagcgca gataccaaat 2580
actgtccttc tagtgtagcc gtagttaggc caccacttca agaactctgt agcaccgcct 2640
acatacctcg ctctgctaat cctgttacca gtggctgctg ccagtggcga taagtcgtgt 2700
cttaccgggt tggactcaag acgatagtta ccggataagg cgcagcggtc gggctgaacg 2760
gggggttcgt gcacacagcc cagcttggag cgaacgacct acaccgaact gagataccta 2820
cagcgtgagc tatgagaaag cgccacgctt cccgaaggga gaaaggcgga caggtatccg 2880
gtaagcggca gggtcggaac aggagagcgc acgagggagc ttccaggggg aaacgcctgg 2940
tatctttata gtcctgtcgg gtttcgccac ctctgacttg agcgtcgatt tttgtgatgc 3000
tcgtcagggg ggcggagcct atggaaaaac gccagcaacg cggcctttt acggttcctg 3060
gccttttgct ggccttttgc tcacatgtcc tgcaggcagc tgcgcgctcg ctcgctcact 3120
gaggccgccc gggcaaagcc cgggcgtcgg gcgacctttg tcgcccggc ctcagtgagc 3180
gagcgagcgc gcagagaggg agtggccaac tccatcacta ggggttcctg cggccgcgat 3240
atctgtagtt aatgattaac ccgccatgct acttatctac agatctcaat attggccatt 3300
agccatatta ttcattggtt atatagcata aatcaatatt ggctattggc cattgcatac 3360
gttgtatcta tatcataata tgtacattta tattggctca tgtccaatat gaccgccatg 3420
ttggcattga ttattgacta gttattaata gtaatcaatt acgggtcat tagttcatag 3480
cccatatatg gagttccgcg ttacataact tacggtaaat ggcccgcctg gctgaccgcc 3540
caacgacccc cgcccattga cgtcaataat gacgtatgtt cccatagtaa cgccaatagg 3600
gactttccat tgacgtcaat gggtggagta tttacggtaa actgcccact ggcagtaca 3660
tcaagtgtat catatgccaa gtccgccccc tattgacgtc aatgacggta atggcccgc 3720
ctggcattat gcccagtaca tgaccttacg ggactttcct acttggcagt acatctacgt 3780
attagtcatc gctattacca tggtgatgcg gttttggcag tacaccaatg ggcgtggata 3840
gcggtttgac tcacggggat ttccaagtct ccaccccatt gacgtcaatg ggagtttgtt 3900
ttggcaccaa aatcaacggg actttccaaa atgtcgtaac aactgcgatc gcccgccccg 3960
ttgacgcaaa tgggcggtag gcgtgtacgg tgggaggtct atataagcag agctcgttta 4020
gtgaaccgtc agatcactag gctagctatt gcggtagttt atcacagtta aattgctaac 4080
gcagtcagtg cttctgacac aacagtctcg aacttaagct gcagtgactc tcttaaggta 4140
gccttgcaga gttggtcgt gaggcactgg gcaggtaagt atcaaggtta caagacaggt 4200
ttaaggagac caatagaaac tgggcttgtc gagacagaga agactcttgc gtttctgata 4260
ggcacctatt ggtcttactg acatccactt tgcctttctc tccacaggtg tccactccca 4320
gttcaattac agctcttaag gctagagtac ttaatacgac tcactataga atacgactca 4380
ctataggggag acgctagcgt cga                                          4403
```

```
SEQ ID NO: 36           moltype = DNA  length = 5073
FEATURE                 Location/Qualifiers
misc_feature            1..5073
                        note = pAAV-CMV-moFGF21
source                  1..5073
                        mol_type = other DNA
                        organism = synthetic construct SEQUENCE: 36
ggggctagcg ccaccatgga atggatgaga agcagagtgg gcaccctggg cctgtgggtg   60
cgactgctgc tggctgtgtt tctgctgggc gtgtaccagg cctaccccat ccctgactct  120
agccccctgc tgcagtttgg cggacaagtg cggcagagat acctgtacac cgacgacgac  180
caggacaccg aggcccacct ggaaatccgc gaggatggca cagtcgtggg cgctgctcac  240
agaagccctg agagcctgct ggaactgaag gccctgaagc ccggcgtgat ccagatcctg  300
ggcgtgaagg ccagcagatt cctgtgccag cagcctgacg gcgccctgta cggctctcct  360
cacttcgatc ctgaggcctg cagcttcaga gagctgctgc tggaggacgg ctacaacgtg  420
taccagtctg aggcccacgg cctgcccctg agactgcctc agaaggacag ccctaaccag  480
gacgccacaa gctggggacc tgtgcggttc ctgcctatgc ctggactgct gcacgagccc  540
caggatcagg ctggctttct gcctcctgag cctccagacg tgggcagcag cgaccctctg  600
agcatggtgg aacctctgca gggcagaagc cccagctacg cctcttgaga atgcgggccc  660
ggtacccct cgacggtacc agcgctgtcg aggccgcttc gagcagacat gataagatac  720
attgatgagt ttgacaaac cacaactaga atgcagtgaa aaaaatgctt tatttgtgaa  780
atttgtatg ctattgcttt atttgtaacc attataagct gcaataaaca agttaacaac  840
aacaattgca ttcattttat gtttcaggtt cagggggaga tgtgggaggt tttttaaagc  900
aagtaaaacc tctacaaatg tggtaaaatc gattaggatc ttcctagagc atggctacct  960
agacatggct cgacagatca gcgctcatgc tctggaagat ctcgatttaa atgcggccgc 1020
aggaacccct agtgatggag ttggccactc cctctctgcg cgctcgctcg ctcactgagg 1080
ccgggcgacc aaaggtcgcc cgacgcccgg gctttgcccg ggcggcctca gtgagcgagc 1140
gagcgcgcag ctgcctgcag gggcgcctga tgcggtattt tctccttacg catctgtgcg 1200
gtatttcaca ccgcatacgt caaagcaacc atagtacgcg ccctgtagcg cgcattaag 1260
cgcggcgggt gtggtggtta cgcgcagcgt gaccgctaca cttgccagcg ccctagcgcc 1320
cgctcctttc gctttcttcc cttcctttct cgccacgttc gccggctttc cccgtcaagc 1380
tctaaatcgg gggctccctt tagggttccg atttagtgct ttacggcacc tcgaccccaa 1440
aaaacttgat ttgggtgatg gttcacgtag tgggccatcg ccctgataga cggttttttcg 1500
cccttgacg ttggagtcca cgttctttaa tagtggactc ttgttccaaa ctggaacaac 1560
actcaaccct atctcgggct attcttttga tttataaggg attttgccga tttcggccta 1620
ttggttaaaa aatgagctga tttaacaaaa atttaacgcg aatttttaaca aaatattaac 1680
gtttacaatt ttatggtgca ctctcagtac aatctgctct gatgccgcat agttaagcca 1740
gccccgacac ccgccaacac ccgctgacgc gccctgacgg gcttgtctgc tcccggcatc 1800
cgcttacaga caagctgtga ccgtctccgg gagctgcatg tgtcagaggt tttcaccgtc 1860
atcaccgaaa cgcgcgagac gaaagggcct cgtgatacgc ctatttttat aggttaatgt 1920
catgataata atggtttctt agacgtcagg tggcactttt cggggaaatg tgcgcggaac 1980
ccctatttgt ttatttttct aaatacattc aaatatgtat ccgctcatga caataaccct 2040
ctgataaatg cttcaataat attgaaaaag gaagagtatg agtattcaac atttccgtgt 2100
cgcccttatt ccttttttg cggcattttg ccttcctgtt tttgctcacc cagaaacgct 2160
ggtgaaagta aaagatgctg aagatcagtt gggtgcacga gtgggttaca tcgaactgga 2220
tctcaacagc ggtaagatcc ttgagagttt tcgccccgaa gaacgttttc caatgatgag 2280
cacttttaaa gttctgctat gtggcgcggt attatcccgt attgacgccg ggcaagagca 2340
actcggtcgc cgcatacact attctcagaa tgacttggtt gagtactcac cagtcacaga 2400
aaaagcatct tacgatggca tgacagtaag agaattatgc agtgctgcca taaccatgag 2460
tgataacact gcggccaact tacttctgac aacgatcgga ggaccgaagg agctaaccgc 2520
ttttttgcac aacatggggg atcatgtaac tcgccttgat cgttgggaac cggagctgaat 2580
tgaagccata ccaaacgacg agcgtgacac cacgatgcct gtagcaatgg caacaacgtt 2640
gcgcaaacta ttaactggcg aactacttac tctagcttcc cggcaacaat taatagactg 2700
gatggaggcg gataaagttg caggaccact tctgcgctcg gcccttccgg ctggctggtt 2760
tattgctgat aaatctggag ccggtgagcg tgggtctcgc ggtatcattg cagcactggg 2820
gccagatggt aagccctccc gtatcgtagt tatctacacg acggggagtc aggcaactat 2880
ggatgaacga aatagacaga tcgctgagat aggtgcctca ctgattaagc attggtaact 2940
gtcagaccaa gtttactcat atatacttta gattgattta aaacttcatt tttaatttaa 3000
aaggatctag gtgaagatcc tttttgataa tctcatgacc aaaatccctt aacgtgagtt 3060
ttcgttccac tgagcgtcag acccgtaga aagatcaaa ggatcttctt gagatccttt 3120
ttttctgcgc gtaatctgct gcttgcaaac aaaaaaacca ccgctaccag cggtggtttg 3180
tttgccggat caagagctac caactctttt tccgaaggta actggcttca gcagagcgca 3240
gataccaaat actgtccttc tagtgtagcc gtagttaggc caccacttca agaactctgt 3300
agcaccgcct acatacctcg ctctgctaat cctgttacca gtggctgctg ccagtggcgc 3360
taagtcgtgt cttaccgggt tggactcaag acgatagtta ccggataagg cgcagcggtc 3420
gggctgaacg gggggttcgt gcacacagcc cagcttggag cgaacgacct acaccgaact 3480
gagataccta cagcgtgagc tatgagaaag cgccacgctt cccgaaggga aaaggcgga 3540
caggtatccg gtaagcggca gggtcggaac aggagagcgc acgagggagc ttccaggggg 3600
aaacgcctgg tatctttata gtcctgtcgg gtttcgccac ctctgacttg agcgtcgatt 3660
tttgtgatgc tcgtcagggg ggcggagcct atggaaaaac gccagcaacg cggcctttt 3720
acggttcctg gccttttgct ggccttttgc tcacatgtcc tgcaggcagc tgcgcgctcg 3780
ctcgctcact gaggccgccc gggcaaagcc cgggcgtcgg cgacctttg tcgccggc 3840
ctcagtgagc gagcgagcgc gcagagaggg agtggccaac tccatcacta ggggttcctg 3900
cggccgcgat atctgtagtt aatgattaac cgcgcatcgt acttatctac agatctcaat 3960
attggccatt agccatatta ttcattggtt atatagcata aatcaatatt ggctattggc 4020
cattgcatac gttgtatcta tatcataata tgtacattta tattggctca tgtccaatat 4080
gaccgccatg ttggcattga ttattgacta gttattaata gtaatcaatt acggggtcat 4140
tagttcatag cccatatatg gagttccgcg ttacataact tacggtaaat ggcccgcctg 4200
gctgaccgcc caacgacccc cgcccattga cgtcaataat gacgtatgtt cccatagtaa 4260
```

```
cgccaatagg gactttccat tgacgtcaat gggtggagta tttacggtaa actgcccact   4320
tggcagtaca tcaagtgtat catatgccaa gtccgccccc tattgacgtc aatgacggta   4380
aatggcccgc ctggcattat gcccagtaca tgaccttacg ggactttcct acttggcagt   4440
acatctacgt attagtcatc gctattacca tggtgatgcg gttttggcag tacaccaatg   4500
ggcgtggata gcggtttgac tcacggggat ttccaagtct ccaccccatt gacgtcaatg   4560
ggagtttgtt ttggcaccaa aatcaacggg actttccaaa atgtcgtaac aactgcgatc   4620
gcccgccccg ttgacgcaaa tgggcggtag gcgtgtacgg tgggaggtct atataagcag   4680
agctcgttta gtgaaccgtc agatcactag gctagctatt gcggtagttt atcacagtta   4740
aattgctaac gcagtcagtg cttctgacac aacagtctcg aacttaagct gcagtgactc   4800
tcttaaggta gccttgcaga agttggtcgt gaggcactgg gcaggtaagt atcaaggtta   4860
caagacaggt ttaaggagac caatagaaac tgggcttgtc gagacagaga agactcttgc   4920
gtttctgata ggcacctatt ggtcttactg acatccactt tgcctttctc tccacaggtg   4980
tccactccca gttcaattac agctcttaag gctagagtac ttaatacgac tcactataga   5040
atacgactca ctataggggag acgctagcgt cga                              5073

SEQ ID NO: 37              moltype = DNA   length = 7292
FEATURE                    Location/Qualifiers
misc_feature               1..7292
                           note = pAAV-CAG-cloFGF21-dmiRT
source                     1..7292
                           mol_type = other DNA
                           organism = synthetic construct
SEQUENCE: 37
ggccgctaat tctagatcgc gaacaaacac cattgtcaca ctccagtata cacaaacacc   60
attgtcacac tccagatatc acaaacacca ttgtcacact ccaaggcgaa caaacaccat   120
tgtcacactc caaggctatt ctagatcgcg aattacatac ttctttacat tccagtatac   180
attacatact tctttacatt ccagatatca ttacatactc ttttacattc caaggcgaat   240
tacatacttc tttacattcc aaggctacct gaggcccggg ggtacctctt aattaactgg   300
cctcatgggc cttccgctca ctgcccgctt tccagtcggg aaacctgtcg tgccagtcag   360
gtgcaggctg cctatcagaa ggtggtggct ggtgtggcca atgccctggc tcacaaatac   420
cactgagatc ttttttccctc tgccaaaaat tatggggaca tcatgaagcc ccttgagcat   480
ctgacttctg gctaataaag gaaatttatt ttcattgcaa tagtgtgttg gaattttttg   540
tgtctctcac tcggaaggac atatgggagg gcaaatcatt taaaacatca gaatgagtat   600
ttggtttaga gtttggcaac atatgcccat atgctggctg ccatgaacaa aggttggcta   660
taaagaggtc atcagtatat gaaacagccc cctgctgtcc attccttatt ccatagaaaa   720
gccttgactt gaggttagat tttttttata ttttgttttg tgttattttt ttctttaaca   780
tccctaaaat tttccttaca tgttttacta gccagatttt tcctcctctc ctgactactc   840
ccagtcatag ctgtccctct tctcttatgg agatccctcg acctgcagcc caagctgtag   900
ataagtagca tggcgggtta tcattaact acaaggaacc cctagtgatg gagttggcca   960
ctccctctct gcgcgctcgc tcgctcactg aggccgggcg accaaaggtc gcccgacgcc   1020
cgggctttgc ccgggcggcc tcagtgagcg agcgagcgcg cagctggcgt aaagtgagcg   1080
agcgagcgcg cagctgcatt aatgaatcgg ccaacgcgcg gggagaggcg gtttgcgtat   1140
tgggcgctct ccgcttcct cgctcactga ctcgctgcgc tcggtcgttc ggctgcggcg   1200
agcggtatca gctcactcaa aggcggtaat acggttatcc acagaatcag gggataacgc   1260
aggaaagaac atgtgagcaa aaggccagca aaaggccagg aaccgtaaaa aggccgcgtt   1320
gctggcgttt ttccataggc tccgcccccc tgacgagcat cacaaaaatc gacgctcaag   1380
tcagaggtgg cgaaacccga caggactata aagataccag gcgtttcccc ctggaagctc   1440
cctcgtgcgc tctcctgttc cgaccctgcc gcttaccgga tacctgtccg cctttctccc   1500
ttcgggaagc gtggcgcttt ctcatagctc acgctgtagg tatctcagtt cggtgtaggt   1560
cgttcgctcc aagctgggct gtgtgcacga accccccgtt cagcccgacc gctgcgcctt   1620
atccggtaac tatcgtcttg agtccaaccc ggtaagacac gacttatcgc cactggcagc   1680
agccactggt aacaggatta gcagagcgag gtatgtaggc ggtgctacag agttcttgaa   1740
gtggtggcct aactacggct acactagaag aacagtattt ggtatctgcg ctctgctgaa   1800
gccagttacc ttcggaaaaa gagttggtag ctcttgatcc ggcaaacaaa ccaccgctgg   1860
tagcggtggt ttttttgttt gcaagcagca gattacgcgc agaaaaaaag gatctcaaga   1920
agatcctttg atcttttcta cggggtctga cgctcagtgg aacgaaaact cacgttaagg   1980
gattttggtc atgagattat caaaaaggat cttcacctag atccttttaa attaaaaatg   2040
aagttttaaa tcaatctaaa gtatatatga gtaaacttgg tctgacagtt accaatgctt   2100
aatcagtgag gcacctatct cagcgatctg tctatttcgt tcatccatag ttgcctgact   2160
ccccgtcgtg tagataacta cgatacggga gggcttacca tctggcccca gtgctgcaat   2220
gataccgcga gacccacgct caccggctcc agatttatca gcaataaacc agccagccgg   2280
aagggccgag cgcagaagtg gtcctgcaac tttatccgcc tccatccagt ctattaattg   2340
ttgccgggaa gctagagtaa gtagttcgcc agttaatagt ttgcgcaacg ttgttgccat   2400
tgctacaggc atcgtggtgt cacgctcgtc gtttggtatg gcttcattca gctccggttc   2460
ccaacgatca aggcgagtta catgatcccc catgttgtgc aaaaaagcgg ttagctcctt   2520
cggtcctccg atcgttgtca gaagtaagtt ggccgcagtg ttatcactca tggttatggc   2580
agcactgcat aattctctta ctgtcatgcc atccgtaaga tgcttttctg tgactggtga   2640
gtactcaacc aagtcattct gagaatagtg tatgcggcga ccgagttgct cttgcccggc   2700
gtcaatacgg gataataccg cgccacatag cagaacttta aaagtgctca tcattggaaa   2760
acgttcttcg gggcgaaaac tctcaaggat cttaccgctg ttgagatcca gttcgatgta   2820
acccactcgt gcacccaact gatcttcagc atcttttact ttcaccagcg tttctgggtg   2880
agcaaaaaca ggaaggcaaa atgccgcaaa aaagggaata agggcgacac ggaaatgttg   2940
aatactcata ctcttccttt ttcaatatta ttgaagcatt tatcagggtt attgtctcat   3000
gagcggatac atatttgaat gtatttagaa aaataaacaa ataggggttc cgcgcacatt   3060
tccccgaaaa gtgccacctg acgtctaaga aaccattatt atcatgacat taacctataa   3120
aaataggcgt atcacgaggc cctttcgtct cgcgcgtttc ggtgatgacg gtgaaaacct   3180
ctgacacatg cagctcccgg agacggtcac agcttgtctg taagcggatg ccgggagcag   3240
acaagcccgt cagggcgcgt cagcgggtgt tggcgggtgt cggggctggc ttaactatgc   3300
ggcatcagag cagattgtac tgagagtgca ccatatgcgg tgtgaaatac cgcacagatg   3360
```

```
cgtaaggaga aaataccgca tcaggcgatt ccaacatcca ataaatcata caggcaaggc   3420
aaagaattag caaaattaag caataaaagc tcagagcata aagctaaatc ggttgtacca   3480
aaaacattat gaccctgtaa tacttttgcg ggagaagcct ttatttcaac gcaaggataa   3540
aaattttttg aaccctcata tattttaaat gcaatgcctg agtaatgtgt aggtaaagat   3600
tcaaacgggt gagaaaggcc ggagacagtc aaatcaccat caatatgata ttcaaccgtt   3660
ctagctgata aattcatgcc ggagagggta gctatttttg agaggtctct acaaaggcta   3720
tcaggtcatt gcctgagagt ctggagcaaa caagagaatc gatgaacggt aatcgtaaaa   3780
ctagcatgtc aatcatatgt accccggttg ataatcagaa aagccccaaa aacaggaaga   3840
ttgtataagc aaatatttaa attgtaagcg ttaatatttt gttaaaattc gcgttaaatt   3900
tttgttaaat cagctcattt tttaaccaat aggccgaaat cggcaaaatc ccttataaat   3960
caaaagaata gaccgagata gggttgagtg ttgttccagt ttggaacaag agtccactat   4020
taaagaacgt ggactccaac gtcaaagggc gaaaaaccgt ctatcagggc gatggcccac   4080
tacgtgaacc atcaccctaa tcaagttttt tggggtcgag gtgccgtaaa gcactaaatc   4140
ggaaccctaa agggagcccc cgatttagag cttgacgggg aaagccggcg aacgtggcga   4200
gaaaggaagg gaagaaagcg aaaggagcgg gcgctagggc gctggcaagt gtagcggtca   4260
cgctgcgcgt aaccaccaca cccgccgcgc ttaatgcgcc gctacagggc gcgtactatg   4320
gttgctttga cgagcacgta taacgtgctt tcctcgttag aatcagagcg ggagctaaac   4380
aggaggccga ttaaagggat tttagacagg aacggtacgc cagaatcctg agaagtgttt   4440
ttataatcag tgaggccacc gagtaaaaga gtctgtccat cacgcaaatt aaccgttgtc   4500
gcaatacttc tttgattagt aataacatca cttgcctgag tagaagaact caaactatcg   4560
gccttgctgg taatatccag aacaatatta ccgccagcca ttgcaacgga atcgccattc   4620
gccattcagg ctgcgcaact gttgggaagg gcgatcggtg cgggcctctt ccactgagcg   4680
ccagctgcgc gctcgctcgc tcactgaggc cgcccgggca aagcccgggc gtcgggcgac   4740
ctttggtcgc ccgcctcag tgagcgagcg agcgcgcaga gagggagtgg ccaactccat   4800
cactaggggg tccttgtagt taatgattaa cccgccatgc tacttatcta ctcgacattg   4860
attattgact agttattaat agtaatcaat tacggggtca ttagttcata gcccatatat   4920
ggagttccgc gttacataac ttacggtaaa tggcccgcct ggctgaccgc ccaacgaccc   4980
ccgcccattg acgtcaataa tgacgtatgt tcccatagta acgccaatag ggactttcca   5040
ttgacgtcaa tgggtggagt atttacggta aactgcccac ttggcagtac atcaagtgta   5100
tcatatgcca agtacgcccc ctattgacgt caatgacggt aaatggcccg cctggcatta   5160
tgcccagtac atgaccttat gggactttcc tacttggcag tacatctacg tattagtcat   5220
cgctattacc atggtcgagg tgagccccac gttctgcttc actctcccca tctcccccccc   5280
ctccccaccc ccaattttgt atttatttat ttttaatta ttttgtgcag cgatgggggc   5340
ggggggggg ggggggcgcg cgccaggcgg ggcggggcgg ggcgagggggc ggggcggggc   5400
gaggcgagga ggtgcggcgg cagccaatca gagcggcgcg ctccgaaagt ttccttttat   5460
ggcgaggcgg cggcggcggc ggccctataa aaagcgaagc gcgcggcggg cgggagtcgc   5520
tgcgttgcct tcgcccgtg cccgctccg cgccgcctcg cgccgcccgc cccggctctg   5580
actgaccgcg ttactcccac aggtgagcgg gcgggacggc ccttctcctc cgggctgtaa   5640
ttagcgcttg gtttaatgac ggcttgtttc ttttctgtgg ctgcgtgaaa gccttgaggg   5700
gctccgggag ggccctttgt gcggggggag cggctcgggg ggtgcgtgcg tgtgtgtgtg   5760
cgtggggagc gccgcgtgcg gctccgcgct gcccggcggc tgtgagcgct gcgggcgcgg   5820
cgcggggctt tgtgcgctcc gcagtgtgcg cgagggggagc gcggccgggg gcggtgcccc   5880
gcggtgcggg gggctgcgag gggaacaaag gctgcgtgcg gggtgtgtgc gtgggggggt   5940
gagcagggggg tgtgggcgcg tcggtcgggc tgcaacccccc cctgcacccc cctccccgag   6000
ttgctgagca cggcccggct tcgggtgcgg ggctccgtac ggggcgtggc gcggggctcg   6060
ccgtgccggg cgggggtgg cggcaggtgg gggtgccggg cggggcgggg ccgcctcggg   6120
ccggggaggg ctcggggag gggcgcggcg gcccccgagg cgccggcggc tgtcgaggcg   6180
cggcgagccg cagccattgc cttttatggt aatcgtgcga gagggcgcag ggacttcctt   6240
tgtcccaaat ctgtgcggag ccgaaatctg ggaggcgccg ccgcacccccc tctagcgggc   6300
gcggggcgaa gcggtgcggc gccggcagga aggaaatggg cggggagggc cttcgtgcgt   6360
cgccgcgccg ccgtccccctt ctccctctcc agcctcgggg ctgtccgcgg ggggacgggt   6420
gccttcgggg gggacgggc agggcggggt tcggcttctg gcgtgtgacc ggcggctcta   6480
gagcctctgc taaccatgtt catgccttct tcttttttcct acagctcctg ggcaacgtgc   6540
tggttattgt gctgtctcat cattttggca aagaattgat taattcgagc gaacgcgtcg   6600
agtcgctcgg tacgatttaa attgaattgg cctcgagcgc aagcttgagc tagcgccacc   6660
atgggatggg ctgaggctgg attcgaacac ctgggactct gggtgccgt cctggccgtg   6720
ctgctcctgg aggcttgcag ggctcatccc atccctgaca gctccccact cctgcagttt   6780
ggaggacagg tgaggcagcg gtacctgtat accgacgatg cccaggagac agaagctcac   6840
ctgaaattc gggctgatgg aacagtggtc ggagctgccc gacagtcccc agagtctctc   6900
ctggaactga aggcccctcaa acccggagtg atccagattc tgggcgtcaa gacttctaga   6960
ttcctgtgcc agggaccaga cggcacccctg tacggcagcc tgcatttcga tcctgtggcc   7020
tgttcctttc gagagctcct gctcgaagac ggctacaaca tctatcactc tgagaccctg   7080
ggactcccac tgcgactcag acctcataat agtgcctatc gagatctggc tcccagggggc   7140
ccagctaggt ttctgccact ccccggactg tcccctgccc cacctgagcc acccgggcatt   7200
ctggctccag aacctccaga cgtgggctct agtgatcctcac tgagtatggt cggcccctca   7260
caggggaggt cacctagcta cgccagctga gc                                  7292
```

SEQ ID NO: 38              moltype = DNA  length = 6278
FEATURE                   Location/Qualifiers
misc_feature              1..6278
                          note = pGG2-hAAT-cloFGF21
source                    1..6278
                          mol_type = other DNA
                          organism = synthetic construct
SEQUENCE: 38
ggccgcttcc ctttagtgag ggttaatgct tcgagcagac atgataagat acattgatga   60
gtttggacaa accacaacta gaatgcagtg aaaaaaatgc tttatttgtg aaatttgtga   120
tgctattgct ttatttgtaa ccattataag ctgcaataaa caagttaaca acaacaattg   180
cattcatttt atgtttcagg ttcaggggga gatgtggtag gttttttaaa gcaagtaaaa   240
```

```
cctctacaaa tgtggtaaaa tccgataagg gactagagca tggctacgta gataagtagc    300
atggcgggtt aatcattaac tacaaggaac ccctagtgat ggagttggcc actccctctc    360
tgcgcgctcg ctcgctcact gaggccgggc gaccaaaggt cgcccgacgc ccgggctttg    420
cccgggcggc ctcagtgagc gagcgagcgc gccagctggc gtaatagcga agaggcccgc    480
accgatcgcc cttcccaaca gttggcgagc ctgaatgcga aatggaattc cagacgattg    540
agcgtcaaaa tgtaggtatt tccatgagcg ttttttccgtt gcaatggctg gcggtaatat    600
tgttctggat attaccagca aggccgatag tttgagttct tctactcagg caagtgatgt    660
tattactaat caaagaagta ttgcgacaac ggttaatttg cgtgatggac agactctttt    720
actcggtggc ctcactgatt ataaaaacac ttctccaggat tctggcgtac cgttcctgtc    780
taaaatccct ttaatcggcc tcctgtttag ctccccgctct gattctaacg aggaaagcac    840
gttatacgtg ctcgtcaaag caaccatagt acgcgccctg tagcggcgca ttaagcgcgg    900
cgggtgtggt ggttacgcgc agcgtgaccg ctacacttgc cagcgcccta gcgcccgctc    960
ctttcgcttt cttcccttcc tttctcgcca cgttcgccgg ctttccccgt caagctctaa   1020
atcgggggct ccctttaggg ttccgattta gtgctttacg gcacctcgac cccaaaaaac   1080
ttgattaggg tgatggttca cgtagtgggc catcgccctg atagacggtt tttcgccctt   1140
tgacgttgga gtccacgttc tttaatagtg gactcttgtt ccaaactgga acaacactca   1200
accctatctc ggtctattct tttgatttat aagggatttt gccgatttcg gcctattggt   1260
taaaaaatga gctgatttaa caaaaattta acgcgaattt taacaaaata ttaacgtcta   1320
caatttaaat atttgcttat acaatcttcc tgttttgggg gctttctga ttatcaaccg   1380
gggtacatat gattgacatg ctagttttac gattaccgtt catcgattct cttgtttgct   1440
ccagactctc aggcaatgac ctgatagcct ttgtagagac ctctcaaaaa tagctaccct   1500
ctccggcatg aatttatcag ctagaacggt tgaatatcat attgatggtg atttgactgt   1560
ctccggcctt tctcacccgt ttgaatcttt acctacacat tactcaggca ttgcatttaa   1620
aatatatgag ggttctaaaa attttttatcc ttgcgttgaa ataaaggctt ctcccgcaaa   1680
agtattacag ggtcataatg tttttggtac aaccgattta gctttatgct ctgaggcttt   1740
attgcttaat tttgctaatt ctttgccttg cctgtatgat ttattggatg ttggaatcga   1800
ctgatgcggt attttctcct tacgcatctg tgcggtattt cacaccgcat atggtgcact   1860
ctcagtacaa tctgctctga tgccgcatag ttaagccagc cccgacaccc gccaacaccc   1920
gctgacgcgc cctgacgggc ttgtctgctc ccggcatccg cttacagaca agctgtgacc   1980
gtctccggga gctgcatgtg tcagaggttt tcaccgtcat caccgaaacg cgcgagacga   2040
aagggcctcg tgatacgcct attttttatag gttaatgtca tgataataat ggtttcttag   2100
acgtcaggtg gcactttctcg gggaaatgtg cgcggaaccc ctatttgttt attttttctaa   2160
atacattcaa atatgtatcc gctcatgaga caataaccct gataaatgct tcaataatat   2220
tgaaaaagga agagtatgag tattcaacat ttccgtgtcg cccttattcc cttttttgcg   2280
gcattttgcc ttcctgtttt tgctcaccca gaaacgctgg tgaaagtaaa agatgctgaa   2340
gatcagttgg gtgcacgagt gggttacatc gaactggatc tcaacagcgg taagatcctt   2400
gagagttttc gccccgaaga acgttttcca atgatgagca cttttaaagt tctgctatgt   2460
ggcgcggtat tatcccgtat tgacgccggg caagagcaac tcggtcgccg catacactat   2520
tctcagaatg acttggttga gtactcacca gtcacagaaa agcatcttac ggatggcatg   2580
acagtaagag aattatgcag tgctgccata accatgagtg ataacactgc ggccaactta   2640
cttctgacaa cgatcggagg accgaaggag ctaaccgctt ttttgcacaa catgggggat   2700
catgtaactc gccttgatcg ttgggaaccg gagctgaatg aagccatacc aaacgacgag   2760
cgtgacacca cgatgcctgt agcaatggca acaacgttgc gcaaactatt aactggcgaa   2820
ctacttactc tagcttcccg gcaacaatta atagactgga tggaggcgga taaagttgca   2880
ggaccacttc tgcgctcggc ccttccggct ggctggttta ttgctgataa atctggagcc   2940
ggtgagcgtg ggtctcgcgg tatcattgca gcactggggc cagatggtaa gccctcccgt   3000
atcgtagtta tctacacgac ggggagtcag gcaactatgg atgaacgaaa tagacagatc   3060
gctgagatag gtgcctcact gattaagcat tggtaactgt cagaccaagt ttactcatat   3120
atactttaga ttgatttaaa acttcatttt taatttaaaa ggatctaggt gaagatcctt   3180
tttgataatc tcatgaccaa aatcccttaa cgtgagtttt cgttccactg agcgtcagac   3240
cccgtagaaa agatcaaagg atcttcttga gatcctttttt ttctgcgcgt aatctgctgc   3300
ttgcaaacaa aaaaaccacc gctaccagcg gtggtttgtt tgccggatca gagctacca    3360
actctttttc cgaaggtaac tggcttcagc agagcgcaga taccaaatac tgtccttcta   3420
gtgtagccgt agttaggcca ccacttcaag aactctgtag caccgcctac atacctcgct   3480
ctgctaatcc tgttaccagt ggctgctgcc agtggcgata agtcgtgtct taccgggttg   3540
gactcaagac gatagttacc ggataaggcg cagcggtcgg gctgaacggg gggttcgtgc   3600
acacagccca gcttggagcg aacgacctac accgaactga gatacctaca gcgtgagcta   3660
tgagaaagcg ccacgcttcc cgaagggaga aaggcggaca ggtatccggt aagcggcagg   3720
gtcggaacag gagagcgcac gagggagctt ccagggggaa acgcctggta tctttatagt   3780
cctgtcgggt ttcgccacct ctgacttgag cgtcgatttt tgtgatgctc gtcaggggg    3840
cggagcctat ggaaaaacgc cagcaacgcg gcctttttac ggttcctggc cttttgctgg   3900
ccttttgctc acatgttctt tcctgcgtta tcccctgatt ctgtggataa ccgtattacc   3960
gcctttgagt gagctgatac cgctcgccgc agccgaacga ccgagcgcag cgagtcagtg   4020
agcgaggaag cggaagagcg cccaatacgc aaaccgcctc tccccgcgcg ttggccgatt   4080
cattaatgca gcagctgcgc gctcgctcgc tcactgaggc cgcccgggca aagcccgggc   4140
gtcgggcgac ctttggtcgc ccggcctcag tgagcgagcg agcgcgcaga gagggagtgg   4200
ccaactccat cactagggggt tccttgtagt taatgattaa cccgccatgc tacttatcta   4260
cgtagccatg ctctagacat ggctcgacag atctgatatc atcgatgaat tcgagctcgg   4320
tacccggccg cagatttagg tgacactata gaatatacat cactagtaag cttgcgaatt   4380
ccagtctaca gagaggtctc tgacctctgc cccagctcca aggtcagcag gcagggaggg   4440
ctgtgtgttt gctgtttgct gcttgcaatg tttgcccatt ttagggacat gagtaggctg   4500
aagtttgttc agtgtggact tcagaggcag cacacaaaca gcaagcttgc gaattccagt   4560
ctacagagag gtctctgacc tctgcccag ctccaaggtc agcaggcagg gagggctgtg   4620
tgtttgctgt ttgctgcttg caatgtttgc ccattttagg gacatgagta ggctgaagtt   4680
tgttcagtgt ggacttcaga ggcagcacac aaacagcaag cttgcgaatt ccagtctaca   4740
gagaggtctc tgacctctgc cccagctcca aggtcagcag gcagggaggg ctgtgtgttt   4800
gctgtttgct gcttgcaatg tttgcccatt ttagggacat gagtaggctg aagtttgttc   4860
agtgtggact tcagaggcag cacacaaaca gcaagctttg ctctagactg gaattcgtcg   4920
acgagctccc tatagtgagt cgtattagag gccgactgac ccggtacccg gggatcttgc   4980
```

-continued

```
taccagtgga acagccacta aggattctgc agtgagagca gagggccagc taagtggtac   5040
tctcccagag actgtctgac tcacgccacc ccctccacct tggacacagg acgctgtggt   5100
ttctgagcca ggtacaatga ctcctttcgg taagtgcagt ggaagctgta cactgcccag   5160
gcaaagcgtc cgggcagcgt aggcgggcga ctcagatccc agccagtgga cttagcccct   5220
gtttgctcct ccgataactg gggtgacctt ggttaatatt caccagcagc ctcccccgtt   5280
gcccctctgg atccactgct taaatacgga cgaggacagg gccctgtctc ctcagcttca   5340
ggcaccacca ctgacctggg acagtgaatg tcccctgat ctgcggccgt gactctctta   5400
aggtagcctt gcagaagttg gtcgtgaggc actgggcagg taagtatcaa ggttacaaga   5460
caggtttaag gagaccaata gaaactgggc ttgtcgagac agagaagact cttgcgtttc   5520
tgataggcac ctattggtct tactgacatc cactttgcct ttctctccac aggtgtccac   5580
tcccagttca attacagctc ttaaggctag agtacttaat acgactcact ataggctagc   5640
gccaccatgg gatgggctga ggctggattc gaacacctgg gactctgggt gcccgtcctg   5700
gccgtgctgc tcctggaggc ttgcagggct catcccatcc ctgacagctc cccactcctg   5760
cagtttggag gacaggtgag gcagcggtac ctgtataccg ggagcacaga ggagacagaa   5820
gctcacctgg aaaattcgggc tgatggaaca gtggtcggag ctgcccgaca gtccccagag   5880
tctctcctgg aactgaaggc cctcaaaccc ggagtgatcc agattctggg cgtcaagact   5940
tctagattcc tgtgccaggg accagacggc accctgtacg gcagcctgca tttcgatcct   6000
gtggcctgtt cctttcgaga gctcctgctc gaagacggct acaacatcta tcactctgag   6060
accctgggac tcccactgcg actcagacct cataatagtg cctatcgaga tctggctccc   6120
agggggcccag ctaggtttct gccactcccc ggactgctcc ctgctccacc tgagccaccc   6180
ggcattctgg ctccagaacc tccagacgtg ggctctagtg atccactgag tatggtcggc   6240
ccctcacagg ggaggtcacc tagctacgcc agctgagc                            6278
```

```
SEQ ID NO: 39          moltype = DNA   length = 6278
FEATURE                Location/Qualifiers
misc_feature           1..6278
                       note = pGG2-hAAT-hsFGF21
source                 1..6278
                       mol_type = other DNA
                       organism = synthetic construct
SEQUENCE: 39
gatctgatat catcgatgaa ttcgagctcg gtacccggcc gcagatttag gtgacactat   60
agaatatgca tcactagtaa gcttgcgaat tccagtctac agagaggtct ctgacctctg   120
ccccagctcc aaggtcagca ggcagggagg gctgtgtgtt tgctgtttgc tgcttgcaat   180
gtttgcccat tttagggaca tgagtaggct gaagtttgtt cagtgtggac ttcagaggca   240
gcacacaaac agcaagcttg cgaattccag tctacagaga ggtctctgac ctctgcccca   300
gctccaaggt cagcaggcag ggagggctgt gtgtttgctg tttgctgctt gcaatgtttg   360
cccattttag ggacatgagt aggctgaagt ttgttcagtg tggacttcag aggcagcaca   420
caaacagcaa gcttgcgaat tccagtctac agagaggtct ctgacctctg ccccagctcc   480
aaggtcagca ggcagggagg gctgtgtgtt tgctgtttgc tgcttgcaat gtttgcccat   540
tttagggaca tgagtaggct gaagtttgtt cagtgtggac ttcagaggca gcacacaaac   600
agcaagcttt gctctagact ggaattcgtc gacgagctcc ctatagtgag tcgtattaga   660
ggccgactga cccggtaccc gggatcttg ctaccagtgg aacagccact aaggattctg   720
cagtgagagc agagggccag ctaagtggta ctctcccaga gactgtctga ctcacgccac   780
ccctccacc ttggacacag acgctgtggt tttctgagcc aggtacaatg actcctttcg   840
gtaagtgcag tggaagctgt acactgccca ggcaaagcgt ccgggcagcg taggcgggcg   900
actcagatcc cagccagtgg acttagcccc tgtttgctcc tccgataact ggggtgacct   960
tggttaatat tcaccagcag cctcccccgt tgcccctctg gatccactgc ttaaatacgg   1020
acgaggacag ggccctgtct cctcagcttc aggcaccacc actgacctgg gacagtgaat   1080
gtccccctga tctgcggccg tgactctctt aaggtagcct tgcagaagtt ggtcgtgagg   1140
cactgggcag gtaagtatca aggttacaag acaggtttaa ggagaccaat agaaactggg   1200
cttgtcgaga cagagaagac tcttgcgttt ctgataggca cctattggtc ttactgacat   1260
ccactttgcc tttctctcca caggtgtcca ctcccagttc aattacagct cttaaggcta   1320
gagtacttaa tacgactcac tataggctag cgccaccatg gactcggacg agaccgggtt   1380
cgagcactca ggactgtggg tttctgtgct ggctggtctt ctgctgggag cctgccaggc   1440
acaccccatc cctgactcca gtcctctcct gcaattcggg ggccagtcc ggcagcggta   1500
cctctacaca gatgatgccc agcagacaga agcccacctg gagatcaggg aggatgggac   1560
ggtgggggggc gctgctgacc agagccccga aagtctcctg cagctgaaag ccttgaagcc   1620
gggagttatt caaatcttgg gagtcaagac atccaggttc ctgtgccagc ggccagatgg   1680
ggccctgtat ggatcgctcc actttgaccc tgaggcctgc agcttccggg agctgcttct   1740
tgaggacgga tacaatgttt accagtccga agcccacggc ctcccgctgc acctgccagg   1800
gaacaagtcc ccacaccggg accctgcacc ccgaggacca gctcgcttcc tgccactacc   1860
aggcctgccc cccgcactcc cggagccacc cggaatcctg ccccccagc ccccgatgt   1920
gggctcctcg gaccctctga gcatggtggg accttcccag accttgccc ctgcagcgagcc   1980
ttcctgagcg gccgcttccc tttagtgagg gttaatgctt cgagcagaca tgataagata   2040
cattgatgag tttggacaaa ccacaactag aatgcagtga aaaaaatgct ttatttgtga   2100
aatttgtgat gctattgctt tatttgtaac cattataagc tgcaataaac aagttaacaa   2160
caacaattgc attcatttta tgtttcaggt tcaggggggag atgtgggagg ttttttaaag   2220
caagtaaaac ctctacaaat gtggtaaaat ccgataaggg actagagcat ggctacgtag   2280
ataagtagca tggcgggtta atcattaact acaaggaacc cctagtgatg gagttggcca   2340
ctccctctct gcgcgctcgc tcgctcactg aggccgggcg accaaaggtc gcccgacgcc   2400
cgggctttgc ccgggcggcc tcagtgagcg agcgagcgcg ccagctggcg taatagcgaa   2460
gaggcccgca ccgatcgccc ttcccaacag ttgcgcagcc tgaatggcga atggaattcc   2520
agacgattag cgctcaaaat gtaggtattt ccatgagcgt ttttcgttg caatgatggc   2580
cggtaatatt gttctggata ttaccagcaa ggccgatagt ttgagttctt ctactcaggc   2640
aagtgatgtt attactaatc aaagaagtat tgcgacaacg gttaatttgc gtgatggaca   2700
gactctttta ctcggtggcc tcactgatta taaaaacact tctcaggatt ctggcgtacc   2760
gttcctgtct aaaatccctt taatcggcct cctgtttagc tcccgctctg attctaacga   2820
ggaaagcacg ttatacgtgc tcgtcaaagc aaccatagta cgcgccctgt agcggcgcat   2880
```

```
taagcgcggc gggtgtggtg gttacgcgca gcgtgaccgc tacacttgcc agcgccctag    2940
cgcccgctcc tttcgctttc ttcccttcct ttctcgccac gttcgccggc tttccccgtc    3000
aagctctaaa tcgggggctc cctttagggt tccgatttag tgctttacgg cacctcgacc    3060
ccaaaaaact tgattagggt gatggttcac gtagtgggcc atcgccctga tagacggttt    3120
ttcgcccttt gacgttggag tccacgttct ttaatagtgg actcttgttc caaactggaa    3180
caacactcaa ccctatctcg gtctattctt ttgatttata agggatttttg ccgatttcgg    3240
cctattggtt aaaaaatgag ctgatttaac aaaaatttaa cgcgaatttt aacaaaatat    3300
taacgtctac aatttaaata tttgcttata caatcttcct gtttttgggg cttttctgat    3360
tatcaaccgg ggtacatatg attgacatgc tagttttacg attaccgttc atcgattctc    3420
ttgtttgctc cagactctca ggcaatgacc tgatagcctt tgtagagacc tctcaaaaat    3480
agctaccctc tccggcatga atttatcagc tagaacggtt gaatatcata ttgatggtga    3540
tttgactgtc tccggccttt ctcacccgtt tgaatcttta cctacacatt actcaggcat    3600
tgcatttaaa atatatgagg gttctaaaaa tttttatcct tgcgttgaaa taaaggcttc    3660
tcccgcaaaa gtattacagg gtcataatgt ttttggtaca accgatttag ctttatgctc    3720
tgaggcttta ttgcttaatt ttgctaattc tttgccttgc ctgtatgatt tattggatgt    3780
tggaatcgcc tgatgcggta ttttctcctt acgcatctgt gcggtatttc acaccgcata    3840
tggtgcactc tcagtacaat ctgctctgat gccgcatagt taagccagcc ccgacacccg    3900
ccaacacccg ctgacgcgcc ctgacgggct tgtctgctcc cggcatccgc ttacagacaa    3960
gctgtgaccg tctccgggag ctgcatgtgt cagaggtttt caccgtcatc accgaaacgc    4020
gcgagacgaa agggcctcgt gatacgccta ttttttatagg ttaatgtcat gataataatg    4080
gtttcttaga cgtcaggtgg cacttttcgg ggaaatgtgc gcggaacccc tatttgttta    4140
tttttctaaa tacattcaaa tatgtatccg ctcatgagac aataaccctg ataaatgctt    4200
caataatatt gaaaaaggaa gagtatgagt attcaacatt tccgtgtcgc ccttattccc    4260
ttttttgcgg cattttgcct tcctgttttt gctcacccag aaacgctggt gaaagtaaaa    4320
gatgctgaag atcagttggg tgcacgagtg ggttacatcg aactggatct caacagcggt    4380
aagatccttg agagttttcg ccccgaagaa cgttttccaa tgatgagcac ttttaaagtt    4440
ctgctatgtg gcgcggtatt atcccgtatt gacgccgggc aagagcaact cggtcgccgc    4500
atacactatt ctcagaatga cttggttgag tactcaccag tcacagaaaa gcatcttacg    4560
gatggcatga cagtaagaga attatgcagt gctgccataa ccatgagtga taacactgcg    4620
gccaacttac ttctgacaac gatcggagga ccgaaggagc taaccgcttt tttgcacaac    4680
atgggggatc atgtaactcg ccttgatcgt tgggaaccgg agctgaatga agccatacca    4740
aacgacgagc gtgacaccac gatgcctgta gcaatggcaa caacgttgcg caaactatta    4800
actggcgaac tacttactct agcttcccgg caacaattaa tagactggat ggaggcggat    4860
aaagttgcag gaccacttct gcgctcggcc cttccggctg gctggtttat tgctgataaa    4920
tctggagccg gtgagcgtgg gtctcgcggt atcattgcag cactggggcc agatggtaag    4980
ccctcccgta tcgtagttat ctacacgacg gggagtcagg caactatgga tgaacgaaat    5040
agacagatcg ctgagatagg tgcctcactg attaagcatt ggtaactgtc agaccaagtt    5100
tactcatata ctttttagat tgatttaaaa cttcattttt aatttaaaag gatctaggtg    5160
aagatccttt ttgataatct catgaccaaa atcccttaac gtgagttttc gttccactga    5220
gcgtcagacc ccgtagaaaa gatcaaagga tcttcttgag atcctttttt tctgcgcgta    5280
atctgctgct tgcaaacaaa aaaaccaccg ctaccagcgg tggtttgttt gccggatcaa    5340
gagctaccaa ctctttttcc gaaggtaact ggcttcagca gagcgcagat accaaatact    5400
gtccttctag tgtagccgta gttaggccac cacttcaaga actctgtagc accgcctaca    5460
tacctcgctc tgctaatcct gttaccagtg gctgctgcca gtggcgataa gtcgtgtctt    5520
accgggttgg actcaagacg atagttaccg gataaggcgc agcggtcggg ctgaacgggg    5580
ggttcgtgca cacagcccag cttggagcga acgacctaca ccgaactgag atacctacag    5640
cgtgagctat gagaaagcgc cacgcttccc gaagggagaa aggcggacag gtatccggta    5700
agcggcaggg tcggaacagg agagcgcacg agggagcttc cagggggaaa cgcctggtat    5760
ctttatagtc ctgtcgggtt tcgccaccttc tgacttgagc gtcgatttttt gtgatgctcg    5820
tcaggggggc ggagcctatg gaaaaacgcc agcaacgcgg cctttttacg gttcctggcc    5880
ttttgctgac ttttttgctca catgttctttt cctgcgttat ccctgattc tgtggataac    5940
cgtattaccg cctttgagtg agctgatacc gctcgccgca gccgaacgac cgagcgcagc    6000
gagtcagtga gcgaggaagc ggaagagcgc ccaatacgca aaccgcctct ccccgcgcgt    6060
tggccgattc attaatgcag cagctgcgcg ctcgctcgct cactgaggcc gcccgggcaa    6120
agcccgggcg tcgggcgacc tttggtcgcc cggcctcagt gagcgagcga gcgcgcagag    6180
agggagtggc caactccatc actaggggtt ccttgtagtt aatgattaac cgccatgct    6240
acttatctac gtagccatgc tctagacata gctcgaca                           6278
```

```
SEQ ID NO: 40          moltype = DNA   length = 6278
FEATURE                Location/Qualifiers
misc_feature           1..6278
                       note = pGG2-hAAT-hsoFGF21 variant 1
source                 1..6278
                       mol_type = other DNA
                       organism = synthetic construct
SEQUENCE: 40
gatctgatat catcgatgaa ttcgagctcg gtacccggcc gcagatttag gtgacactat    60
agaatatgca tcactagtaa gcttgcgaat tccagtctac agagaggtct ctgacctctg    120
ccccagctcc aaggtcagca ggcagggagg gctgtgtgtt tgctgtttgc tgcttgcaat    180
gtttgcccat tttagggaca tgagtaggct gaagtttgt cagtgtggac ttcagaggca    240
gcacacaaac agcaagcttg cgaattccag tctacagaga ggtctctgac ctctgcccca    300
gctccaaggt cagcaggcag ggagggctgt gtgtttgctg tttgctgctt gcaatgtttg    360
cccattttag ggacatgagt aggctgaagt tgttcagtg tggacttcag aggcagcaca    420
caaacgcaa gcttgcgaat tccagtctac agagaggtct ctgacctctg cccagctcc    480
aaggtcagca ggcagggagg gctgtgtgtt tgctgtttgc tgcttgcaat gtttgcccat    540
tttagggaca tgagtaggct gaagtttgtt cagtgtggac ttcagaggca gcacacaaac    600
agcaagcttt gctctagact ggaattcgtc gacgagctcc ctatagtgag tcgtattaga    660
ggccgactga ccccggtaccc ggggatcttg ctaccagtgg aacagccact aaggattctg    720
cagtgagagc agagggccag ctaagtggta ctctcccaga gactgtctga ctcacgccac    780
```

-continued

```
cccctccacc ttggacacag gacgctgtgg tttctgagcc aggtacaatg actcctttcg    840
gtaagtgcag tggaagctgt acactgccca ggcaaagcgt ccgggcagcg taggcgggcg    900
actcagatcc cagccagtgg acttagcccc tgtttgctcc tccgataact ggggtgacct    960
tggttaatat tcaccagcag cctcccccgt tgccctctg gatccactgc ttaaatacgg    1020
acgaggacag ggccctgtct cctcagcttc aggcaccacc actgacctgg gacagtgaat    1080
gtccccctga tctgcggccg tgactctctt aaggtagcct tgcagaagtt ggtcgtgagg    1140
cactgggcag gtaagtatca aggttacaag acaggtttaa ggagaccaat agaaactggg    1200
cttgtcgaga cagagaagac tcttgcgttt ctgataggca cctattggtc ttactgacat    1260
ccactttgcc tttctctcca caggtgtcca ctcccagttc aattacagct cttaaggcta    1320
gagtacttaa tacgactcac tataggctag cgccaccatg gattctgatg agacaggctt    1380
cgagcacagc ggcctgtggg tttcagttct ggctggactg ctgctgggag cctgtcaggc    1440
acaccctatt ccagatagca gccctctgct gcagttcggc ggacaagtgc ggcagagata    1500
cctgtacacc gacgacgccc agcagacaga agcccacctg gaaatcagag aggatggcac    1560
agttggcgga gccgccgatc agtctcctga atctctgctc cagctgaagg ccctgaagcc    1620
tggcgtgatc cagatcctgg gcgtgaaaac cagccggttc ctgtgccaaa gacctgacgg    1680
cgccctgtat ggcagcctgc actttgatcc tgaggcctgc agcttcagag agctgctgct    1740
tgaggacggc tacaacgtgt accagtctga ggcccatggc ctgcctctgc atctgcctgg    1800
aaacaagagc cctcacagag atcccgctcc tagaggccct gccagatttc tgcctcttcc    1860
tggattgcct cctgctctgc cagagcctcc tggaattctg gctcctcagc ctcctgatgt    1920
gggcagctct gatcctctga gcatggtcgg acctagccag ggcagatctc ctagctacgc    1980
ctcttgagcg gccgcttccc tttagtgagg gttaatgctt cgagcagaca tgataagata    2040
cattgatgag tttggacaaa ccacaactag aatgcagtga aaaaaatgct ttatttgtga    2100
aatttgtgat gctattgctt tatttgtaac cattataagc tgcaataaac aagttaacaa    2160
caacaattgc attcatttta tgtttcaggt tcaggggggag atgtgggagg tttttttaaag    2220
caagtaaaac ctctacaaat gtggtaaaat ccgataaggg actagagcat ggctacgtag    2280
ataagtagca tggcgggtta atcattaact acaaggaacc cctagtgatg gagttggcca    2340
ctccctctct gcgcgctcgc tcgctcactg aggccgggcg accaaaggtc gcccgacgcc    2400
cgggctttgc ccgggcggcc tcagtgagcg agcgagcgcg ccagctggcg taatagcgaa    2460
gaggcccgca ccgatcgccc ttcccaacag ttgcgcagcc tgaatggcga atggaattcc    2520
agacgattga gcgtcaaaat gtaggtattt ccatgagcgt ttttccgttg caatggctgg    2580
cggtaatatt gttctggata ttaccagcaa ggccgatagt ttgagttctt ctactcaggc    2640
aagtgatgtt attactaatc aaagaagtat tgcgacaacg gttaatttgc gtgatggaca    2700
gactctttta ctcggtggcc tcactgatta taaaaacact tctcaggatt ctggcgtacc    2760
gttcctgtct aaaatccctt taatcggcct cctgtttagc tcccgctctg attctaacga    2820
ggaaagcacg ttatacgtgc tcgtcaaagc aaccatagta cgcgccctga gcggcgcat    2880
taagcgcggc gggtgtggtg gttacgcgca gcgtgaccgc tacacttgcc agcgccctag    2940
cgcccgctcc tttcgctttc ttcccttcct ttctcgccac gttcgccggc tttccccgtc    3000
aagctctaaa tcgggggctc cctttagggt tccgatttag tgctttacgg cacctcgacc    3060
ccaaaaaact tgattagggt gatggttcac gtagtgggcc atcgccctga tagacggttt    3120
ttcgcccttt gacgttggag tccacgttct ttaatagtgg actcttgttc caaactggaa    3180
caacactcaa ccctatctcg gtctattctt ttgatttata agggattttg ccgatttcgg    3240
cctattggtt aaaaaatgag ctgatttaac aaaaatttaa cgcgaatttt aacaaaatat    3300
taacgtctac aatttaaata tttgcttata caatcttcct gtttttgggg cttttctgat    3360
tatcaaccgg ggtacatatg attgacatgc tagttttacg attaccgttc atcgattctc    3420
ttgtttgctc cagactctca ggcaatgacc tgatagcctt tgtagagacc tctcaaaaat    3480
agctaccctc tccggcatga atttatcagc tagaacggtt gaatatcata ttgatggtga    3540
tttgactgtc tccggccttt ctcacccgtt tgaatcttta cctacacatt actcaggcat    3600
tgcatttaaa atatatgagg gttctaaaaa ttttttatcct tgcgttgaaa taaaggcttc    3660
tcccgcaaaa gtattacagg gtcataatgt tttttggtaca accgatttag ctttatgctc    3720
tgaggcttta ttgcttaatt ttgctaattc tttgccttgc ctgtatgatt tattggatgt    3780
tggaatcgcc tgatgcggta ttttctcctt acgcatctgt gcggtatttc acaccgcata    3840
tggtgcactc tcagtacaat ctgctctgat gccgcatagt taagccagcc ccgacacccg    3900
ccaacacccg ctgacgcgcc ctgacgggct tgtctgctcc cggcatccgc ttacagacaa    3960
gctgtgaccg tctccgggag ctgcatgtgt cagaggtttt caccgtcatc accgaaacgc    4020
gcgagacgaa agggcctcgt gatacgccta tttttatagg ttaatgtcat gataataatg    4080
gtttcttaga cgtcaggtgg cacttttcgg ggaaatgtgc gcggaacccc tatttgttta    4140
tttttctaaa tacattcaaa tatgtatccg ctcatgagac aataaccctg ataaatgctt    4200
caataatatt gaaaaaggaa gagtatgagt attcaacatt tccgtgtcgc ccttattccc    4260
ttttttgcgg cattttgcct tcctgttttt gctcacccag aaacgctggt gaaagtaaaa    4320
gatgctgaag atcagttggg tgcacgagtg ggttacatcg aactggatct caacagcggt    4380
aagatccttg agagttttcg ccccgaagaa cgttttccaa tgatgagcac ttttaaagtt    4440
ctgctatgtg gcgcggtatt atcccgtatt gacgccgggc aagagcaact cggtcgccgc    4500
atacactatt ctcagaatga cttggttgag tactcaccag tcacagaaaa gcatcttacg    4560
gatggcatga cagtaagaga attatgcagt gctgccataa ccatgagtga taacactgcg    4620
gccaacttac ttctgacaac gatcggagga ccgaaggagc taaccgcttt tttgcacaac    4680
atgggggatc atgtaactcg ccttgatcgt tgggaaccgg agctgaatga agccatacca    4740
aacgacgagc gtgacaccac gatgcctgta gcaatggcaa caacgttgcg caaactatta    4800
actggcgaac tacttactct agcttcccgg caacaattaa tagactggat ggaggcggat    4860
aaagttgcag gaccacttct gcgctcggcc cttccggctg gctggtttat tgctgataaa    4920
tctggagccg gtgagcgtgg gtctcgcggt atcattgcag cactggggcc agatggtaag    4980
ccctcccgta tcgtagttat ctacacgacg gggagtcagg caactatgga tgaacgaaat    5040
agacagatcg ctgagatagg tgcctcactg attaagcatt ggtaactgtc agaccaagtt    5100
tactcatata ctttagat tgatttaaaa cttcattttt aatttaaaag gatctaggtg    5160
aagatccttt ttgataatct catgaccaaa atcccttaac gtgagttttc gttccactga    5220
gcgtcagacc ccgtagaaaa gatcaaagga tcttcttgag atcctttttt tctgcgcgta    5280
atctgctgct tgcaaacaaa aaaaccaccg ctaccagcgg tggtttgttt gccggatcaa    5340
gagctaccaa ctctttttcc gaaggtaact ggcttcagca gagcgcagat accaaatact    5400
gtccttctag tgtagccgta gttaggccac cacttcaaga actctgtagc accgcctaca    5460
tacctcgctc tgctaatcct gttaccagtg gctgctgcca gtggcgataa gtcgtgtctt    5520
```

```
accgggttgg actcaagacg atagttaccg gataaggcgc agcggtcggg ctgaacgggg   5580
ggttcgtgca cacagcccag cttggagcga acgacctaca ccgaactgag atacctacag   5640
cgtgagctat gagaaagcgc cacgcttccc gaagggagaa aggcggacag gtatccggta   5700
agcggcaggg tcggaacagg agagcgcacg agggagcttc caggggggaaa cgcctggtat   5760
ctttatagtc ctgtcgggtt tcgccacctc tgacttgagc gtcgattttt gtgatgctcg   5820
tcaggggggc ggagcctatg gaaaaacgcc agcaacgcgg cctttttacg gttcctggcc   5880
ttttgctggc cttttgctca catgttcttt cctgcgttat ccctgattc tgtggataac   5940
cgtattaccg cctttgagtg agctgatacc gctcgccgca gccgaacgac cgagcgcagc   6000
gagtcagtga gcgaggaagc ggaagagcgc ccaatacgca aaccgcctct ccccgcgcgt   6060
tggccgattc attaatgcag cagctgcgcg ctcgctcgct cactgaggcc gcccgggcaa   6120
agcccgggcg tcgggcgacc tttggtcgcc cggcctcagt gagcgagcga gcgcgcagag   6180
agggagtggc caactccatc actaggggtt ccttgtagtt aatgattaac ccgccatgct   6240
acttatctac gtagccatgc tctagacatg gctcgaca                          6278
```

SEQ ID NO: 41            moltype = DNA  length = 6278
FEATURE                  Location/Qualifiers
misc_feature             1..6278
                         note = pGG2-hAAT-hsoFGF21 variant 2
source                   1..6278
                         mol_type = other DNA
                         organism = synthetic construct
SEQUENCE: 41

```
cagcagctgc gcgctcgctc gctcactgag gccgcccggg caaagcccgg gcgtcgggcg   60
acctttggtc gcccggcctc agtgagcgag cgagcgcgca gagagggagt ggccaactcc   120
atcactaggg gttccttgta gttaatgatt aacccgccat gctacttatc tacgtagcca   180
tgctctagac atggctcgac agatctgata tcatcgatga attcgagctc ggtacccggc   240
cgcagattta ggtgacacta tagaatatgc atcactagta agcttgcgaa ttccagtcta   300
cagagaggtc tctgacctct gccccagctc caaggtcagc aggcagggag ggctgtgtgt   360
ttgctgtttg ctgcttgcaa tgtttgccca ttttagggac atgagtaggc tgaagtttgt   420
tcagtgtgga cttcagaggc agcacacaaa cagcaagctt gctgaattcca gtctacagag   480
aggtctctga cctctgcccc agtccaagg tcagcaggca gggagggctg tgtgtttgct   540
gtttgctgct tgcaatgttt gcccatttta gggacatgag taggctgaag tttgttcagt   600
gtggacttca gaggcagcac acaaacagca gcttgcgaa ttccagtcta cagagaggtc   660
tctgacctct gccccagctc caaggtcagc aggcagggag ggctgtgtgt ttgctgtttg   720
ctgcttgcaa tgtttgccca ttttagggac atgagtaggc tgaagtttgt tcagtgtgga   780
cttcagaggc agcacacaaa cagcaagctt gctctagac tggaattcgt cgacgagctc   840
cctatagtga gtcgtattag aggccgactg acccggtacc cggggatctt gctaccagtg   900
gaacagccac taaggattct gcagtgagag cagagggcca gctaagtggt actctcccag   960
agactgtctg actcacgcca ccccctccac cttggacaca ggacgctgtg gtttctgagc   1020
caggtacaat gactcctttc ggtaagtgca gtggaagctg tacactgccc aggcaaagc   1080
tccgggcagc gtaggcgggc gactcagatc ccagccagtg gacttagccc ctgtttgctc   1140
ctccgataac tgggggtgacc ttggttaata ttcaccagca gcctccccg ttgcccctct   1200
ggatccactg cttaaatacg gacgaggaca gggccctgtc tcctcagctt caggcaccac   1260
cactgacctg ggacagtgaa tgtcccctg atctgcggcc gtgactctct taaggtagc   1320
ttgcagaagt tggtcgtgag gcactgggca ggtaagtatc aaggttacaa gacaggttta   1380
aggagaccaa tagaaactgg gcttgtcgag acagagaaga ctcttgcgtt tctgataggc   1440
acctattggt cttactgaca tccactttgc ctttctctcc acaggtgtcc actcccagtt   1500
caattacagc tcttaaggct agagtactta atacgactca ctataggcta gcgccaccat   1560
ggacagcgat gaaaccgggt tcgagcacag cggtctgtgg gtgtccgtgc tggccggact   1620
gctcctggga gcctgtcagg cgcacccat ccctgactcc tcgccgctgc tgcaattcgg   1680
cggacaagtc cgcccagagat acctgtacac cgacgacgcc cagcagaccg aagcccacct   1740
ggaaattcgg gaggacggga ctgtgggagg cgctgcagat cagtcacccg agtccctcct   1800
ccaactgaag gccttgaagc ccggcgtgat tcagatcctg ggcgtgaaaa cttcccgctt   1860
cctttgccaa cggccggatg gagctctgta cggatccctg cacttcgacc ccgaagcctg   1920
ctcattccgc gagctgctcc ttgaggacgg ctataacgtg taccagtctg aggcccatgg   1980
actcccctg catctgcccg gcaacaagtc ccctcaccgg gatcctgccc caagaggccc   2040
agctcggttt ctgcctctgc cgggactgcc tccagcgttg cccgaacccc ctggtatcct   2100
ggccccgcaa ccacctgacg tcggttcgtc ggacccgctg agcatggtcg gtccgagcca   2160
gggaaggtcc ccgtcctacg catcctgagc ggccgcttcc ctttagtgag ggttaatgct   2220
tcgagcagac atgataagat acattgatga gtttggacaa accacaacta gaatgcagtg   2280
aaaaaaatgc tttatttgtg aaatttgtga tgctattgct ttatttgtaa ccattataag   2340
ctgcaataaa caagttaaca acaacaattg cattcatttt atgtttcagg ttcaggggga   2400
gatgtgggag gttttttaaa gcaagtaaaa cctctacaaa tgtggtaaaa tccgataagg   2460
gactagagca tggctacgta gataagtagc atggcgggtt aatcattaac tacaaggaac   2520
ccctagtgat ggagttggcc actccctctc tgcgcgctcg ctcgctcact gaggccgggc   2580
gaccaaaggt cgcccgacgc ccgggctttg cccgggcggc ctcagtgagc gagcgagcgc   2640
gccagctggc gtaatagcga gagggcccgc accgatcgcc cttcccaaca gttgcgcagc   2700
ctgaatggcg aatggaattc cagacgattg agcgtcaaaa tgtaggtatt tccatgaggc   2760
tttttccgtt gcaatggctg gcggtaatat tgttctggat attaccagca aggccgatag   2820
tttgagttct tctactcagg caagtgatgt tattactaat caaagaagta ttgcgacaac   2880
ggttaatttg cgtgatggac agactctttt actcggtggc ctcactgatt ataaaaacac   2940
ttctcaggat tctggcgtac cgttcctgtc taaatccct ttaatcggcc tcctgtttag   3000
ctcccgctct gattctaacg aggaaagcac gttatacgtg ctcgtcaaag caaccatagt   3060
acgcgccctg tagcggcgca ttaagcgcgg cgggtgtggt ggttacgcgc agcgtgaccg   3120
ctacacttgc cagcgcccta gcgcccgctc ctttcgcttt cttcccttcc tttctcgcca   3180
cgttcgccgg ctttccccgt caagctctaa atcgggggct ccctttaggg ttccgattta   3240
gtgctttacg gcacctcgac cccaaaaaac ttgattaggg tgatggttca cgtagtgggc   3300
catcgccctg atagacggtt tttcgccctt tgacgttgga gtccacgttc tttaatagtg   3360
gactcttgtt ccaaactgga acaacactca accctatctc ggtctattct tttgatttat   3420
```

```
aagggatttt gccgatttcg gcctattggt taaaaaatga gctgatttaa caaaaattta   3480
acgcgaattt taacaaaata ttaacgtcta caatttaaat atttgcttat acaatcttcc   3540
tgttttgggg gctttctga ttatcaaccg gggtacatat gattgacatg ctagttttac    3600
gattaccgtt catcgattct cttgtttgct ccagactctc aggcaatgac ctgatagcct   3660
ttgtagagac ctctcaaaaa tagctaccct ctccggcatg aatttatcag ctagaacggt   3720
tgaatatcat attgatggtg atttgactgt ctccggcctt tctcacccgt ttgaatcttt   3780
acctacacat tactcaggca ttgcatttaa aatatatgag ggttctaaaa atttttatcc   3840
ttgcgttgaa ataaaggctt ctcccgcaaa agtattacag ggtcataatg tttttggtac   3900
aaccgattta gctttatgct ctgaggcttt attgcttaat tttgctaatt ctttgccttg   3960
cctgtatgat ttattggatg ttggaatcgc ctgatgcggt attttctcct tacgcatctg   4020
tgcggtattt cacaccgcat atggtgcact ctcagtacaa tctgctctga tgccgcatag   4080
ttaagccagc cccgacaccc gccaacaccc gctgacgcgc cctgacgggc ttgtctgctc   4140
ccggcatccg cttacagaca agctgtgacc gtctccggga gctgcatgtg tcagaggttt   4200
tcaccgtcat caccgaaacg cgcgagacga aagggcctcg tgatacgcct attttatag    4260
gttaatgtca tgataataat ggtttcttag acgtcaggtg gcactttcg gggaaatgtg    4320
cgcggaaccc ctatttgttt attttctaa atacattcaa atatgtatcc gctcatgaga    4380
caataaccct gataaatgct tcaataatat tgaaaaagga agagtatgag tattcaacat    4440
ttccgtgtcg cccttattcc cttttttgcg gcattttgcc ttcctgtttt tgctcaccca    4500
gaaacgctgg tgaaagtaaa agatgctgaa gatcagttgg gtgcacgagt gggttacatc    4560
gaactggatc tcaacagcgg taagatcctt gagagttttc gccccgaaga acgttttcca    4620
atgatgagca cttttaaagt tctgctatgt ggcgcggtat tatcccgtat tgacgccggg    4680
caagagcaac tcggtcgccg catacactat tctcagaatg acttggttga gtactcacca    4740
gtcacagaaa agcatcttac ggatggcatg acagtaagag aattatgcag tgctgccata    4800
accatgagtg ataacactgc ggccaactta cttctgacaa cgatcggagg accgaaggag    4860
ctaaccgctt ttttgcacaa catgggggat catgtaactc gccttgatcg ttgggaaccg    4920
gagctgaatg aagccatacc aaacgacgag cgtgacacca cgatgcctgt agcaatggca    4980
acaacgttgc gcaaactatt aactggcgaa ctacttactc tagcttcccg gcaacaatta    5040
atagactgga tggaggcgga taaagttgca ggaccacttc tgcgctcggc ccttccggct    5100
ggctggttta ttgctgataa atctggagcc ggtgagcgtg ggtctcgcgg tatcattgca    5160
gcactggggc cagatggtaa gccctcccgt atcgtagtta tctacacgac ggggagtcag    5220
gcaactatgg atgaacgaaa tagacagatc gctgagatag gtgcctcact gattaagcat    5280
tggtaactgt cagaccaagt ttactcatat atactttaga ttgatttaaa acttcatttt    5340
taatttaaaa ggatctaggt gaagatcctt tttgataatc tcatgaccaa aatcccttaa    5400
cgtgagtttt cgttccactg agcgtcagac cccgtagaaa agatcaaagg atcttcttga    5460
gatccttttt ttctgcgcgt aatctgctgc ttgcaaacaa aaaaaccacc gctaccagcg    5520
gtggtttgtt tgccggatca agagctacca actcttttc cgaaggtaac tggcttcagc     5580
agagcgcaga taccaaatac tgtccttcta gtgtagccgt agttaggcca ccacttcaag    5640
aactctgtag caccgcctac atacctcgct ctgctaatcc tgttaccagt ggctgctgcc    5700
agtggcgata agtcgtgtct taccgggttg gactcaagac gatagttacc ggataaggcg    5760
cagcggtcgg gctgaacggg gggttcgtgc acacagccca gcttggagcg aacgacctac    5820
accgaactga gatacctaca gcgtgagcta tgagaaagcg ccacgcttcc cgaagggaga    5880
aaggcggaca ggtatccggt aagcggcagg gtcggaacag gagagcgcac gagggagctt    5940
ccaggggggaa acgcctggta tctttatagt cctgtcgggt ttcgccacct ctgacttgag    6000
cgtcgatttt tgtgatgctc gtcaggggg cggagcctat ggaaaaacgc cagcaacgcg     6060
gcctttttac ggttcctggc cttttgctgg ccttttgctc acatgttctt tcctgcgtta    6120
tcccctgatt ctgtggataa ccgtattacc gcctttgagt gagctgatac cgctcgccgc    6180
agccgaacga ccgagcgcag cgagtcagtg agcgaggaag cggaagagcg cccaatacgc    6240
aaaccgcctc tccccgcgcg ttggccgatt cattaatg                          6278
```

```
SEQ ID NO: 42              moltype = DNA  length = 6278
FEATURE                    Location/Qualifiers
misc_feature               1..6278
                           note = pGG2-hAAT-hsoFGF21 variant 3
source                     1..6278
                           mol_type = other DNA
                           organism = synthetic construct
SEQUENCE: 42
cagcagctgc gcgctcgctc gctcactgag gccgcccggg caaagcccgg gcgtcgggcg   60
acctttggtc gcccggcctc agtgagcgag cgagcgcgca gagagggagt ggccaactcc   120
atcactaggg gttccttgta gttaatgatt aacccgccat gctacttatc tacgtagcca   180
tgctctagac atggctcgac agatctgata tcatcgatga attcgagctc ggtacccggc   240
cgcagattta ggtgacacta gaaatatgc atcactagta agcttgcgaa ttccagtcta     300
cagagaggtc tctgacctct gccccagctc caaggtcagc aggcagggag ggctgtgtgt   360
ttgctgtttg ctgcttgcaa tgtttgccca ttttagggac atgagtaggc tgaagtttgt   420
tcagtgtgga cttcagaggc agcacacaaa cagcaagctt gcgaattcca gtctacagag   480
aggtctctga cctctgcccc agctccaagg tcagcaggca gggagggctg tgtgtttgct   540
gtttgctgct tgcaatgttt gcccatttta gggacatgag taggctgaag tttgttcagt   600
gtggacttca gaggcagcac acaaacagca gcttgcgaa ttccagtcta cagagaggtc    660
tctgacctct gccccagctc caaggtcagc aggcagggag ggctgtgtgt ttgctgtttg   720
ctgcttgcaa tgtttgccca ttttagggac atgagtaggc tgaagtttgt tcagtgtgga   780
cttcagaggc agcacacaaa cagcaagctt gctctagac tggaattcgt cgacgagctc    840
cctatagtga gtcgtattag aggccgactg acccggtacc cggggatctt gctaccagtg   900
gaacagccac taaggattct gcagtgagag cagagggcca gctaagtggt actctcccag   960
agactgtctg actcacgcca ccccctccac cttggacgagc ggctgtg gttctgagc      1020
caggtacaat gactcctttc ggtaagtgca gtggaagctg tacactgccc aggcaaagcg   1080
tccgggcagc gtaggcgggc gactcagatc ccagccagtg gacttagccc ctgtttgctc   1140
ctccgataac tggggtgacc ttggttaata ttcaccagca gcctcccccg ttgcccctct   1200
ggatccactg cttaaatacg gacgaggaca gggccctgtc tcctcagctt caggcaccac   1260
cactgacctg ggacagtgaa tgtcccctg atctgcggcc gtgactctct taaggtagcc   1320
```

-continued

```
ttgcagaagt tggtcgtgag gcactgggca ggtaagtatc aaggttacaa gacaggttta  1380
aggagaccaa tagaaactgg gcttgtcgag acagagaaga ctcttgcgtt tctgataggc  1440
acctattggt cttactgaca tccactttgc ctttctctcc acaggtgtcc actcccagtt  1500
caattacagc tcttaaggct agagtactta atacgactca ctataggcta gcgccaccat  1560
ggattccgac gaaactggat ttgaacattc agggctgtgg gtctctgtgc tggctggact  1620
gctgctgggg gcttgtcagg ctcaccccat ccctgacagc tcccctctgc tgcagttcgg  1680
aggacaggtg cggcagagat acctgtatac cgacgatgcc cagcagacag aggcacacct  1740
ggagatcagg gaggacggaa ccgtgggagg agcagccgat cagtctcccg agagcctgct  1800
gcagctgaag gccctgaagc ctggcgtgat ccagatcctg ggcgtgaaga catctcggtt  1860
tctgtgccag cggcccgacg gcgccctgta cggctccctg cacttcgatc ccgaggcctg  1920
ttcttttagg gagctgctgc tggaggacgg ctacaacgtg tatcagagcg aggcacacgg  1980
cctgccactg cacctgcctg gcaataagtc ccctcaccgc gatccagcac ccaggggccc  2040
agcacgcttc ctgcctctgc caggcctgcc ccctgccctg ccagagccac ccggcatcct  2100
ggcccccag cctccagatg tgggctccag cgatcctctg tcaatggtgg ggccaagtca  2160
ggggcggagt ccttcatacg catcataagc ggccgcttcc ctttagtgag ggttaatgct  2220
tcgagcagac atgataagat acattgatga gtttggacaa accacaacta gaatgcagtg  2280
aaaaaaatgc tttatttgtg aaatttgtga tgctattgct ttatttgtaa ccattataag  2340
ctgcaataaa caagttaaca acaacaattg cattcatttt atgtttcagg ttcaggggga  2400
gatgtgggag gttttttaaa gcaagtaaaa cctctacaaa tgtggtaaaa tccgataagg  2460
gactagagca tggctacgta gataagtagc atggcgggtt aatcattaac tacaaggaac  2520
ccctagtgat ggagttggcc actccctctc tgcgcgctcg ctcgctcact gaggccgggc  2580
gaccaaaggt cgcccgacgc ccgggctttg cccgggcggc ctcagtgagc gagcgagcgc  2640
gccagctggc gtaatagcga gaggcccgc accgatcgcc cttcccaaca gttgcgcagc  2700
ctgaatggcg aatggaattc cagacgattg agcgtcaaaa tgtaggtatt tccatgagcg  2760
tttttccgtt gcaatggctg gcggtaatat tgttctggat attaccagca aggccgatag  2820
tttgagttct tctactcagg caagtgatgt tattactaat caaagaagta ttgcgacaac  2880
ggttaatttg cgtgatggac agactctttt actcggtggc ctcactgatt ataaaaacac  2940
ttctcaggat tctggcgtac cgttcctgtc taaaatccct ttaatcggcc tcctgtttag  3000
ctcccgctct gattctaacg aggaaagcac gttatacgtg ctcgtcaaag caaccatagt  3060
acgcgccctg tagcggcgca ttaagcgcgg cgggtgtggt ggttacgcgc agcgtgaccg  3120
ctacacttgc cagcgcccta gcgcccgctc ctttcgcttt cttcccttcc tttctcgcca  3180
cgttcgccgg ctttccccgt caagctctaa atcgggggct ccctttaggg ttccgattta  3240
gtgctttacg gcacctcgac cccaaaaaac ttgattaggg tgatggttca cgtagtgggc  3300
catcgccctg atagacggtt tttcgccctt tgacgttgga gtccacgttc tttaatagtg  3360
gactcttgtt ccaaactgga acaacactca accctatctc ggtctattct tttgatttat  3420
aagggatttt gccgatttcg gcctattggt taaaaaatga gctgatttaa caaaaattta  3480
acgcgaattt taacaaaata ttaacgtcta caatttaaat atttgcttat acaatcttcc  3540
tgtttttggg gcttttctga ttatcaaccg gggtacatat gattgacatg ctagttttac  3600
gattaccgtt catcgattct cttgtttgct ccagactcag aggcaatgac ctgatagcct  3660
ttgtagagac ctctcaaaaa tagctaccct ctccggcatg aatttatcag ctagaacggt  3720
tgaatatcat attgatggtg atttgactgt ctccggcctt tctcacccgt ttgaatcttt  3780
acctacacat tactcaggca ttgcatttaa aatatatgag ggttctaaaa attttttatcc  3840
ttgcgttgaa ataaaggctt ctcccgcaaa agtattacag agtggttcag tttttggtac  3900
aaccgattta gctttatgct ctgaggcttt attgcttaat tttgctaatt ctttgccttg  3960
cctgtatgat ttattggatg ttggaatcgc ctgatgcggt attttctcct tacgcatctg  4020
tgcggtattt cacaccgcat atggtgcact ctcagtacaa tctgctctga tgccgcatag  4080
ttaagccagc cccgacaccc gccaacaccc gctgacgcgc cctgacgggc ttgtctgctc  4140
ccggcatccg cttacagaca agctgtgacc gtctccggga gctgcatgtg tcagaggttt  4200
tcaccgtcat caccgaaacg cgcgagacga aagggcctcg tgatacgcct atttttatag  4260
gttaatgtca tgataataat ggtttcttag acgtcaggtg gcacttttcg gggaaatgtg  4320
cgcggaaccc ctatttgttt attttctaa atacattcaa atatgtatcc gctcatgaga  4380
caataaccct gataaatgct tcaataatat tgaaaaagga agagtatgag tattcaacat  4440
ttccgtgtcg cccttattcc cttttttgcg gcattttgcc ttcctgtttt tgctcaccca  4500
gaaacgctgg tgaaagtaaa agatgctgaa gatcagttgg gtgcacgagt gggttacatc  4560
gaactggatc tcaacagcgg taagatcctt gagagttttc gccccgaaga acgttttcca  4620
atgatgagca cttttaaagt tctgctatgt ggcgcggtat tatcccgtat tgacgccggg  4680
caagagcaac tcggtcgccg catacactat tctcagaatg acttggttga gtactcacca  4740
gtcacagaaa agcatcttac ggatggcatg acagtaagag aattatgcag tgctgccata  4800
accatgagtg ataacactgc ggccaactta cttctgacaa cgatcgggag gaccgaaggag  4860
ctaaccgctt ttttgcacaa catgggggat catgtaactc gccttgatcg ttgggaaccg  4920
gagctgaatg aagccatacc aaacgacgag cgtgacacca cgatgcctgt agcaatggca  4980
acaacgttgc gcaaactatt aactggcgaa ctacttactc tagcttcccg gcaacaatta  5040
atagactgga tggaggcgga taaagttgca ggaccacttc tgcgctcggc ccttccggct  5100
ggctggttta ttgctgataa atctggagcc ggtgagcgtg ggtctcgcgg tatcattgca  5160
gcactgggggc cagatggtaa gccctcccgt atcgtagtta tctacacgac ggggagtcag  5220
gcaactatgg atgaacgaaa tagacagatc gctgagatag gtgcctcact gattaagcat  5280
tggtaactgt cagaccaagt ttactcatat atactttaga ttgatttaaa acttcatttt  5340
taatttaaaa ggatctaggt gaagatcctt tttgataatc tcatgaccaa aatcccttaa  5400
cgtgagtttt cgttccactg agcgtcagac cccgtagaaa agatcaaagg atcttcttga  5460
gatccttttt ttctgcgcgt aatctgctgc ttgcaaacaa aaaaaccacc gctaccagcg  5520
gtggtttgtt tgccggatca agagctacca actctttttc cgaaggtaac tggcttcagc  5580
agagcgcaga taccaaatac tgtccttcta gtgtagccgt agttaggcca ccacttcaag  5640
aactctgtag caccgcctac atacctcgct ctgctaatcc tgttaccagt ggctgctgcc  5700
agtggcgata agtcgtgtct taccgggttg gactcaagac gatagttacc ggataaggcg  5760
cagcggtcgg gctgaacggg gggttcgtgc acacagccca gcttggagcg aacgacctac  5820
accgaactga gatacctaca gcgtgagcta tgagaaagcg ccacgcttcc cgaagggaga  5880
aaggcggaca ggtatccggt aagcggcagg gtcggaacag gagagcgcac gagggagctt  5940
ccagggggaa acgcctggta tctttatagt cctgtcgggt ttcgccacct ctgacttgag  6000
cgtcgatttt tgtgatgctc gtcagggggg cggagcctat ggaaaaacgc cagcaacgcg  6060
```

```
gccttttac ggttcctggc cttttgctgg ccttttgctc acatgttctt tcctgcgtta    6120
tcccctgatt ctgtggataa ccgtattacc gcctttgagt gagctgatac cgctcgccgc    6180
agccgaacga ccgagcgcag cgagtcagtg agcgaggaag cggaagagcg cccaatacgc    6240
aaaccgcctc tccccgcgcg ttggccgatt cattaatg                            6278
```

```
SEQ ID NO: 43            moltype = DNA   length = 133
FEATURE                  Location/Qualifiers
misc_feature             1..133
                         note = Chimeric intron composed of introns from human
                          beta-globin and immunoglobulin heavy chain genes
source                   1..133
                         mol_type = other DNA
                         organism = synthetic construct
SEQUENCE: 43
gtaagtatca aggttacaag acaggtttaa ggagaccaat agaaactggg cttgtcgaga    60
cagagaagac tcttgcgttt ctgataggca cctattggtc ttactgacat ccactttgcc    120
tttctctcca cag                                                       133
```

```
SEQ ID NO: 44            moltype = DNA   length = 1671
FEATURE                  Location/Qualifiers
misc_feature             1..1671
                         note = CAG promoter
source                   1..1671
                         mol_type = other DNA
                         organism = synthetic construct
SEQUENCE: 44
gacattgatt attgactagt tattaatagt aatcaattac ggggtcatta gttcatagcc    60
catatatgga gttccgcgtt acataactta cggtaaatgg cccgcctggc tgaccgccca    120
acgacccccg cccattgacg tcaataatga cgtatgttcc catagtaacg ccaatagggga   180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct     300
ggcattatgc ccagtacatg accttatggg actttcctac ttggcagtac atctacgtat    360
tagtcatcgc tattaccatg gtcgaggtga gccccacgtt ctgcttcact ctccccatct    420
ccccccctc cccacccca attttgtatt tatttatttt ttaattattt tgtgcagcga     480
tgggggcggg ggggggggg gggcgcgcgc caggcggggc ggggcggggc gaggggcgga     540
gcggggcgag gcggagaggt gcggcggcag ccaatcagag cggcgcgctc cgaaagtttc    600
ctttttatggc gaggcggcgg cggcggcggc cctataaaaa gcgaagcgcg cggcgggcgg   660
gagtcgctgc gttgccttcg ccccgtgccc cgctccgcgc cgcctcgcgc cgcccgcccc    720
ggctctgact gaccgcgtta ctcccacagg tgagcgggcg ggacggccct tctcctccgg    780
gctgtaatta gcgcttggtt taatgacggc ttgtttcttt tctgtggctg cgtgaaagcc    840
ttgagggggct ccgggagggc cctttgtgcg ggggagcgg ctcggggggt gcgtgcgtgt    900
gtgtgtgcgt ggggagcgcc gcgtgcggct ccgcgctgcc cggcggctgt gagcgctgcg    960
ggcgcgggcac ggggctttgt gcgctccgca gtgtgcgcga ggggagcgcg ggcggggcct   1020
gtgccccgcg gtgcgggggg ctgcgagggg aacaaaggct gcgtgcgggg tgtgtgcgtg    1080
gggggggtgag caggggggtgt gggcgcgtcg gtcgggctgc aacccccct gcacccccct    1140
ccccgagttg ctgagcacgg cccggcttcg ggtgcggggc tccgtacggg gcgtggccgcg   1200
gggctcgccg tgccgggcgg ggggtgcgg caggtgggg gcggggcgcg gcgcggggcg       1260
cctcgggccg gggagggctc gggggagggg cgcggcggcc cccggagcgc cggcggctgt    1320
cgaggcgcgg cgagccgcag ccattgcctt ttatggtaat cgtgcgagag ggcgcaggga    1380
cttccttttgt cccaaatctg tgcggagccg aaatctggga ggcgccgccg cacccctct     1440
agcgggcgg gggcgaagcg gtgcggcgcc ggcaggaagg aaatgggcgg gaggggcctt      1500
cgtgcgtcgc cgcgccgccg tcccccttctc cctctccagc ctcgggggctg tccgcgggggg  1560
gacggctgcc ttcggggggg acggggcagg gcgggggttcg gcttctggcg tgtgaccggc    1620
ggctctagag cctctgctaa ccatgttcat gccttcttct ttttcctaca g             1671
```

```
SEQ ID NO: 45            moltype = DNA   length = 212
FEATURE                  Location/Qualifiers
misc_feature             1..212
                         note = CMV promoter
source                   1..212
                         mol_type = other DNA
                         organism = synthetic construct
SEQUENCE: 45
gtgatgcggt tttggcagta caccaatggg cgtggatagc ggtttgactc acggggattt    60
ccaagtctcc accccattga cgtcaatggg agtttgtttt ggcaccaaaa tcaacgggac    120
tttccaaaat gtcgtaacaa ctgcgatcgc ccgccccgtt gacgcaaatg ggcggtaggc    180
gtgtacggtg ggaggtctat ataagcagag ct                                  212
```

```
SEQ ID NO: 46            moltype = DNA   length = 380
FEATURE                  Location/Qualifiers
misc_feature             1..380
                         note = CMV enhancer
source                   1..380
                         mol_type = other DNA
                         organism = synthetic construct
SEQUENCE: 46
ggcattgatt attgactagt tattaatagt aatcaattac ggggtcatta gttcatagcc    60
catatatgga gttccgcgtt acataactta cggtaaatgg cccgcctggc tgaccgccca    120
acgacccccg cccattgacg tcaataatga cgtatgttcc catagtaacg ccaatagggga   180
```

```
ctttccattg acgtcaatgg gtggagtatt tacggtaaac tgcccacttg gcagtacatc  240
aagtgtatca tatgccaagt ccgcccccta ttgacgtcaa tgacggtaaa tggcccgcct  300
ggcattatgc ccagtacatg accttacggg actttcctac ttggcagtac atctacgtat  360
tagtcatcgc tattaccatg                                               380

SEQ ID NO: 47              moltype = DNA   length = 397
FEATURE                   Location/Qualifiers
misc_feature              1..397
                          note = hAAT promoter
source                    1..397
                          mol_type = other DNA
                          organism = synthetic construct
SEQUENCE: 47
gatcttgcta ccagtggaac agccactaag gattctgcag tgagagcaga gggccagcta  60
agtggtactc tcccagagac tgtctgactc acgccacccc ctccaccttg gacacaggac  120
gctgtggttt ctgagccagg tacaatgact cctttcggta agtgcagtgg aagctgtaca  180
ctgcccaggc aaagcgtccg ggcagcgtag gcgggcgact cagatcccag ccagtggact  240
tagcccctgt ttgctcctcc gataactggg gtgaccttgg ttaatattca ccagcagcct  300
cccccgttgc ccctctggat ccactgctta aatacggacg aggacagggc cctgtctcct  360
cagcttcagg caccaccact gacctgggac agtgaat                            397

SEQ ID NO: 48              moltype = DNA   length = 128
FEATURE                   Location/Qualifiers
misc_feature              1..128
                          note = Truncated AAV2 5'ITR
source                    1..128
                          mol_type = other DNA
                          organism = synthetic construct
SEQUENCE: 48
gcgcgctcgc tcgctcactg aggccgcccg ggcaaagccc gggcgtcggg cgacctttgg  60
tcgcccggcc tcagtgagcg agcgagcgcg cagagaggga gtggccaact ccatcactag  120
gggttcct                                                            128

SEQ ID NO: 49              moltype = DNA   length = 128
FEATURE                   Location/Qualifiers
misc_feature              1..128
                          note = Truncated AAV2 3'ITR
source                    1..128
                          mol_type = other DNA
                          organism = synthetic construct
SEQUENCE: 49
aggaacccct agtgatggag ttggccactc cctctctgcg cgctcgctcg ctcactgagg  60
ccgggcgacc aaaggtcgcc cgacgcccgg gctttgcccg gcggcctca gtgagcgagc   120
gagcgcgc                                                            128

SEQ ID NO: 50              moltype = DNA   length = 122
FEATURE                   Location/Qualifiers
misc_feature              1..122
                          note = SV40 polyadenylation signal
source                    1..122
                          mol_type = other DNA
                          organism = synthetic construct
SEQUENCE: 50
taagatacat tgatgagttt ggacaaacca caactagaat gcagtgaaaa aaatgcttta  60
tttgtgaaat ttgtgatgct attgctttat ttgtaaccat tataagctgc aataaacaag  120
tt                                                                  122

SEQ ID NO: 51              moltype = DNA   length = 449
FEATURE                   Location/Qualifiers
misc_feature              1..449
                          note = Rabbit beta-globin polyadenylation signal
source                    1..449
                          mol_type = other DNA
                          organism = synthetic construct
SEQUENCE: 51
gatctttttc cctctgccaa aaattatggg gacatcatga gccccttga gcatctgact   60
tctggctaat aaaggaaatt tattttcatt gcaatagtgt gttggaattt tttgtgtctc  120
tcactcggaa ggacatatgg gagggcaaat catttaaaac atcagaatga gtatttggtt  180
tagagtttgg caacatatgc ccatatgctg gctgccatga acaaaggttg gctataaaga  240
ggtcatcagt atatgaaaca gccccctgct gtccattcct attccatag aaaagccttg   300
acttgaggtt agatttttttt tatattttgt tttgtgttat ttttttcttt aacatcccta  360
aaattttcct tacatgtttt actagccaga tttttcctcc tctcctgact actcccagtc  420
atagctgtcc ctcttctctt atggagatc                                    449

SEQ ID NO: 52              moltype = DNA   length = 592
FEATURE                   Location/Qualifiers
misc_feature              1..592
                          note = CMV promoter and CMV enhancer
source                    1..592
```

```
                          mol_type = other DNA
                          organism = synthetic construct
SEQUENCE: 52
ggcattgatt attgactagt tattaatagt aatcaattac ggggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaataggga   180
ctttccattg acgtcaatgg gtggagtatt tacggtaaac tgcccacttg gcagtacatc   240
aagtgtatca tatgccaagt ccgcccccta ttgacgtcaa tgacggtaaa tggcccgcct   300
ggcattatgc ccagtacatg accttacggg actttcctac ttggcagtac atctacgtat   360
tagtcatcgc tattaccatg gtgatgcggt tttggcagta caccaatggg cgtggatagc   420
ggtttgactc acggggattt ccaagtctcc accccattga cgtcaatggg agtttgtttt   480
ggcaccaaaa tcaacgggac tttccaaaat gtcgtaacaa ctgcgatcgc ccgcccgtt    540
gacgcaaatg ggcggtaggc gtgtacggtg ggaggtctat ataagcagag ct          592

SEQ ID NO: 53              moltype = DNA   length = 154
FEATURE                   Location/Qualifiers
misc_feature              1..154
                          note = Hepatocyte control region (HCR) enhancer from
                           apolipoprotein E
source                    1..154
                          mol_type = other DNA
                          organism = synthetic construct
SEQUENCE: 53
cagagaggtc tctgacctct gccccagctc caaggtcagc aggcagggag ggctgtgtgt    60
ttgctgtttg ctgcttgcaa tgtttgccca ttttagggac atgagtaggc tgaagtttgt   120
tcagtgtgga cttcagaggc agcacacaaa cagc                               154

SEQ ID NO: 54              moltype = DNA   length = 651
FEATURE                   Location/Qualifiers
misc_feature              1..651
                          note = mini/aP2 promoter
source                    1..651
                          mol_type = other DNA
                          organism = synthetic construct
SEQUENCE: 54
gattaacccg ccatgctact tatctactcg acattgatta ttgactaggg gaattccagc    60
aggaatcagg tagctggaga atcgcacaga gccatgcgat tcttggcaag ccatgcgaca   120
aaggcagaaa tgcacatttc acccagagag aagggattga tgtcagcagg aagtcaccac   180
ccagagagca aatggagttc ccagatgcct gacatttgcc ttcttactgg atcagagttc   240
actagtggaa gtgtcacagc ccaaacactc cccaaagct cagcccttcc ttgccttgta   300
acaatcaagc cgctcctgga tgaactgctc cgccctctgt ctctttggca gggttggagc   360
ccactgtggc ctgagcgact tctatggctc ccttttctgt gattttcatg gtttctgagc   420
tcttttcccc cgctttatga ttttctcttt ttgtctctct cttgctaaac ctccttcgta   480
tatatgccct ctcaggtttc atttctgaat catctactgt gaactattcc cattgtttgc   540
cagaagcccc ctggttcttc cttctagaca ccaggcaagg ggcaggaggt aagaggcagg   600
agtccataaa acagccctga gagcctgctg ggtcagtgcc tgctgtcaga a            651

SEQ ID NO: 55              moltype = DNA   length = 722
FEATURE                   Location/Qualifiers
misc_feature              1..722
                          note = mini/UCP1 promoter
source                    1..722
                          mol_type = other DNA
                          organism = synthetic construct
SEQUENCE: 55
gacgtcacag tgggtcagtc acccttgatc acactgcacc agtcttcacc tttccacgct    60
tcctgccaga gcatgaatca ggctctctgg ggataccggc ctcacccta ctgaggcaaa    120
ctttctccca cttctcagag gctctgaggg cagcaaggtc agccctttct ttggaatcta   180
gaaccactcc ctgtcttgag ctgacatcac agggcaggca gatgcagcag ggaagggct    240
gggactggga cgttcatcct acaagaaagc tgtggaactt ttcagcaaca tctcagaaat   300
cagatcgcac ttattcaaag gagccaggcc ctgctctgcg ccctggtgga ggctcctcat   360
gtgaagagtg acaaaaggca ccatgttgtg gatacggggc gaagcccctc cggtgtgtcc   420
tccaggcatc atcaggaact agtgccaaag cagaggtgct ggccagggct ttgggagtga   480
cgcgcgtctg ggaggcttgt gcgcccaggg cacgcccctg cctgattccca ctagcaggtc   540
ttgggggacc tgggccggct ctgcccctcc tccagcaatc gggctataaa gctcttccaa   600
gtcagggcgc agaagtgccg ggcgatccgg gcttaaagag cgagaggaag ggacgctcac   660
ctttgagctc ctccacaaat agccctggtg gctgccacag aagttcgaag ttgagagttc   720
gg                                                                  722

SEQ ID NO: 56              moltype = DNA   length = 326
FEATURE                   Location/Qualifiers
misc_feature              1..326
                          note = C5-12 promoter
source                    1..326
                          mol_type = other DNA
                          organism = synthetic construct
SEQUENCE: 56
cggccgtccg ccttcggcac catcctcacg acacccaaat atggcgacgg gtgaggaatg    60
gtggggagtt attttagag cggtgaggaa ggtgggcagg cagcaggtgt tggcgctcta   120
```

-continued

```
aaaataactc ccgggagtta ttttttagagc ggaggaatgg tggacaccca aatatggcga   180
cggttcctca cccgtcgcca tatttggggtg tccgccctcg gccgggggccg cattcctggg   240
ggccgggcgg tgctcccgcc cgcctcgata aaaggctccg gggccggcgg cggcccacga   300
gctaccggga ggagcgggag gcgcca                                        326

SEQ ID NO: 57        moltype = DNA  length = 4930
FEATURE              Location/Qualifiers
misc_feature        1..4930
                    note = pAAV-EF1a-mmFGF21-pA
source              1..4930
                    mol_type = other DNA
                    organism = synthetic construct
SEQUENCE: 57
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac tagggggttcc tgcggccgcg gctccggtgc ccgtcagtgg gcagagcgca   180
catcgcccac agtccccgag aagttggggg gagggggtcgg caattgaacc ggtgcctaga   240
gaaggtggcg cggggtaaac tgggaaagtg atgtcgtgta ctggctccgc cttttttcccg   300
agggtggggg agaaccgtat ataagtgcag tagtcgccgt gaacgttctt tttcgcaacg   360
ggtttgccgc cagaacacag gtaagtgccg tgtgtggttc ccgcggggcct ggcctcttta   420
cgggttatgg cccttgcgtg ccttgaatta cttccactgg ctgcagtacg tgattcttga   480
tcccgagctt cgggttggaa gtggggtggga gagttcgaagg ccttgcgctt aaggagcccc   540
ttcgcctcgt gcttgagttg aggcctggcc tgggcgctgg ggcgccgcg tgcgaatctg   600
gtggcacctt cgcgcctgtc tcgctgcttt cgataagtct ctagccattt aaaattttg   660
atgacctgct gcgacgcttt ttttctggca agatagtctt gtaaatgcgg gccaagatct   720
gcacactggt atttcggttt ttggggccgc gggcggcgac ggggcccgtg cgtcccagcg   780
cacatgttcg gcgaggcggg gcctgcgagc gcggccaccg agaatcggac gggggtagtc   840
tcaagctggc cggcctgctc tggtgcctgg cctcgcgccg ccgtgtatcg ccccgccctg   900
ggcggcaagg ctggcccggt cggcaccagt tgcgtgagcg aaagatggc cgcttcccgg   960
ccctgctgca gggagctcaa aatggaggac gcggcgctcg ggagagcggg cgggtgagtc   1020
acccacacaa aggaaaaggg cctttccgtc ctcagccgtc gcttcatgtg actccacgga   1080
gtaccgggcg ccgtccaggc acctcgatta gttctcgagc ttttggagta cgtcgtcttt   1140
aggttggggg gaggggtttt atgcgatgga gtttccccac actgagtggg tggagactga   1200
agttaggcca gcttggcact tgatgtaatt ctccttggaa tttgcccttt ttgagtttga   1260
atcttggttc attctcaagc ctcagacagt ggttcaaagt tttttttcttc catttcaggt   1320
gtcgtgagga atttcgactg ctagcacgcg tgatatcaat ggaatggatg agatctagag   1380
ttgggaccct gggactgtgg gtccgactgc tgctggctgt cttcctgctg ggggtctacc   1440
aagcataccc catccctgac tccagccccc tcctccagtt tgggggtcaa gtccggcaga   1500
ggtacctcta cacagatgac gaccaagaca ctgaagccca cctggagatc agggaggatg   1560
gaacagtggt aggcgcagca caccgcagtc cagaaagtct cctggagctc aaagccttga   1620
agccaggggt cattcaaatc ctgggtgtca aagcctctag gtttctttgc caacagcag   1680
atggagctct ctatggatcg cctcactttg atcctgaggc ctgcagcttc agagaactgc   1740
tgctggagga cggttacaat gtgtaccagt ctgaagccca tggcctgccc ctgcgtctga   1800
ctcagaagga ctccccaaac caggatgcaa catcctgggg acctgtgcgc ttcctgccca   1860
tgccaggcct gctccacgag ccccaagacc aagcaggatt cctgccccca gagcccccag   1920
atgtgggctc ctctgacccc ctgagcatgg tagagccttt acaggggccga agccccagct   1980
atgcgtcctg agatatcaaa gaattctaag cttgtcgacg aatgcaattg ttgttaatta   2040
attgttaact tgtttattgc agcttataat ggttacaaat aaagcaatag catcacaaat   2100
ttcacaaata aagcattttt ttcactgcat tctagttgtg gtttgtccaa actcatcaat   2160
gtatcttagt cgagttaatt aacggcgggcc gcaggaaccc ctagtgatgg agttggccac   2220
tccctctctg cgcgctcgct cgctcactga ggccgggcga ccaaaggtcg cccgacgccc   2280
gggctttgcc cgggcggcct cagtgagcga gcgagcgcgc agctgcctgc aggggcgcct   2340
gatgcggtat tttctcctta cgcatctgtg cggtatttca caccgcatac gtcaaagcaa   2400
ccatagtacg cgccctgtag cggcgcatta gcgcggcgg gtgtggtggt tacgcgcagc   2460
gtgaccgcta cacttgccag cgccctagcg cccgctcctt tcgctttctt cccttccttt   2520
ctcgccacgt tcgccggctt tccccgtcaa gctctaaatc ggggctccc tttagggttc   2580
cgatttagtg ctttacggca cctcgacccc aaaaaacttg atttgggtga tggttcacgt   2640
agtgggccat cgccctgata cggttttt cgccctttga cgttggagtc cacgttcttt   2700
aatagtggac tcttgttcca aactggaaca acactcaacc ctatctcggg ctattctttt   2760
gatttataag ggattttgcc gatttcggcc tattggttaa aaaatgagct gatttaacaa   2820
aaatttaacg cgaatttaa caaaatatta acgtttacaa ttttatggtg cactctcagt   2880
acaatctgct ctgatgccgc atagttaagc cagccccgac acccgccaac acccgctgac   2940
gcgccctgac gggcttgtct gctcccggca tccgcttaca gacaagctgt gaccgtctcc   3000
gggagctgca tgtgtcagag gttttcaccg tcatcaccga aacgcgcgag acgaaagggc   3060
ctcgtgatac gcctattttt ataggttaat gtcatgataa taatggtttc ttagacgtca   3120
ggtggcactt ttcggggaaa tgtgcgcgga acccctattt gtttattttt ctaaatacat   3180
tcaaatatgt atccgctcat gagacaataa ccctgataaa tgcttcaata atattgaaaa   3240
aggaagagta tgagtattca acatttccgt gtcgccctta ttcccttttt tgcggcattt   3300
tgccttcctg tttttgctca cccagaaacg ctggtgaaag taaaagatgc tgaagatcag   3360
ttgggtgcac gagtgggtta tcgaactg atctcaaca gcggtaagat ccttgagagt   3420
tttcgccccg aagaacgttt tccaatgatg agcactttta aagttctgct atgtggcgcg   3480
gtattatccc gtattgacgc cgggcaagag caactcggtc gccgcataca ctattctcag   3540
aatgacttgg ttgagtactc accagtcaca gaaaagcatc ttacggatgg catgacagta   3600
agagaattat gcagtgctgc cataaccatg agtgataaca ctgcggccaa cttacttctg   3660
acaacgatcg aggaccgaa ggagctaacc gcttttttgc acaacatggg ggatcatgta   3720
actcgccttg atcgttggga accggagctg aatgaagcca taccaaacga cgagcgtgac   3780
accacgatgc ctgtagcaat ggcaacaacg ttgcgcaaac tattaactgg cgaactactt   3840
actctagctt cccggcaaca attaatagac tggatggagg cggataaagt tgcaggacca   3900
cttctgcgct cggcccttcc ggctggctgg tttattgctg ataaatctgg agccggtgag   3960
```

```
cgtgggtctc gcggtatcat tgcagcactg gggccagatg gtaagccctc ccgtatcgta  4020
gttatctaca cgacggggag tcaggcaact atggatgaac gaaatagaca gatcgctgag  4080
ataggtgcct cactgattaa gcattggtaa ctgtcagacc aagtttactc atatatactt  4140
tagattgatt taaaacttca tttttaattt aaaaggatct aggtgaagat ccttttttgat  4200
aatctcatga ccaaaatccc ttaacgtgag ttttcgttcc actgagcgtc agaccccgta  4260
gaaaagatca aaggatcttc ttgagatcct tttttctgc gcgtaatctg ctgcttgcaa  4320
acaaaaaaac caccgctacc agcggtggtt tgtttgccgg atcaagagct accaactctt  4380
tttccgaagg taactggctt cagcagagcg cagataccaa atactgtcct tctagtgtag  4440
ccgtagttag gccaccactt caagaactct gtagcaccgc ctacatacct cgctctgcta  4500
atcctgttac cagtggctgc tgccagtggc gataagtcgt gtcttaccgg gttggactca  4560
agacgatagt taccggataa ggcgcagcgg tcgggctgaa cggggggttc gtgcacacag  4620
cccagcttgg agcgaacgac ctacaccgaa ctgagatacc tacagcgtga gctatgagaa  4680
agcgccacgc ttcccgaagg gagaaaggcg gacaggtatc cggtaagcgg cagggtcgga  4740
acaggagagc gcacgaggga gcttccaggg ggaaacgcct ggtatcttta tagtcctgtc  4800
gggtttcgcc acctctgact tgagcgtcga tttttgtgat gctcgtcagg ggggcgggagc  4860
ctatggaaaa acgccagcaa cgcggccttt ttacggttcc tggccttttg ctggcctttt  4920
gctcacatgt                                                          4930
```